US008014961B2

(12) United States Patent
Bass et al.

(10) Patent No.: US 8,014,961 B2
(45) Date of Patent: Sep. 6, 2011

(54) INTEGRATED SYSTEMS AND METHODS FOR DIVERSITY GENERATION AND SCREENING

(75) Inventors: Steven H. Bass, Hillsborough, CA (US); Simon Christopher Davis, San Francisco, CA (US); Phillip A. Patten, Portola Valley, CA (US); Matthew Tobin, San Carlos, CA (US); Jeremy S. Minshull, Los Altos, CA (US); Mark Welch, Fremont, CA (US); Claus Gustafsson, Belmont, CA (US); Brian Carr, Raleigh, NC (US); Stephan J. Jenne, Foster City, CA (US); Sun Ai Raillard, Mountain View, CA (US); Andreas Crameri, Mountain View, CA (US); Willem P. C. Stemmer, Los Gatos, CA (US); Robin Emig, Belmont, CA (US); Pascal Longchamp, Lausanne (CH); Stanley Goldman, Walnut Creek, CA (US); Lorraine J. Giver, Sunnyvale, CA (US); Joseph A. Affholter, Zephyr Cove, NV (US)

(73) Assignee: Codexis Mayflower Holdings, LLC, Redwood City, CA (US)

( * ) Notice: Subject to any disclaimer, the term of this patent is extended or adjusted under 35 U.S.C. 154(b) by 1083 days.

(21) Appl. No.: 11/677,505

(22) Filed: Feb. 21, 2007

(65) Prior Publication Data
US 2008/0015116 A1 Jan. 17, 2008

Related U.S. Application Data

(63) Continuation of application No. 10/154,936, filed on May 23, 2002, now Pat. No. 7,462,469, which is a continuation of application No. 09/760,010, filed on Jan. 10, 2001, now abandoned.

(60) Provisional application No. 60/175,551, filed on Jan. 11, 2000, provisional application No. 60/213,947, filed on Jun. 23, 2000.

(51) Int. Cl.
G01N 33/48 (2006.01)
(52) U.S. Cl. ........................................ 702/20
(58) Field of Classification Search ............ 702/20
See application file for complete search history.

(56) References Cited

U.S. PATENT DOCUMENTS

| 4,591,567 | A | 5/1986 | Britten et al. |
| 5,158,875 | A | 10/1992 | Miller et al. |
| 5,503,980 | A | 4/1996 | Cantor |
| 5,512,463 | A | 4/1996 | Stemmer |
| 5,514,588 | A | 5/1996 | Varadaraj |
| 5,545,531 | A | 8/1996 | Rava et al. |
| 5,585,275 | A | 12/1996 | Hudson et al. |
| 5,591,646 | A | 1/1997 | Hudson et al. |
| 5,605,793 | A | 2/1997 | Stemmer |
| 5,712,171 | A | 1/1998 | Zambias et al. |
| 5,763,239 | A | 6/1998 | Short et al. |
| 5,763,263 | A | 6/1998 | Dehlinger |
| 5,789,228 | A | 8/1998 | Lam et al. |
| 5,811,238 | A | 9/1998 | Stemmer et al. |
| 5,814,473 | A | 9/1998 | Warren et al. |
| 5,824,469 | A | 10/1998 | Horwitz et al. |
| 5,830,696 | A | 11/1998 | Short |
| 5,830,721 | A * | 11/1998 | Stemmer et al. ............ 506/10 |
| 5,834,252 | A | 11/1998 | Stemmer et al. |
| 5,837,458 | A | 11/1998 | Minshull et al. |
| 5,852,498 | A | 12/1998 | Youvan et al. |
| 5,859,700 | A | 1/1999 | Yang |
| 5,866,363 | A | 2/1999 | Pieczenik |
| 5,876,997 | A | 3/1999 | Kretz |
| 5,910,437 | A | 6/1999 | Kent et al. |
| 5,914,245 | A | 6/1999 | Bylina et al. |
| 5,925,749 | A | 7/1999 | Mathur et al. |
| 5,928,905 | A | 7/1999 | Stemmer et al. |
| 5,939,250 | A | 8/1999 | Short |
| 5,939,300 | A | 8/1999 | Robertson et al. |
| 5,942,430 | A | 8/1999 | Robertson et al. |
| 5,945,522 | A | 8/1999 | Cohen et al. |
| 5,948,666 | A | 9/1999 | Callen et al. |
| 5,958,672 | A | 9/1999 | Short |
| 5,958,751 | A | 9/1999 | Murphy et al. |
| 5,962,258 | A | 10/1999 | Mathur et al. |
| 5,962,283 | A | 10/1999 | Warren et al. |
| 5,965,408 | A | 10/1999 | Short |
| 5,985,646 | A | 11/1999 | Murphy et al. |
| 6,001,574 | A | 12/1999 | Short et al. |
| 6,004,788 | A | 12/1999 | Short |

(Continued)

FOREIGN PATENT DOCUMENTS
EP 0911396 A2 4/1999
(Continued)

OTHER PUBLICATIONS

Zhao et al., "Optimization of DNA Shuffling for High Fidelity Recombination," Nucleic Acids Research (1997) vol. 25, No. 6, pp. 1307-1308.*

(Continued)

*Primary Examiner* — Jerry Lin
(74) *Attorney, Agent, or Firm* — Weaver Austin Villeneuve & Sampson LLP

(57) ABSTRACT

Integrated systems and methods for diversity generation and screening are provided. The systems use common fluid and array handling components to provide nucleic acid diversification, transcription, translation, product screening and subsequent diversification reactions.

15 Claims, 40 Drawing Sheets

U.S. PATENT DOCUMENTS

| | | |
|---|---|---|
| 6,030,779 A | 2/2000 | Short |
| 6,054,267 A | 4/2000 | Short |
| 6,057,103 A | 5/2000 | Short |
| 6,096,548 A | 8/2000 | Stemmer |
| 6,117,679 A | 9/2000 | Stemmer |
| 6,132,970 A | 10/2000 | Stemmer |
| 6,159,368 A | 12/2000 | Moring et al. |
| 6,165,793 A | 12/2000 | Stemmer |
| 6,168,919 B1 | 1/2001 | Short |
| 6,171,820 B1 | 1/2001 | Short |
| 6,174,673 B1 | 1/2001 | Short et al. |
| 6,180,341 B1 | 1/2001 | Iverson et al. |
| 6,180,351 B1 | 1/2001 | Cattell |
| 6,180,406 B1 | 1/2001 | Stemmer |
| 6,238,884 B1 | 5/2001 | Short et al. |
| 6,264,891 B1 | 7/2001 | Heyneker et al. |
| 6,270,961 B1 | 8/2001 | Drmanac |
| 6,287,765 B1 | 9/2001 | Cubicciotti |
| 6,291,165 B1 | 9/2001 | Borchert et al. |
| 6,319,714 B1 | 11/2001 | Crameri et al. |
| 6,358,740 B1 | 3/2002 | Patten et al. |
| 6,368,861 B1 | 4/2002 | Crameri et al. |
| 6,376,246 B1 | 4/2002 | Crameri et al. |
| 6,403,312 B1 | 6/2002 | Dahiyat et al. |
| 6,406,910 B1 | 6/2002 | Patten et al. |
| 6,406,921 B1 | 6/2002 | Wagner et al. |
| 6,413,745 B1 | 7/2002 | Patten et al. |
| 6,423,542 B1 | 7/2002 | Crameri et al. |
| 6,426,224 B1 | 7/2002 | Crameri et al. |
| 6,479,652 B1 | 11/2002 | Crameri et al. |
| 6,521,427 B1 | 2/2003 | Evans |
| 6,521,453 B1 | 2/2003 | Crameri et al. |
| 6,586,182 B1 | 7/2003 | Patten et al. |
| 7,462,469 B2 | 12/2008 | Bass et al. |
| 2001/0039014 A1 | 11/2001 | Bass |
| 2001/0041349 A1 | 11/2001 | Patron et al. |
| 2001/0055763 A1 | 12/2001 | Singh |
| 2002/0012926 A1 | 1/2002 | Quake et al. |
| 2002/0042063 A1 | 4/2002 | Kilian |
| 2002/0048749 A1 | 4/2002 | Lipshutz et al. |
| 2002/0055099 A1 | 5/2002 | Fisher |
| 2002/0055112 A1 | 5/2002 | Patil et al. |
| 2002/0090649 A1 | 7/2002 | Chan et al. |
| 2002/0094533 A1 | 7/2002 | Hess et al. |
| 2002/0106667 A1 | 8/2002 | Yamamoto et al. |
| 2002/0119484 A1 | 8/2002 | Weidenhammer et al. |
| 2002/0142309 A1 | 10/2002 | Dattagupta |
| 2002/0142314 A1 | 10/2002 | Dong et al. |
| 2002/0142339 A1 | 10/2002 | Bardhan et al. |
| 2002/0146704 A1 | 10/2002 | Head et al. |
| 2002/0150917 A1 | 10/2002 | Weidenhammer et al. |
| 2002/0150921 A1 | 10/2002 | Barany et al. |
| 2002/0160369 A1 | 10/2002 | Dorsel et al. |
| 2002/0164634 A1 | 11/2002 | Patil et al. |
| 2002/0164656 A1 | 11/2002 | Hoeffler et al. |
| 2002/0168669 A1 | 11/2002 | Huang |
| 2002/0183934 A1 | 12/2002 | Selifonov et al. |
| 2003/0054384 A1 | 3/2003 | Bass et al. |
| 2003/0064393 A1 | 4/2003 | Bass et al. |
| 2008/0220990 A1 | 9/2008 | Fox |
| 2009/0312196 A1 | 12/2009 | Colbeck et al. |

FOREIGN PATENT DOCUMENTS

| | | |
|---|---|---|
| EP | 0911396 A3 | 5/1999 |
| EP | 0934999 A1 | 8/1999 |
| WO | WO 97/07205 | 2/1997 |
| WO | WO 97/20078 | 6/1997 |
| WO | WO 97/25410 | 7/1997 |
| WO | WO 97/31256 | 8/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/54312 | 12/1998 |
| WO | WO 98/55026 | 12/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/14318 | 3/1999 |
| WO | WO 99/14373 | 3/1999 |
| WO | WO 99/19341 | 4/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/58661 | 11/1999 |
| WO | WO 99/60170 | 11/1999 |
| WO | WO 99/65927 | 12/1999 |
| WO | WO 00/18906 | 4/2000 |
| WO | WO 00/23564 | 4/2000 |
| WO | WO 00/42559 | 7/2000 |
| WO | WO 00/42560 | 7/2000 |
| WO | WO 00/42561 | 7/2000 |
| WO | WO 00/48004 | 8/2000 |
| WO | WO 00/52155 | 9/2000 |
| WO | WO 00/53744 | 9/2000 |
| WO | WO 00/58517 | 10/2000 |
| WO | WO 01/79849 | 10/2001 |

OTHER PUBLICATIONS

Sun, "Modeling DNA Shuffling," Proceedings of the Second Annual International Conference on Computational Molecular Biology (1998) pp. 251-257.*

Chang, C., et al. (1999) "Evolution of a cytokine using DNA family shuffling." *Nature Biotechnology* 17:793-797.

Christians, F.C. et al., (1999) "Directed evolution of thymidine kinase for AZT phosphorylation using DNA family shuffling." *Nature Biotechnology* 17:259-264.

Coco et al., (2001) "DNA shuffling method for generating highly recombined genes and evolved enzymes" *Nature Biotechnology* vol. 19 pp. 354-359.

Crameri et al., (1993) "10(20)-Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194-195.

Crameri, A, et al. (1996) "Improved green fluorescent protein by molecular evolution using DNA shuffling." *Nature Biotechnology* 14:315-319.

Crameri, A. et al. (1996) "Construction and evolution of antibody-phage libraries by DNA shuffling." *Nature Medicine* 2:100-103.

Crameri, A. et al., (1997) "Molecular evolution of an arsenate detoxification pathway by DNA shuffling." *Nature Biotechnology* 15:436-438.

Crameri, A. et al., (1998) "DNA shuffling of a family of genes from diverse species accelerates directed evolution." *Nature* 391:288-291.

Gates, C.M. et al., (1996) "Affinity selective isolation of ligands from peptide libraries through display on a lac repressor headpiece dimer". *Journal of Molecular Biology* 255:373-386.

Minshull, J., Stemmer, W.P.C. (1999) "Protein evolution by molecular breeding." *Current Opinion in Chemical Biology* 3:284-290.

Ness, J. et al., (1999) "DNA shuffling of subgenominc sequences of subtilisin." *Nature Biotechnology* 17:893-896.

Patten, P.A. et al., (1997) "Application of DNA Shuffling to Pharmaceuticals and Vaccines." *Current Opinion in Biotechnology* 8:724-733.

Pelletier, Joelle N., (2001) "A Rachitt for our toolbox" *Nature Biotechnology* vol. 19, p. 314-315.

Stemmer, W.P.C. (1994) "DNA Shuffling by random fragmentation and reassembly: In vitro recombination for molecular evolution." *PNAS* 91:10751.

Stemmer, W.P.C. (1994) "Rapid evolution of a protein in vitro by DNA shuffling." *Nature* 370:389-391.

Stemmer, W.P.C. (1995) "The Evolution of Molecular Computation." *Science* 270:1510.

Stemmer, W.P.C. (1995) "Searching Sequence Space." *Bio/Technology* 13:549-553.

Stemmer, W.P.C. (1996) "Sexual PCR and Assembly PCR." In: *The Encyclopedia of Molecular Biology*. VCH Publishers, New York. pp. 447-457.

Stemmer, W.P.C. & Soong, N. W. (1999) "Molecular breeding of viruses for targeting and other clinical properties." *Tumor Targeting* 4:59-62.

Zhang, J. et al., (1997) "Directed evolution of an effective fucosidase from a galactosidase by DNA shuffling and screening." *Proceedings of the National Academy of Sciences, USA* 94:4504-4509.

Chou, H.P. et al (1999) "A Microfabricated Device for Sizing and Sorting DNA Molecules." *Proc. Nat'l Acad. Sci.* 96:11-113.

DeSilva et al. (1998) "Rapid Genotyping and Quantification on the LightCycler with Hybridization Probes" *Biochimica* 2:12-15.

DeSilva et al. (1998) "The LightCycler—The Smartest Innovation for More Efficient PCR" *Biochemica* 2:4-7.

Fu, A.Y. et al (1999) "A Microfabricated Fluorescence-Activated Cell Sorter," *Nat. Biotechnol.* 17:1109-1111.

Hanes and Pluckthun (1997) "In vitro Selection and Evolution of Functional Proteins by Using Ribosome Display." *Biochemistry* 94:4937-4942.

Hanes et al. (1988) "Ribosome Display Efficiently Selects and Evolves High-Affinity Antibodies in vitro from Immune Libraries" *PNAS* 95:14130-14135.

Hanes et al. (1999) "Comparison of *E. Coli* and rabbit reticulocyte ribosome display systems" *FEBS Lett.* 450(1-2):105-10.

Hays et al. (1981) "Recombination of uracil-containing Lambda bacteriophages." *J. Bacteriol.* 145(1):306-320.

Jermutus et al. (1998) "Recent advances in producing and selecting functional proteins by using cell-free translation" *Curr. Opin. Biotechnol.* 9(5):534-48.

Kopp et al. (1998) "Chemical Amplification: Continuous flow PCR on a Chip" *Science* 280:1046-1047.

Kreuzer et al. (1999) "LightCycler technology for the quantitation of bcr/ab1 fusion transcripts" *Cancer Research* 59(13):3171-4.

Laurendeau et al. (1999) "Quantitation of MYC gene expression in sporadic breast tumors with a real-time reverse transcriptionPCR assay" *Clin Chem* 59(12):2759-65.

Laurendeau et al. (1999) "TaqMan PCR-based gene dosage asay for predictive testing in individuals from a cancer family with INK4 locus haploinsufficiency" *Clin Chem* 45(7):982-6.

Lindner et al. (1997) "Specific Detection of His-tagged Proteins with Recombinant anti-His tag scFv-Phosphatase or scFv-phage fusions" *Biotechniques* 22(1):140-149.

Moore et al. (1997) "Strategies for the in vitro evolution of protein function: enzyme evolution by random recombination of improved sequences" *Journal of Mol. Bio.* 3:336-347.

Muller et al. (1998) "Tandem Immobilized Metal Ion Affinity Chromatography/Immunoaffinity purification of His-tagged proteins—evaluation of two anti-His-tag monoclonal antibodies" *Anal Biochem.* 259(1):54-61.

Nieba et al. (1997) "BIACORE analysis of histadine-tagged proteins using a chelating NTA sensor chip." *Anal. Biochem* 22(2):217-218.

Tyagi and Kramer (1996) "Molecular beacons: probes that fluoresce upon hybridization." *Nat Biotechnol* 14, 303-308.

Unger, M. et al (1999) "Single Molecule Fluorescence Observed with Mercury Lamp Illumination," *Biotechniques* 27:1008-1013.

Wang et al. (1997) "Biocatalytic plastics as active and stable materials for biotransformations" *Nat Biotechnol* 2:15(8):789-93.

Warner et al. (1981) "Synthesis and Metabolism of uracil-containing deoxyribonucleic acid in *Escherichia coli*" *J. Bacteriol.* 145(2):687-695.

Zhao et al. (1997) "Functional and nonfunctional mutations distinguished by random recombination of homologous genes" *Proc. Natl. Acad. Sci.* vol. 94:7997-8000.

Moore, J.C., et al., *J. Mol. Biol.* (1997) 272:336-347.

Zhao, H., et al., *PNAS(USA)* (1997) 94:7997-8000.

\* cited by examiner

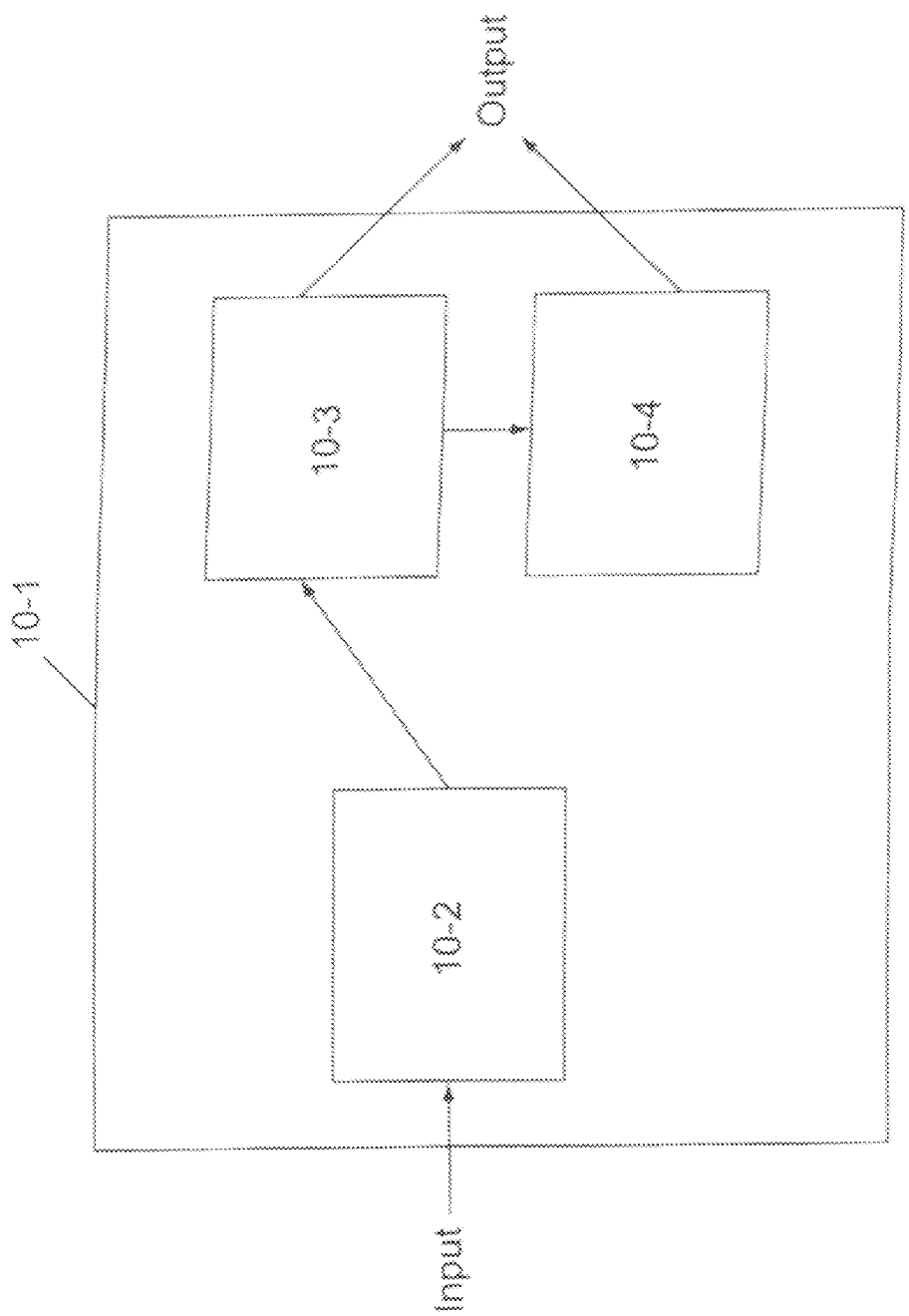

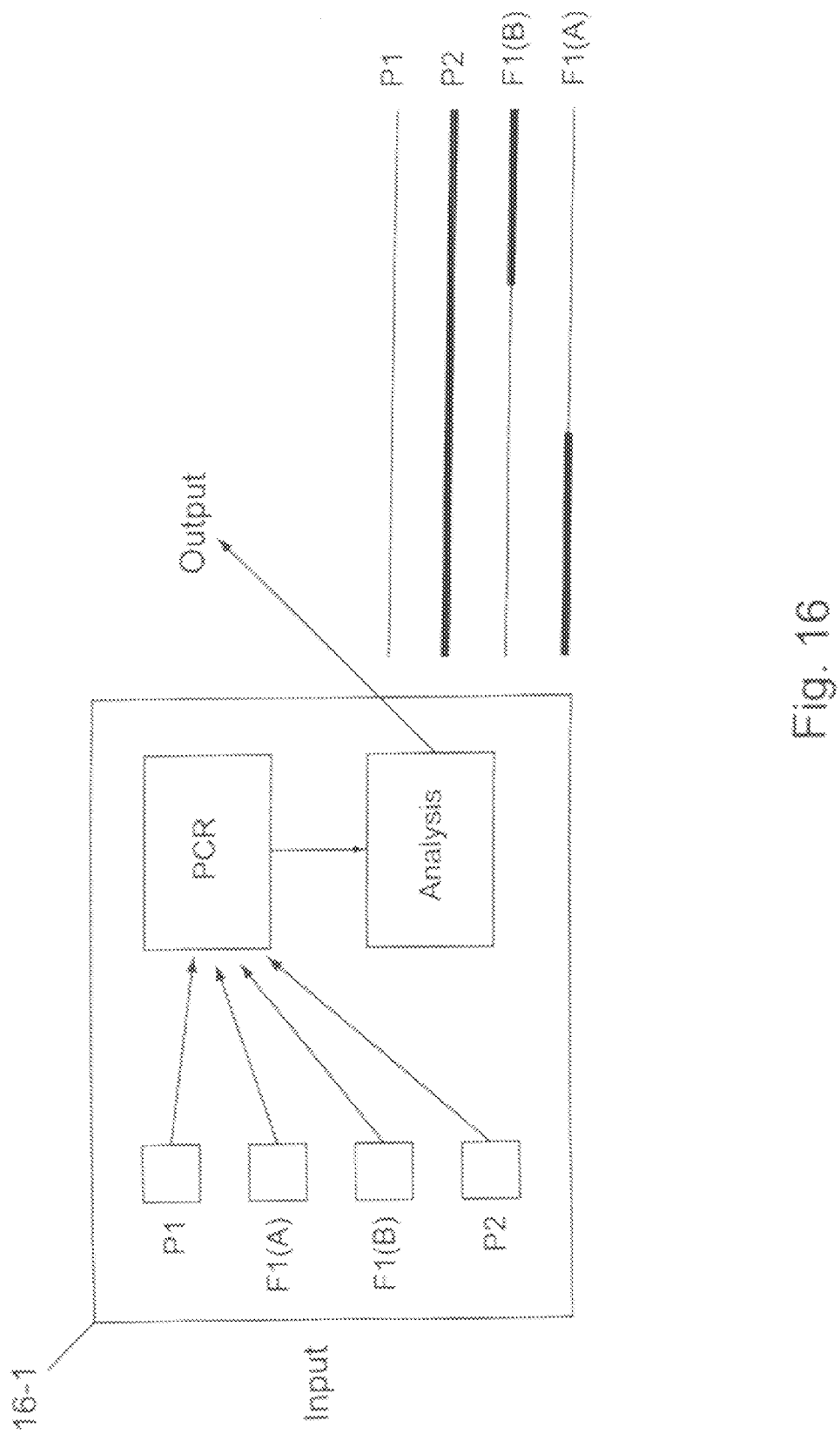

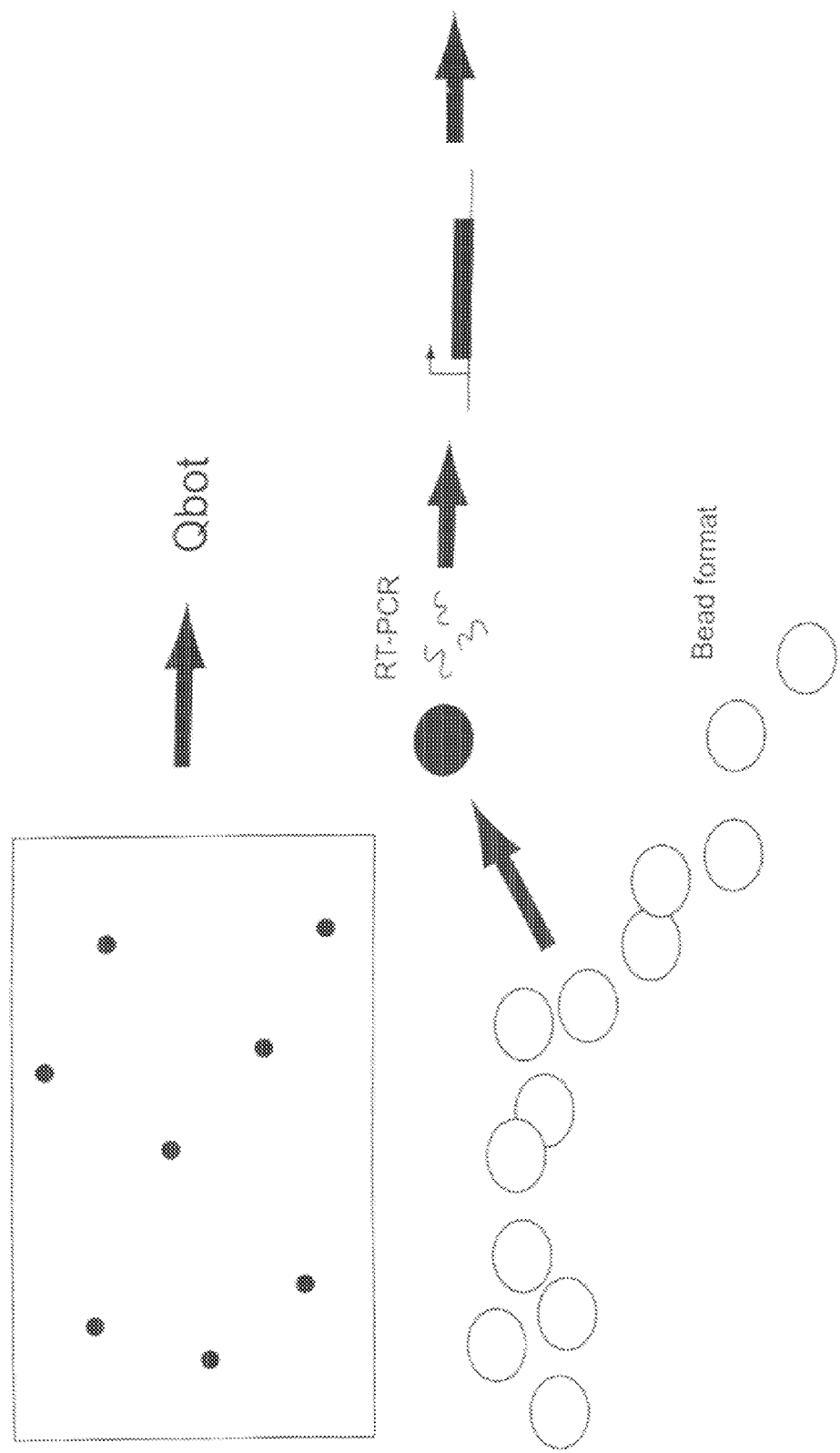

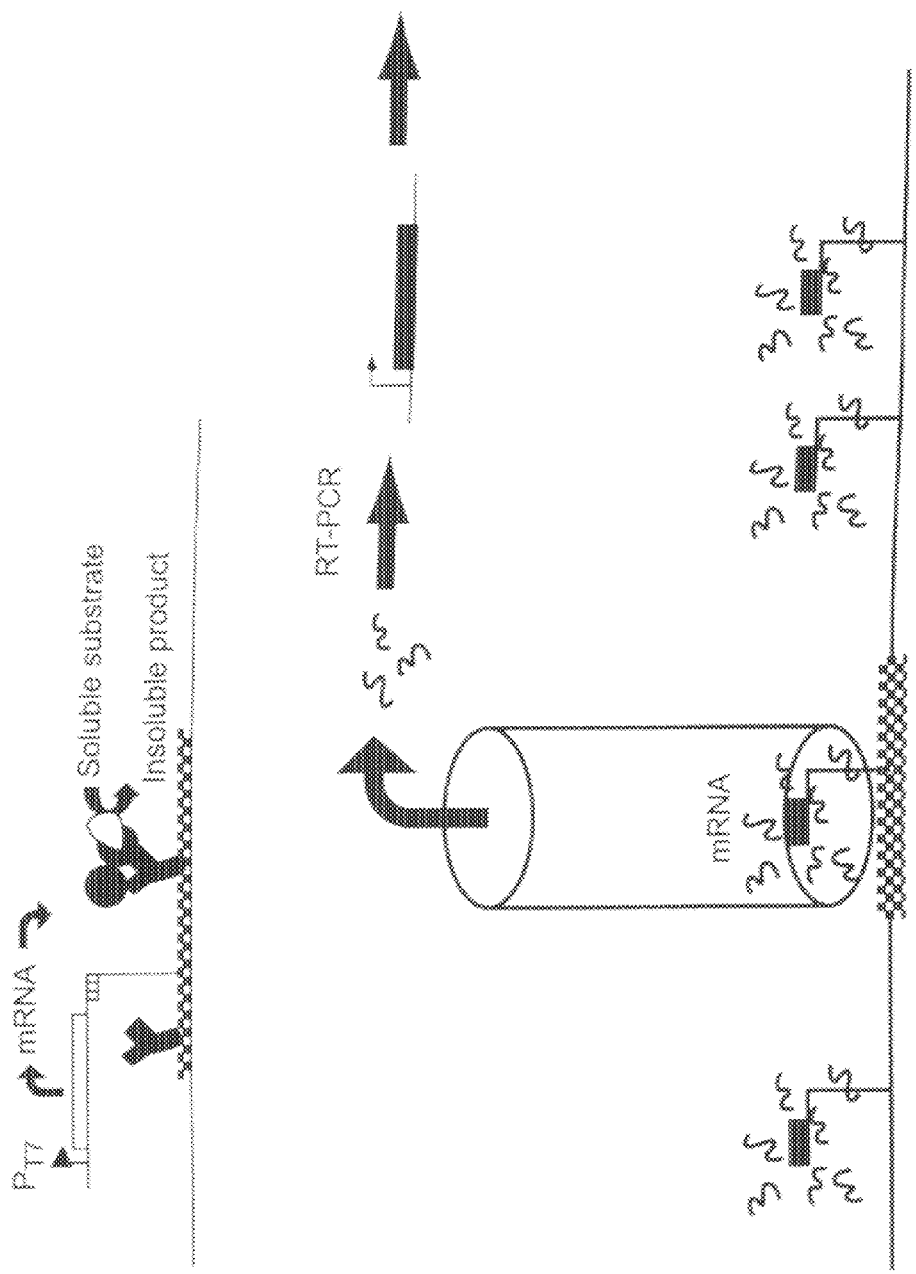

INTEGRATED SYSTEMS AND METHODS FOR DIVERSITY GENERATION AND SCREENING

CROSS REFERENCE TO RELATED APPLICATIONS

This application is a continuation of U.S. Ser. No. 10/154,936, filed May 23, 2002, which is a continuation of U.S. Ser. No. 09/760,010, filed Jan. 10, 2001, which claims the benefit under 35 U.S.C. §119(e) of US provisional patent applications INTEGRATED SYSTEMS AND METHODS FOR DIVERSITY GENERATION AND SCREENING by Bass et al. U.S. Ser. No. 60/175,551 filed Jan. 11, 2000 and INTEGRATED SYSTEMS AND METHODS FOR DIVERSITY AND SCREENING by Bass et al. U.S. Ser. No. 60/213,947 filed Jun. 23, 2000. Each of the above documents is incorporated herein by reference in their entireties and for all purposes.

FIELD OF THE INVENTION

The present invention relates to automated devices and systems for performing nucleic acid recombination, mutation, shuffling and other diversity generating reactions in vitro, as well as related methods of performing automated diversity generation reactions. The devices and systems can include, e.g., modules for generating diversity in nucleic acids, for recombining these nucleic acids, for arraying the nucleic acids, for making or copying arrays of reaction mixtures comprising the nucleic acids and for performing in vitro translation and/or transcription of diverse libraries of nucleic acids. Related methods for performing such shuffling reactions in vitro are also provided.

BACKGROUND OF THE INVENTION

Today's laboratory attempts to meet the dramatically increasing need for analytical data brought about by the increased pace of new product development, increased research, demands for stricter quality control, and the like. Labs deliver data in a timely, cost-efficient way while ensuring precise results, clear documentation, and minimal use of skilled (and, therefore, expensive) personnel. For example, automated systems have been proposed to assess a variety of biological phenomena, including, e.g., expression levels of genes in response to selected stimuli (Service (1998) "Microchips Arrays Put DNA on the Spot" *Science* 282:396-399), high throughput DNA genotyping (Zhang et al. (1999) "Automated and Integrated System for High-Throughput DNA Genotyping Directly from Blood" *Anal. Chem.* 71:1138-1145) and many others. Similarly, integrated systems for performing mixing experiments, DNA amplification, DNA sequencing and the like are also available (See, e.g., Service (1998) "Coming Soon: the Pocket DNA Sequencer" *Science* 282: 399-401).

Improvements in laboratory automation continually increase the productivity of laboratory workers and provide for more precise results, clearer documentation and the like, as compared to the performance of unautomated tasks. The automation of laboratory procedures using devices and/or systems dedicated to particular tasks in the laboratory substantially enhances the speed and reproducibility of a variety of experimental tasks. Product research, regulatory approval and quality control in industries such as pharmaceuticals, chemicals, and biotechnology routinely involve the testing of thousands (or even hundreds of thousands) of samples.

Automated systems typically perform, e.g., repetitive fluid handling operations (e.g., pipetting) for transferring material to or from reagent storage systems such as microtiter trays, which are used as basic container elements for a variety of automated laboratory methods. Similarly, the systems manipulate, e.g., microtiter trays and control a variety of environmental conditions such as temperature, exposure to light or air, and the like.

Many such automated systems are commercially available. For example, a variety of automated systems are available from the Zymark Corporation (Zymark Center, Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.).

More recently, microfluidic systems have established the potential for even greater automation and laboratory productivity increases. In these microfluidic systems, automated fluid handling and other sample manipulations are controlled at the microscale level. Such systems are now commercially available. For example, the Hewlett-Packard (Agilent Technologies) HP2100 bioanalyzer utilizes LabChip™ technology to manipulate extremely small sample volumes. In this "lab-on-a-chip," system, sample preparation, fluid handling and biochemical analysis steps are carried out within the confines of a microchip. The chips have microchannels fabricated, e.g., in glass, providing interconnected networks of fluid reservoirs and pathways.

While many automated systems are now available, the application of automated systems to non-routine sample handling and analysis remains challenging. In particular, the application of automation to new technologies in the field of molecular biology would be desirable. For example, some of the most significant new classes of techniques in molecular biology are found in the field of rapid forced molecular evolution. In rapid evolution processes, diversity is generated in nucleic acids of interest via mutation, recombination, or other mechanisms, which are screened for one or more desirable activities, or encoded activities. These processes are repeated until a nucleic acid possessing or encoding a desired activity level is produced. The present invention provides significant new automated systems and methods which facilitate nucleic acid shuffling and other diversity generating/screening processes of interest.

SUMMARY OF THE INVENTION

The present invention provides automated devices for performing nucleic acid shuffling and other diversity generating reactions in vitro and in vivo. The devices can include, e.g., modules for generating diversity in nucleic acids, for recombining these nucleic acids, for arraying the nucleic acids, for making or copying arrays of reaction mixtures comprising shuffled mutated or otherwise diversified nucleic acids and for performing in vitro translation and/or transcription of diverse libraries of nucleic acids (including in an array-based format). Related methods for performing automated mutation, recombination and/or shuffling reactions in vitro and in vivo are also provided.

For example, the present invention comprises, e.g., devices and/or integrated systems which include a physical or logical array of reaction mixtures. The reaction mixtures include one or more diversified (e.g., shuffled or mutagenized) nucleic acids and/or one or more transcribed shuffled or transcribed mutagenized nucleic acids and one or more in vitro transcription and/or translation reagents. A variety of variant forms and implementations of these devices/integrated systems, as well as related methods are described herein.

The devices and integrated systems optionally include any of a variety of component or module elements. These can include, e.g., one or more duplicates of the physical or logical array. A bar-code based sample tracking module, which includes a bar code reader and a computer readable database comprising at least one entry for at least one array or at least one array member can also be included, in which the entry is corresponded to at least one bar code. The device or integrated system can include a long term storage device such as a refrigerator; an electrically powered cooling device, a device capable of maintaining a temperature of <0 C, a freezer, a device which uses liquid nitrogen or liquid helium for cooling storing or freezing samples, a container comprising wet or dry ice, a constant temperature and/or constant humidity chamber or incubator; or an automated sample storage or retrieval unit. The device or integrated can also include one or more modules for moving arrays or array members into the long term storage device.

The device or integrated system can, and often do, include a copy array comprising a copy of each of a plurality of members of the one or more shuffled or mutagenized nucleic acids in a physically or logically accessible arrangement of the members. A plurality of the reaction mixtures can include one or more translation products or one or more transcription products, or both one or more translation products and one or more transcription products. The array of reaction mixtures can be in a solid phase, liquid phase or mixed phase array which includes one or more of: the one or more shuffled or mutated nucleic acids, the one or more transcribed shuffled nucleic acids, and the one or more in vitro translation reagents. The one or more shuffled or mutated nucleic acids are optionally homologous or heterologous. The one or more transcribed shuffled or mutated nucleic acid(s) typically, though not necessarily, includes an mRNA.

The one or more in vitro translation reagents which are optionally present in the array typically include transcription reagents, e.g., reticulocyte lysates, rabbit reticulocyte lysates, canine microsome translation mixtures, wheat germ in vitro translation (IVT) mixtures, $E. coli$ lysates, or the like. As already noted, the arrays optionally further include one or more in vitro transcription reagents, such as an $E. coli$ lysate, an $E. coli$ extract, an $E. coli$ s20 extract, a canine microsome system, a HeLa nuclear extract in vitro transcription component, an SP6 polymerase, a T3 polymerase a T7 RNA polymerase, or the like.

The device or integrated system can include a nucleic acid shuffling or mutagenesis module, which accepts input nucleic acids or character strings corresponding to input nucleic acids and manipulates the input nucleic acids or the character strings corresponding to input nucleic acids to produce output nucleic acids, which include the one or more shuffled or mutagenized nucleic acids in the reaction mixture array. The output nucleic acids optionally comprise one or more sequence which controls transcription or translation. Such modules include a DNA shuffling module, which accepts input DNAs or character strings corresponding to input DNAs and manipulates the input DNAs or the character strings corresponding to input DNAs to produce output DNAs, which output DNAs include the one or more shuffled DNAs in the reaction mixture array. The nucleic acid shuffling or mutagenesis module is optionally preceded in the system or device by a module which allows overlapping synthetic oligonucleotides to be first assembled into oligonucleotide multimers or functional open reading frames prior to entering the mutagenesis or shuffling module. The module (s) can be operatively linked to or include a thermocycling device, or a mutagenesis module. In one aspect, the nucleic acid shuffling or mutagenesis module fragments the input nucleic acids to produce nucleic acid fragments. Alternately, the input nucleic acids optionally include cleaved or synthetic nucleic acid fragments. Optionally, the shuffling or mutagenesis module is mechanically, electronically, robotically or fluidically coupled to at least one other array operation module. The nucleic acid shuffling or mutagenesis module can perform any of a variety of operations, including PCR, StEP PCR, uracil incorporation, chain termination, or the like. Optionally, the nucleic acid shuffling module separates, identifies, purifies or immobilizes any product elongated nucleic acid.

The nucleic acid shuffling module optionally includes an identification portion which identifies one or more nucleic acid portion or subportion (e.g., by sequencing or any other product deconvolution method). Similarly, the nucleic acid shuffling module optionally includes a fragment length purification portion which purifies selected length fragments of the nucleic acid fragments. In one embodiment, the nucleic acid shuffling module permits hybridization of the nucleic acid fragments. The module can also include a polymerase which elongates the hybridized nucleic acid.

The module can control incorporation of features into product nucleic acids. For example, the nucleic acid shuffling module can combine one or more translation or transcription control sequence into elongated product nucleic acids. The translation or transcription control sequence(s) can be combined into the elongated nucleic acid using the polymerase, or a ligase, or both. The nucleic acid shuffling module optionally determines a recombination frequency or a length, or both a recombination frequency and a length, for any product nucleic acid(s). Similarly, the nucleic acid shuffling module can determine nucleic acid length by detecting incorporation of one or more labeled nucleic acid or nucleotide into the resulting elongated nucleic acid. For example, the nucleic acid shuffling module optionally determines nucleic acid length by detecting one or more label (e.g., dye, radioactive label, biotin, dioxin, or a fluorophore) associated with any product nucleic acid. For example, the nucleic acid shuffling module can determine nucleic acid length with a fluorogenic 5' nuclease assay.

The devices and integrated systems can utilize conventional or microscale construction. Thus, in one aspect, the physical or logical array of reaction mixtures is optionally incorporated into a microscale device, or at least one of the reaction mixtures is incorporated into a microscale device, or the one or more shuffled or mutagenized nucleic acids or the one or more transcribed shuffled or mutagenized nucleic acids is found within a microscale device, or the one or more in vitro translation reagents is optionally found within a microscale device. The nucleic acid shuffling module optionally comprises one or more microscale channel (e.g., a microcapillary or chip) through which a shuffling reagent or product is flowed. Liquid flow through the device is mediated, e.g., by capillary flow, differential pressure between one or more inlets and outlets, electroosmosis, hydraulic or mechanical pressure, or peristalsis.

Nucleic acid fragments for use in the systems and devices of the invention are optionally contacted in a single pool, or in multiple pools. For example, the nucleic acid shuffling module optionally dispenses the resulting elongated nucleic acids into one or more multiwell plates, or onto one or more solid substrates, or into one or more microscale systems, or into one or more containers. The nucleic acid shuffling module optionally pre-dilutes any product nucleic acids and dispenses them into one or more multiwell plates, e.g., at a selected density per well of the product nucleic acid(s).

For example, in one embodiment, the nucleic acid shuffling module dispenses elongated nucleic acids into one or more master multiwell plates and/or PCR amplifies the resulting master array of elongated nucleic acids to produce an amplified array of elongated nucleic acids. Optionally, the module includes a array copy system which transfers aliquots from the wells of the one or more master multiwell plates to one or more copy multiwell plates. The array of reaction mixtures is optionally formed by separate or simultaneous addition of an in vitro transcription reagent and an in vitro translation reagent to the one or more copy multiwell plates, or to a duplicate set thereof.

In one embodiment, the device or integrated system, further includes one or more sources of one or more nucleic acids. The one or more sources collectively or individually can include a first population of nucleic acids, wherein shuffled or mutant nucleic acids are produced by recombining the one or more members of the first population of nucleic acids. The one or more sources of nucleic acids include, e.g., at least one nucleic acid selected from: a synthetic nucleic acid, a DNA, an RNA, a DNA analogue, an RNA analogue, a genomic DNA, a cDNA, an mRNA, a DNA generated by reverse transcription, an nRNA, an aptamer, a polysome associated nucleic acid, a cloned nucleic acid, a cloned DNA, a cloned RNA, a plasmid DNA, a phagemid DNA, a viral DNA, a viral RNA, a YAC DNA, a cosmid DNA, a fosmid DNA, a BAC DNA, a P1-mid, a phage DNA, a single-stranded DNA, a double-stranded DNA, a branched DNA, a catalytic nucleic acid, an antisense nucleic acid, an in vitro amplified nucleic acid, a PCR amplified nucleic acid, an LCR amplified nucleic acid, a QƎ-replicase amplified nucleic acid, an oligonucleotide, a nucleic acid fragment, a restriction fragment and a combination thereof.

The device or integrated system optionally includes a population destination region, wherein, during operation of the device, one or more members of the first population are moved from the one or more sources of the one or more nucleic acids to the one or more destination regions (e.g., in the form of a solid phase array, a liquid phase array, a container, a microtiter tray, a microtiter tray well, a microfluidic component, a microfluidic chip, a test tube, a centrifugal rotor, a microscope slide, an organism, a cell, a tissue, a liposome, a detergent particle, or any combination thereof). Thus, the device or integrated system can include nucleic acid movement means (e.g., a fluid pressure modulator, an electrokinetic fluid force modulator, a thermokinetic modulator, a capillary flow mechanism, a centrifugal force modulator, a robotic armature, a pipettor, a conveyor mechanism, a peristaltic pump or mechanism, a magnetic field generator, an electric field generator, one or more fluid flow path, etc.) for moving the one or more members from the one or more sources of the one or more nucleic acids to the one or more destination regions (for example, nucleic acids to be recombined can be moved into contact with one another). During operation of the device, the in vitro transcription reagent or an in vitro translation reagent is typically flowed into contact with the members of the first population. Optionally, members of the first population are fixed (immobilized) at the one or more sources of one or more nucleic acids or at the one or more destination regions. During operation of the device, the first population of nucleic acids is optionally arranged into one or more physical or logical recombinant nucleic acid arrays, which are optionally duplicated.

The device or integrated system can include one or more reaction mixture arraying modules which move one or more of the one or more shuffled (or mutated) nucleic acids or the one or more transcribed shuffled or mutated nucleic acids or the in vitro translation reactant components into one or more selected spatial positions. This places the one or more shuffled mutated or otherwise diversified nucleic acids or the one or more transcribed shuffled or otherwise diversified nucleic acids or the in vitro translation reactant component into one or more locations in the array of reaction mixtures. Thus, this module can be used to generate a recombined/mutated/shuffled nucleic acid master or duplicate array which physically or logically corresponds to positions of mutated, shuffled or other product nucleic acids in a reaction mixture array. The device or integrated system can include a nucleic acid amplification module, which module amplifies members of the mutated or shuffled nucleic acid master array, or a duplicate thereof. The arraying and amplification modules can be integrated in one module or device.

The amplification module can include a heating or cooling element (e.g., to perform PCR, LCR or the like). For example, in one embodiment, the amplification module includes a DNA micro-amplifier. For example, the micro-amplifier can include a programmable resistor, a micromachined zone heating chemical amplifier, a Peltier solid state heat pump, a heat pump, a heat exchanger, a hot air blower, a resistive heater, a refrigeration unit, a heat sink, a Joule Thompson cooling device, or any combination thereof. The arraying/amplification module can produce a duplicate amplified array which produces amplicons of the nucleic acid master array, or duplicates thereof.

During operation of the overall device or system, the array of reaction mixtures produces an array of reaction mixture products. The device or integrated system can include one or more product identification or purification modules, which product identification modules identify one or more members of the array of reaction products. For example, product identification or purification modules can include one or more of: a gel, a polymeric solution, a liposome, a microemulsion, a microdroplet, an affinity matrix, a plasmon resonance detector, a BIACORE, a GC detector, an ultraviolet or visible light sensor, an epifluorescence detector, a fluorescence detector, a fluorescent array, a CCD, a digital imager, a scanner, a confocal imaging device, an optical sensor, a FACS detector, a micro-FACS unit, a temperature sensor, a mass spectrometer, a stereo-specific product detector, an Elisa reagent, an enzyme, an enzyme substrate an antibody, an antigen, a refractive index detector, a polarimeter, a pH detector, a pH-stat device, an ion selective sensor, a calorimeter, a film, a radiation sensor, a Geiger counter, a scintillation counter, a particle counter, an H2O2 detection system, an electrochemical sensor, ion/gas selective electrodes, or a capillary electrophoresis element. For ease of detection, the one or more reaction product array members are optionally moved into proximity to the product identification module, or the product identification module can perform an xyz translation, thereby moving the product identification module proximal to the array of reaction products. Similarly, the one or more reaction product array members are optionally flowed into proximity to the product identification module, where an in-line purification system purifies the one or more reaction product array members from associated materials.

Typical reaction products include, e.g., one or more polypeptide, one or more nucleic acid, one or more catalytic RNA (e.g., a ribozyme), or one or more biologically active RNA (e.g., an anti-sense RNA). In one class of embodiments, the device or integrated system can include a source of one or more lipid which is flowed into contact with the one or more polypeptide, or into contact with the physical or logical array of reaction mixtures, or into contact with the one or more transcribed shuffled or mutagenized nucleic acids, thereby producing one or more liposomes or micelles comprising the polypeptide, reaction mixture components, or one or more transcribed shuffled or mutagenized nucleic acids. The reaction products can include one or more polypeptide which can be further modified by the system, e.g., by incubation with one or more protein refolding reagent. For example, refolding agents such as guanidine, guanidinium, urea, detergents, chelating agents, DTT, DTE, chaperonins and the like can be flowed into contact with the protein of interest.

Product identification or purification modules in the device or integrated system can include a protein detector, a protein purification means, or the like. The product identification or purification modules can also include an instruction set for discriminating between members of the array of reaction products based upon, e.g., a physical characteristic of the members, an activity of the members, concentrations of the members, or combinations thereof.

The device or integrated system can include a secondary product array produced by re-arraying members of the reaction product array such that the secondary product array has a selected concentration of product members in the secondary product array. The selected concentration is optionally approximately the same for a plurality of product members in the secondary product array. This facilitates comparison of activity or detectable feature levels across or among members of the secondary product array. In an alternate or complementary aspect, the device or integrated system can include an instruction set or physical or logical filter for determining a correction factor which accounts for variation in polypeptide concentration at different positions in the amplified physical or logical array of polypeptides.

The device or integrated system of can include a substrate addition module which adds one or more substrate to a plurality of members of the product array or the secondary product array. In this embodiment, a substrate conversion detector is provided to monitor formation of a product produced by contact between the one or more substrate and one or more of the plurality of members of the product array or the secondary product array. Formation of product or disappearance of substrate is monitored directly or indirectly, for example, by monitoring loss of the substrate or formation of product over time. Formation of the product or disappearance of substrate is optionally monitored enantioselectively, regioselectively or stereo selectively. For example, formation of the product or disappearance of substrate is optionally monitored by adding at least one isomer, enantiomer or stereoisomer in substantially pure form (e.g., independent of other potential isomers). Formation of the product is optionally monitored by detecting any detectable product, e.g., by monitoring formation of peroxide, protons, or halides, or reduced or oxidized cofactors, changes in heat or entropy which result from contact between the substrate and the product, changes in mass, charge, fluorescence, epifluorescence, by chromatography, luminescence or absorbance, of the substrate or the product, which result from contact between the substrate and the product.

The device or integrated system optionally includes an array correspondence module, which identifies, determines or records the location of an identified product in the array of reaction mixture products which is identified by the one or more product identification modules, or which array correspondence module determines or records the location of at least a first nucleic acid member of the shuffled or mutant nucleic acid master array, or a duplicate thereof, or of an amplified duplicate array, where the member corresponds to the location of one or more member of the array of reaction products.

The device or integrated system optionally includes one or more secondary selection module which selects at least the first member for further recombination, which selection is based upon the location of a product identified by the product identification module(s).

The device or integrated system optionally includes a screening or selection module. For example, the module can include one or more of: an array reader, which detects one or more member of the array of reaction products; an enzyme which converts one or more member of the array of reaction products into one or more detectable products; a substrate which is converted by the one or more member of the array of reaction products into one or more detectable products; a cell which produces a detectable signal upon incubation with the one or more member of the array of reaction products; a reporter gene which is induced by one or more member of the array of reaction products; a promoter which is induced by one or more member of the array of reaction products, which promoter directs expression of one or more detectable products; and an enzyme or receptor cascade which is induced by the one or more member of the array of reaction products.

The device or integrated system can include a secondary recombination module, which physically contacts the first member, or an amplicon thereof, to an additional member of the shuffled or mutant nucleic acid master array, or the duplicate thereof, or the amplified duplicate array, thereby permitting physical recombination between the first and additional members.

The device or integrated system optionally includes a DNA fragmentation module which can include a recombination region. The DNA fragmentation module can include, e.g., one or more of: a nuclease, a mechanical shearing device, a polymerase, a random primer, a directed primer, a nucleic acid cleavage reagent, a chemical nucleic acid chain terminator, and an oligonucleotide synthesizer. During operation of the device, fragmented DNAs produced in the DNA fragmentation module are optionally recombined in the recombination region to produce one or more mutated, shuffled or otherwise altered nucleic acids.

Common operations for the device or system include modules which perform one or more of: error prone PCR, site saturation mutagenesis, or site-directed mutagenesis. Many other diversity generating reactions which can be practiced in modules of the devices or systems are set forth herein.

The device or integrated system optionally includes a data structure embodied in a computer, such as an analog computer or a digital computer, or in a computer readable medium. The data structure corresponds to the one or more shuffled or otherwise modified nucleic acid(s).

The device or integrated system optionally includes one or more reaction mixtures which include one or more mutated or shuffled nucleic acids arranged in a microtiter tray at an average of approximately 0.1-100 shuffled or otherwise modified nucleic acids per well, e.g., an average of approximately 1-5 such nucleic acids per well.

The device or integrated system optionally includes a diluter which pre-dilutes the concentration of the one or more shuffled, modified or mutated nucleic acids prior to addition of the shuffled or mutant nucleic acids to the reaction mixtures. The concentration of the one or more modified, mutated or shuffled nucleic acids after pre-dilution is about 0.01 to 100 molecules per microliter.

In one class of embodiments, the reaction mixtures are produced in the device or system by adding the in vitro translation reactant and, optionally, an in vitro transcription reagent, to a duplicate shuffled or mutated nucleic acid array. The duplicate shuffled or mutated nucleic acid array is duplicated from a master array of the shuffled or mutated nucleic acids produced by spatially or logically separating members of a population of the shuffled or mutated nucleic acids to produce a physical or logical array of the shuffled or mutated nucleic acids. For example, the array can be produced by one or more arraying technique, including (1) lyophilizing members of the population of mutated, shuffled or otherwise altered nucleic acids on a solid surface, thereby forming a solid phase array, (2) chemically coupling members of the population of mutated, shuffled or otherwise altered nucleic acids to a solid surface, thereby forming a solid phase array, (3) rehydrating members of the population of mutated, shuffled or otherwise altered nucleic acids on a solid surface, thereby forming a liquid phase array, (4) cleaving chemically coupled members of the population of mutated, shuffled or otherwise altered nucleic acids from a solid surface, thereby forming a liquid phase array, (5) accessing one or more physically separated logical array members from one or more sources of mutated, shuffled or otherwise altered nucleic acids and flowing the physically separated logical array members to one or more destination, the one or more destinations constituting a logical array of the mutated, shuffled or otherwise altered nucleic acids, and (6) printing members of a population of mutated, shuffled or otherwise altered nucleic acids onto a solid material to form a solid phase array. Optionally, greater than about 1% of the physical or logical array of reaction mixtures comprise shuffled or mutant nucleic acids having one or more base changes relative to a parental nucleic acid.

In one aspect, one or more mutated, recombined (e.g., shuffled) or otherwise modified nucleic acids are produced by synthesizing a set of overlapping oligonucleotides, or by cleaving a plurality of homologous nucleic acids to produce a set of cleaved homologous nucleic acids, or both, and permitting recombination to occur between the set of overlapping oligonucleotides, the set of cleaved homologous nucleic acids, or both the set of overlapping oligonucleotides and the set of cleaved homologous nucleic acids.

In one aspect, the invention provides a diversity generation device. The device includes a programmed thermocycler and a fragmentation module operably coupled to the programmed thermocycler. The programmed thermocycler typically includes a thermocycler operably coupled to a computer which includes one or more instruction set, e.g., for calculating an amount of uracil and an amount of thymidine for use in the programmed thermocycler, calculating one or more crossover region between two or more parental nucleotides calculating an annealing temperature, calculating an extension temperature, selecting one or more parental nucleic acid sequence, or the like.

The one or more instruction set receives user input data and sets up one or more cycle to be performed by the programmed thermocycler. The input data typically includes one or more parental nucleic acid sequence, a desired crossover frequency, an extension temperature, and/or an annealing temperature, or other features which control the reaction of interest.

In one aspect, the one or more instruction set calculates an amount of uracil and an amount of thymidine based on a desired fragment size. In other aspects, the one or more instruction set directs the one or more cycle on the diversity generation device, e.g., amplifies the one or more parental nucleic acid sequence, fragments the one or more parental nucleic acid sequence to produce one or more nucleic acid fragment, reassembles the one or more nucleic acid fragment to produce one or more mutated, shuffled or otherwise altered nucleic acid, and/or amplifies the one or more mutated, shuffled or otherwise altered nucleic acid. For example, the set can direct amplifying the one or more parental nucleic acid sequence in the presence of uracil. Optionally, the one or more cycle pauses between steps to allow addition of one or more fragmentation reagent.

The one or more instruction set optionally performs one or more calculation based on one or more theoretical prediction of a nucleic acid melting temperature or on one or more set of empirical data, which empirical data comprises a comparison of one or more nucleic acid melting temperature. The one or more instruction set optionally instructs the fragmentation module to fragment the parental nucleic acids to produce one or more nucleic acid fragments having a desired mean fragment size.

The programmed thermocycler comprises a thermocycler and, optionally, software for performing one or more shuffling calculations, which software is embodied on a web page, an attached computer, an intranet server, or, e.g., installed directly in the thermocycler.

In one aspect, a similar diversity generation device is provided. The device includes a computer, which includes at least a first instruction set for creating one or more nucleic acid fragment sequence from one or more parental nucleic acid sequence and a synthesizer module, which synthesizes the one or more nucleic acid fragment sequence. The device also includes a thermocycler which generates one or more diverse sequence from the one or more nucleic acid fragment sequence. The first instruction set optionally limits or expands diversity of the one or more nucleic acid fragment sequence by adding or removing one or more amino acid having similar diversity; selecting a frequently used amino acid at one or more specific position; using one or more sequence activity calculation; using a calculated overlap with one or more additional oligonucleotide; based on an amount of degeneracy, or based on a melting temperature. In one aspect, the thermocycler performs an assembly/rescue PCR reaction.

The diversity generation device can include a synthesizer module having a microarray oligonucleotide synthesizer. For example, the synthesizer module optionally includes an ink-jet printer head based oligonucleotide synthesizer. The synthesizer module optionally synthesizes the one or more nucleic acid fragment sequences on a solid support. The synthesizer module optionally uses one or more mononucleotide coupling reactions or one or more trinucleotide coupling reactions to synthesize the one or more nucleic acid fragment sequence.

The computer optionally comprises at least a second instruction set, which second instruction set determines at least a first set of conditions for the assembly/rescue PCR reaction.

The device optionally further includes a screening module for screening the one or more diverse sequence for a desired characteristic. For example, the screening module optionally comprises a high-throughput screening module.

In a related aspect, a diversity generation kit is provided. For example, the kit can include the diversity generation devices above and one or more reagent for diversity generation. Example reagents include *E. coli.*, a PCR reaction mixture comprising a mixture of uracil and thymidine, one or more uracil cleaving enzyme, and a PCR reaction mixture comprising standard dNTPs. The one or more uracil cleaving enzyme optionally includes a uracil glycosidase and an endonuclease. The mixture of uracil and thymidine comprises a desired ratio of uracil to thymidine, which desired ratio is calculated by the diversity generation device, based upon user selected inputs.

Optionally, the diversity generation kit can include one or more artificially evolved enzyme such as an artificially evolved polymerase. The kit can also include, e.g., packaging materials, a container adapted to receive the device or reagents, and instructional materials for use of the device.

The devices and integrated systems herein can include data tracking modules such as a bar-code based sample tracking module, which includes, e.g., a bar code reader and a computer readable database comprising at least one entry for at least one array or at least one array member, which entry is corresponded to at least one bar code. Long term storage devices can also be incorporated into the devices and integrated systems herein (and the methods herein can include storage in such long term storage modules). For example, as noted, the storage module can include, e.g., a refrigerator, an electrically powered cooling device, a device capable of maintaining a temperature of <0 C; a freezer, a device which uses liquid nitrogen or liquid helium for cooling storing or freezing samples, a container comprising wet or dry ice, a constant temperature and/or constant humidity chamber or incubator, an automated sample storage or retrieval unit, a dessicator or moisture minimizing or reducing device, one or more modules for moving arrays or array members into the long term storage device etc.

As noted in more detail herein, the invention provides devices and integrated systems, e.g., which include a physical or logical array of reaction mixtures, each reaction mixture comprising one or more shuffled or mutagenized nucleic acids and one or more transcribed shuffled or transcribed mutagenized nucleic acids or one or more in vitro translation reagents. Also provided are libraries of shuffled or mutated or mutagenized nucleic acids formatted in a logical and physical array based on at least one physical and one activity parameter. Devices or integrated systems which use a fluorescent or visible signal to sort a shuffled or mutagenized nucleic acid library into a spatial array of cells, particles or molecules are also provided. These include, e.g., a physical or logical array of comprising one or more shuffled or mutagenized nucleic acids or one or more transcribed shuffled or transcribed mutagenized nucleic acids or one or more in vitro translation reagents.

The present invention also provides a number of related methods, both for use with the integrated systems and devices of the invention and for use separate from the devices and systems.

For example, in one class of methods of the invention, methods of processing shuffled or mutagenized nucleic acids are provided. In the methods, a physical (e.g., solid or liquid phase) or logical array of reaction mixtures is provided. A plurality of the reaction mixtures include one or more member of a first population of nucleic acids. The first population of nucleic acids include one or more shuffled or mutagenized nucleic acids, or one or more transcribed shuffled or mutagenized nucleic acids. A plurality of the plurality of reaction mixtures typically further include an in vitro translation reactant. One or more in vitro translation products produced by a plurality of members of the physical or logical array of reaction mixtures is then detected. Any of the various array configurations noted above or herein for the devices and integrated systems of the invention are can be used in these methods.

For example, in one embodiment, a population of nucleic acids (which can be homologous or heterologous) is physically arrayed on a solid substrate, such as a chip, slide, membrane, or well of a microtiter tray or plate. The arrayed nucleic acids are recombined with one or more additional nucleic acids, thereby providing an arrayed library of recombinant nucleic acids. These recombinant nucleic acids are then amplified and screened to identify members of the array that possess a desired property. In some embodiments, an oligonucleotide primer is tethered to the solid substrate and an additional single-stranded nucleic acid is annealed to the oligonucleotide which is then extended with a nucleic acid polymerase. In alternative embodiments, a single-stranded template polynucleotide is hybridized with a set of partially overlapping complementary nucleic acid fragments which are extended to produce an arrayed library of recombinant nucleic acids. For example, one or more template nucleic acids are immobilized on a solid support. Partially overlapping complementary nucleic acid fragments are annealed to the template polynucleotide, and extended or ligated to produce a heteroduplex comprising the template nucleic acid and a substantially full-length heterolog complementary to the template nucleic acid. The heterolog is recovered and, optionally, further diversified.

A number of variants of this basic methodology are set forth herein, as are a variety of products produced by the methods and their variants and apparatus and kits for performing the methods.

For example, the one or more mutated, shuffled or otherwise altered nucleic acids are optionally produced in an automatic DNA shuffling, recombination, or mutation module. Optionally, the method includes inputting DNAs or character strings corresponding to input DNAs into the DNA shuffling module and accepting output DNAs from the DNA shuffling module, where the output DNAs include the one or more mutated, shuffled or otherwise altered nucleic acids in the reaction mixture array. The input DNA in the DNA shuffling module can be cleaved to produce DNA fragments, or provide the input DNAs can include cleaved or synthetic DNA fragments. DNA fragments, e.g., of a selected length can be purified in the DNA shuffling module. Purified DNA fragments can be hybridized and elongated with a polymerase. The resulting elongated nucleic acids can be separated, identified, cloned, purified, or the like. A recombination frequency or a length, or both a recombination frequency and a length for the resulting elongated DNAs can be determined, e.g., by detecting incorporation of one or more labeled nucleic acid or nucleotide into the elongated DNAs.

The invention provides for a variety of physical manipulations of the various reagents and products of the invention, including, flowing, e.g., a shuffling reagent or product through a microscale channel in the DNA shuffling module, contacting the components in single or multiple pools, dispensing materials into one or more multiwell plates, dispensing materials into one or more multiwell plates at a selected density per well of the elongated DNAs, dispensing the product elongated DNAs into one or more master multiwell plates and PCR amplifying the resulting master array of elongated nucleic acids to produce an amplified array of elongated nucleic acids, etc. Optionally, the shuffling module includes an array copy system which transfers aliquots from the wells of the one or more master multiwell plates to one or more copy multiwell plates.

The methods optionally include determining an extent of PCR amplification by any available technique, including, e.g., incorporation of a label into one or more amplified elongated nucleic acid, applying a fluorogenic 5' nuclease assay or the like.

In one aspect, the array of reaction mixtures is formed by separate or simultaneous addition of in vitro transcription reagents and an in vitro translation reactant to the one or more copy multiwell plates, or to a duplicate set thereof, wherein the elongated DNAs comprise the one or more mutated, shuffled or otherwise altered nucleic acids. Typically, the array of reaction mixtures produces an array of reaction mixture products, e.g., comprising one or more polypeptide. The methods optionally include re-folding the one or more polypeptide by contacting the one or more polypeptide with a refolding reagent such as guanidine, urea, DTT, DTE, and/or a chaperonin. The one or more polypeptide with one or more lipid to produce one or more liposome or micelle, which liposome or micelle comprises the one or more polypeptide.

The methods optionally include moving the one or more reaction product array members into proximity to a product identification module, or moving a product identification module into proximity to the reaction product array members. The one or more reaction product array members are optionally flowed into proximity to a product identification module. In-line purification of the one or more reaction product array members can be performed.

In one aspect, the method further includes reading the array of reaction mixture products with an array reader which detects one or more member of the array of reaction products. In another aspect, one or more member of the array of reaction products is converted with an enzyme into one or more detectable products. Similarly, one or more substrates can be converted by the one or more member of the array of reaction products into one or more detectable products. These detectable products are optionally detected in the array reader.

A cell can be contacted to one or more member of the array of reaction products, which cell or reaction product, or both, produce a detectable signal upon contacting the one or more member of the array of reaction products.

A variety of detectable events can be induced, including inducing a reporter gene with one or more member of the array of reaction products, inducing a promoter with one or more member of the array of reaction products which directs expression of one or more detectable products, including inducing an enzyme or receptor cascade with one or more member of the array of reaction products which is induced by the one or more member of the array of reaction products.

Methods of recombining members of a physical or logical array of nucleic acids are also provided. In the methods, a first population of nucleic acids is provided, or a data structure (e.g., embodied in a computer, an analog computer, a digital computer, or a computer readable medium) comprising character strings corresponding to the first population of nucleic acids (e.g., embodied in a computer, an analog computer, a digital computer, or a computer readable medium) is provided. One or more members of the first population of nucleic acids are recombined, thereby providing a first population of recombinant nucleic acids. Alternatively, one or more character strings corresponding to one or more members of the first population of nucleic acids are recombined, thereby providing a population of character strings corresponding to the first population of recombinant nucleic acids. In this embodiment, the population of character strings corresponding to the first population of recombinant nucleic acids is converted into the first population of recombinant nucleic acids, thereby providing the first population of recombinant nucleic acids. In either case, members of the population of recombinant nucleic acids are spatially or logically separated to produce a physical or logical array of recombinant nucleic acids. The recombinant nucleic acids in the physical or logical array of recombinant nucleic acids are amplified in vitro (e.g., by enzymatic or synthetic means) to provide an amplified physical or logical array of recombinant nucleic acids. Alternately, members of the population of recombinant nucleic acids are amplified (or synthesized) and physically or logically separated to produce an amplified physical or logical array of recombinant nucleic acids. Typically, the amplified physical or logical array of recombinant nucleic acids, or a duplicate thereof, is screened for one or more desired property. Optionally, the amplified physical or logical array of recombinant nucleic acids, or a duplicate thereof, is screened for a desired property. A variety of variants of this basic class of methods are set forth herein, as are a variety of products produced by the methods and their variants and kits and apparatus for practicing the methods.

Spatially or logically separating members of the population of recombinant nucleic acids to produce a physical or logical array of recombinant nucleic acids or amplified recombinant nucleic acids optionally includes plating the nucleic acids in a microtiter tray at an average of approximately 0.1-10 (e.g., 1-5) array members per well. Optionally, spatially or logically separating the members of the population of recombinant nucleic acids includes diluting the members of the population with a buffer. The concentration of the population of recombinant nucleic acids after dilution is typically about 0.01 to 100 molecules per microliter.

Spatially or logically separating members of the population of recombinant nucleic acids to produce a physical or logical array of recombinant nucleic acids can also include one or more of: (i) lyophilizing members of the population of recombinant nucleic acids on a solid surface, thereby forming a solid phase array; (ii) chemically coupling members of the population of recombinant nucleic acids to a solid surface, thereby forming a solid phase array; (iii) rehydrating members of the population of recombinant nucleic acids on a solid surface, thereby forming a liquid phase array; (iv) cleaving chemically coupled members of the population of recombinant nucleic acids from a solid surface, thereby forming a liquid phase array; and, (v) accessing one or more physically separated logical array members from one or more sources of recombinant nucleic acids and flowing the physically separated logical array members to one or more destination.

Methods of recombining members of a physical or logical array of nucleic acid are provided. In the methods, at least a first population of nucleic acids is arranged in a physical or logical array. One or more members of the first population of nucleic acids is recombined with one or more additional nucleic acid, thereby providing a first physical or logical array comprising a population of recombined nucleic acids. The recombined nucleic acids in the physical or logical array of recombined nucleic acids are amplified, usually in vitro, to provide an amplified physical or logical array of recombined nucleic acids. The first or amplified physical or logical array of recombined nucleic acids, or one or more duplicate thereof, is then screened for one or more desired properties. As above, a number of variants of this basic class of methods are set forth herein. In some embodiments, the recombination of nucleic acids is performed on a solid substrate such as a slide, membrane or "chip." For example, a population of nucleic acids is physically arrayed on a solid substrate, such as a chip, slide, membrane, or well of a microtiter tray or plate. The arrayed nucleic acids are recombined with one or more additional nucleic acids, thereby providing an arrayed library of recombinant nucleic acids. These recombinant nucleic acids are then amplified and a screened to identify members of the array that possess a desired property. In some embodiments, an oligonucleotide primer is tethered to the solid substrate and an additional single-stranded nucleic acid is annealed to the oligonucleotide which is then extended with a nucleic acid polymerase. In alternative embodiments, a single-stranded template polynucleotide is hybridized with a set of partially overlapping complementary nucleic acid fragments which are extended to produce an arrayed library of recombinant nucleic acids. For example, one or more template nucleic acids are immobilized on a solid support. Partially overlapping complementary nucleic acid fragments are annealed to the template polynucleotide, and extended or ligated to produce a heteroduplex comprising the template nucleic acid and a substantially full-length heterolog complementary to the template nucleic acid. The heterolog is recovered and, optionally, further diversified. A variety of products produced by the methods and their variants and kits and apparatus for practicing the methods are similarly described.

In the above methods, the first population of nucleic acids or the population of recombinant nucleic acids are typically arranged in a physical or logical matrix at an average of approximately 0.1-10 (e.g., 0.5-5) array members per array position. The first population of nucleic acids or the population of recombinant nucleic acids optionally include a solid phase or a liquid phase array. Optionally, the first population of nucleic acids is provided by one or more of: synthesizing a set of overlapping oligonucleotides, cleaving a plurality of homologous nucleic acids to produce a set of cleaved homologous nucleic acids, step PCR of one or more target nucleic acid, uracil incorporation and cleavage during copying of one or more target nucleic acids, and incorporation of a cleavable nucleic acid analogue into a target nucleic acid and cleavage of the resulting target nucleic acid. In another approach, the first population of nucleic acids is provided by synthesizing a set of overlapping oligonucleotides, by cleaving a plurality of homologous nucleic acids to produce a set of cleaved homologous nucleic acids, or both. The set of overlapping oligonucleotides or the set of cleaved homologous nucleic acids are optionally flowed into one or more selected physical locations.

The first population of nucleic acids is optionally provided by sonicating, cleaving, partially synthesizing, random primer extending or directed primer extending one or more of: a synthetic nucleic acid, a DNA, an RNA, a DNA analogue, an RNA analogue, a genomic DNA, a cDNA, an mRNA, a DNA generated by reverse transcription, an nRNA, an aptamer, a polysome associated nucleic acid, a cloned nucleic acid, a cloned DNA, a cloned RNA, a plasmid DNA, a phagemid DNA, a viral DNA, a viral RNA, a YAC DNA, a cosmid DNA, a fosmid DNA, a BAC DNA, a P1-mid, a phage DNA, a single-stranded DNA, a double-stranded DNA, a branched DNA, a catalytic nucleic acid, an antisense nucleic acid, an in vitro amplified nucleic acid, a PCR amplified nucleic acid, an LCR amplified nucleic acid, a QƎ-replicase amplified nucleic acid, an oligonucleotide, a nucleic acid fragment, a restriction fragment and/or a combination thereof.

The first population of nucleic acids is optionally modified by purifying one or more member of the first population of nucleic acids. Optionally, the first population of nucleic acids is provided by transporting one or more members of the population from one or more sources of one or more members of the first population to one or more destinations of the one or more members of the first population of nucleic acids. For example, the transporting optionally includes flowing the one or more members from the source to the destination. The one or more sources of nucleic acids can include any of: a solid phase array, a liquid phase array, a container, a microtiter tray, a microtiter tray well, a microfluidic chip, a test tube, a centrifugal rotor, a microscope slide, and/or a combination thereof.

Amplifying the recombinant nucleic acids in the physical or logical array of recombinant nucleic acids, or amplifying the elongated nucleic acids in the master array optionally includes one or more amplification technique selected from: PCR, LCR, SDA, NASBA, TMA and QƎ-replicase amplification. Optionally, amplifying the recombinant nucleic acids in the physical or logical array or amplifying the elongated nucleic acids in the master array comprises heating or cooling the physical or logical array or the master array, or a portion thereof.

Amplifying the recombinant nucleic acids in the physical or logical array or amplifying the elongated nucleic acids in the master array can include incorporating one or more transcription or translation control subsequence into one or more of: the elongated nucleic acids, the recombinant nucleic acids in the physical or logical array, an intermediate nucleic acid produced using the elongated nucleic acids or the recombinant nucleic acids in the physical or logical array as a template, or a partial or complete copy of the elongated nucleic acids or the recombinant nucleic acids in the physical or logical array. The one or more transcription or translation control subsequence is optionally ligated to into one or more of: the elongated nucleic acids, the recombinant nucleic acids in the physical or logical array, an intermediate nucleic acid produced using the elongated nucleic acids or the recombinant nucleic acids in the physical or logical array as a template, and a partial or complete copy of the elongated nucleic acids or the recombinant nucleic acids in the physical or logical array. The one or more transcription or translation control subsequence is optionally hybridized or partially hybridized to one or more of: the elongated nucleic acids, the recombinant nucleic acids in the physical or logical array, an intermediate nucleic acid produced using the elongated nucleic acids or the recombinant nucleic acids in the physical or logical array as a template, or a partial or complete copy of the elongated nucleic acids or the recombinant nucleic acids in the physical or logical array.

In one aspect, the recombinant nucleic acids in the physical or logical array or the elongated nucleic acids in the master array are amplified in a DNA micro-amplifier. The micro-amplifier can include one or more of: a programmable resistor, a micromachined zone heating chemical amplifier, a chemical denaturation device, an electrostatic denaturation device, and/or a microfluidic electrical fluid resistance heating device. Similarly, the physical or logical array, or portion thereof or the master array or portion thereof, is heated or cooled by one or more of: a Peltier solid state heat pump, a heat pump, a resistive heater, a refrigeration unit, a heat sink, and a Joule Thompson cooling device. The methods optionally include producing a duplicate amplified physical or logical array of recombinant nucleic acids.

The methods can similarly include in vitro transcribing members of the amplified physical or logical array of recombinant nucleic acids to produce an amplified array of in vitro transcribed nucleic acids. In one aspect, screening the amplified physical or logical array of recombinant nucleic acids, or a duplicate thereof, for a desired property comprises assaying a protein or product nucleic acid encoded by one or more members of the amplified physical or logical array of recombinant nucleic acids for one or more property.

In one aspect, the invention provides recombination of nucleic acids using a single-stranded template. In the methods, a first population of single-stranded template polynucleotides is provided. The template polynucleotides are the same or different. The templates are recombined by: (i) annealing a plurality of partially overlapping complementary nucleic acid fragments; and, (ii) extending the annealed fragments to produce a physical or logical array comprising a first population of recombinant nucleic acids. In one embodiment, a physical array comprising the first population of template polynucleotides is provided immobilized on a solid support (e.g., a glass support, a plastic support, a silicon support, a chip, a bead, a pin, a filter, a membrane, a microtiter plate, a slide or the like). In one embodiment, the first population of template polynucleotides comprises substantially an entire genome (e.g., a bacterial or fungal genome). In another embodiment, the first population of template polynucleotides comprises substantially all of the expression products of a cell (e.g., eukaryotic or prokaryotic), tissue or organism. Optionally, the first population of template polynucleotides comprises a subset of the expression products of a cell, tissue or organism. The first population of template polynucleotides optionally comprises a library of genomic nucleic acids or cellular expression products (e.g., mRNAs, cDNAs, etc.).

The template polynucleotides optionally include one or more of: a coding RNA, a coding DNA, an antisense RNA, and antisense DNA, a non-coding RNA, a non-coding DNA, an artificial RNA, an artificial DNA, a synthetic RNA, a synthetic DNA, a substituted RNA, a substituted DNA, a naturally occurring RNA, a naturally occurring DNA, a genomic RNA, a genomic DNA, a cDNA, or the like.

In one aspect, members of the amplified physical or logical arrays of recombinant nucleic acids herein are transcribed to produce an amplified array of transcribed nucleic acids. These can be translated to produce an amplified physical or logical array of polypeptides. The concentration of polypeptide or transcribed nucleic acids can be determined at one or more positions in the amplified physical or logical array of polypeptides.

In one aspect, the invention provides for re-arraying the amplified physical or logical array of polypeptides or in vitro transcribed nucleic acids in a secondary polypeptide or in vitro transcribed nucleic acid array which has an approximately uniform concentration of polypeptides or in vitro transcribed nucleic acids at a plurality of locations in the secondary polypeptide array. Alternately, or in conjunction, a correction factor which accounts for variation in polypeptide or in vitro transcribed nucleic acid concentrations at different positions in the amplified physical or logical array of polypeptides or in vitro transcribed nucleic acids can be applied to normalize detectable data.

In one aspect, one or more substrate is added to a plurality of members of the logical array of polypeptides or in vitro transcribed nucleic acids. Formation of a product produced by contact between the one or more substrate and one or more of the plurality of members of the logical array of polypeptides can be monitored, directly or indirectly. Formation of the product is detected, e.g., by a coupled enzymatic reaction which detects the product or the substrate or a secondary product of the product or substrate. For example, peroxide production can be monitored. Similarly, formation of the product is optionally detected by monitoring production of heat or entropy which results from the formation of the product.

The physical or logical array of polypeptides is optionally selected for a desired property, thereby identifying one or more selected member of the physical or logical array of polypeptides which has a desired property, and identifying one or more selected member of the amplified physical or logical array of recombinant nucleic acids that encodes the one or more member of the physical or logical array of polypeptides. For example, the selecting is optionally performed in a primary screening assay, comprising one or more of: (i) re-selecting the one or more selected member of the amplified physical or logical array of recombinant nucleic acids in a secondary screening assay; (ii) quantifying protein levels at one or more location in the physical or logical array of polypeptides; (iii) purifying proteins from one or more locations in the physical or logical array of polypeptides; (iv) normalizing activity levels in the primary screen by compensating for protein quantitation at a plurality of locations in the physical or logical array of polypeptides; (v) determining a physical characteristic of the one or more selected members; and, (vi) determining an activity of the one or more selected members. In a further aspect, the one or more selected member of the amplified physical or logical array of recombinant nucleic acids are recombined with one or more additional nucleic acids, in vivo, in vitro or in silico.

One or more member of the amplified physical or logical array, or a duplicate thereof, can be selected based upon the screening of the amplified physical or logical array for a desired property. Optionally, a plurality of members of the amplified physical or logical array or duplicate thereof are selected, recombined and re-arrayed to form a secondary array of recombined selected nucleic acids, which secondary array is re-screened for the desired property, or for a second desired property.

Methods of detecting or enriching for in vitro transcription or translation products are also provided. In the methods, one or more first nucleic acids which encode one or more moieties are localized proximal to one or more moiety recognition agents which specifically bind the one or more moieties. The one or more nucleic acids are in vitro translated or transcribed, producing the one or more moieties (e.g., polypeptides or biologically active RNAs such as anti-sense or ribozyme molecules, or other product molecules). The one or more moieties diffuse or flow into contact with the one or more moiety recognition agents. Binding of the one or more moieties to the one or more moiety recognition agents is permitted and the one or more moieties are detected or enriched for by detecting or collecting one or more materials proximal to, within or contiguous with the moiety recognition agent (the material comprises at least one of the one or more moieties, where the moieties comprise one or more in vitro translation or transcription product). Optionally, the one or more moieties are pooled by pooling the material which is collected. Here again, a variety of variants of this basic class of methods are set forth herein as are a variety of products produced by the methods and their variants.

Optionally, the one or more moieties (e.g., polypeptides or RNAs) are pooled by pooling the material which is collected. The moiety recognition agents noted above optionally include one or more antibody or one or more second nucleic acids. The first nucleic acids optionally include a related population of mutated, shuffled or otherwise altered nucleic acids. In another aspect, the first nucleic acids optionally include a related population of mutated, shuffled or otherwise altered nucleic acids which encode an epitope tag bound by the moiety or the one or more moiety recognition agents.

In one aspect, the first nucleic acids comprise a related population of mutated, shuffled or otherwise altered nucleic acids and a PCR primer binding region. Alternately, the first nucleic acids optionally comprise a related population of mutated, shuffled or otherwise altered nucleic acids and a PCR primer binding region. In this embodiment, the method further includes identifying one or more target first nucleic acid by proximity to the moieties which are bound to the one or more moiety recognition agent, and amplifying the target first nucleic acid by hybridizing a PCR primer to the PCR primer binding region and extending the primer with a polymerase. The method optionally includes PCR amplifying a set of parental nucleic acids to produce the related population of mutated, shuffled or otherwise altered nucleic acids.

In one typical embodiment, the first nucleic acids comprise an inducible or constitutive heterologous promoter. The first nucleic acids and the one or more moiety recognition agents are typically localized on a solid substrate (e.g., a bead, chip, slide or the like). In one embodiment, the first nucleic acids and the one or more moiety recognition agents are localized on the solid substrate by one or more of: a cleavable linker chemical linker, a gel, a colloid, a magnetic field, and an electrical field.

An activity of the moiety or moiety recognition agent is typically detected and the one or more first nucleic acid coupled to the moiety or moiety recognition agent is picked with an automated robot, e.g., by placing a capillary on a region comprising the detected activity of the moiety or moiety recognition agent. The moiety or moiety in contact with the moiety recognition agent is optionally cleaved at a cleavable linker which attaches the first nucleic acid to a solid substrate, providing for isolation of the first nucleic acid.

Methods of producing duplicate arrays of shuffled or mutagenized nucleic acids are provided. In the methods, a physical or logical array of shuffled or mutagenized nucleic acids or transcribed shuffled or transcribed mutagenized nucleic acids is provided. A duplicate array of copies (generated, e.g., using a polymerase or nucleic acid synthesizer) of the shuffled or mutagenized nucleic acids or copies of the transcribed shuffled or transcribed mutagenized nucleic acids is formed by physically or logically organizing the copies into a physical or logical array. Once again, a variety of variants of this basic class of methods are set forth herein, as are a variety of products produced by the methods and their variants.

In one aspect, an array of reaction mixtures which corresponds to the physical or logical array of shuffled or mutagenized nucleic acids or transcribed shuffled or transcribed mutagenized nucleic acids is formed. The reaction mixtures include members of the array of shuffled or mutagenized nucleic acids or transcribed shuffled or transcribed mutagenized nucleic acids or the duplicate array of copies of the shuffled or mutagenized nucleic acids or copies of the transcribed shuffled or transcribed mutagenized nucleic acids, or a derivative copy thereof. The reaction mixtures typically further include one or more in vitro transcription or translation reagent.

Methods of normalizing an array of reaction mixtures are provided. In the methods, a physical or logical array of diversified (e.g., shuffled or mutagenized) nucleic acids or transcribed shuffled or transcribed mutagenized nucleic acids is in vitro transcribed or translated to produce an array of products. A correction factor is determined which accounts for variation in concentration of the products at different sites in the array of products. Typically, a secondary product array is produced which comprises selected concentrations of the products at one or more sites in the secondary array, e.g., by transferring aliquots from a plurality of sites in the array of products to a plurality of secondary sites in the secondary array. Optionally, the products are diluted while being transferred or after transfer to the secondary sites, thereby selecting the concentration of the products at the secondary sites in the secondary array.

In one aspect, the invention provides methods of directing nucleic acid fragmentation using a computer. The method includes calculating a ratio of uracil to thymidine, which ratio when used in a fragmentation module produces one or more nucleic acid fragment of a selected length.

In another aspect, methods of directing PCR using a computer are provided. The method includes calculating one or more crossover region between two or more parental nucleic acid sequence using one or more annealing temperature or extension temperature. For example, the method optionally includes calculating the one or more crossover region using one or more theoretical prediction or one or more set of empirical data to calculate a melting temperature.

Methods of selecting one or more parental nucleic acids for diversity generation using a computer are also provided. In the method, an alignment between two or more potential parental nucleic acid sequences is performed. A number of mismatches between the aligned sequences is calculated and a melting temperature for one or more window of w bases in the alignment is calculated. One or more window of w bases having a melting temperature greater than x is determined and one or more crossover segment in the alignment is identified, which one or more crossover segment comprises two or more windows having a melting temperature greater than x, which two or more windows are separated by no more than n nucleotides. A dispersion of the one or more crossover segments is calculated and a first score for each alignment based on the number of windows having a melting temperature greater that x, the dispersion, and the number of crossover segments identified is calculated. A second score based on the number of mismatches, the number of windows having a melting temperature greater than x, the dispersion, and the number of crossover segments identified is determined, and one or more parental nucleic acid is selected based on the first score and/or the second score. These steps are optionally repeated, e.g., starting with the one or more parental nucleic acid which are selected.

In this method, the alignment optionally comprises a pairwise alignment. W optionally comprises an odd number, e.g., about 21. The method optionally includes calculating the melting temperature for the one or more window of w bases in the alignment from one or more set of empirical data or one or more melting temperature prediction algorithm. Example values for x include about 65° C. Example values for n include about 2. In the methods, the dispersion typically comprises the inverse of the average number of bases between crossover segments in the alignment.

Typically, the instruction set selects the two or more potential parental nucleic acid sequences by searching one or more database for one or more nucleic acid sequence of interest and one or more homolog of the one or more nucleic acid sequence of interest.

The invention further provides embodiments in a web page, e.g., for directing nucleic acid diversity generation, the web page comprising a computer readable medium that causes a computer to perform any of the methods herein.

Products produced by any of the processes herein are a feature of the invention.

Kits embodying the methods and comprising various components of the device/apparatus/integrated systems herein are also provided. Use of the methods and/or device/systems for any of the purposes indicated herein are also a feature of the invention.

BRIEF DESCRIPTION OF THE FIGURES

FIG. 10 is a schematic of an example DNA shuffling machine.

FIG. 16 is a schematic of a recombination analysis module.

DEFINITIONS

Figure 1A:
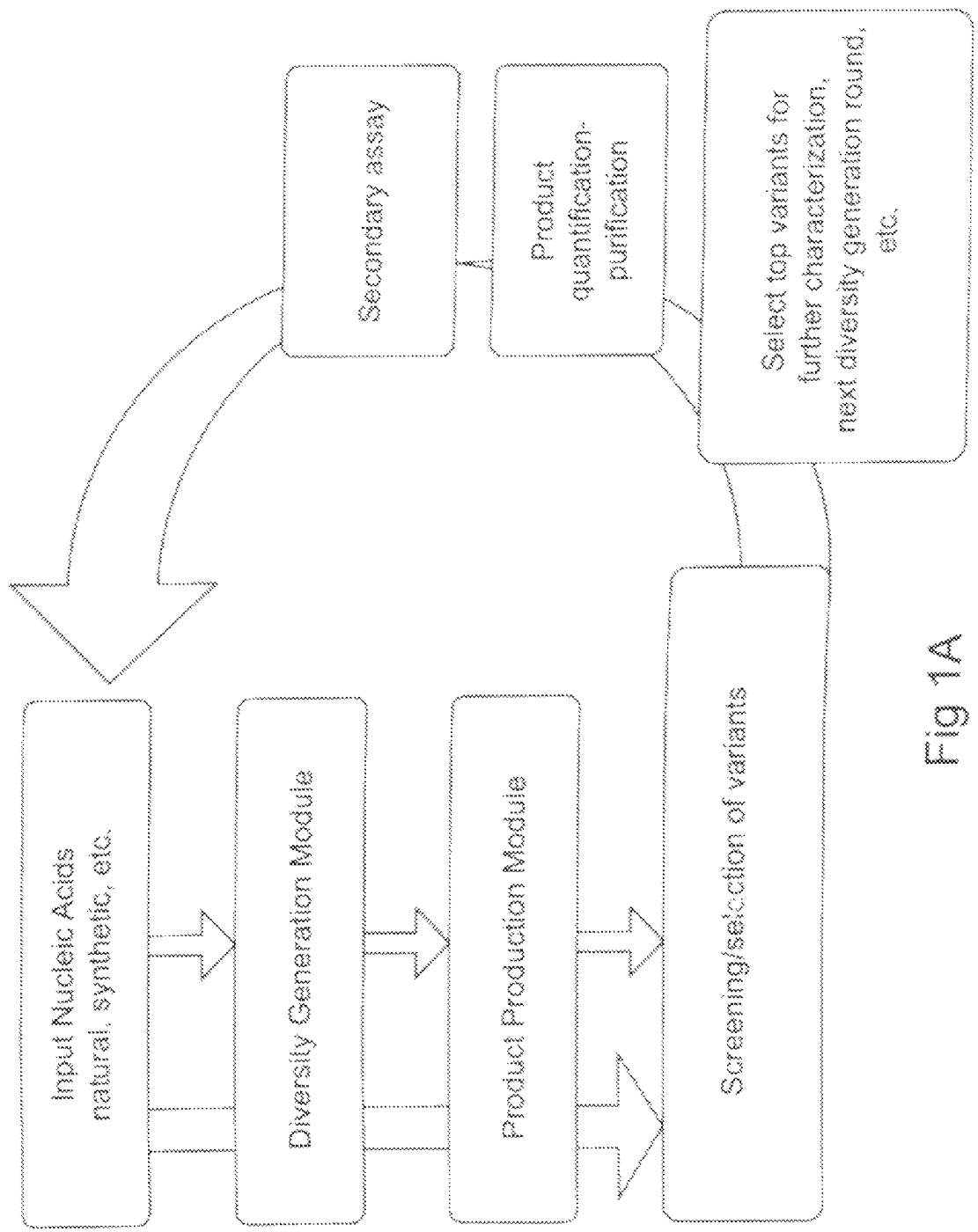
FIG. 1, Panels A and B is a schematic flow chart of an integrated system of the invention, beginning with input nucleic acids.

The following definitions supplement those common in the art for the terms specified.

A "physical array" is a set of specified elements arranged in a specified or specifiable spatial arrangement. A "logical array" is a set of specified elements arranged in a manner which permits access to the elements of the set. A logical array can be, e.g., a virtual arrangement of the set in a computer system, or, e.g., an arrangement of set elements produced by performing a specified physical manipulation on one or more set element or components of set elements. For example, a logical array can be described in which set elements (or components that can be combined to produce set elements) can be transported or manipulated to produce the set. A "duplicate" or "copy" array is an array which can be at least partially corresponded to a parental array. In simplest form, this correspondence takes the form of simply replicating all or part of the parental array, e.g., by taking an aliquot of material from each position in the parental array and placing the aliquot in a defined position in the duplicate array. However, any method which results in the ability to correspond members of the duplicate array to the parental array can be used for array duplication, including the use of simple or complex storage algorithms, partially or purely in silico arrays, and pooling approaches which partially combine some elements of the parental array into single locations (physical or virtual) in the duplicate array. The duplicate or copy array duplicates some or all components of a parental array. For example, an array of reaction mixtures optionally includes nucleic acids and translation or transcription reagents at sites in the array, while the duplicate/copy array can also include the complete reaction mixtures, or, alternately, can include, e.g., the nucleic acids, without the other reaction mixture components.

A "shuffled" nucleic acid is a nucleic acid produced by a shuffling procedure such as any shuffling procedure set forth herein. Shuffled nucleic acids are produced by recombining (physically or virtually) two or more nucleic acids (or character strings), e.g., in an artificial, and optionally recursive, fashion. Generally, one or more screening steps are used in shuffling processes to identify nucleic acids of interest; this screening step can performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

A "mutagenized nucleic acid" is a nucleic acid which has been physically altered as compared to a parental nucleic acid (e.g., such as a naturally occurring nucleic acid), e.g., by modifying, deleting, rearranging, or replacing one or more nucleotide residue in the mutagenized nucleic acid as compared to the parental nucleic acid.

A "transcribed" nucleic acid is a nucleic acid produced by copying a parental nucleic acid, where the parental nucleic acid is a different nucleic acid type than the copied nucleic acid. For example, an RNA copy of a DNA molecule (e.g., as occurs during classical transcription) or a DNA copy of an RNA molecule (e.g., as occurs during classical reverse transcription) can be a "transcribed nucleic acid" as that term is intended herein. Similarly, artificial nucleic acids, including peptide nucleic acids, can be used as either the parental or the copied nucleic acid (and artificial nucleotides can be incorporated into either parental or copied molecules). Copying can be performed, e.g., using appropriate polymerases, or using in vitro artificial chemical synthetic methods, or a combination of synthetic and enzymatic methods.

An "in vitro translation reagent" is a reagent which is necessary or sufficient for in vitro translation, or a reagent which modulates the rate or extent of an in vitro translation reaction, or which alters the parameters under which the reaction is operative. Examples include ribosomes, and reagents which include ribosomes, such as reticulocyte lysates, bacterial cell lysates, cellularractions thereof, amino acids, t-RNAs, etc.

A "translation product" is a product (typically a polypeptide) produced as a result of the translation of a nucleic acid. A "transcription product" is a product (e.g., an RNA, optionally including mRNA, or, e.g., a catalytic or biologically active RNA) produced as a result of transcription of a nucleic acid.

A "solid phase array" is an array in which the members of the array are fixed to or within a solid or semi-solid substrate. The fixation can be the result of any interaction that tends to immobilize components, including chemical linking, heat treatment, hybridization, ligand/receptor interactions, metal chelation interactions, ion exchange, hydrogen bonding and hydrophobic interactions and the like. For semi-solid substrates such as gels and gel droplets, linking may require nothing more than mixing of the member with the substrate material during or after solidification. A "solid substrate" has a fixed organizational support matrix, such as silica, glass, polymeric materials, membranes, filters, beads, pins, slides, microtiter plates or trays, etc. In some embodiments, at least one surface of the substrate is partially planar, but in others, the solid substrate is a discrete element such as a bead which can be dispensed into an organization matrix such as a microtiter tray. Solid support materials include, but are not limited to, glass, polacryloylmorpholide, silica, controlled pore glass (CPG), polystyrene, polystyrene/latex, polyacrylate, polyacrylamide, agar, agarose, chemically modified agars and agaroses, carboxyl modified teflon, nylon and nitrocellulose. The solid substrates can be biological, nonbiological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art. Often, the surface of the solid substrate will contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. The surface may also be chemically modified or functionalized in such a way as to allow it to establish binding interactions with functional groups intrinsic to or specifically associated with the nucleic acids or polypeptides to be immobilized.

A "liquid phase array" is an array in which the members of the array are free in solution, e.g., on a microtiter tray, or in a series of containers such as a set of test tubes or other containers. Most often, members of a liquid phase array are separated in space by subdividing the volume containing the members of the array into multiple discrete chambers such that each chamber contains less than a complete library of members, and ideally less than about 10% of the discrete members in the library. Such separation or fractionation of a population containing a plurality of unique sequences can be accomplished by sorting, dilution, serial dilution, and a variety of other methods.

Nucleic acids are "homologous" when they derive (artificially or naturally) from a common ancestor. Where there is no direct knowledge of the relatedness of two or more nucleic acids, homology is often inferred by consideration of the percent identity or by identification of discrete sequence motifs within sets of low identity sequences of the relevant nucleic acids. As described in more detail herein, commonly available software programs such as BLAST and PILEUP can be used to calculate relatedness of nucleic acids.

Nucleic acids "hybridize" when they preferentially associate in solution. As described in more detail below, a variety of parameters such as temperature, ionic buffer conditions and the presence or absence of organic solvents affect hybridization of two or more nucleic acids.

A "translation control sequence" is a nucleic acid subsequence which affects the initiation, rate or extent of translation of a nucleic acid, such as ribosome binding sites, stop codons and the like. A variety of such sequences are known and described in the references set forth herein and many more are fully available to one of skill.

A "transcription control sequence" is a nucleic acid subsequence which affects the initiation, rate or extent of transcription of a nucleic acid, such as a promoter, enhancer or terminator sequences. A variety of such sequences are known and described in the references set forth herein, and many more are fully available to one of skill.

DETAILED DISCUSSION OF THE INVENTION

The present invention takes advantage of a variety of technologies to automate nucleic acid shuffling and other diversity-generation dependent processes. Each aspect of diversity generation and downstream screening processes can be automated (and used individually in separate modules or collectively in an integrated system or an overall device), providing devices, systems and methods which greatly increase throughput for generating diverse nucleic acids (e.g., by recombination methods such as DNA shuffling, or via other mutagenesis methods, or combinations thereof) and screening for desirable properties of those nucleic acids (e.g., encoded RNAs, proteins, or the like).

The invention provides, among other things, methods, kits, devices and integrated systems. For example, devices and integrated systems comprising a physical or logical array of reaction mixtures are provided. Each reaction mixture comprises one or more recombinant, shuffled or otherwise diversified nucleic acids (e.g., diversified by mutagenesis, optionally including recombination or other methods), or corresponding transcribed nucleic acids (e.g., cDNAs or mRNAs). The reaction mixtures of the array also include one or more in vitro transcription and/or translation reagents.

As will be described in more detail below, arrays can be, and commonly are, partially or completely duplicated in the methods and systems of the invention. For example, aliquots of reaction mixtures or products can be taken and copy arrays formed from the aliquots. Similarly, master arrays comprising, e.g., the nucleic acids found in the reaction mixtures (e.g., arrays constituted of duplicate amplified sets of diversified nucleic acids) can be produced. The precise manner of production of array copies varies according to the physical nature of the array. For example, where arrays are formed in microtiter trays, copy arrays are conveniently formed in microtiter trays, e.g., by automated pipetting of aliquots of material from an original array. However, arrays can also change form in the copying process, i.e., liquid phase copies can be formed from solid phase arrays, or vice versa, or a logical array can be converted to a simple or complex spatial array in the process of forming the copy (e.g., by moving or creating an aliquot of material corresponding to a member of the logical array, and, subsequently, placing the aliquot with other array members in an accessible spatial relationship such as a gridded array), or vice versa (e.g., array member positions can be recorded and that information used as the basis for logical arrays that constitute members of multiple spatial arrays—a common process when identifying "hits" having an activity of interest).

The arrays can include both reaction mixture and product components. For example, in addition to the nucleic acids, transcription regents and translation reagents noted above, the arrays can also include products of the reaction mixture such as RNAs (e.g., mRNAs, biologically active nucleic acids (e.g., ribozymes, aptamers, antisense molecules, etc.) proteins, or the like. Thus, the reaction mixtures can comprise one or more translation products or one or more transcription products, or both.

Similarly, the arrays can have any of a variety of physical configurations, including solid or liquid phase(s). Some or all of the components of the reaction mixtures can be fixed in position, e.g., the nucleic acids in the reaction mixtures can be relatively fixed in position (e.g., in a solid or immobilized phase), while the other components of the array can diffuse across the array (e.g., through a gel or other immobilizing matrix). Alternatively, some or all of the members of the array can be immobilized to a single general spatial location (e.g., by being present in wells of a microtiter dish, either by being fixed to the surface of the dish or in solution in the wells of the dish). Thus, the array of reaction mixtures can comprises a solid phase or a liquid phase array of any of the components of the reaction mixtures, e.g., the diversified nucleic acids (or transcribed products thereof), in vitro translation reagents, etc.

I. An Overview of Integrated Diversity Generation/Screening Systems

Figure 1B:
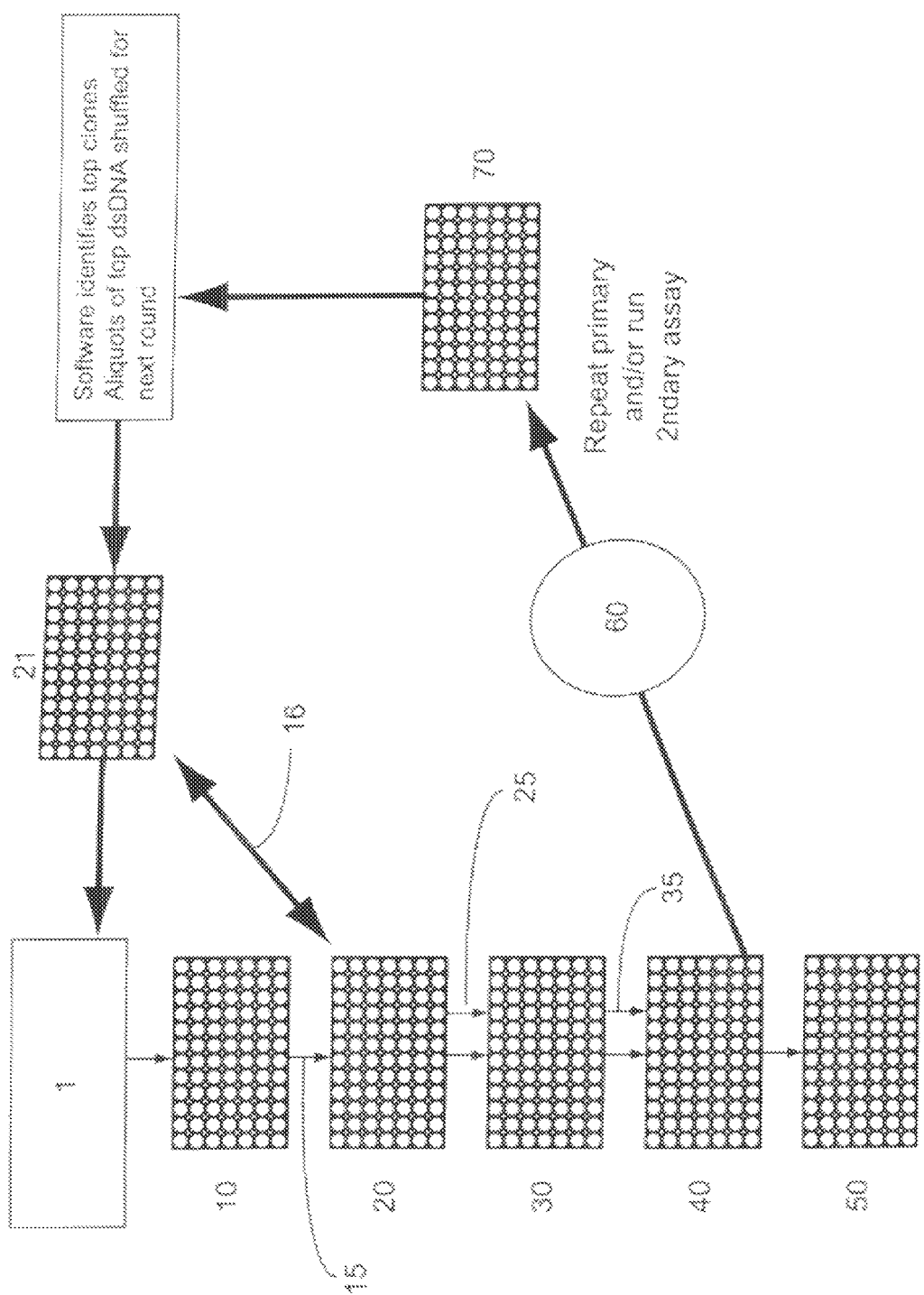

FIG. 1, panels A and B provides a schematic overview of an example integrated system of the invention. In some contexts, some of the listed elements are omitted; conversely, many additional elements are optionally included.

As shown, nucleic acids (DNA, RNA, etc.) or corresponding character strings (e.g., characters in a computer system) are input into the system. A diversity generation module (e.g., a shuffling and/or mutagenesis module) recombines, mutagenizes or otherwise modifies the input nucleic acids to produce a diverse set of nucleic acids that are used to produce one or more product (a protein, bioactive RNA, or the like) in a product production module. Variant nucleic acids are then selected (typically by screening products from the production module) for a desired encoded activity (encoded protein or RNA, level of RNA expression, level of protein expression, etc.). Top variants are then selected for further characterization, additional rounds of diversity generation (e.g., recombination of the top variants with each other or with additional nucleic acids, or both).

Typically, a product quantification module can be used to normalize selection results (i.e., to account for differences in concentrations of protein, catalytic RNAs or other products). Optionally, one or more additional secondary assay can be performed to further select for one or more additional property of interest in any product.

FIG. 1, panel B provides additional details of the example integrated system. As shown, nucleic acids are dispensed from diversity generation module 1 into microtiter trays (as described below, many alternative configurations that do not use such trays, instead using other liquid (e.g., microfluidic) or solid phase arrays). For example, the diversified DNAs (or other nucleic acids) are dispensed into first tray or set of trays 10 at about 0-100 unique DNA molecules/well to provide for straightforward interpretation of results from the system. Commonly, each well can contain 0-10 unique molecules. For example, each well can contain, on average, 0-5, or e.g., 0-3 unique molecules. That is, if there are only 1 or a few nucleic acid molecule member types per array position it is easier to identify which array members produce a desirable activity. However, arrays of pooled members can be used, in which pools having an activity of interest are subsequently deconvoluted (e.g., re-arrayed by limiting dilution and the pool members tested for any activity of interest). In this context, the term "unique" refers to nucleic acids of differing lengths or sequences.

A nucleic acid master array is produced by amplifying the members of the first tray (the amplified members are accessible for further operations), e.g., as indicated by PCR process amplification step(s) 15. One or more copies of this master array (20, 21) is optionally produced (e.g., by aliquotting or otherwise transferring materials from the original to the copies) for further access by the system in subsequent procedures. Either the original or the duplicate of the master array can be in vitro transcribed (if appropriate—the copying procedure (represented by in vitro transcription process step 25) can produce DNA or RNA copies (e.g., as represented by mRNA copy array 30), and the original can be DNA or RNA, as desired) and/or translated in vitro to produce a product of interest (e.g., a biologically active RNA, protein, or the like, represented by protein/RNA array 40). This is represented by in vitro transcription process step(s) 35.

The product is assayed as appropriate on primary assay plate 50 which optionally includes substrates or other relevant components. Secondary assays (i.e., assays for activities which differ from the first activity) can also be run in secondary assay modules.

Typically, a product quantification module such as a protein quantification/purification module 60 is used to normalize the activity level of the product, i.e., to detect and/or account for variation in product concentrations. Protein quantitation module 60 allows arraying at uniform concentration for specific activities. Aliquots of existing proteins can be rearrayed and reassayed, e.g., on secondary assay plate 70. New protein can be reproduced from mRNA or dsDNA, quantified and reassayed.

Detector elements are typically included in protein quantitation module 60 to detect product activities of interest (hits). Optionally, hit picking software and or hardware is used to select hits (other software elements control sample manipulation and transfer between modules and respond to user inputs). The system determines which nucleic acids in the master array that the hits correspond to and either identifies the hits to the user or uses corresponding nucleic acids from the original or copy master array in subsequent diversity generation reactions, such as in additional shuffling reactions in the diversity generation module.

In general in FIG. 1, arrows between plates indicate processes that can be used to produce new plates, or which can be performed on existing plates.

II. Methods and System Elements for Generating Nucleic Acid Diversity

A variety of diversity generating protocols (e.g., mutation, including recombination and other methods) are available and described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to provide diverse sequence variants.

The result of any of the diversity generating procedures described herein can be the generation of one or more nucleic acids, which can be selected or screened for nucleic acids that encode proteins or bioactive RNAs (e.g., catalytic RNAs) with or which confer new or desirable properties. Following diversification by one or more of the methods herein, or otherwise available to one of skill, any nucleic acids that are produced can be selected for a desired activity or property, e.g. for use in the automated systems and methods herein. This can include identifying any activity that can be detected, for example, in an automated or automatable format, by any of the assays in the art or herein. A variety of related (or even unrelated) properties can be evaluated, in serial or in parallel, at the discretion of the practitioner.

As noted, a variety of diversity generating/product screening reactions can be automated by the methods set forth herein. One important class of such reactions are "nucleic acid shuffling" or "DNA shuffling" methods. In these methods, any of a variety of recombination-based diversity generating procedures can be used to diversify starting nucleic acids, or organisms comprising nucleic acids, or even to diversify character strings which are "in silico" (in computer) representations of nucleic acids (or both). Diverse nucleic acids/character strings/organisms which are generated by such methods are typically screened for one or more activity. Nucleic acids, character strings, or organisms which comprise nucleic acids are then optionally used as substrates in subsequent recombination reactions, the products of which are, again, screened for one or more activity. This process is optionally repeated recursively until one or more desirable product is produced.

A variety of diversity generating protocols, including nucleic acid shuffling protocols, are available and fully described in the art. The following publications describe a variety of recursive recombination and other mutational procedures and/or methods which can be incorporated into such procedures, as well as other diversity generating protocols: Soong, N. et al. (2000) "Molecular breeding of viruses" *Nat Genet.* 25(4):436-439; Stemmer, et al., (1999) "Molecular breeding of viruses for targeting and other clinical properties. Tumor Targeting" 4:1-4; Ness et al. (1999) "DNA Shuffling of subgenomic sequences of subtilisin" *Nature Biotechnology* 17:893-896; Chang et al. (1999) "Evolution of a cytokine using DNA family shuffling" *Nature Biotechnology* 17:793-797; Minshull and Stemmer (1999) "Protein evolution by molecular breeding" *Current Opinion in Chemical Biology* 3:284-290; Christians et al. (1999) "Directed evolution of thymidine kinase for AZT phosphorylation using DNA family shuffling" *Nature Biotechnology* 17:259-264; Crameri et al. (1998) "DNA shuffling of a family of genes from diverse species accelerates directed evolution" *Nature* 391:288-291; Crameri et al. (1997) "Molecular evolution of an arsenate detoxification pathway by DNA shuffling," *Nature Biotechnology* 15:436-438; Zhang et al. (1997) "Directed evolution of an effective fucosidase from a galactosidase by DNA shuffling and screening" *Proceedings of the National Academy of Sciences, U.S.A.* 94:4504-4509; Patten et al. (1997) "Applications of DNA Shuffling to Pharmaceuticals and Vaccines" *Current Opinion in Biotechnology* 8:724-733; Crameri et al. (1996) "Construction and evolution of antibody-phage libraries by DNA shuffling" *Nature Medicine* 2:100-103; Crameri et al. (1996) "Improved green fluorescent protein by molecular evolution using DNA shuffling" *Nature Biotechnology* 14:315-319; Gates et al. (1996) "Affinity selective isolation of ligands from peptide libraries through display on a lac repressor 'headpiece dimer'" *Journal of Molecular Biology* 255: 373-386; Stemmer (1996) "Sexual PCR and Assembly PCR" In: *The Encyclopedia of Molecular Biology.* VCH Publishers, New York. pp. 447-457; Crameri and Stemmer (1995) "Combinatorial multiple cassette mutagenesis creates all the permutations of mutant and wildtype cassettes" *BioTechniques* 18:194-195; Stemmer et al., (1995) "Single-step assembly of a gene and entire plasmid form large numbers of oligodeoxyribonucleotides" *Gene,* 164:49-53; Stemmer (1995) "The Evolution of Molecular Computation" *Science* 270: 1510; Stemmer (1995) "Searching Sequence Space" *Bio/Technology* 13:549-553; Stemmer (1994) "Rapid evolution of a protein in vitro by DNA shuffling" *Nature* 370:389-391; and Stemmer (1994) "DNA shuffling by random fragmentation and reassembly: In vitro recombination for molecular evolution." *Proceedings of the National Academy of Sciences, U.S.A.* 91:10747-10751.

Additional available mutational methods of generating diversity include, for example, site-directed mutagenesis (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237: 1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100: 468-500 (1983); *Methods in Enzymol.* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100:468-500; and Zoller & Smith (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749-8764; Taylor et al. (1985) "The rapid generation of oligonucleotide-directed mutations at high frequency using phosphorothioate-modified DNA" *Nucl. Acids Res.* 13: 8765-8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679-9698; Sayers et al. (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide" *Nucl. Acids Res.* 16: 803-814); mutagenesis using gapped duplex DNA (Kramer et al. (1984) "The gapped duplex DNA approach to oligonucleotide-directed mutation construction" *Nucl. Acids Res.* 12: 9441-9456; Kramer & Fritz (1987) *Methods in Enzymol.* "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987-6999).

Additional suitable methods include point mismatch repair (Kramer et al. (1984) "Point Mismatch Repair" *Cell* 38:879-887), mutagenesis using repair-deficient host strains (Carter et al. (1985) "Improved oligonucleotide site-directed mutagenesis using M13 vectors" *Nucl. Acids Res.* 13: 4431-4443; and Carter (1987) "Improved oligonucleotide-directed mutagenesis using M13 vectors" *Methods in Enzymol.* 154: 382-403), deletion mutagenesis (Eghtedarzadeh & Henikoff (1986) "Use of oligonucleotides to generate large deletions" *Nucl. Acids Res.* 14: 5115), restriction-selection and restriction-purification (Wells et al. (1986) "Importance of hydrogen-bond formation in stabilizing the transition state of subtilisin" *Phil. Trans. R. Soc. Lond. A* 317: 415-423), mutagenesis by total gene synthesis (Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducin)" *Nucl. Acids Res.* 14: 6361-6372; Wells et al. (1985) "Cassette mutagenesis: an efficient method for generation of multiple mutations at defined sites" *Gene* 34:315-323; and Grundström et al. (1985) "Oligonucleotide-directed mutagenesis by microscale 'shotgun' gene synthesis" *Nucl. Acids Res.* 13: 3305-3316), double-strand break repair (Mandecki (1986) "Oligonucleotide-directed double-strand break repair in plasmids of *Escherichia coli*: a method for site-specific mutagenesis" *Proc. Natl. Acad. Sci. USA,* 83:7177-7181; and Arnold (1993) "Protein engineering for unusual environments" *Current Opinion in Biotechnology* 4:450-455). Additional details on many of the above methods can be found in *Methods in Enzymology Volume* 154, which also describes useful controls for trouble-shooting problems with various mutagenesis methods.

Additional details regarding DNA shuffling and other diversity generating methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

In addition, details and formats for recursive recombination, e.g., DNA shuffling and other diversity generating protocols are found in a variety of PCT and foreign patent application publications, including: Stemmer and Crameri, "DNA MUTAGENESIS BY RANDOM FRAGMENTATION AND REASSEMBLY" WO 95/22625; Stemmer and Lipschutz "END COMPLEMENTARY POLYMERASE CHAIN REACTION" WO 96/33207; Stemmer and Crameri "METHODS FOR GENERATING POLYNUCLEOTIDES HAVING DESIRED CHARACTERISTICS BY ITERATIVE SELECTION AND RECOMBINATION" WO 97/0078; Minshul and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION" WO 99/41383; Punnonen et al. "GENETIC VACCINE VECTOR ENGINEERING" WO 99/41369; Punnonen et al. OPTIMIZATION OF IMMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGANISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO9813487.

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION", by del Cardayre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

As review of the foregoing publications, patents, published applications and U.S. patent applications reveals, recursive recombination and other mutation methods for modifying nucleic acids to provide new nucleic acids with desired (e.g., new or improved) properties can be carried out by a number of established methods and these procedures can be combined with any of a variety of other diversity generating methods. The following exemplify some of the different formats for diversity generation in the context of the present invention, including, e.g., certain recombination based diversity generation formats. Many additional formats are provided in the references above and herein, and can be adapted to use in the systems and methods herein.

For example, several different general classes of recombination methods are applicable to the present invention and set forth in the references above. First, nucleic acids can be recombined in vitro by any of a variety of techniques discussed in the references above, including e.g., DNAse digestion of nucleic acids to be recombined followed by ligation and/or PCR reassembly of the nucleic acids. Second, nucleic acids can be recursively recombined in vivo, e.g., by allowing recombination to occur between nucleic acids in cells. Third, whole genome recombination methods can be used in which whole genomes of cells or other organisms are recombined, optionally including spiking of the genomic recombination mixtures with desired library components. Fourth, synthetic recombination methods can be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard, single nucleotide addition methods, or by methods in which dinucleotides, trinucleotides or longer oligomers are added in at least one synthetic cycle, for example, to limit or expand the number of codons which may be present at a given position within a synthetic or semi-synthetic gene. Moreover, recombined nucleic acids may be generated either from a starting pool of single stranded oligonucleotides or by first annealing at least one single-stranded oligomer to a complement sequence, thus forming a starting pool of preannealed double stranded oligonucleotides. Fifth, in silico methods of recombination can be effected in which genetic algorithms are used in a computer to recombine sequence strings which correspond to nucleic acid homologues (or even non-homologous sequences). The resulting recombined sequence strings are optionally converted into nucleic acids by synthesis of nucleic acids which correspond to the recombined sequences, e.g., in concert with oligonucleotide synthesis/gene reassembly techniques. Sixth, methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be used. Any of the preceding general recombination formats can be practiced in a reiterative fashion to generate a more diverse set of recombinant nucleic acids.

Thus, as noted, nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants are described in several of the references above, e.g., in Stemmer (1994) Proc. Natl. Acad. Sci. USA 91:10747-10751. The present invention provides various automated formats and related devices for practicing such methods.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Here again, the present invention provides various automated formats and related devices for practicing such methods.

In addition, whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination." The present invention provides various automated formats and related devices for practicing such methods.

As noted, synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide or other synthetic approaches. Details regarding such approaches are found in the references noted above, including, e.g., "OLIGONUCLEOTIDE MEDIATED NUCLEIC ACID RECOMBINATION" by Crameri et al., filed Sep. 28, 1999 (U.S. Ser. No. 09/408,392), and "OLIGO-NUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202); "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579). These procedures are especially amenable to use in the automated systems and methods herein.

For example, in silico methods of recombination can be effected in which genetic algorithms (GAs) or genetic operators (GOs) are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579). Extensive details regarding in silico recombination methods are found in these applications.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length, ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "SINGLE-STRANDED NUCLEIC ACID TEMPLATE-MEDIATED RECOMBINATION AND NUCLEIC ACID FRAGMENT ISOLATION" by Affholter, U.S. Ser. No. 09/656,549, filed Sep. 6, 2000. Further details on adaptation of these methods to the present invention are found supra.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein. Further details on this approach are provided herein.

Any of the preceding general mutation or recombination formats can be practiced in a reiterative fashion (e.g., one or more cycles of mutation/recombination or other diversity generation methods, optionally followed by one or more selection methods) to generate a more diverse set of recombinant nucleic acids.

In general, the above references provide many basic mutation and recombination formats as well as many modifications of these formats. Regardless of the format which is used, the nucleic acids of the invention can be recombined (with each other or with related (or even unrelated) to produce a diverse set of recombinant nucleic acids, including, e.g., sets of homologous nucleic acids.

Following recombination and/or other forms of mutation, any nucleic acids which are produced can be selected for a desired activity. In the context of the present invention, this can include testing for and identifying any activity that can be detected in an automatable format, by any of the assays in the art. A variety of related (or even unrelated) properties can be assayed for, using any available assay. These methods are automated according to the present invention as described herein. As noted, DNA recombination and other forms of mutagenesis, separately or in combination, provide robust, widely applicable, means of generating diversity useful for the engineering of nucleic acids, proteins, pathways, cells and organisms to provide new or improved characteristics.

It is often desirable to combine multiple diversity generating methodologies when generating diversity. For example, in conjunction with (or separately from) shuffling methods, a variety of mutation methods can be practiced and the results (i.e., diverse populations of nucleic acids) screened for in the systems of the invention. Additional diversity can be introduced by methods which result in the alteration of individual nucleotides or groups of contiguous or non-contiguous nucleotides, i.e., mutagenesis methods. Further details on certain example mutation methodologies are provided below.

In one aspect, error-prone PCR is used, in which, e.g., PCR is performed under conditions where the copying fidelity of the DNA polymerase is low, such that a high rate of point mutations is obtained along the entire length of the PCR product. Examples of such techniques are found in the references above and, e.g., in Leung et al., (1989) *Technique*, 1:11-15 (1989) and Caldwell et al. (1992) *PCR Methods Applic.* 2:28-33. Similarly, assembly PCR can be used, in a process which involves the assembly of a PCR product from a mixture of small DNA fragments. A large number of different PCR reactions can occur in parallel in the same vial, with the products of one reaction priming the products of another reaction. Sexual PCR mutagenesis can be used in which homologous recombination occurs between DNA molecules of different but related DNA sequence in vitro, by random fragmentation of the DNA molecule based on sequence homology, followed by fixation of the crossover by primer extension in a PCR reaction. This process is described in the references above, e.g., in Stemmer (1994) *PNAS* 91:10747-10751. Recursive ensemble mutagenesis can be used in which an algorithm for protein mutagenesis is used to produce diverse populations of phenotypically related mutants whose members differ in amino acid sequence. This method uses a feedback mechanism to control successive rounds of combinatorial cassette mutagenesis. Examples of this approach are found in Arkin and Youvan *PNAS USA* 89:7811-7815 (1992).

As noted, oligonucleotide directed mutagenesis can be used in a process which allows for the generation of site-specific mutations in any cloned DNA segment of interest. Examples of such techniques are found in the references above and, e.g., in Reidhaar-Olson et al. (1988) *Science*, 241:53-57. Similarly, cassette mutagenesis can be used in a process which replaces a small region of a double stranded DNA molecule with a synthetic oligonucleotide cassette that differs from the native sequence. The oligonucleotide can contain, e.g., completely and/or partially randomized native sequence(s).

In vivo mutagenesis can be used in a process of generating random mutations in any cloned DNA of interest which involves the propagation of the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

Exponential ensemble mutagenesis can be used for generating combinatorial libraries with a high percentage of unique and functional mutants, where small groups of residues are randomized in parallel to identify, at each altered position, amino acids which lead to functional proteins. Examples of such procedures are found in Delegrave and Youvan (1993) *Biotechnology Research,* 11:1548-1552. Similarly, random and site-directed mutagenesis can be used. Examples of such procedures are found in Arnold (1993) *Current Opinion in Biotechnology,* 4:450-455.

Many kits for mutagenesis are also commercially available. For example, kits are available from, e.g., Stratagene (e.g., the QuickChange site-directed mutagenesis kit; and the Chameleon double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology ltd (e.g., using the Carter/Winter method above).

Any of the described shuffling or mutagenesis techniques can be used in conjunction with procedures which introduce additional diversity into a genome, e.g. a eukaryotic or bacterial genome. For example, in addition to the methods above, techniques have been proposed which produce chimeric nucleic acid multimers suitable for transformation into a variety of species, including *E. coli* and *B. subtilis* (see, e.g., Schellenberger U.S. Pat. No. 5,756,316 and the references above). When such chimeric multimers consist of genes that are divergent with respect to one another, (e.g., derived from natural diversity or through application of site directed mutagenesis, error prone PCR, passage through mutagenic bacterial strains, and the like), are transformed into a suitable host, this provides a source of nucleic acid diversity for DNA diversification.

In one aspect, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multi-species expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

Chimeric multimers transformed into host species are suitable as substrates for in vivo shuffling protocols. Alternatively, a multiplicity of polynucleotides sharing regions of partial sequence similarity can be transformed into a host species and recombined in vivo by the host cell. Subsequent rounds of cell division can be used to generate libraries, members of which, comprise a single, homogenous population of monomeric or pooled nucleic acid. Alternatively, the monomeric nucleic acid can be recovered by standard techniques and recursively recombined in any of the described shuffling formats.

Chain termination methods of diversity generation have also been proposed (see, e.g., U.S. Pat. No. 5,965,408 and the references above). In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., uv, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are chimeric with respect to the starting population of DNA molecules. Optionally, the products or partial pools of the products can be amplified at one or more stages in the process. Polynucleotides produced by a chain termination method, such as described above are suitable substrates for DNA shuffling according to any of the described formats.

Diversity can also be generated using, for example, incremental truncation for the creation of hybrid enzymes (ITCHY) described in Ostermeier et al. (1999) "A combinatorial approach to hybrid enzymes independent of DNA homology" *Nature Biotech* 17:1205, can be used to generate an initial recombinant library which serves as a substrate for one or more rounds of in vitro or in vivo shuffling methods. Any homology or non-homology based mutation/recombination format can be used to generate diversity, separately or in combination.

In some applications, it is desirable to preselect or pre-screen libraries (e.g., an amplified library, a genomic library, a cDNA library, a normalized library, etc.) or other substrate nucleic acids prior to shuffling, or to otherwise bias the substrates towards nucleic acids that encode functional products (shuffling procedures can also, independently have these effects). For example, in the case of antibody engineering, it is possible to bias the shuffling process toward antibodies with functional antigen binding sites by taking advantage of in vivo recombination events prior to DNA shuffling by any described method. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to DNA shuffling according to, any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations, including, but not restricted to, DNA shuffling. A library comprising the mutagenized homologues is then screened for a desired activity, which can be the same as or different from the initially specified activity. An example of such a procedure is proposed in U.S. Pat. No. 5,939,250. Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from a hybridization probe used in the capture, with or without prior release from the capture medium or by a wide variety of other strategies known in the art. Alternatively, the isolated single-stranded genomic DNA population can be fragmented without further cloning and used directly in a shuffling-based gene reassembly process. In one such method the fragment population derived the genomic library(ies) is annealed with partial, or, often approximately full length ssDNA or RNA corresponding to the opposite strand. Assembly of complex chimeric genes from this population is the mediated by nuclease-based removal of non-hybridizing fragment ends, polymerization to fill gaps between such fragments and subsequent single stranded ligation. The parental strand can be removed by digestion (if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. As set detailed, e.g., in "SINGLE-STRANDED NUCLEIC ACID TEMPLATE-MEDIATED RECOMBINATION AND NUCLEIC ACID FRAGMENT ISOLATION" by Affholter, U.S. Ser. No. 60/186,482 filed Mar. 2, 2000, and U.S. Ser. No. 09/656,549, Filed Sep. 6, 2000 shuffling using single-stranded templates and nucleic acids of interest which bind to a portion of the template can also be performed.

"Non-Stochastic" methods of generating nucleic acids and polypeptides are proposed in Short "Non-Stochastic Generation of Genetic Vaccines and Enzymes" WO 00/46344. These methods, including proposed non-stochastic polynucleotide reassembly and site-saturation mutagenesis methods can be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297-300; Reidhaar-Olson et al. (1991) "Random mutagenesis of protein sequences using oligonucleotide cassettes" *Methods Enzymol.* 208:564-86; Lim and Sauer (1991) "The role of internal packing interactions in determining the structure and stability of a protein" *J. Mol. Biol.* 219:359-76; Breyer and Sauer (1989) "Mutational analysis of the fine specificity of binding of monoclonal antibody 51F to lambda repressor" *J. Biol. Chem.* 264:13355-60); and "Walk-Through Mutagenesis" (Crea, R; U.S. Pat. Nos. 5,830,650 and 5,798,208, and EP Patent 0527809 B1.

In one approach, described in more detail herein, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for any of the shuffling reactions described herein.

It will further be appreciated that any of the above described techniques suitable for enriching a library prior to shuffling can be used to screen the products generated by the methods of DNA shuffling.

The above references provide many mutational formats, including recombination, recursive recombination, mutation by non-recombination directed methods, recursive mutation in any format as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

Non-PCR Based Recombination Methods

As noted above, site-directed or oligonucleotide-directed mutagenesis methods can be used to generate chimeras between 2 or more parental genes. Many methods are described in the literature and some are listed herein that do not depend on PCR, though PCR-based methods are also fully described herein and useful in the context of the present invention.

A common theme to many non-PCR based methods is preparation of a single-stranded template to which primers (e.g., synthetic oligonucleotides, single-stranded DNA or RNA fragments) are annealed, then elongated by a DNA or RNA polymerase in the presence of dNTPs and appropriate buffer. The gapped duplex can be sealed with DNA ligase prior to transformation or electroporation into *E. coli*. In some instances, e.g., where a substantially coextensive heterolog is generated by annealing of multiple primers to a template, ligase alone is sufficient to produce a recombinant DNA strand. In some instances, e.g., where there are "flaps" of nucleic acid which do not hybridize to the template, an exo- or endo-nuclease can be used to eliminate unhybridized portions of a bound nucleic acid prior to polymerase and/or ligase treatment.

The newly synthesized strand is replicated and generates a chimeric gene with contributions from the oligo in the context of the single-stranded (ss) parent. The ss template can be prepared, e.g., by incorporation of the phage IG region into the plasmid and use of a helper phage such as M13KO7 or R408 to package ss plasmids into filamentous phage particles. The ss template can also be generated by denaturation of a double-stranded template and annealing in the presence of the primers. Methods vary, e.g., in the enrichment protocols for isolation of the newly synthesized chimeric strand over the parental template strand and are described in the references below. The "Kunkel" method uses uracil-containing templates. The Eckstein method uses phosphorothioate-modified DNA. The use of restriction selection or purification can be used in conjunction with mismatch repair deficient strains.

In the context of the present invention, the "mutagenic" primer described in these methods can be one or more synthetic oligonucleotides encoding any type of randomization, insertion, deletion, family gene shuffling oligonucleotides based on sequence diversity of homologous genes, etc. Oligos that randomize particular sequences (eg. NNG/C), encode conservative replacements for particular residues (eg. NUN for hydrophobic residues), spiked oligos where the correct nucleotide sequence is synthesized in the background of a low level of all 3 mismatched nucleotides, incorporation of deoxyinosine or other ambiguous nucleotide analogs, incorporation, insertions, deletions, error prone PCR, etc. can be used. The primer(s) can also be, e.g., fragments of homologous genes that are annealed to the ss parent template. In this way chimeras between 2 or more parental genes can be generated.

Multiple primers can anneal to a given template and be extended to create multiply chimeric genes. The use of a DNA polymerase such as those from phages T4 or T7 are good for this purpose as they will not degrade or displace a downstream primer from the template.

In one class of preferred embodiments, the ss template or one or more primers (e.g., mutagenic primers) is immobilized on a solid substrate such as a chip or a membrane. In other embodiments, annealing and extension occurs in a liquid phase array, such as in a reaction solution within wells of a microtiter plate or an arrangement of test tubes.

Example: DNA Shuffling Using Uracil Containing Templates

For example, in one aspect, a gene of interest is cloned into an *E. coli* plasmid containing the filamentous phage intergenic (IG, ori) region. Single stranded (ss) plasmid DNA is packaged into phage particles upon infection with a helper phage such as M13KO7 (Pharmacia) or R408 and is purified by methods such as phenol/chloroform extraction and ethanol precipitation. If this DNA is prepared in a dut⁻ ung⁻ strain of *E. coli*, a small number of uracil residues are incorporated into it in place of normal thymine residues. The ratio of the amount of uracil residues to the amount of thymidine residues used typically depends on the desired nucleic acid fragment size. The ratio is optionally calculated using appropriate software or instruction sets as described below. The instructions are typically programmed into a diversity generation device of the invention, e.g., in a computer readable format in a computer operably coupled to a diversity generation device or directly into a thermocycler used in a diversity generation device.

One or more primers as defined above are annealed to the ss uracil-containing template by heating to 90° C. and slowly cooling to room temperature. An appropriate buffer containing all 4 deoxyribonucleotides, T7 DNA polymerase and T4 DNA ligase is added to the annealed template/primer mix and incubated between room temperature –37° C. for ≧1 hour. The T7 DNA polymerase extends from the 3' end of the primer and synthesizes a complementary strand to the template incorporating the primer. DNA ligase seals the gap between the 3' end of the newly synthesized strand and the 5' end of the primer. If multiple primers are used, then the polymerase will extend to the next primer, stop (preferentially, polymerases that are arrested by downstream bound nucleic acids are used for this purpose) and ligase will seal the gap. As noted above, an exonuclease can be employed, e.g., prior to polymerase treatment.

The products of these reactions are then transformed into an ung⁺ strain of *E. coli* and antibiotic selection for the plasmid is applied. Uracil N-glycosylase (the ung gene product) enzyme in the host cell recognizes the uracil in the template strand and removes it, creating apyrimidinic sites that are either not replicated or which are corrected by the host repair systems using the newly synthesized strand as a template. The resulting plasmids predominantly contain the desired change in the gene if interest. If multiple primers are used then it is possible simultaneously to introduce numerous changes in a single reaction. If the primers are derived from fragments of homologous genes, then multiply chimeric genes can be generated.

Any of these diversity generating methods (shuffling, mutagenesis, etc.) can be combined with each other, in any combination selected by the user, to produce nucleic acid diversity, which may be screened for using any available screening method. The section below entitled "Diversity Generation Modules" provides further details regarding generation of diversity in the devices, modules and systems of the present invention.

A. Diversity Generation Modules

The automated production of diverse libraries can be used to increase the throughput of forced evolution methods. A variety of diversity production strategies can be used. Shuffling and other diversity generating modules of the invention provide a convenient way to generate diversity from starting nucleic acids. Diversity generation modules automate one or more relevant diversity generating process.

For example, the diversity generation module can take the form of a nucleic acid shuffling or mutagenesis module which can accept input nucleic acids or character strings corresponding to input nucleic acids and can manipulate the input nucleic acids or the character strings corresponding to input nucleic acids to produce output nucleic acids. In addition, the diversity generation modules of the invention are optionally used to select appropriate input nucleic acids or character strings corresponding to input nucleic acids which are typically shuffled to produce output nucleic acids. In any case, the output nucleic acids can comprise the one or more shuffled or mutagenized nucleic acids in the reaction mixture arrays of the invention, or fragments thereof. In addition to performing diversity-generation reactions, the diversity generation module optionally separates, identifies, purifies, immobilizes or otherwise treats diversified nucleic acids for further analysis.

Common formats for the diversity generation module can include computer systems for designing and selecting nucleic acids, oligonucleotide synthesizers, liquid handlers for moving and mixing reagents (e.g., microwell plates, automatic pipettors, peristaltic pumps, etc.). The nucleic acid shuffling module can include one or more microscale channel through which a shuffling reagent or product is flowed which can be integrated in a chip, or present in a series of microcapillaries.

For example, in addition to, in conjunction with, or in place of a standard automatic pipetting station and set of microwell plates, devices or integrated systems can include physical or logical arrays of reaction mixtures incorporated into the automatic pipetting station and set of microwell plates, or into a microscale device. Alternately, at least one of the reaction mixtures can be incorporated into a microscale device or a delivery system which interfaces with the automatic pipetting station and set of microwell plates. In one embodiment, the one or more shuffled or mutagenized nucleic acids (or a transcribed form thereof) can be found within a microscale device or the microwell plates, or the one or more in vitro transcription or translation reagents can be found within the plates or the microscale device. Any reagent associated with any operation of the module can be found within standard robotic systems, or in a microscale device, or in microwell plates, or on solid substrates or other storage systems as noted herein and any operation or set of operations for the module can be performed in a microscale or milliscale format. Thus, all or part of the module can be embodied in one or more automatic pipetting station, robotic fluid handling systems, in microcapillary systems (e.g., including integrated microchannel devices). or combinations thereof.

(1.) Selection and Acquisition of Targets for Diversity Generation Processes

The identification and acquisition of nucleic acid targets for diversity generation can be performed by the diversity generating modules of the invention. For example, selection algorithms can be used to identify sequences in public or proprietary databases which meet any user-selected criterion as a target for diversity generation. These user criteria include activity, encoded activity, homology, public availability, and any other criteria of interest. In addition, character strings corresponding to nucleic acids (or their derived polypeptides) can be generated according to any set of criteria selected by the user, including similarity to existing sequences, modification of an existing sequence according to any desired modification parameter (genetic algorithm, etc.), random or non-random (e.g., weighted) sequence generation, etc. Data structures comprising diverse sequences can be formed in a digital or analog computer or in a computer readable medium and the data structures converted from character strings to nucleic acids (e.g., via automated synthesis protocols) for subsequent physical manipulations. Alternatively, the character strings are manipulated or shuffled "in silico" to produce diverse nucleic acids, based upon any genetic algorithm or operator selected by the practitioner.

Either computer data or nucleic acids can be "data structures," a term which refers to the organization and optionally associated device for the storage of information, typically comprising multiple "pieces" of information. The data structure can be a simple recordation of the information (e.g., a list) or the data structure can contain additional information (e.g., annotations) regarding the information contained therein, can establish relationships between the various "members" (information "pieces") of the data structure, and can provide pointers or be linked to resources external to the data structure. The data structure can be intangible but is rendered tangible when stored/represented in tangible medium (e.g., in a computer medium, a nucleic acid or set of nucleic acids, or the like). The data structure can represent various information architectures including, but not limited to simple lists, linked lists, indexed lists, data tables, indexes, hash indices, flat file databases, relational databases, local databases, distributed databases, thin client databases, and/or the like.

Nucleic acids can be selected by the user based upon sequence similarity to one or more additional nucleic acid. Different types of similarity and considerations of various stringency and character string length can be detected and recognized in the target acquisition phase of the invention. For example, many homology determination methods have been designed for comparative analysis of sequences of biopolymers, for spell-checking in word processing, and for data retrieval from various databases. With an understanding of double-helix pair-wise complement interactions among the principal nucleobases in natural polynucleotides, models that simulate annealing of complementary homologous polynucleotide strings can also be used as a foundation of sequence alignment or other operations typically performed on the character strings corresponding to the sequences of interest (e.g., word-processing manipulations, construction of figures comprising sequence or subsequence character strings, output tables, etc.). An example of a dedicated software package with genetic algorithms for calculating sequence similarity and other operations of interest is BLAST, which can be used in the present invention to select target sequence (e.g., based upon homology) for acquisition and supply to the diversity generating modules of the invention.

BLAST is described in Altschul et al., *J. Mol. Biol.* 215: 403-410 (1990). Software for performing BLAST analyses is publicly available through the National Center for Biotechnology Information. This algorithm first identifies high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

As noted, the diversity generation module can comprise a DNA shuffling module. In one preferred embodiment, this module accepts input nucleic acids such as DNAs or character strings corresponding to input DNAs and manipulates the input DNAs or the character strings corresponding to input DNAs to produce output DNAs, which output DNAs comprise the one or more shuffled DNAs in the reaction mixture array. This can be performed by physical manipulation of nucleic acids as noted above, or character strings in computer systems, or both. For example, in addition to simply selecting nucleic acids of interest, computer systems can be used to produce character strings which correspond to nucleic acid targets for diversity generation. A variety of genetic algorithms for modifying character strings which correspond to biopolymers are set forth in detail in, e.g., "METHODS FOR MAKING CHARACTER STRINGS, POLYNUCLEOTIDES & POLYPEPTIDES HAVING DESIRED CHARACTERISTICS" by Selifonov et al., filed Feb. 5, 1999 (U.S. Ser. No. 60/118,854), U.S. Ser. No. 09/416,375 filed Oct. 12, 1999, Application No. PCT/US00/01202, filed Jan. 18, 2000, and, e.g., U.S. Ser. No. 09/618,579 filed Jul. 18, 2000. These genetic algorithms (GAs) include, e.g., modifying nucleic acid sequences to correspond to physical mutation events such as point mutation, nucleotide insertion, deletion, recombination and the like. Sequences can also be tested for fitness or any other parameter, including multidimensional parameters, by parameterizing any selection criteria and then selecting sequences which fall within the hyperspace defined by the set of parameters. Combinations of automated design (e.g., protein design automation, or "PDA"), e.g., to select crossover points for recombination based upon, e.g., physical (e.g., presence of encoded protein or other domains) or statistical (e.g., principal component analysis ("PCA"), Markov modeling, neural networks, etc.) criteria and random approaches (e.g., physical recombination of synthesized nucleic acids) can also be used. Further details on such approaches are found in the applications noted above.

For example, the present methods for selecting nucleic acids for shuffling are used to insure that the parental sequences chosen for diversity generation supply sufficient diversity yet can be recombined or shuffled in practice. Typically, sequences are chosen for recombination/shuffling based on percent homology, or based on phylogenetic relationships. Typically, a level of at least 50% sequence homology is required for efficient recombination between a pair of sequences. However, this general limit can be overcome by the introduction of additional (wild type, naturally occurring or synthetic) sequences which the 'bridge' the diversity within any given sequence pair. This module may act to enhance recombinational efficiency within a sequence population by further prescribing the synthesis or addition of a limited set of additional sequences not resident within the initial parental sequences. The likelihood that any two or more parents are compatible for recombination/shuffling is a consequence of the chance of recombination occurring during the process. Frequency of recombination is a direct consequence of the melting point of the hybrid molecule. Phylogenetic relationship and/or percent homology provide indirect measurements of the same thing. Therefore, the following method is optionally used to provide an improved selection of sequences for diversity generation. The method is an automated process by which parental sequences are found, scored and chosen for shuffling based on melting temperature. In addition, parental divergence is calculated and scored to enable an experimenter to make an informed decision upon choosing parental nucleic acids for shuffling.

In one embodiment, a set of nucleic acid sequences or character strings corresponding to nucleic acid sequences is selected using a computer or set of instructions embodied in a computer readable medium, e.g., on a web page. Such a method typically comprises performing an alignment, e.g., a pairwise alignment, between two or more potential parental nucleic acid sequences, e.g., using clustalw or one or more of the programs described herein. Potential parental nucleic acid sequences are also optionally selected using a computer, e.g., by searching one or more database for one or more nucleic acid sequence of interest and one or more homolog of the one or more nucleic acid sequence of interest.

The number of mismatches between the alignment is then calculated. Melting temperatures for one or more window of w bases in the alignment are also calculated, identifying those windows having a melting temperature greater than x. Melting temperatures are optionally calculated from one or more set of empirical data or one or more melting temperature prediction algorithm. A window of w bases typically comprises, e.g., about 21 bases. Preferably, w is an odd number and the melting temperature cutoff, x, is typically about 65° C.

Figure 33:
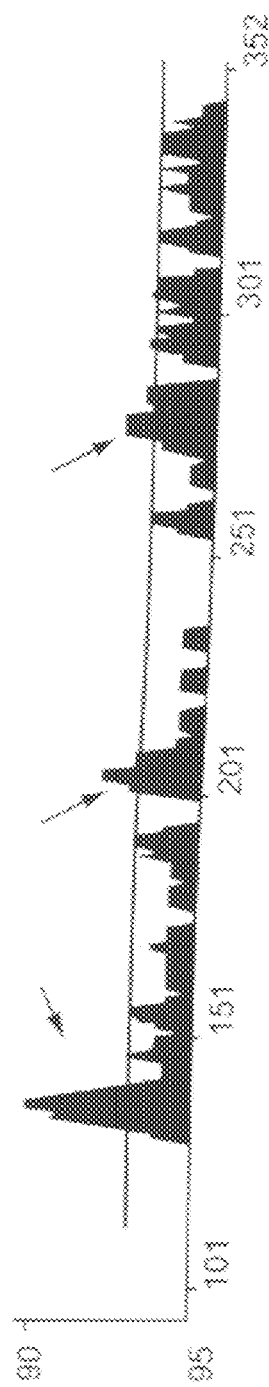
FIG. 33 is an illustration of the melting temperature for a nucleic acid pairwise hybridization showing various crossover segments.

One or more crossover segment in the alignment is then identified. A crossover segment is one comprising two or more windows having a melting temperature greater than x, which two or more windows are separated by no more than n nucleotides, with n typically about 2. FIG. 33 illustrates the melting temperature for a pairwise hybridization. In this example, the line indicates the melting temperature cutoff point and the arrows indicate various crossover segments.

The dispersion, e.g., the inverse of the average number of bases between crossover segments in the alignment, for the crossover segments identified is then typically calculated. The above calculations are then combined to provide two scores, e.g., a shuffleability score and a diversity capture score, for each alignment pair.

The shuffleability score is based on the number of windows having a melting temperature greater that x, the dispersion, and the number of crossover segments identified. For example, the number of windows, the dispersion, and the number of segments are multiplied together. This score reflects how well the aligned sequences would cross over during a shuffling reaction, e.g., in silico shuffling or shuffling in another diversity generation device of the invention, and how much of the sequences are likely to be shuffled.

The diversity capture score is based on the number of mismatches in the alignment, the number of windows having a melting temperature greater that x, the dispersion, and the number of crossover segments identified. The score is representative not only of how well the sequences would recombine, but also of how well recombining these sequences together would create diversity.

The sequences are then ranked according to one or both of the above scores and sequences for shuffling are selected based on the ranks. To further evaluate the sequences for shuffleability, the above steps are optionally repeated, e.g., starting with the one or more parental nucleic acid selected in the first cycle. Alternatively, the steps are repeated starting with the same or different potential parental nucleic acid sequences using one or more different input parameters, e.g., for calculating the melting temperature.

The above methods are optionally used, e.g., with varying potential parental sequences and melting temperature parameters, e.g., to optimize the diversity capture score while minimizing the amount of parental sequences needed for shuffling. In addition, the algorithm is optionally used with certain restrictions, e.g., that a particularly desirable parent or parents must be included in the final set of parents. For example, the method could be set up to walk between two parental sequences of interest. "Walking" refers to the process by which recombinations are obtained between two low homology parental sequences via intermediate sequences, i.e., A recombines with B, which recombines with C, which recombines with D, wherein A and D do not directly recombine.

Other parameters are also optionally optimized in the selection of parents or to modify the scoring. Such parameters include, but are not limited to, the activity of the various parents, freedom to operate clearance, e.g., by an automatic search through a patent or literature database, the feasibility of obtaining the parents, the expression levels of the parents, and the compatibility of the parents coding sequences with the codon bias of one or more organisms.

For example, the above method is optionally used as described below, e.g., in an automated computerized format. A researcher submits a small molecule substrate or product, e.g., to a computer program, e.g., embodied in a diversity generation device or on a web page. A chemical structure comparison search is performed on the small molecule, e.g., using ISIS or another such database. Such comparison is optionally performed manually or using a computer. The small molecule and related structures or homologs are used to search one or more databases, e.g., KEGG, WIT, or the like, for genes that are related to or have an activity on one or more of the compounds of interest. The genes are used to find homologs for shuffling, e.g., by searching databases, such as BLAST, HMMR, fasta, Smith Waterman, and the like. The gene sequences found are reverse translated, e.g., to optimize shuffleability, optimize codon usage for a given host, and/or maximize the difference from a parent that is prohibited by a lack freedom to operate. In some embodiments, it is desirable to have as few genes as possible for shuffling. Therefore, the genes are optionally weighted based on activity, species, environment, or diversity. A final set of parental sequences is determined based on the scores obtained as described above and the various weights given to each sequence. Oligonucleotides or character strings that correspond to oligonucleotides for gene synthesis based on the selected parental nucleic acids are then created, e.g., for synthetic shuffling or in silico shuffling.

Nucleic acids which hybridize to one another are often provided to the system as starting nucleic acids for recombination-based diversity generation procedures. Further, nucleic acid hybridization can be estimated and used as a basis for selection in a computer system, in a manner similar to selecting for sequence similarity as set forth above (similar sequences typically hybridize). Nucleic acids "hybridize" when they associate, typically in solution. Nucleic acids hybridize due to a variety of well characterized physicochemical forces, such as hydrogen bonding, solvent exclusion, base stacking and the like and, thus, these interactions can be modeled. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. For purposes of the present invention, generally, "highly stringent" hybridization and wash conditions are selected to be about 5° C. lower than the thermal melting point ($T_m$) for the specific sequence at a defined ionic strength and pH. The $T_m$, is the temperature (under defined ionic strength and pH) at which 50% of the test sequence hybridizes to a perfectly matched probe. Very stringent conditions are selected to be equal to the $T_m$, for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization. Comparative hybridization can be used to identify nucleic acids as inputs to the systems of the invention.

Providing nucleic acids which are identified or generated as noted above optionally takes one of two basic forms.

First, where a nucleic acid is selected which corresponds to a physically existent nucleic acid, that nucleic acid can be acquired by cloning, PCR amplification or other nucleic acid isolation methods as is common in the art. An introduction to such methods is found in available standard texts, including Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). Examples of techniques sufficient to direct persons of skill through in vitro amplification methods, useful in identifying, isolating and cloning nucleic acid diversity targets, including the polymerase chain reaction (PCR) the ligase chain reaction (LCR), Qβ-replicase amplification and other RNA polymerase mediated techniques (e.g., NASBA), are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Host cells can be transduced with nucleic acids of interest, e.g., cloned into vectors, for production of nucleic acids and expression of encoded molecules (these encoded molecules can be used, e.g., as controls to determine a baseline activity to compare encoded activities of a diverse library of nucleic acids to). In addition to Berger, Sambrook and Ausubel, a variety of references, including, e.g., Freshney (1994) *Culture of Animal Cells, a Manual of Basic Technique, third edition*, Wiley-Liss, New York and the references cited therein, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla. provide additional details on cell culture, cloning and expression of nucleic acids in cells.

Sources for physically existent nucleic acids include nucleic acid libraries, cell and tissue repositories, the NIH, USDA and other governmental agencies, the ATCC, zoos, nature and many others familiar to one of skill. For example, a wide variety of samples can be obtained from nature which are suitable for use in the present invention. These include, but are not limited to, environmental isolates from remote, unusual, contaminated or common soils, clays, aquifers and marine localities; high and low moisture environments; living, dead, decayed or partially decayed tissues of plants or animals; environmental isolates containing a plurality of microorganisms; extracts from the gut flora of vertebrates and invertebrates, including symbiotic and endosymbiotic microorganisms. While these diverse sources provide many nucleic acids, there are many others which exist only as a result of computer algorithms as described above, or, even though existent, are difficult to acquire from nature (but often straightforward to synthesize, given an appropriate sequence).

The second basic method for acquiring nucleic acids does not rely on the physical pre-existence of a nucleic acid. Instead, nucleic acids are generated synthetically, e.g., using well-established nucleic acid synthesis methods. For example, nucleic acids can be synthesized using commercially available nucleic acid synthesis machines which utilize standard solid-phase methods. Typically, fragments of up to about 100 bases are individually synthesized, then joined (e.g., by enzymatic or chemical ligation methods, or polymerase mediated recombination methods) to form essentially any desired continuous sequence or sequence population. For example, the polynucleotides and oligonucleotides of the invention can be prepared by chemical synthesis using, e.g., the classical phosphoramidite method described by Beaucage et al., (1981) *Tetrahedron Letters* 22:1859-69, or the method described by Matthes et al., (1984) *EMBO J.* 3: 801-05., e.g., as is typically practiced in automated synthetic methods. According to the phosphoramidite method, oligonucleotides are synthesized, e.g., in an automatic DNA synthesizer, assembled and, optionally, cloned in appropriate vectors. In addition, essentially any nucleic acid can be custom ordered from any of a variety of commercial sources, such as The Midland Certified Reagent Company (mcrc@oligos.com), The Great American Gene Company, ExpressGen Inc., Operon Technologies Inc. (Alameda, Calif.) and many others. Similarly, peptides and antibodies (useful in various embodiments noted below) can be custom ordered from any of a variety of sources, such as PeptidoGenic (pkim@ccnet.com), HTI Bio-products, inc., BMA Biomedicals Ltd (U.K.), Bio. Synthesis, Inc., Research Genetics (Huntsville, Ala.) and many others.

Synthetic approaches to nucleic acid generation have the advantage of easy automation. Oligonucleotide synthesis machines can easily be interfaced with a digital system that instructs which nucleic acids to be synthesized (indeed, such digital interfaces are generally part of standard oligonucleotide synthesis devices). Similarly, ordering nucleic acids from commercial sources can be automated through simple computer programming and use of the internet (e.g., by having the user select nucleic acids which are desired and providing an automated ordering system), with provisions for user inputs (nucleic acid selection) and outputs (synthesis of nucleic acids which are ordered).

Synthetic approaches can also be used to automate simultaneous sequence acquisition and diversity generation, i.e., through "oligonucleotide shuffling" and related technologies (see also, "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392) and USSN PCT/US00/01203 filed Jan. 18, 2000; and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); and "METHODS FOR MAKING CHARACTER STRINGS, POLYNUCLEOTIDES & POLYPEPTIDES HAVING DESIRED CHARACTERISTICS" by Selifonov et al. filed Feb. 5, 1999 (U.S. Ser. No. 60/118,854), U.S. Ser. No. 09/416, 375 filed Oct. 12, 1999, Application No. PCT/US00/01202, filed Jan. 18, 2000, and, e.g., U.S. Ser. No. 09/618,579 filed Jul. 18, 2000). In these methods, nucleic acid oligonucleotides corresponding to multiple parental nucleic acids are synthesized, mixed and assembled via polymerase (e.g., PCR) or ligase (or both) mediated methods to produce recombinant nucleic acids which have subsequences corresponding to multiple parental nucleic acid types.

(2.) Sources and Destinations for Nucleic Acids in the Module

The assays of the invention are optionally partially or completely performed in a flowing format. That is, nucleic acids or other relevant reaction reagents are optionally flowed from sources (wells, channels, oligonucleotide synthesis elements, etc.) to destinations (reaction wells, channels, arrays, etc.), with reactions optionally being controlled by flowing reactants into contact in the system.

Thus, the nucleic acids which are selected and/or acquired optionally include one or more sources of one or more nucleic acids which both collectively or individually comprise a first population of nucleic acids. The diversified nucleic acids are produced by recombining or otherwise mutating one or more members of the first population of nucleic acids. This source of nucleic acids can be an in vitro, in vivo or virtual (in a digital system, i.e., "in silico") source.

Sources of nucleic acids can include at least one nucleic acid, including, e.g., any of: a synthetic nucleic acid, a DNA, an RNA, a DNA analogue, an RNA analogue, a genomic DNA, a cDNA, an mRNA, an nRNA, an aptamer, a cloned nucleic acid, a cloned DNA, a cloned RNA, a plasmid DNA, a viral DNA, a viral RNA, a YAC DNA, a cosmid DNA, a BAC DNA, a P1-mid, a phage DNA, a single-stranded DNA, a double-stranded DNA, a branched DNA, a catalytic nucleic acid, an antisense nucleic acid, an in vitro amplified nucleic acid, a PCR amplified nucleic acid, an LCR amplified nucleic acid, a Qβ-replicase amplified nucleic acid, an oligonucleotide, a nucleic acid fragment, a restriction fragment or any combination thereof; or other nucleic acid forms which are available. Alternately, the sources can be virtual or virtual and synthetic, and can include one or more character string corresponding to such sources. In addition to virtual sources, data structures (which can be physical or virtual) can be sources of nucleic acids (e.g., by combining character strings with synthetic methods), including diversified nucleic acids.

In addition to a source of nucleic acid, the module can include a population destination region. During operation of the device, one or more members of the first population are optionally moved from one or more sources of the one or more nucleic acids to the one or more destination regions.

In general, the devices and systems can include nucleic acid movement means for moving the one or more members from the one or more sources of the one or more nucleic acids to the one or more destination regions (a variety of fluidic and non-fluidic means of moving components are described herein).

Sources, destinations and source and destination regions can be physically embodied in many different ways. For example, they can be microtiter wells or dishes, fritted microtiter trays (e.g., for coupling to column chromatographic methods) microfluidic systems, microchannels, containers, data structures, computer systems, combinations thereof; or the like. Examples of sources/destinations include solid phase arrays, liquid phase arrays, containers, microtiter trays, microtiter tray wells, microfluidic components, microfluidic chips, test tubes, centrifugal rotors, microscope slides, an organism, a cell, a tissue, and combinations thereof.

As is noted in more detail herein, the systems of the invention also can similarly include sources of in vitro transcription or translation reagents, where, during operation of the device, the in vitro transcription reagent or an in vitro translation reagent is flowed from a source into contact with nucleic acids to be transcribed/translated. Sources and destinations for other reactants as noted herein are also optionally provided.

Any of the operations to be performed on individual array members can be performed sequentially or in parallel. As noted throughout, certain physical array formats such as microtiter tray-based approaches are well suited to parallel operations (i.e., having the same or similar operations performed by approximately simultaneous additions of relevant reagents to the array, or approximately simultaneous removal of materials from the array (e.g., for re-plating (e.g., for array duplication), purification of materials, and/or other downstream operations. As discussed herein, conventional high-throughput robotics provide one convenient way of performing these operations, which may, of course, also be provided by manual manipulations, microfluidic approaches, or other available methods. In some array formats, sequential operations are more conveniently performed, e.g., where the array is a logical array with members which are not located in formats that provide for parallel manipulations.

In either case, robotic or other manipulations can be performed uniformly to the array, or can be selectively performed to individual array members. These manipulations, and the actual motions used to achieve selective or parallel manipulations can be controlled by appropriate controller devices, e.g., computers linked to robotic elements with software comprising instruction sets for regulating the robotic or other material manipulative elements. The software is optionally user programmable, i.e., to provide for parallel or selective operations, e.g., to select "hits" for further manipulations.

Generally, as noted herein, master arrays or data sets (or both) can be maintained that preserve information regarding the spatial location of array elements in the system. Generally, duplicate arrays are acted upon by system elements (e.g., reagents are added to or material removed from one or more duplicate array members), rather than the preserved master array members or data set elements.

In addition to flowable formats, nucleic acids, transcription reagents, translation reagents or other relevant reactants are optionally fixed at one or more sources or at one or more destination regions. In these "fixed" or "partially flowing" formats, reagents can be localized to one or more locations and cognate reagents either fixed in proximity, or flowed (e.g., via pipetting) or otherwise delivered (e.g., via aerosolization, lyophilization, etc.) into contact with reagents of interest.

Movement means for moving nucleic acids and other reagents include fluid pressure modulators (e.g., pipettors or other pressure-driven channel systems), electrokinetic fluid force modulators, electroosmotic flow modulators, electrophoretic flow modulators, centrifugal force modulators, robotic armatures, pipettors, conveyor mechanisms, stepper motors, robotic plate manipulators, peristaltic pumps, magnetic field generators, electric field generators, fluid flow paths and the like.

For example, the diversity generating module can include one or more recombination modules which move one or more members of a population of nucleic acids into contact with one another, thereby facilitating recombination of the first population of nucleic acids. Similarly, the diversity generation module can include one or more reaction mixture arraying modules, which move one or more of the one or more diverse (e.g., shuffled) nucleic acids into one or more spatial positions. The system can also provide for moving in vitro transcription/translation reactant components into desired locations in the array of reaction mixtures.

(3.) Dilution/Concentration Module

Shuffling/recombination/diversification module(s), or other modules herein, optionally include a dilution or concentration function. In particular, it is often desirable to normalize the level of reactant or product at an array position (e.g., in a duplicate diluted or concentrated array) so that product activities can be directly compared across an array. This typically involves determining the concentration of products (proteins, nucleic acids, etc.) or reactants (nucleic acids, transcription buffers, translation buffers, etc.) at sites in the array and diluting or concentrating the products or reactants appropriately. The dilution/concentration module or module function can form new diluted arrays or can dilute reactants or products at array sites. For example, the dilution/concentration module can re-array amplified physical or logical array of polypeptides or in vitro transcribed nucleic acids in a secondary polypeptide or in vitro transcribed nucleic acid array which has an approximately uniform concentration of polypeptides or in vitro transcribed nucleic acids at a plurality of locations in the secondary polypeptide array.

To be able easily to recover nucleic acids which encode products of interest, it is generally desirable to limit the number of different nucleic acids at defined sites in an array. For example, when arranged in a microtiter tray or other physical array, e.g., for subsequent amplification or processing it is useful to dilute or concentrate array members to an average of approximately 0.1-100 nucleic acids (e.g., unique nucleic acids) per well or other storage site. This is particularly relevant at the start of the arraying process following initial extraction, mutagenesis or cloning of member nucleic acids. Typically, nucleic acids are arranged at about 1-10, and often at an average of approximately 1-10 or 1-5 nucleic acids per well prior to amplification. Subsequent amplification in preparation for array duplication can increase this by, e.g., about 2-about 100 fold or more. In contrast, subsequent amplification for purposes of conducting transcription, translation and/or screening can increase the concentration of member nucleic acids by, e.g., about >100-fold or more.

The diluter can operate prior to or after diversity generation or between any reaction steps. For example, one embodiment includes a diluter which pre-dilutes one or more shuffled or otherwise diversified nucleic acids (e.g., by diluting members of a population with a buffer prior to arraying the members, e.g., in the reaction mixture arrays herein). In other aspects, the diluter dilutes nucleic acids as part of producing copy arrays from amplified arrays of nucleic acids.

Typical concentration ranges for diluted nucleic acids are in the range of about 0.01 to 100 molecules per microliter (although, in certain embodiments where lipid vesicles are used as reaction vessels, this concentration can be somewhat different, as described supra).

Typical dilution/concentration operations are performed by any available method, including the addition of buffers (e.g., by pipetting), lyophilization, osmosis, precipitation, chromatography and the like.

In one example, DNA is diluted and aliquoted into wells such that the concentration approaches a statistical approximation of the desired concentration. The DNA is fluorescently labeled, during or after diversity generation, followed by FACS or other fluorescence-based cell sorting. The sorting and isolation of individual DNA fragments is optionally coupled to a dispensing device such as a fraction collector such that a collection array (e.g., microtiter tray) receives about 1 molecule/well. The DNA is affinity tagged such that, e.g., one affinity tag exists per molecule. Subsequent binding to an assay vehicle allows a single dsDNA molecule to bind each compartment in the assay.

DNA tagging formats include, e.g., 5' termini DNA/RNA labeling by aminotag phosphoramidites, such as those described in Olejnik et al. (1998) "Photocleavable Aminotag Phorphoramidites for 5' termini DNA/RNA labeling" *Nucleic Acids Res.* 26(15):3572-3576, in which a photocleavable amine can be introduced on the 5' terminal phosphate and conjugated with a variety of amine-reactive markers such as biotin, digoxigenin or tetramethylrhodamine. The assay vehicles for compartmentalization of affinity tagged dsDNA can bind the DNA to a derivatized microtiter plate directly or to, e.g., beads which are subsequently dispensed at a rate of, e.g., one bead per well. The bound DNA can be used to isolate hybridizing fragments or other hybridizing shuffled variants.

More than one DNA fragment can be dispensed into separate wells, with the diversity generation and assaying steps being run as small pools of samples of interest. In some cases, this partially pooled approach is preferred, e.g., for assaying larger libraries of diversified nucleic acids, or where the cost of reagents (e.g., transcription/translation reagents) is limiting. However, there are some drawbacks to this approach, such as a dilution of average activity in the wells, inhibition of individual pool members by other members in the wells, etc.

(4.) Processing of Acquired Nucleic Acids to Increase Diversity—Fragmentation Based Methods As noted, the nucleic acid diversity generation (e.g., shuffling) module can permit hybridization of the nucleic acid fragments followed by elongation with a polymerase which elongates the hybridized nucleic acid. Several (though not all) diversity generation methods rely initially on the production of fragmented DNA. In general, one or more shuffled nucleic acid(s) can be produced by synthesizing a set of overlapping oligonucleotides, or by cleaving a plurality of homologous nucleic acids to produce a set of cleaved homologous nucleic acids, or both, and permitting recombination to occur between the set of overlapping oligonucleotides, the set of cleaved homologous nucleic acids, or a combined set of overlapping oligonucleotides and set of cleaved homologous nucleic acids. Fragmented DNA is recombined, e.g., taking advantage of hybridization and PCR or LCR gene reconstruction methods described in the references above to produce full-length, diversified recombinant nucleic acid libraries. These libraries are optionally screened for the expression of products of interest. Thus, the diversity module optionally fragments input nucleic acids to produce nucleic acid fragments, or the input nucleic acids can themselves include cleaved or synthetic nucleic acid fragments.

A number of automated approaches can be used to produce "fragmented" nucleic acids. Fragmented nucleic acids can be provided by mechanically shearing nucleic acids, by enzymatically or chemically cleaving nucleic acids, by partially synthesizing nucleic acids, by random primer extending or directed primer extending double-stranded or single-stranded nucleic acid templates, by incorporating cleavable elements into the nucleic acids during synthesis, or the like. Templates or starting materials for such procedures include naturally occurring nucleic acids, synthetic nucleic acids, DNA in any form, RNA in any form, DNA analogues, RNA analogues, genomic DNAs, cDNAs, mRNAs, nRNAs, cloned nucleic acids, cloned DNAs, cloned RNAs, plasmid DNAs, viral DNAs, viral RNAs, YAC DNAs, cosmid DNAs, branched DNAs, DNA and/or RNA isolated from heterogeneous microbial populations, catalytic nucleic acids, antisense nucleic acids, in vitro amplified nucleic acids, PCR amplified nucleic acids, LCR amplified nucleic acids, SDA nucleic acids, Qꓱ-replicase amplified nucleic acids, nucleic acid sequence-based amplified (NASBA) nucleic acids, transcription-mediated amplified (TMA) nucleic acids, oligonucleotides, nucleic acid fragments, restriction fragments, combinations thereof and any other available material. Nucleic acids can be partially or substantially purified prior to fragmentation, or can be unpurified.

For example, nucleic acids can be fragmented enzymatically, e.g., DNA can be fragmented using a nuclease such as a DNAse. In the context of the present invention, a fragmentation module can include containers such as microtiter plates or microfluidic chips into which parental nucleic acids (e.g., homologous DNAs) are dispensed, mixed and fragmented by the addition of DNAse. In addition, the fragmentation module is optionally operably coupled to a programmed thermocycler and/or computer for directing fragmentation. For example, a computer is used to calculate conditions for fragmentation that produce desired length fragments. For example, when uracil incorporation and cleavage is used to produce nucleic acid fragments, a computer optionally calculates the amount of uracil residues to be used in relation to thymidine residues, e.g., based on user input comprising the desired fragment length. The reaction is allowed to proceed for a selected period of time, or in parallel reactions having different time periods, to produce one or multiple sets of nucleic acid fragments. The addition of DNAse or other cleavage enzymes can occur before or after dispensing the parental nucleic acids into one or more systems which facilitate downstream processing (e.g., prior to dispensing into microwell plates, microchips, or the like). The nucleic acid fragments can be contacted to one another in a single pool, or in multiple pools.

Alternately, or in combination, nucleic acids are mechanically sheared, e.g., by vortexing, sonicating, point-sink shearing or other similar operations, before or after addition to the one or more systems which facilitate downstream processing. Mechanical shearing of nucleic acids has the advantage of being largely sequence independent, which, at times, is desirable, e.g. where no bias is desired in the sheared nucleic acid fragments. For example, the point-sink shearing method is described in Thorstenson et al., (1998) "An Automated Hydrodynamic Process for Controlled, Unbiased DNA shearing," *Genome Research* 8:848-855. Basically, this method consists of forcing a solution of DNA into a narrowed region of a channel, putting sufficient force on the DNA to break it up. Although this method typically generated relatively large DNA fragments (500-1000 bp), the size of fragments can be reduced by increasing the velocity of the solution, decreasing the size of the channel, vibrating the channel, e.g., at the channel entrance (e.g., using a circular piezo-electric device), or the like.

In a second alternate embodiment, nucleic acids are "fragmented" by synthesis of fragments (rather than cleavage) which correspond in sequence to subsequences of one or more parental nucleic acids. For example, synthetic oligonucleotide "fragments" can be made in an automatic synthesizer which correspond to any sequence of interest. This method has the advantage of easy combination with in silico approaches (e.g., in silico recombination of character strings can be performed, followed by synthesis of the oligonucleotides which correspond to any desired character string). Indeed, the oligonucleotides which are generated can provide any desired diversity in products which are formed using the oligonucleotides—thus, sequence acquisition and at least a first round of diversity generation can be performed simultaneously. Further details regarding Oligonucleotide synthetic approaches and "in silico" shuffling approaches are found in OLIGONUCLEOTIDE MEDIATED NUCLEIC ACID RECOMBINATION" by Crameri et al., supra., and "USE OF CODON-BASED OLIGONUCLEOTIDE SYNTHESIS FOR SYNTHETIC SHUFFLING" by Welch et al., supra., and "METHODS FOR MAKING CHARACTER STRINGS, POLYNUCLEOTIDES & POLYPEPTIDES HAVING DESIRED CHARACTERISTICS" by Selifonov et al., supra., and further details on these methods are also found, supra.

In a third and also preferred embodiment, DNA fragmentation is achieved via incorporation of cleavage targets into nucleic acids of interest. In this embodiment, modified nucleotides or other structures are incorporated into nucleic acids during synthesis (whether chemical, enzymatic, or both) of the nucleic acids. These modified nucleotides or other structures become cleavage points within a nucleic acid into which they are incorporated. One example of this approach is described, e.g., in PCT US96/19256. As noted in the '256 application, nucleic acid synthesis can be conducted to produce nucleic acids of interest (e.g., via PCR, e.g., using a computer or computer program to calculate the uracil/thymidine ratio necessary to produce nucleic acid fragments of a desired size or synthetic methods), incorporating uracil into the nucleotides in a stochastic or directed fashion. The PCR products are then fragmented by digestion with UDG-glycosylase, which forms strand breaks at the uracil residues. Further details on this procedure are found below.

Similarly, RNA nucleotides can be incorporated into DNA chains (synthetically or via enzymatic incorporation); these nucleotides then serve as targets for cleavage via RNA endonucleases. A variety of other cleavable residues are known, including certain residues which are specific or non-specific targets for enzymes, or other residues which serve as cleavage points in response to light, heat or the like. Where polymerases are currently not available with activity permitting incorporation of a desired cleavage target, such polymerases can be produced using shuffling methods to modify the activity of existing polymerases, or to acquire new polymerase activities.

Simple chain termination methods can also be used to produce nucleic acid fragments, e.g., by incorporating dideoxy nucleotides into the reaction mixture(s) of interest.

In any case, once fragmentation is performed to the extent desired, the reaction is transferred to a recombination/resynthesis module. This module optionally dispenses resulting elongated nucleic acids into one or more multiwell plates, or onto one or more solid substrates, or into one or more microscale systems, or into one or more containers for further operations by the system.

In one embodiment, diversity generation module(s) (or any other module herein) can include a fragment length purification portion which purifies selected length fragments of the nucleic acid fragments. Fragment purification can be performed by electrophoresis (e.g., gel electrophoresis), column chromatography, incorporation of a label, incorporation of a purification tag, or any other currently available method.

As noted above, the diversity module also optionally dilutes or concentrates nucleic acids (e.g., produced by elongation of fragment populations) and dispenses them. For example, elongated nucleic acids produced after PCR or ligase-mediated gene reconstruction can be dispensed into one or more multiwell plates or other array configurations at a selected density per well (or chamber, channel, container, etc., depending on the configuration) of the elongated nucleic acids. This dilution/concentration function is useful in normalizing assay results. That is, having array members at similar (or otherwise defined) concentrations permits analysis of results (e.g., concentration or activity levels of products). Similarly, where product concentrations are different, it is useful to dilute or concentrate products to similar or at least defined concentrations to facilitate result interpretation.

In one embodiment, the device or integrated system includes a nucleic acid fragmentation module and a recombination region. The fragmentation module includes, e.g., a nuclease, a mechanical shearing device, a polymerase, a random primer, a directed primer, a nucleic acid cleavage reagent, a chemical nucleic acid chain terminator, an oligonucleotide synthesizer, or other element for producing fragmented nucleic acids as described above. During operation of the device, fragmented DNAs or other nucleic acids produced in the fragmentation module, are recombined in the recombination region (a well, channel, chamber or other container or substrate or surface) to produce one or more shuffled nucleic acids.

As noted, fragments (or full-length nucleic acids in other modules herein) are often purified prior for further operations by the system. This purification incorporate any of the purification methods common to DNA or RNA purification, including electrophoresis (in gels, capillary channels, etc.), chromatography or the like.

An Improved StEP

The effectiveness of DNA shuffling by staggered extension process (StEP) depends in certain formats in part on the rapidity of thermocycling between denaturation and extension steps. Very rapid thermocycling can be used to limit extension. The more limited the extension, the smaller the resulting fragments and the finer the "granularity" of the resulting recombination. Controlled incorporation of uracil into parental templates with uracil glycosylase to generate AP sites are used to provide an alternate method of controlling fragment size. The granularity of recombination is controlled, e.g., by the frequency of apurinic sites in parental templates, as these sites serve as replication terminators in the StEP reaction. A further improvement uses a thermostable uracil glycosylase and dUTP in the StEP reaction to add replication terminators to newly synthesized DNA fragments, assuring recombination throughout the StEP reaction.

Fragmentation Example: Ung-End Fragmentation:
Use in Single-Tube DNA Shuffling Reactions This example describes single-tube DNA shuffling according to the present invention including simplification of DNase enzymatic fragmentation, size fractionation and purification of DNA by agarose gel electrophoresis or other procedures. An alternative to laborious and hard-to-control standard fragmentation protocols includes the use of controlled uracil incorporation into starting DNA, e.g., via PCR with dUTP, followed by fragmentation of the uracil-containing DNA with two enzymes: Uracil N-Glycosylase (Ung) which hydrolyzes the n-glycosidic bond between the deoxyribose sugar and uracil to generate apurinic (or AP) sites, followed by the use of a 5' AP endonuclease, such as Endonuclease IV (End) which cleaves a single strand of DNA 5' to AP sites, leaving a 3'-hydroxy-nucleotide and 5'-deoxyribose phosphate termini. See also, Freidberg et al. (1995) *DNA Repair and Mutagenesis*. pp. 1-698. ASM Press. Washington, D.C.

A fundamental advantage of Ung-End fragmentation over DNAse I treatment, is that fragmentation is simply a function of uracil content (which is easily controlled in PCR), rather than time of reaction and size of DNA (which is difficult to control). Size fractionation and purification may be obviated by the use of Ung-End fragmentation, since the reaction goes to completion, with the average fragment size being a function of uracil content only. Note that, as with conventional DNase fragmentation and size fractionation, Ung-End fragmentation is used for shuffling a single DNA sequence or family of related DNA sequences. The use of Ung-End fragmentation along with PCR assembly provides for single-tube DNA shuffling, which can be carried out, e.g., in microtiter plates.

Important considerations in the design of a single-tube shuffling reaction include methods for minimizing carry-over of the plasmid template DNA used to generate uracil-containing DNA for shuffling. A simple solution is to incorporate uracil into the plasmid template via growth in a dut-1 ung-1 double mutant of *Escherichia coli*, such as strain CJ236 (Warner et al. (1981) "Synthesis and metabolism of uracil-containing deoxyribonucleic acid in *Escherichia coli*" *J. Bacteriol.* 145(2):687-695; Kunkel et al. (1987) "Rapid and efficient site-specific mutagenesis without phenotypic selection" *Methods Enzymol.* 15:367-382) or by PCR. Likewise, incorporation of uracil into primers for generating uracil-containing DNA minimizes carry-over of primers into the assembly reaction. Reduction in transformation efficiency of shuffled product using Ung-End fragmentation can result due to residual uracil. Where this is problematic, transformation of shuffled products into an ung mutant of *E. coli* assists in cloning processes.

Growth of plasmid in a dut-1 ung-1 *E. coli* mutant (e.g. strain CJ236) for uracil incorporation followed by Ung-End fragmentation and PCR assembly provides a quick, single-tube method of shuffling a whole plasmid or family of plasmids. Growth of plasmids in an *E. coli* dut ung strain bearing a strong mutator allele (e.g. dut ung mutD5) or combination of mutator alleles for in vivo mutagenesis, as well as, uracil incorporation into plasmid DNA coupled with Und-End fragmentation and PCR assembly is a powerful and simple means of rapidly evolving the function of a plasmid. Uracil content of plasmid DNA (and consequently average fragment size following Ung-End fragmentation) following growth in a dot ung strain is modulated by the addition of exogenous uridine or thymidine. In addition, uracil content is effected using strains bearing alternative dut and/or ung alleles, such as the leaky dut-4 allele for less frequent uracil incorporation (Hays et al. (1981) "Recombination of uracil-containing Lambda bacteriophages" *J. Bacteriol.* 145(1):306-320) or be using other alleles which effect cellular dUTP levels or uracil incorporation or removal from DNA. Also, plasmid multimerization generated by Und-End fragmentation and PCR assembly of uracil-containing plasmid can be directly transformed into naturally competent bacteria, such as *Bacillus subtilus* 168 derivatives, which are more efficiently transformed by plasmid multimers.

Note that uracil glycosylases and 5' AP endonucleases are ubiquitous. They have been characterized in both eukaryotic and prokaryotic cells, as well as viruses (Freidberg et al. (1995) *DNA Repair and Mutagenesis*. pp. 1-698. ASM Press. Washington, D.C.). Many of these can be used for Ung-End fragmentation.

In addition to cleaving 5' to AP sites, AP nucleases (such as Exonuclease III, Endonuclease IV, and Endonuclease V) recognize and cleave DNA at sites damaged by oxidizing agents or alkylating agents. Endonculease V additionally cleaves DNA at A/C and A/A mismatches and at deoxyinosine. Thus, the use of controlled dITP incorporation (e.g., during oligonucleotide synthesis used in construction of the nucleic acid of interest) and Endonuclease V treatment enables a single enzyme method for DNA fragmentation. Reagents and bacterial strains for Ung-End fragmentation can easily be incorporated along with PCR reagents into a simple DNA shuffling kit.

Amplifications with Decreasing Uracil Concentrations:

The following protocol provides an illustrative example of performing amplifications at multiple Uracil concentrations. In an automated process, e.g., in an integrated diversity generation device, appropriate uracil concentrations are optionally calculated, e.g., based on empirical data, to produce a desired fragment length and optimize diversity generation. For example a programmed thermocycler is optionally used to create appropriate nucleic acids for shuffling, e.g., having a desired amount of uracil incorporation. The programmed thermocycler can be operably coupled to a fragmentation device that produces fragments of a desired length from the uracil containing nucleic acids. The fragments are then used to generate diverse nucleic acids.

First, 50 μl 10 mM dUTP Stock Mixtures are prepared for a dUTP titration.

100 mM dNTPs stocks are prepared as follows:

|  | 10 mM dUTP | 8 mM dUTP | 6 mM dUTP | 4 mM dUTP | 2 mM dUTP | 0 mM dUTP |
|---|---|---|---|---|---|---|
| 100 mM dGTP | 5 | 5 | 5 | 5 | 5 | 5 |
| 100 mM dCTP | 5 | 5 | 5 | 5 | 5 | 5 |
| 100 mM dATP | 5 | 5 | 5 | 5 | 5 | 5 |
| 100 mM dTTP | 0 | 1 | 2 | 3 | 4 | 5 |
| 100 mM dUTP | 5 | 4 | 3 | 2 | 1 | 0 |
| smp H$_2$O | 30 | 30 | 30 | 30 | 30 | 30 |

Second, 100 µl PCR Reactions are made:

|  | /100 µl | /800 µl |
|---|---|---|
| smp H2O | 45 µl | 360 µl |
| 3.3 X TthXL Buffer | 33 | 264 |
| 25 mM MgOAC | 10 | 60 |
| 10 mM dNTP Mix | 4 | 32 |
| 20 pmol/µl Protease Forward | 2.5 | 20 |
| 20 pmol/µl Protease Reverse | 2.5 | 20 |
| "100 ng/µl plasmid p3RcC112 (XL1-Blue) | 1 | 6 |
| 2 U/µl TthXL | 2 | 16 |

Third, Reaction Mixes are prepared with all components except the dNTP Mix. 96 µl of Reaction Mix are aliquoted into, e.g., 6 PCR tubes. 4 µl of each of the dNTP Mixes are added to samples of Reaction Mix. The tubes are placed in a Stratagene RoboCycler using the following settings:

| 1x | 2 min @ 94° C. |
|---|---|
|  | 30 sec @ 50° C. |
|  | 1 min @ 72° C. |
| 29x | 30 sec @ 94° C. |
|  | 30 sec @ 50° C. |
|  | 1 min @ 72° C. |

Finally, 10 µl of each amplification is run on a standard 0.7% Agarose/TBE gel or other separation system.

Enzymatic Treatment with Uracil N-Glycosylase and/or Endonuclease IV:

10 µl of the 0.32, 0.24, 0.16, and 0.0 mM dUTP reactions are aliquoted into 4 wells of a PCR strip. No enzyme is added to the first aliquot, 0.5 µl of 1 U/µl Hk™-UNG N-Glycosylase (Epicentre Technologies) to the second, 0.5 µl of 2 U/µl E. coli Endonuclease IV (Epicentre Technologies) is added to the third aliquot, and 0.5 µl of each enzyme is added to the fourth aliquot. The reactions are Incubated for 2 hours at 37° C. The reactions are then heated for 10 min at 94° C., then placed on ice. 10 µl of each reaction are then run on a 1.5% Agarose/TBE gel.

Assembly of Fragments:

Uracil titrations and 100 µl amplifications are repeated to generate more test DNA. The QIAGEN QIAquick PCR Purification Kit is used to remove primers and unused dNTPs from reactions according to QIAGEN's instructions, eluting with 55 µl of smp water. The following is added to all 6 per reactions to bring to 100 µl total volume:

|  | /100 µl |
|---|---|
| smp water | 7 µl |
| Reaction in smp water | 50 |
| 3.3 X TthXL Buffer | 33 |
| 25 mM MgOAc | 10 |

To 50 µl of each of the 6 reactions, 2.5 µl of 1 U/ml HK™ UNG N-Glycosylase and 2 U/µl E. coli Endonuclease IV is added. The reactions are incubated for 2 hours at 37° C., then for 10 min at 94° C., and then cooled to 4° C. in a Thermocycler. Untreated reactions are saved for agarose gel analysis. 25 µl of each reaction is removed and saved for agarose gel analysis. To the remaining 25 µl, 25 µl of the following Assembly Mix is added:

|  | /100 µl | /200 µl |
|---|---|---|
| smp water 4 | 45 µl | 90 |
| 33 X TthXL Buffer | 33 | 66 |
| 25 mM MgOAc | 10 | 20 |
| 10 mM dNTP Mix (no Ura) | 80 | 16 |
| 2 U / µl TthXL | 4 | 8 |

The reactions are placed in a Stratagene RoboCycler using the following settings:

| 1x | 2min @ 94° C. |
|---|---|
|  | 30 sec @ 50° C. |
|  | 1 min @ .72° C. |
| 29x | 30 sec @ 94° C. |
|  | 30 sec @ 50° C. |
|  | 1 mm @ 72° C. |

For each uracil concentration, 10 µl of the original PCR reaction is run, 10 µl of fragments, and 10 µl of assembly reaction on a 1.5% Agarose/TBE gel.

Fragments from the assembly reaction are rescued using PCR with nested primers in 100 µl reactions.

Ung-End Fragmentation of E. coli dut ung Grown Plasmid DNA:

Electrocompetent E. coli strain CJ236 (pCJ105 (Cam$^r$ F')// dut1 ung1 thi-1 relA1) is prepared as follows. Strain CJ236 is Streaked on LB+30 µg/ml chloramphenicol and incubated overnight at 37° C. Cells are scraped from the plate into 5 ml LB and inoculated into 250 ml LB to a starting OD$_{600}$ of 0.100. The culture is shaken at 37° C. The culture is placed on ice for ~30 min when at OD$_{600}$ 0.4-0.5 and prepared via standard electrocompetence procedures, freezing in 220 µl aliquots in 10% Glycerol.

Transformation of strain CJ236 with plasmid is performed as follows. 0.5 mg of plasmid are added into 100 ml of electrocompetent strain CJ236 via standard a electroporation protocol. $10^{-1}$ to $10^{-4}$ dilutions are plated on LB+100 µg/µl Ampicillin and incubated overnight at 37° C. A transformation efficiency of about $2\times10^8$ transformants/µg plasmid are observed. 8 transformants are patched to an LB+Amp100 stock plate and incubated overnight at 37° C. CJ236 in inoculated into 3 ml LB Broth+Amp100, unsupplemented, and supplemented with 500 µg/ml Uradine (to see if fragment size is modulated by supplementation). The cultures are shaken overnight at 37° C. Plasmid DNA is prepared from 1.5 ml with the aid of a Qiagen Miniprep Spin Kit, suspending plasmid DNA in 50 µl smp water. A$_{260}$ and A$_{280}$ of a 1:20 dilution in smp water is read and quantitated. Plasmid in CJ236 in LB+Amp100=0.34 μg/μl plasmid in CJ236 in LB+Amp100+Ura500=0.35 μg/μl plasmid in XL1-Blue in LB+Amp100=0.7 μg/μl.

Fragmentation Example: Automated DNA Fragmentation Using DNase Plastic Co-Polymers Fragmentation is currently performed by the addition of DNaseI to DNA in solution. This can result in variable fragmentation. For example, PCR products are often fragmented less well than plasmids, presumably as a result of residual salts following purification of the PCR product. This example provides an automated process in which DNA is fragmented and specific sized fragments are purified, speeding the process greatly.

Immobilized DNase on support resin beads can be used for fragmentation, with DNA to be fragmented passing over a column made of the beads. This avoids the problem of salts in the solution which are removed by gel filtration.

An extension of this procedure is to encapsulate the DNase in a polymeric (plastic) resin. Wang et al. (1997) "Biocatalytic plastics as active and stable materials for biotransformations" *Nat Biotechnol* 2:15(8):789-93 and the references therein describe Biocatalytic plastic technology generally. Resin encapsulation has the advantage of stabilizing the enzyme greatly: no loss of activity is seen even after 30 or more days. Synthesis of a stable DNase resin avoids the need to re-calibrate the column to account for the loss of activity. Using a fixed initial concentration of DNA, DNA fragment size can be determined by the flow rate through the column. Fractions can be collected containing known fragment sizes.

Encapsulated DNAse resin can then be used as a component of an automated DNA shuffling system as set forth herein. That is, fragmentation can be performed in a flowing fashion, across DNAse or other nuclease columns. This flow-through fragmentation can be performed in an "in line" or "off-line" fashion. For example, the columns can be incorporated into the fluid handling module(s) herein and performed as part of a fluid transfer of material to be fragmented (in line fragmentation). Alternately, fragmentation columns can be a separate module in the system.

Although described above in terms of columns for purposes of illustration, it will be appreciated that non-column based methods can utilize particle-bound or encapsulated nucleases, e.g., in a bead panning or chip-based format.

(5.) Recombination/Resynthesis/Amplification Module

The recombination resynthesis module permits hybridization of complementary (or partially complementary) nucleic acids, followed by PCR-based resynthesis of hybridized nucleic acids, typically using multiple cycles of PCR (a variety of PCR-based re-synthesis methods, including staggered extension process ("StEP") PCR are set forth in the references above), or ligation (e.g., via LCR). In general, PCR can be used to "sew" sets of overlapping nucleic acids together, simply by performing multiple cycles of PCR on overlapping nucleic acid fragments. Similarly, ligases can be used to ligate overlapping (or even non-overlapping) nucleic acid fragments (with or without a polynucleotide extension (e.g. polymerase-mediated) step between cycles of ligation). Where PCR is used, the recombination/resynthesis module also optionally performs nucleic acid amplification, i.e., by PCR.

The amplification of arrays and duplicate arrays is also an important feature of the invention, as this amplification provides material for subsequent operations ($2^{nd}$ round diversity generation reactions such as shuffling, cloning, sequencing, etc.). For example a duplicate amplified array can be formed by copying a master array, or a portion thereof, and generating amplicons of the members of the resulting duplicate array to form an amplified array of nucleic acids. Any available amplification methods can be used, including amplifying nucleic acids in physical or logical arrays by PCR, LCR, SDA, NASBA, TMA, Qβ-replicase amplification, etc.

Common physical elements for the resynthesis module include heating and optionally cooling elements to perform PCR, containers to hold nucleic acids to be resynthesized (microtiter trays, chips, test tubes, etc.). For example, standard PCR thermocyclers can be incorporated into this module, i.e., in combination with appropriate instruction sets to perform synthesis recombination and amplification. For example, a set of instructions is optionally embodied in a programmed thermocycler, a computer operably coupled to a thermocycler, or in a web page that can be used to instruct a thermocycler. The set of instructions typically receives user input data and sets up cycles to be performed on the thermocycler, e.g., a programmed thermocycler. The user input data typically includes one or more parental nucleic acid sequence, a desired crossover frequency, an extension temperature, and/or an annealing temperature, and the like. From such user input data, a set of instructions, e.g., embodied in a computer readable medium, creates a cycle which is performed by the programmed thermocycler. For example, a set of instructions optionally sets up a cycle to amplify one or more parental nucleic acid sequence and fragment the one or more parental nucleic acid sequence to produce one or more nucleic acid fragment. In some embodiments, the cycle is programmed or instructed to pause before fragmenting to allow the addition of fragmentation enzymes, e.g., to fragment nucleic acids that have had uracil residues incorporated therein. The fragments are then reassembled to produce one or more shuffled nucleic acid; which is optionally amplified, all according to the set of instructions or calculations.

Amplifiers typically include some sort of heating element and can also include a cooling element. Such elements commonly include (but are not limited to) resistive elements, programmable resistors, micromachined zone heating chemical amplifiers, Peltier solid state heat pumps, heat pumps, resistive heaters, refrigeration units, heat sinks, Joule Thompson cooling devices, a heat exchanger, a hot air blower, etc. Any of the above elements are optionally operably coupled to a computer comprising a set of instructions which directs or instructs the elements in the amplification process, e.g., according to user input data or computer calculated predictions.

Recently, attempts have been made to shorten the time required for each cycle of PCR, an advantage in the present method, in that reduction in this time increases the overall throughput of the system. Such methods often reduce the time by, for example, performing the PCR in devices that allow rapid temperature changes. The use of apparatus that allow greater heat transfer, e.g., incorporating thin-walled tubes, turbulent air-based machines, and the like also facilitate the use of shorter cycle times. For example, the RapidCycler™, from Idaho Technologies, Inc. (Salt Lake City, Utah) allows relatively rapid ramping times between each temperature of a PCR and relatively efficient thermal transfer from the cycler to the samples. Similarly, the RAPID (Ruggedized Advanced Pathogen Identification Device) from Idaho Technologies, Inc. provides a thermal cycler with concurrent fluorescence monitoring to speed analysis as well.

As an alternative or adjunct to standard PCR thermocyclic elements, chip-based PCR can also be incorporated into the present invention. A recent example of chip-based PCR was discussed by Kopp et al. (1998) "Chemical Amplification:

Continuous Flow PCR on a Chip" Science 280:1046-1047. Kopp et al. describe a microfluidic continuous flow PCR system where the PCR reactants were flowed through a chip having three discrete temperature zones. The reagents within the channel underwent essentially instantaneous changes in temperature. Thus, the cycle time in this system reflected the time at each temperature, with no substantial temporal contribution from ramping times.

Additional chip-based PCR methods are set forth in U.S. Pat. No. 5,587,128 to Wilding et al. Dec. 24, 1996 "MESOSCALE POLYNUCLEOTIDE AMPLIFICATION DEVICES") which similarly incorporate hot zones and fluid flow to achieve temperature cycling. PCR can also be performed by fluid resistance heating in microchips. For example, U.S. Pat. No. 5,965,410, to Chow, et al., Oct. 12, 1999, "ELECTRICAL CURRENT FOR CONTROLLING FLUID PARAMETERS 1N MICROCHANNELS" describe such devices.

In certain embodiments, non-thermocyclic polymerase mediated amplification can be achieved, i.e., using a chemical denaturation device or an electrostatic denaturation device. For example U.S. Pat. No. 5,939,291 by Loewy et al., Aug. 17, 1999 "MICROFLUIDIC METHOD FOR NUCLEIC ACID AMPLIFICATION" describes such devices. This invention can also be used with polymerases capable of performing under unusual or biochemically challenging environments such as are created under extreme shear forces, temperatures, salt concentrations, or the presence of one or more non-aqueous solvents and other chemicals. Such enzymes may be generated via the shuffling and mutagenesis techniques disclosed here and elsewhere in the art.

(6.) PCR Amplification of Individual Fragments

It is generally preferable to amplify diversified nucleic acids by PCR or any of the other amplification techniques herein prior to an in vitro transcription and translation step. This is desirable because single copy genes can become damaged or otherwise compromised during the course of the transcription/translation or assay steps, making rescue of the genetic material problematic. Also, PCR amplification of a single gene copy can be suboptimal, although it is known to be possible (Ohuchi et al. (1998) "In vitro Generation of protein libraries using PCR amplification of a single DNA molecule and coupled protein transcription/translation," *Nucleic Acids Res.* 26(19):4339-4346). The true number of starting genes in each reaction can be estimated using quantitative PCR. Such quantification involves, e.g., imaging of the amplified products via methods involving fluorescence detection, fluorescence resonance energy transfer, autoradiography, chemiluminescence or visible dyes.

(7.) Measuring Diversity/Library Quality Module

The diversity generation module can include a nucleic acid deconvolution module (or this module can exist separately to identify nucleic acids in other portions of the system). For example, the diversity generation module can include an identification portion, which identifies one or more nucleic acid portion or subportion.

A variety of nucleic acid deconvolution methods can be used, including nucleic acid sequencing, restriction enzyme digestion, dye incorporation and the like. The module can determine a recombination frequency (e.g., by dye incorporation, labeled nucleotide incorporation, sequencing, restriction enzyme digestion, rescue PCR, etc.) or a length of product (by any molecular sizing technology, or by dye incorporation, nucleotide incorporation, sequencing, restriction enzyme digestion, rescue PCR, etc.), or both a recombination frequency and a length, for the resulting elongated nucleic acids. Detection can be by detecting labels associated with nucleic acid products (e.g., detection of a dye, radioactive label, biotin, dioxin, a fluorophore, etc.), or simply by detecting the nucleic acid directly. Secondary assays such as fluorogenic 5' nuclease assays can be used for detection. For example, the extent of PCR amplification can be determined by incorporation of a label into one or more amplified elongated nucleic acid, a fluorogenic 5' nuclease assay, TaqMan, FRET, etc.

In general, an important factor in producing diverse nucleic acids in the diversity generation module(s) is the ability to measure the diversity which is generated. For example, if there is limited recombination in a shuffling reaction, the library of nucleic acids which is produced is often not sufficiently diverse for optimal screening of an activity of interest. Thus, in preferred embodiments, the shuffling module assesses the degree of diversity, generally before any screening is performed.

Diversity assessment can be performed in a number of ways. Aliquots of diverse populations of nucleic acids can be cloned or amplified (e.g., via standard primers which provide for amplification of all or least some members of the pool) by limiting dilution. These nucleic acids can then be sequenced, e.g., using automated sequencing methods and apparatus. The diversity of the population is then assessed, e.g., using sequence alignment algorithms, by visual inspection, or the like. Pools which are determined to be diverse can then be selected for activity of interest, used as substrates in additional recombination reactions, or the like.

Sometimes it is possible to make a determination, or an approximation, of diversity without having to sequence members of the population of nucleic acids. For example, a rescue PCR or LCR reaction can be performed that is designed to preferentially amplify recombined nucleic acids. In such rescue reactions, rescue PCR or LCR primers are provided which correspond to a subset (and, occasionally, only one) of the original parental nucleic acids that were acquired as noted above. By performing combinatorial PCR or LCR reactions using such primers, it is possible to determine whether recombination has taken place between two or more parental nucleic acids. That is, nucleic acids which are produced are optionally only amplified in the rescue PCR or LCR process if they have sequences corresponding to two or more parental nucleic acids (excluding PCR/LCR control reactions). Recombination events are detected for using appropriate combination of primers in the rescue reaction.

PCR/LCR products can be detected in solution, eliminating the need for separation or sequencing (although these approaches can be used, if desired, to provide more complete information of what sequences are rescued). For example, the amount of double-stranded DNA in the rescued pool provides an indication as to whether a PCR/LCR was successful. Thus, If there is double-stranded DNA following a rescue PCR/LCR amplification on a subset of the pool, then it is likely that the assembly reaction worked properly, producing recombinant nucleic acids. Simply monitoring double-strand DNA specific dye incorporation in a PCR/LCR rescue reaction provides at least a first approximation of the efficiency of the fragmentation and reassembly process.

For example, the PicoGreen dsDNA quantitation reagent (available e.g., from Molecular Probes) can be used to monitor and quantitate dsDNA. Similarly, the OliGreen ssDNA reagent can be used to monitor and quantitate ssDNA (including oligonucleotides) and the RiboGreen RNA quantitation reagent can be used to monitor RNA. See, e.g., Haugland (1996) *Handbook of Fluorescent Probes and Research Chemicals Sixth Edition* by Molecular Probes, Inc. (Eugene Oreg.) and http://www.probes.com/handbook (the on-line 1999 version of the *Handbook of Fluorescent Probes and Research Chemicals Sixth Edition* by Molecular Probes, Inc.) (Molecular Probes, 1999). For example, Molecular Probes 1999, Chapter 8 (e.g., section 8.2) provides details regarding quantitation of DNA in solution.

The PicoGreen reagent (e.g., Molecular Probes Nos. P-7581, P-11495) and Kit (Molecular Probes Nos. P-7589, P-11496) accurately quantitate as little as 25 pg/mL of double-stranded DNA (dsDNA) in a fluorometer or 250 pg/mL (typically 50 pg in a 200 μL volume) in a fluorescence microplate reader. The PicoGreen assay is greater than 10,000 times more sensitive than conventional UV absorbance measurements at 260 nm (an A260 of 0.1 corresponds to a 5 μg/mL dsDNA solution). Although the PicoGreen reagent is not actually specific for dsDNA, it shows a>1000-fold fluorescence enhancement upon binding to dsDNA, and less fluorescence enhancement upon binding to single-stranded DNA (ssDNA) or RNA, making it possible to quantitate dsDNA in the presence of ssDNA, RNA, proteins or other materials. Thus, the PicoGreen reagent allows direct quantitation of PCR amplicons without purification from the reaction mixture and makes it possible to detect low levels of DNA contamination in recombinant protein products.

Protocols for the PicoGreen assay are amenable to high-throughput screening in the systems herein. The dye is added to the sample (e.g., in a microtiter tray) and incubated for about five minutes, and then the fluorescence is measured. In addition, the fluorescence signal from binding of the PicoGreen reagent to dsDNA is linear over at least four orders of magnitude with a single dye concentration. Linearity is maintained in the presence of several compounds commonly found in nucleic acid preparations, including salts, urea, ethanol, chloroform, detergents, proteins and agarose.

For detecting oligonucleotides and other ssDNA the OliGreen ssDNA quantitation reagent from Molecular Probes (No. O-7582) and/or (No. O-11492) can be used). The OliGreen ssDNA quantitation reagent enables quantitation of as little as 100 pg/mL of ssDNA—200 pg in a 2 mL assay volume with a standard fluorometer or 200 pg in a 200 μL assay volume using a fluorescence microplate reader. Thus, quantitation with the OliGreen reagent is about 10,000 times more sensitive than quantitation with UV absorbance methods and at least 500 times more sensitive (and far faster, with a greater throughput) than detecting oligonucleotides on electrophoretic gels stained with ethidium bromide.

The OliGreen ssDNA quantitation reagent does exhibit fluorescence enhancement when bound to dsDNA and RNA. Like the PicoGreen assay, the linear detection range of the OliGreen assay in a standard fluorometer extends over four orders of magnitude—from 100 pg/mL to 1 μg/mL—with a single dye concentration. The linearity of the OliGreen assay is also maintained in the presence of several compounds commonly found to contaminate nucleic acid preparations, including salts, urea, ethanol, chloroform, detergents, proteins, ATP and agarose (see, e.g., the OliGreen product information sheet from Molecular Probes); however, many of these compounds do affect signal intensity, so standard curves are typically generated using solutions that closely mimic those of the samples. The OliGreen reagent shows a large fluorescence enhancement when bound to poly(dT) but only a relatively small fluorescence enhancement when bound to poly(dG) and little signal with poly(dA) and poly (dC). Thus, it is helpful to use an oligonucleotide with similar base composition when generating a standard curve for concentration dependence. The OliGreen ssDNA quantitation reagent can be used for quantitation of antisense oligonucleotides, aptamers, genomic DNA isolated under denaturing conditions, LCR/PCR primers, phosphorothioate and phosphodiester oligodeoxynucleotides, sequencing primers, single-stranded phage DNA, etc.

Other dyes such as the Cyanine Dyes and Phenanthridine Dyes can also be used for Nucleic Acid Quantitation in Solution and are, therefore, adaptable to use in the present invention. See, Molecular Probes, Supra, for a discussion of these and many other nucleic acid staining and quantitation dyes.

In one embodiment, a real time PCR assay system such as the "TaqMan" system is used for library quality determinations. Real time PCR product analysis by, e.g., FRET or TaqMan (and related real time reverse-transcription PCR) is a known technique for real time PCR monitoring that has been used in a variety of contexts (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12):2759-65; and Kreuzer et al. (1999) "LightCycler technology for the quantitation of bcr/abl fusion transcripts" *Cancer Research* 59(13):3171-4. Examples of these embodiments are set forth in more detail in the two following examples.

Example: Parallel Determination of Family Library Quality without Cloning or Sequencing A significant rate limiting step in the creation of a shuffled libraries is the determination of library quality. Since chimera formation depends on multiple parameters (fragment size, gene size, GC content, annealing temperature, extension temperature, number of parents, homology between parents) it is difficult to predict the conditions required for a certain cross-over frequency.

An alternative to complete control of the shuffling process is to gain precise control (i.e. for reproducibility) over important parameters (such as fragment size, annealing and extension temperatures, parental representation etc) and then to make multiple libraries in which these are systematically varied, e.g., in a microtitre plate format. The problem then is how to assess rapidly the quality of these libraries without the labor-intensive and costly processes of cloning and sequencing.

There are two common determinants of shuffled libraries: the frequency of recombination used to produce the library members, and the frequency with which frame shifts or deletions prevent the synthesis of full-length protein.

The TaqMan system (Perken Elmer Biosystems) provides one example of available technology that can be adapted to address these problems. TaqMan is a real-time PCR detection system that works as follows. Two oligonucleotides are used as amplification primers, e.g., about two or three hundred bases apart. A third primer, complementary to a section of DNA between these primers, is labeled with a fluorescent dye and a fluorescence quencher. During PCR, the third oligonucleotide anneals to the single stranded product DNA, and is then degraded by the 5' to 3' exonuclease activity of the polymerase as it extends through the region to which the labeled oligonucleotide is annealed. Degradation of the labeled oligonucleotide separates the fluorescent dye from the quencher, resulting in an increase in fluorescence. The cycle number at which an increase in fluorescence appears indicates the abundance of a particular template.

The TaqMan system can be adapted to measure the abundance of various chimeras in a microtiter format. Varying the primers and indicator oligonucleotides used allows detection of different classes of chimeras (see, FIG. 9). A simple tiered screen can used in which libraries are first screened for the presence of a fragment of B or C, incorporated between two fragments of A. Libraries that score well in this test could then be tested for more complex chimera arrangements. Finally the best few (5 or so) libraries are cloned into a translational-coupling vector, and full-length variants are picked, screened and sequenced. This, in turn, generates feedback about the types of chimeras that are the best indicators for a specific function, and the relationship between the simple chimera indicator described here and the real sequences generated.

Figure 9A:
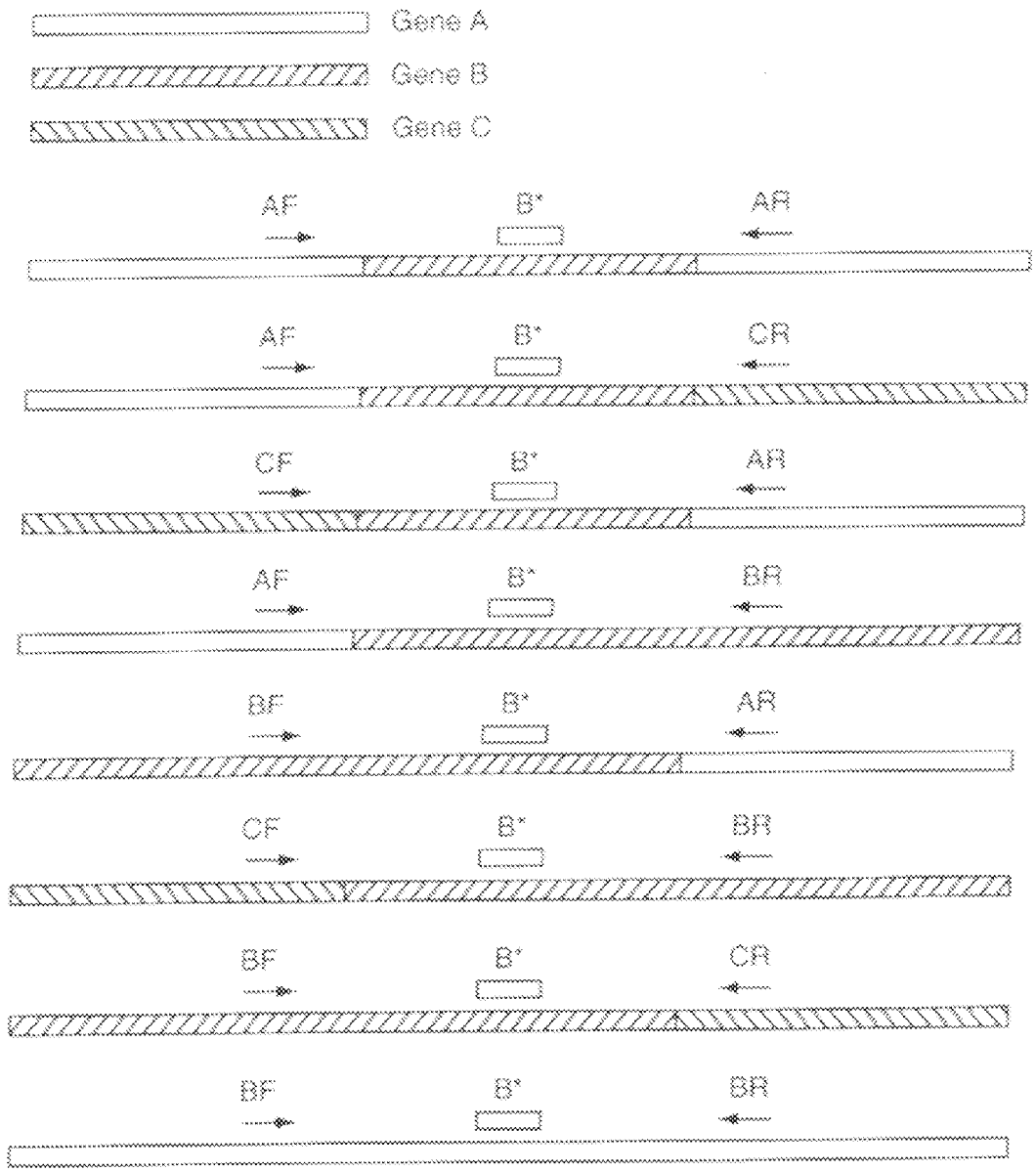
FIG. 9, panels A-B provide a schematic illustration of various detection strategies using single or multiple primers (e.g., via TaqMan).
Figure 9B:
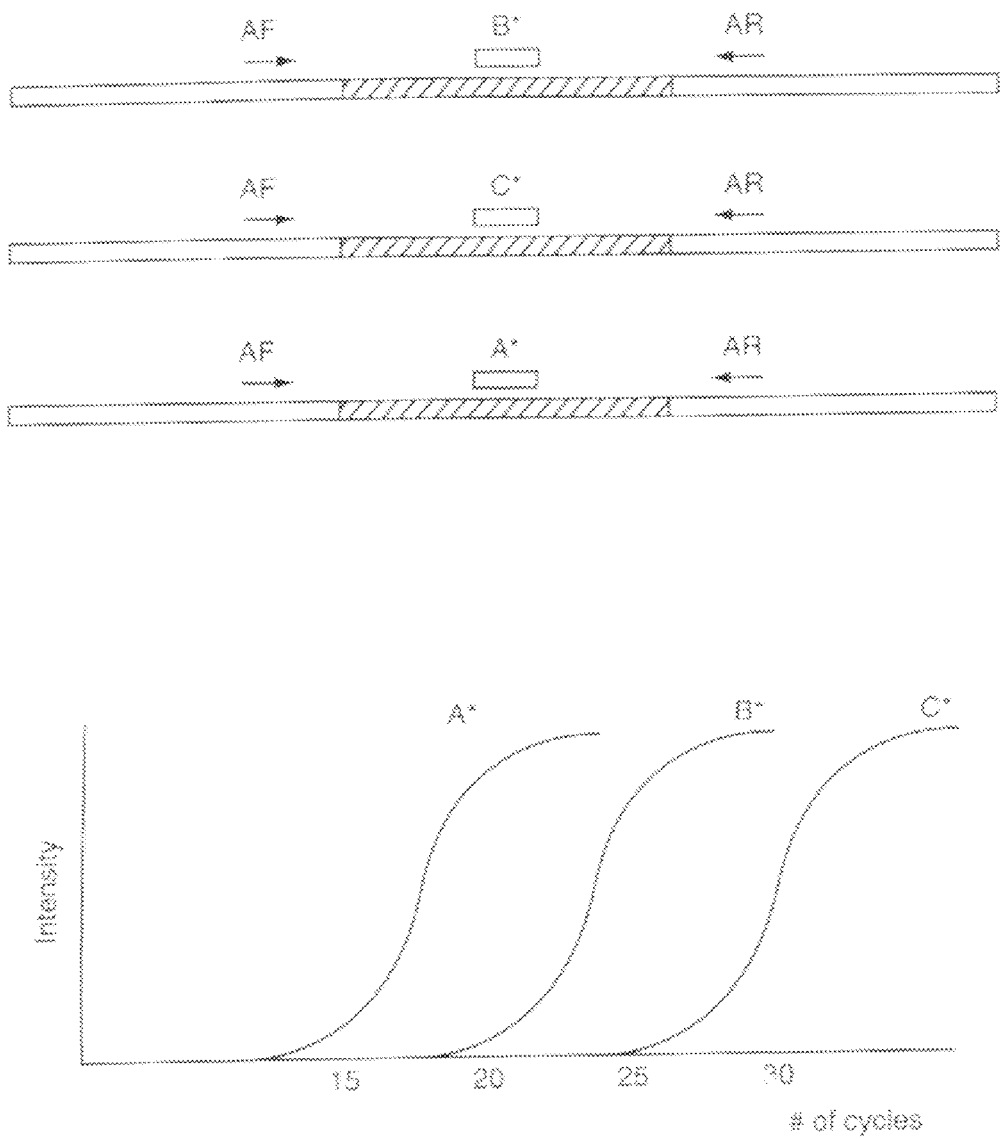

As shown in FIG. 9, a labeled B oligo can be used to measure the relative differences of, e.g., 8 possible crossovers. Alternately, several different fluorescently labeled oligos can be used in the same well of a reaction tray or other container. In this scheme, a library is tested by amplifying with a specific primer and fluorescence of A, B and C for different indicator dyes are measured as a function of the number of cycles (e.g., PCR cycles). This gives an indication of the frequency of the types of crossovers present in the library sample, illustrated schematically.

This kind of library screening dramatically increases the throughput for library assessment as compared to previous methods.

An alternative to TaqMan is the use of molecular beacons to assess library quality. Molecular beacons are oligonucleotide probes that can report the presence of specific nucleic acids in homogeneous solutions (Tyagi and Kramer (1996) "Molecular beacons: probes that fluoresce upon hybridization." *Nat Biotechnol* 14, 303-308. They are used for real-time monitoring of PCR or other amplification reactions and for the detection of RNAs within living cells. Molecular beacons are hairpin-shaped molecules with an internally quenched fluorophore whose fluorescence is restored when they bind to a target nucleic acid (see Tyagi and Kramer, id). They are designed so that the loop portion of the molecule is a probe sequence complementary to a target nucleic acid molecule. The stem is formed by an annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. When the probe encounters a target molecule, it forms a hybrid that is longer and more stable than the stem hybrid and its rigidity and length preclude the simultaneous existence of the stem hybrid. Thus, the molecular beacon undergoes a spontaneous conformational reorganization that forces the stem apart, and causes the fluorophore and the quencher to move away from each other, leading to the restoration of fluorescence which can be detected. Further details on Molecular Beacons and their use can be found in the following references: Tyagi et al. (1998) "Multicolor molecular beacons for allele discrimination" *Nat Biotechnol* 16:49-53; Matuso (1998) "In situ visualization of mRNA for basic fibroblast growth factor in living cells" *Biochimica Biophysica Acta* 1379:178-184; Sokol et al. (1998) "Real time detection of DNA-RNA hybridization in living cells" *Proc Natl Acad Sci USA* 95:11538-11543; Leone et al. (1998) "Molecular beacon probes combined with amplification by NASBA enable homogeneous, real-time detection of RNA" *Nucleic Acids Res* 26:2150-2155; Piatek et al. (1998) "Molecular beacon sequence analysis for detecting drug resistance in *Mycobacterium tuberculosis*" *Nat Biotechnol* 16:359-363; Kostrikis et al. (1998) "Spectral genotyping of human alleles" *Science* 279:1228-1229; Giesendorf et al. (1998) "Molecular beacon: a new approach for semiautomated mutation analysis" *Clin Chem* 44:482-486; Marras et al. (1999) "Multiplex detection of single-nucleotide variations using molecular beacons" *Genet Anal* 14:151-156; and Vet at al. (1999) "Multiplex detection of four pathogenic retroviruses using molecular beacons" *Proc Natl Acad Sci USA* 96:6394-6399.

Thus, the presence or absence of any specific nucleic acid (including any mutated nucleic acid) can be monitored in real time via the use of Molecular Beacons.

Example: Monitoring of Recombination using Fluorescence Energy Transfer

After performing a diversity generation reaction, an extensive analysis of the library can be performed to check whether there was recombination between genes (or other nucleic acids) and at what frequency. An immediate answer to those question speeds up the construction of the relevant libraries. Furthermore, if the monitoring is continuous during the shuffling reaction, the conditions can be changed to optimize recombination, even before the end of the reaction.

The process in this example utilizes real time PCR analysis based upon FRET. The method uses "light cycler" techniques (De Silva et at (1998) *Biochemica* "Rapid Genotyping and Quantification with Hybridization Probes Rapid Genotyping and Quantification on the LightCycler with Hybridisation Probes" 2:12-15, and De Silva et al (1998) *Biochemica* "The LightCycler—The Smartest Innovation for More Efficient PCR" *Biochemica* 2: 4-7).

Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals*, Published by Molecular Probes, Inc., Eugene, Oreg., e.g., at chapter 13).

The Forster radius ($R_o$) is the distance between fluorescent pairs at which energy transfer is 50% efficient (i.e., at which 50% of excited donors are deactivated by FRET. The magnitude of $R_o$ is dependent on the spectral properties of donor and acceptor dyes: $R_o=[(8.8\times10^{23})(K^2)(n^{-4})(QY_D)(J)(S)]^{1/6}$ Å, where: $K^2$=dipole orientation range factor (range 0 to 4, $K^2=\frac{2}{3}$ for randomly oriented donors and acceptors); $QY_D$=fluorescence quantum yield of the donor in the absence of the acceptor; n=refractive index; and, J(S)=spectral overlap integral=$IM_A(S) \cdot F_D S \cdot S^4 dScm^3 M^{-1}$, Where $M_A$=extinction coefficient of acceptor and $F_D$=Fluorescence emission intensity of donor as a fraction of total integrated intensity. Typical donor-acceptor pairs include fluorescein/Cy5, fluorescein/tetramethylrhodamine, IAEDANS/fluorescein, Fluorescein/Fluorescein, BODIPY/BODIPY and EDANS/DABCYL. An extensive compilation of $R_o$ values are found in the literature; see, Haugland (1996) *Handbook of Fluorescent Probes and Research Chemicals* Published by Molecular Probes, Inc., Eugene, Oreg. at page 46 and the references cited therein.

In brief, two probes are labeled with different fluorophores. The two probes are complementary to a specific region of a gene to be analyzed: If the desired genotype (recombination event) is present in the sample, the probes bring two fluorophores into close proximity (e.g., within $R_o$), allowing a transfer of energy between them. This transfer of energy can be monitored using a device such as the one described in the De Silva et al. references (id); see also, the LightCycler from Amersham.

This approach can be used in shuffling or other diversity generating reactions using automated techniques. In order to label the DNA molecules, constructed, e.g., during PCR or LCR reactions, nucleotides labeled with fluorophores are used and are introduced by the DNA polymerase or other enzymes into the molecule, or via automated synthetic approaches. The fluorophores are excited and detected by system.

For example, two genes to be shuffled can be labeled using this method, e.g., one with fluorescein, and the other with Cy5 in a PCR reaction (both fluorophores are available, e.g., from Amersham Pharmacia). The labeled genes are fragmented, e.g., using DNaseI before being shuffled by the system. Recombination between the two genes brings the fluorescein molecule next to the Cy5 molecule, and, e.g., after each cycle the system excites the fluorescein. The fluorescein then transfers its energy either to the Cy5 molecule, if it is proximal, or to the media if it is not. The system then detects light at the wavelength of emission of Cy5, providing an indication of FRET. Similarly, FRET can be used to assess recombination frequency by solution-phase or solid-phase hybridization to differentially labeled fluorescence-coupled oligonucleotide, PCR amplified or restriction fragment-generated probes.

(8.) Non-Coding Control Sequences

Quite commonly, output nucleic acids from the shuffling or mutagenesis module comprise one or more sequences which control transcription or translation or which facilitate downstream processing of the nucleic acid (e.g., cloning). These sequences include promoters, enhancers, ribosome binding sites, translation initiation regions, transcription initiation regions, universal PCR primer binding sites, sequencing primer binding sites, restriction enzyme digestion sequences and other sequences of known activity. Ausubel, Sambrook, Berger and a number of other references herein provide an introduction to sequences useful in genetic engineering. Many such sequences are known and can easily be provided in the present methods, if desired. For example, including such sequences as part of PCR or ligase-directed gene synthesis is a convenient way of incorporating such sequences of interest.

Amplifying recombinant nucleic acids in physical or logical arrays, or amplifying elongated nucleic acids in master arrays, duplicate arrays or other arrays herein can include, as a feature of the amplification, the incorporation of one or more transcription or translation control subsequence into the elongated nucleic acids, recombinant nucleic acids in the physical or logical array, intermediate nucleic acids produced using elongated nucleic acids or recombinant nucleic acids in the physical or logical array as a template, partial or complete copies of elongated nucleic acids or recombinant nucleic acids in the physical or logical arrays, and the like. One or more transcription or translation control subsequence can be ligated to the elongated nucleic acids, the recombinant nucleic acids in the physical or logical array, intermediate nucleic acids produced using the elongated nucleic acids or the recombinant nucleic acids in the physical or logical array as a template, partial or complete copies of the elongated nucleic acids or the recombinant nucleic acids in the physical or logical array, etc. For example, the one or more transcription or translation control subsequences can be hybridized or partially hybridized to the above nucleic acids during any nucleic acid amplification or polymerase or ligase mediated method herein.

(9.) Isolation Of Single DNA Molecules From A Mixed Pool Without Bacterial Transformation This section describes a method that allows pieces of DNA to be singly isolated from a pool and amplified for sequencing or other process (e.g., shuffling or in vitro translation) without the use of a host organism. The method is both faster and more reliable than traditional cloning. The method is based upon the ability to form particles from individual pieces of DNA that can then be isolated and dispensed into individual wells. The particles are degraded and each piece of DNA is amplified to give enough material for sequencing or other downstream operations.

The advantage of this protocol is that the particles are formed due to the physical nature of the DNA polymer, and as such, the protocol is sequence and context independent. Thus all pieces of DNA have approximately the same chance of being amplified at the end of the process, unlike traditional cloning methods.

DNA Library Preparation

When cloning from genomic DNA, the DNA is usually cleaved to suitable size by nuclease (e.g., restriction enzyme) or mechanical treatment. To amplify the DNA, the ends of each fragment are compatible, e.g., for PCR amplification using standard primers. This is true if the DNA molecules have a standard construction with fixed 5' and 3' ends (as is usual for RNA or DNA selection constructs and for expression constructs). For cloning of fragments of unknown DNA (or following mechanical or random cleavage procedures), this is achieved by ligation of standard primers to the end of each fragment for subsequent ligation into a vector. Fluorescent or other tags can be added to the extension to aid handling and analysis. Successfully ligated molecules can be enriched in the pool by PCR and purified, if necessary, by standard methods.

Monomolecular Particle Formation

DNA is a rigid polyanionic linear polymer that exists as a monomer in solution with a large radius of gyration as it floats in a random coil structure. The addition of a polycationic polymer to a solution of DNA causes the DNA to associate with the polycation and condense in a cooperative electrostatic process to yield a compact complex. Due to the electrostatic nature of the process, there is a tendency for multiple copies of the two polymers to associate to give large poorly defined mixtures of particles.

Complexation of DNA with single chain cationic detergents is known to form small monomolecular particles (J. Am. Chem. Soc. 1995, 117, 2401-2408), but these complexes are unstable to reduction of the detergent concentration. The ability of single chain detergents to form complex is based upon the formation of the polycation at the DNA in a template-assisted assembly. Hence addition of such a detergent to a solution of DNA leads to formation of small (~20 nm) complexes which can then be dispensed into individual wells. Dilution of the particles with a PCR mix leads to dissolution of the complex, releasing free DNA ready for amplification.

Complexes formed with detergent can be relatively unstable. However, other methods of forming monomolecular complexes are available. See, e.g., Blessing (1998) *Proc. Natl. Acad. Sci. USA* 95:1427-1431. In this protocol, the single chain cationic detergent contains a chemical moiety such as a thiol group. Once the complex has formed, the detergents are dimerized (by oxidation for thiols) which yields a stable particle. Once the particles are dispensed, the dimerization is reversed (reduction of the disulfide) and the complex degrades to yield free DNA. Addition of lipophilic fluorophores to these complexes leads to production of a fluorescent particle. This can be used to track the complexes for sorting as described below.

Dispensing the Particles

The charged complexes formed by the protocols outlined above are readily sorted by electrophoretic mobility to remove uncomplexed material. Dispensing these particles into separate wells of a microtiter plate uses, e.g., electrophoresis, e.g., in which the particles travel down a capillary (or channel) in single file, much like in a FACS machine (or chip). A fluorescent detector (e.g., LIF, confocal laser with suitable PMT/CCD) set up at the end of the system detects passage of particles and directs particles into the receiving well. Flow cytometry systems which will sort into microtiter plates of any format, are available, e.g., from Cytomation (Fort Collins, Colo.).

Release of the Free DNA

Stability of the DNA-detergent complex is sensitive to reduction in detergent concentration. Thus, dilution of the particles into a PCR mix leads to dissolution of the complex, releasing free DNA for amplification. The PCR product can then be used for the desired purpose (sequencing, in vitro transcription/translation, etc.).

(10.) Array Copy Systems

During operation of the devices of the invention, populations of nucleic acids can be arranged into one or more physical or logical recombinant nucleic acid arrays. In several of the procedures herein, a duplicate of at least one of the one or more physical or logical recombinant nucleic acid arrays is produced in the process of amplifying, sequencing, or expressing members of the nucleic acid array. Thus, in one typical embodiment, the system includes a shuffled nucleic acid master array which physically or logically corresponds to positions of the shuffled nucleic acids in the reaction mixture array. This master array can be accessed as necessary, e.g., where access of reaction mixture or other duplicated nucleic acid arrays is not feasible. See also, FIG. 1b.

In general, the diversity generation module can copy arrays (i.e., the module can include an array copy function) to produce duplicate arrays, master arrays, amplified arrays and the like, e.g., where any operation is contemplated which could make recovery of nucleic acids from an original array problematic (e.g. where a process to be performed destroys the original nucleic acids, e.g., recombination methods that change the nature of product nucleic acids as compared to starting nucleic acids), or where an elevated stability for the array would be helpful (e.g., where an amplified array can be produced to stabilize accessible copies of nucleic acids), or where a normalization of components (e.g., to provide similar concentrations of reactants or products) is useful for recombination, expression or analysis purposes. Copies can be made from master arrays, reaction mixture arrays or any duplicates thereof.

For example, the diversity generation module optionally dispenses nucleic acids into one or more master multiwell plates and, typically, amplifies the resulting master array of elongated nucleic acids (e.g., by PCR) to produce an amplified array of elongated nucleic acids. The shuffling module can include an array copy system which transfers aliquots from the wells of the one or more master multiwell plates to one or more copy multiwell plates.

The array of reaction mixtures can be formed, e.g., by separate or simultaneous addition of an in vitro transcription reagent and an in vitro translation reagent to one or more copy multiwell plates (or other spatially organizing set of containers), or to a duplicate set thereof, to diversified nucleic acids.

In addition to adding reaction mixture components directly to arrays, reaction mixture components are commonly added to duplicate arrays of shuffled or otherwise diversified nucleic acids. For example, the reaction mixtures can be produced by adding in vitro transcription/translation reactants to a duplicate nucleic acid array, which is duplicated from a master array of the shuffled nucleic acids produced by spatially or logically separating members of a population of the shuffled nucleic acids.

Arraying techniques for producing both master and duplicate arrays from populations of shuffled or otherwise diversified nucleic acids can involve any of a variety of methods. For example, when forming solid phase arrays (e.g., as a copy of a liquid phase array, or as an original array), members of the population can by lyophilized or baked on a solid surface to form a solid phase array, or chemically coupled or printed (e.g., using ink jet printing methods) to the solid surface. Similarly, population members can be converted from solid phase to liquid phase by rehydrating members of the population, or by cleaving chemically coupled members of the population of shuffled nucleic acids from the solid surface to form a liquid phase array. One or more physically separated logical or physical array members can be accessed from one or more sources of shuffled or otherwise diversified nucleic acids and moved to one or more array destination site (e.g., by pipetting into microtiter trays), where the one or more destinations constitute a logical array of the shuffled nucleic acids.

Individual members of an array can be copied in a number of ways. For example, members can be amplified and aliquots removed and placed in a duplicate array. Alternately, where the sequences of array members are deconvoluted (e.g., sequenced) copies can be produced synthetically and placed into copy arrays. Two preferred ways of copying array members are to use a polymerase (e.g., in amplification or transcription formats) or to use an in vitro nucleic acid synthesizer for copying operations. Typically, a fluid handling system will deposit copied array members in destination locations, although non-fluid based member transport (e.g., transfer in a solid or gaseous phase) can also be performed.

B. In vitro Transcription/Translation

In one preferred embodiment of the invention, libraries of nucleic acids produced by the various diversity generation methods set forth herein (shuffling, mutation, etc.) are transcribed (i.e., where the diverse nucleic acids are DNAs) into RNA and translated into proteins, which are screened by any appropriate assay. Common in vitro transcription and/or translation reagents include reticulocyte lysates (e.g., rabbit reticulocyte lysates) wheat germ in vitro translation (IVT) mixtures, E. coli lysates, canine microsome systems, HeLa nuclear extracts, the "in vitro transcription component," (see, e.g., Promega technical bulletin 123), SP6 polymerase, T3 polymerase, T7 RNA polymerase (e.g., Promega # TM045), the "coupled in vitro transcription/translation system" (Progen Single Tube Protein System 3) and many others. Many of translation systems are described, e.g., in Ausubel, supra. as well as in the references below, and many transcription/translation systems are commercially available.

Methods of processing (transcribing and/or translating) diversified nucleic acids (shuffled, mutagenized, etc.) are provided. In the methods, a physical or logical array of reaction mixtures is provided, in which a plurality of the reaction mixtures include one or more member of a first population of nucleic acids (including shuffled, mutagenized or otherwise diversified nucleic acids). A plurality of the plurality of reaction mixtures further comprise an in vitro transcription or translation reactant. One or more in vitro translation products produced by a plurality of members of the physical or logical array of reaction mixtures is then detected. The physical or logical array or reaction mixtures produced by these methods are also a feature of the invention.

Generally, cell-free transcription/translation systems can be employed to produce polypeptides from solid or liquid phase arrays of DNAs or RNAs as provided by the present invention. Several transcription/translation systems are commercially available and can be adapted to the present invention by the appropriate addition of transcription and or translation reagents to arrays of diversified nucleic acids, e.g., produced by shuffling target nucleic acids and arraying the resulting nucleic acids. A general guide to in vitro transcription and translation protocols is found in Tymms (1995) *In vitro Transcription and Translation Protocols: Methods in Molecular Biology* Volume 37, Garland Publishing, NY. Any of the reagents used in these systems can be flowed or otherwise directed into contact with nucleic acid array members.

Typically, in the present invention, in vitro transcription and/or translation reagents are added to an array (or duplicate thereof) that embodies the diverse populations of nucleic acids generated by diversity generating procedures. For example, where the nucleic acids of interest are plated on microtiter trays, the in vitro transcription/translation reagents are added to the wells of the trays to form arrays of reaction mixtures that individually comprise the in vitro transcription/translation reagents, the nucleic acids of interest and any other reagents of interest.

Several in vitro transcription and translation systems are well known and described in Tymms (1995), id. For example, an untreated reticulocyte lysate is commonly isolated from rabbits after treatment of the rabbits with acetylphenylhydrazine as a cell-free in vitro translation system. Similarly, coupled transcription/translation systems often utilize an *E. coli* S30 extract. See also, the Ambion 1999 Product Catalogue from Ambion, Inc (Austin Tex.).

A variety of commercially available in vitro transcription and translation reagents are commercially available, including the PROTEINscript-PRO™ kit (for coupled transcription/translation) the wheat germ IVT kit, the untreated reticulocyte lysate kit (each from Ambion, Inc (Austin Tex.)), the HeLa Nuclear Extract in vitro Transcription system, the TnT Quick coupled Transcription/translation systems (both from Promega, see, e.g., Technical bulletin No. 123 and Technical Manual No. 045), and the single tube protein system 3 from Progen. Each of these available systems (as well as many other available systems) have certain advantages which are detailed by the product manufacturer.

In addition, the art provides considerable detail regarding the relative activities of different in vitro transcription translation systems, for example as set forth in Tymms, id.; Jermutus et al. (1999) "Comparison of *E. Coli* and rabbit reticulocyte ribosome display systems" *FEBS Lett.* 450(1-2):105-10 and the references therein; Jermutus et al. (1998) "Recent advances in producing and selecting functional proteins by using cell-free translation" *Curr. Opin. Biotechnol.* 9(5):534-48 and the references therein; Hanes et al. (1988) "Ribosome Display Efficiently Selects and Evolves High-Affinity Antibodies in vitro from Immune Libraries" *PNAS* 95:14130-14135 and the references therein; and Hanes and Pluckthun (1997) "In vitro Selection and Evolution of Functional Proteins by Using Ribosome Display." *Biochemistry* 94:4937-4942 and the references therein.

For example, an untreated rabbit reticulocyte lysate is suitable for initiation and translation assays where the prior removal of endogenous globin mRNA is not necessary. The untreated lysate translates exogenous mRNA, but also competes with endogenous mRNA for limiting translational machinery.

Similarly, The PROTEINscript-PRO™ kit from Ambion is designed for coupled in vitro transcription and translation using an *E. coli* S30 extract. In contrast to eukaryotic systems, where the transcription and translation processes are separated in time and space, prokaryotic systems are coupled, as both processes occur simultaneously. During transcription, the nascent 5'-end of the mRNA becomes available for ribosome binding, allowing transcription and translation to proceed at the same time. This early binding of ribosomes to the mRNA maintains transcript stability and promotes efficient translation. Coupled transcription: translation using the PROTEINscript-PRO Kit is based on this *E. coli* model.

The Wheat Germ IVT™ Kit from Ambion, or other similar systems, is/are a convenient alternative, e.g., when the use of a rabbit reticulocyte lysate is not appropriate for in vitro protein synthesis. The Wheat Germ IVT™ Kit can be used, e.g., when the desired translation product comigrates with globin (approx. 12-15 kDa), when translating mRNAs coding for regulatory factors (such as transcription factors or DNA binding proteins) which may already be present at high levels in mammalian reticulocytes, but not plant extracts, or when an mRNA will not translate for unknown reasons and a second translation system is to be tested.

The TNT® Quick Coupled Transcription/Translation Systems (Promega) are single-tube, coupled transcription/translation reactions for eukaryotic in vitro translation. The TNT® Quick Coupled Transcription/Translation System combines RNA Polymerase, nucleotides, salts and Recombinant RNasin® Ribonuclease Inhibitor with the reticulocyte lysate to form a single TNT® Quick Master Mix. The TNT® Quick Coupled Transcription/Translation System is available in two configurations for transcription and translation of genes cloned downstream from either the T7 or SP6 RNA polymerase promoters. Included with the TNT® Quick System is a luciferase-encoding control plasmid and Luciferase Assay Reagent, which can be used in a non-radioactive assay for rapid (<30 seconds) detection of functionally active luciferase protein.

In addition to coupled in vitro transcription and translation, either step may be done separately from the other by in vitro or cellular means. For example, in vitro transcribed RNA can be provided to cells for subsequent translation by way of mechanical or osmotic microinjection., methods for which are well known in the art. Moreover, cells containing RNA derived by transcription from one or more of the shuffling and mutagenesis methods described (directly or indirectly) herein can be lysed and the RNA obtained for subsequent analysis. The purified or unpurified RNA obtained in this manner can be subjected to in vitro or in situ translation. All such methods can be conducted within or in conjunction with the various arraying approaches described in this invention.

Many other systems are well known, well characterized and set forth in the references noted herein, as well as in other references known to one of skill. It will also be appreciated that one of skill can produce transcription/translation systems similar to those which are commercially available from available materials, e.g., as taught in the references noted above.

The methods of the invention can include in-line or off-line purification of one or more reaction product array members. In line purification is performed as part of the transfer process from an in vitro transcription/translation reaction to a product detection or identification module, whereas off-line purification can be performed before or after transfer, or in a parallel module.

In any case, once expressed, proteins can be purified, either partially or substantially to homogeneity, according to standard procedures known to and used by those of skill in the art. Polypeptides of the invention can be recovered and purified from arrays by any of a number of methods well known in the art, including ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in completing configuration of mature proteins. High performance liquid chromatography (HPLC) can be employed in final purification steps where high purity is desired. Once purified, partially or to homogeneity, as desired, the polypeptides may be used (e.g., as assay components, therapeutic reagents or as immunogens for antibody production).

In addition to the references noted supra, a variety of purification/protein folding methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2$^{nd}$ Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3$^{rd}$ Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein folding and other in vitro protein biosynthetic methods are found in Marszal et al. U.S. Pat. No. 6,033,868 (Mar. 7, 2000).

As noted, those of skill in the art will recognize that after synthesis, expression and/or purification, proteins can possess a conformation substantially different from the native conformations of the relevant parental polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl.

In general, it is occasionally desirable to denature and reduce expressed polypeptides and then to cause the polypeptides to re-fold into the preferred conformation. For example, guanidine, guanidinium, urea, detergents, chelating agents, DTT, DTE, and/or a chaperonin can be added incubated with a transcription product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa:

Various systems are also available for simultaneous synthesis and folding of complex proteins. For example, the control of redox potential, the use of helper proteins (from both bacterial and eukaryotic systems) and the like can be used to provide for improved cell free translation. Optionally, proteins may be added which aid in protein refolding, such as by maintaining solubility of the nascent or partially folded protein (e.g., chaperonins) or by adjusting the configuration of inter- and intra-molecular disulfide bonds (e.g. protein disulfide isomerase).

RNA or protein or other products of a translation reaction can be tagged with any available tag (biotin, His tag, etc.), and captured to an array position following expression, if desired. The products are released, e.g., by cleavage of an incorporated cleavage site, or other releasing methods (salt, heat, acid, base, light, or the like). In alternate embodiments, products are free in solution or encapsulated in mini-reaction compartments such as inverted micelles, liposomes, or gel particles or droplets.

As noted, it can be desirable to reconstitute expression products in liposomes, inverted micelles, or other lipid systems. Thus, the system can include a source of one or more lipid. Typically this lipid is flowed into contact with the one or more polypeptide or other reaction product (or vice-versa), or into contact with the physical or logical array of reaction mixtures. Similarly, the lipid can be flowed into contact with one or more shuffled or mutagenized nucleic acids (or transcription products thereof), thereby producing one or more liposomes or micelles comprising the polypeptide or other reaction product, reaction mixture components, and/or nucleic acids.

Liposomes and related structures are particularly attractive systems for use in the present invention, because they serve to concentrate reagents of interest into small volumes and because they are amenable to FACS and other high-throughput methods. In addition to standard FACS methods, microfabricated FACSs for use in sorting cells and certain subcellular components such as molecules of DNA have also been described in, e.g., Fu, A. Y. et al. (1999) "A Microfabricated Fluorescence-Activated Cell Sorter," *Nat. Biotechnol.* 17:1109-1111; Unger, M., et al. (1999) "Single Molecule Fluorescence Observed with Mercury Lamp Illumination," *Biotechniques.* 27:1008-1013; and Chou, H. P. et al. (1999) "A Microfabricated Device for Sizing and Sorting DNA Molecules," *Proc. Nat'l. Acad. Sci.* 96:11-13. These sorting techniques utilizing microfabricated FACSs generally involve focusing cells using microchannel geometry and can be adapted to the present invention by the inclusion of a chip-based FACS system in the in vitro transcription/translation module of the system.

The following example provides details regarding use of liposomes as reaction vesicles.

(1.) Alternate Format: In Vitro Clone Selection: Direct Isolation of Active Sequences from a DNA Library—Use of Liposomes in the Integrated Systems of the Invention The slowest step in the manipulation of DNA is often the selection of functional DNA constructs in vivo. That is, DNA is often maintained in a form suitable for transformation and growth in a host organism, such as *E. coli*, to allow the selection of positive constructs from the background. This example describes functional assays to be performed on the gene product, which is transcribed directly from a DNA library, leading to the isolation of the specific construct bearing the desired activity. The technique is amenable to the screening of libraries of any size.

This example relies upon the application of a number of techniques in series. In particular, the example uses liposomes as reaction/sorting compartments, in vitro transcription/translation, a fluorescent activity assay and a FACS machine.

The use of in vitro transcription/translation systems to produce small amounts of protein from DNA in solution is described above. The encapsulation of this machinery inside a small compartment (~1 µm), such as an inverted micelle (Tawfik and Griffiths (1998) *Nature Biotech,* 16:652-656) or liposome, enables the machinery to act upon a single DNA molecule. The presence of 1 molecule in a 1 µm diameter sphere corresponds to a concentration of ~2.5 nM. Thus, the effective concentration of the DNA is sufficient for efficient transcription/translation and even a single round of translation gives a useful protein concentration. A single turnover of the enzyme encoded by the DNA also gives nM concentrations of product; therefore, e.g., about 100 catalytic events are sufficient for detection. Detection of this fluorescence by the laser of the FACS machine will then lead to the sorting of the fluorescent compartments (liposomes only, as inverted micelles are incompatible with the FACS machine). In general, FACS machines sort liposomes, cells or other sortable compartments at a rate of thousands per second, which allows millions of liposomal reaction compartments to be sorted routinely. The selected liposomes can then be degraded and the formerly encapsulated DNA isolated and purified. The DNA that encoded a gene product(s) capable of generating fluorescence under the assay conditions are substantially present in this sample. This DNA is further analyzed or used directly in another cycle of this process under more stringent conditions.

For example, Tawfik and Griffiths, id, describes a system in which linear DNA encoding a DNA methylase was isolated from a background of other DNA. The DNA was encapsulated in inverted micelles with suitable transcription/translation machinery, such that only one DNA molecule was encapsulated in each micelle. After the DNA methylase had been translated, it methylated the DNA accessible to it, i.e. present in that micelle. The reaction was quenched and the DNA was isolated from the micelles. The pooled DNA was then exposed to the restriction enzyme corresponding to the methylase, leading to the degradation of unmethylated sequences. The intact DNA was then amplified by PCR and the DNA was found to be highly enriched in the methylase encoding sequence.

A solution of the in vitro transcription/translation machinery with the substrates required for the activity assay is provided, at concentrations sufficient to ensure that each liposome contains a self sufficient transcription/translation/gene product assay system, in a suitable buffer, at 4° C. A DNA library is added at a concentration such that generally only about one or zero DNA molecule(s) are present in each liposome.

The liposomes, are formed using a solvent dispersal method, which allows the direct formation of small unilamellar vesicles of defined size in the starting solution. The starting solution is stirred at a predetermined speed and the lipids are added to the solution in a water miscible solvent. As the solvent disperses (solvent is typically less than 2% final concentration) the lipids are exposed to the aqueous phase which causes them to spontaneously form SUVs of a size defined by the conditions and the choice of lipid mixture. In a typical experiment 30% of the initial solution will be encapsulated in liposomes. The liposomes are purified and the remaining unencapsulated solution can be recycled if desired. The liposomes are then incubated under conditions that favor transcription/translation and later conditions suitable for the activity assay of interest.

The stability of the liposomes and their behavior in solution can be controlled by the choice of the constituent lipids, which form the bilayer. Thus, the compartment for reaction can be tailored to fit the conditions necessary for a specific experiment. Fluorescent lipids can also be incorporated into the bilayer, which can be used as an internal standard for fluorescence produced in the gene product assay e.g., in the FACS machine.

Gene product can be assayed using any of the standard fluorescent formats, such as the production/consumption of a fluorophore in the reaction, fluorescence resonance energy transfer (FRET), or coupled assays that use the product of the reaction performed by the gene product as the substrate for another reaction which generates a fluorophore. The tiny volume of reaction (~4 femtoliters for a ~1 µm diameter vesicle) increases the sensitivity of the solution to changes in the number of ions such as $H^+$ (i.e. pH) and $Ca^{2+}$ for which specific fluorescent detection methods are available. Fluorescent methods are the most commonly used assays for most enzyme classes, which provides general utility for this system.

Once sufficient time has been allowed for the gene product to perform its reaction, the liposome suspension is sorted using a FACS machine. Particles of ~1 µm diameter are readily visualized/sorted at a rate of thousands per second by this technology. Thus, the liposomes which are sufficiently fluorescent (and thus contain an active gene product/DNA construct) are separated from the many which do not meet the predefined criteria. The DNA is then purified from the sorted liposome population using standard methodology.

This approach confers a number of advantages over traditional cloning protocols. Firstly, the entire screening process is performed in a single batch, limiting the amount of liquid handling steps, so that there is virtually no limit to the size of library that can be screened in a single run. The only time the individual DNA constructs are handled individually is when they are sorted in the FACS machine, allowing extremely high throughout screens to be performed. Further, any gene product are handled equally efficiently, with no problems associated with host organism toxicity, protease mediated degradation, or the like. Even membrane associated proteins are screenable, due to the lipid bilayer nature of the liposomes.

Equally powerful particle screening methods are available by use of quantitative (e.g. digital) imaging in association with visible or fluorescent microscopy. In such methods, a library of particles producing a quantifiable emission are distributed on a surface in such a way as to maintain a reasonably fixed positions. Visualization and quantification of emission of light from particle(s) or specified sub-area(s) (as in a grid) is conducted by one of a variety of available of microscopic devices operatively linked to and digital imaging camera. Optionally, these components may be linked to a computer or other high-speed computational device equipped with software capable of correcting for lens curvature, unequal background within the field of view, and the like. Such imaging hardware and software can be used to guide (manually or electronically) the selective 'picking' or removal of particles from the surface. Such particles are then processed, characterized and arrayed as described elsewhere within this disclosure. Particularly useful for the selective 'picking' of particles from a surface are micromanipulation tools such as capillary-actuated clamping devices such as find use in ion channel and patch clamp studies, optical and atomic tweezers, micropipets, syringes, and the like.

Furthermore, because the only components in the system are added by design, there is no interference from overlapping activities of other proteins, etc., leading to a low background and the ability to detect very low levels of activity. Similarly, because no living organism is involved in the process, sensitive or dangerous gene products such as antibiotic resistance genes and factors which mediate infection can be studied without risk of transferring the new activity to pathogens and, therefore, the safety concerns for the systems are relatively reduced. Finally, results of an experiment can be produced quickly without waiting for an incubation period, especially when the host organism is a slow growing yeast or mold.

In addition to liposomes, individual or pooled nucleic acid populations with relevant in vitro transcription or translation reagents may be encapsulated within agar, agarose, carageenan, guar and related biological gels and gums; or in a wide variety of hygroscopic synthetic polymers such as polyacrylates, polymethylmethacrylates, polyacrylamides, polyethyleneimine (crosslinked) membranes, or the like. Methods for using these substances to encapsulate biological materials are known in the art. For example, microdroplets are formed by flowing a mixture of the polymerizing or pre-gelled polymer with a mixture containing the biochemical components of interest. Microdroplet technology is described, e.g., in Weaver et al. (1993) "Microdrop technology: A General Method for Separating Cells by Function and Composition" *METHODS: A Companion to Methods in Enzymology* 2(3) 234-247).

The resulting mixture is passed through a mechanical or aspirating device capable of atomizing the stream into microdroplets of desired size or characteristics. Such microdroplets can be sprayed onto a surface, plate, preformed grid, or the like, directly from the atomizing device, or passed into a separate aspirator, nozzle or ink jet-like device. Commonly, the particles can be sprayed in a random or semi-random manner onto the target surface and allowed to retain a relatively fixed position either by surface tension, gel adhesion or maintenance of a low moisture or low-eddy current capillary layer on a gel or moist surface. The positions of the quantified particles may be used to establish and record an initial array or the particles of interest may be picked and repositioned in a more normal pattern to establish the functional array.

This embodiment facilitates the process of developing biological catalysts for novel functions by giving a direct connection between DNA structure and gene product activity and by decreasing the time required for the interactive evolution of novel activities.

(2.) Alternate Format: Localizing In Vitro Transcription/Translation Products

Methods of detecting or enriching for in vitro transcription or translation products are provided. In the methods, one or more first nucleic acids (e.g., shuffled or otherwise diversified nucleic acids) which encode one or more moieties are localized proximal to one or more moiety recognition agents which specifically bind the one or more moieties. The one or more nucleic acids are in vitro translated or transcribed, producing the one or more moieties (e.g., polypeptides or biologically active RNAs such as anti-sense or ribozyme molecules, or other product molecules). The one or more moieties diffuse or flow into contact with the one or more moiety recognition agents (e.g., antibodies, antigens, etc.). Binding of the one or more moieties to the one or more moiety recognition agents is permitted and the one or more moieties are detected or enriched for by detecting or collecting one or more materials proximal to, within or contiguous with the moiety recognition agent (the material comprises at least one of the one or more moieties, where the moieties comprise one or more in vitro translation or transcription product). Optionally, the one or more moieties are pooled by pooling the material which is collected. Here again, a variety of variants of this basic class of methods are set forth herein as are a variety of products produced by the methods and their variants. The one or more moieties can be pooled by pooling the material which is collected.

For example, the first nucleic acids can include a related population of shuffled nucleic acids which encode an epitope tag, which is bound by the moiety or one or more moiety recognition agents. The first nucleic acids can include transcription or translation control sequences, such as an inducible or constitutive heterologous (or non-heterologous) promoter. In some embodiments, the first nucleic acids include a related population of shuffled nucleic acids and a PCR primer binding region, the method further including PCR amplifying a set of parental nucleic acids to produce the related population of shuffled nucleic acids.

Optionally, the first nucleic acids can include a related population of shuffled nucleic acids and a PCR primer binding region. In this case, the method can include identifying one or more target first nucleic acid by proximity to the moieties which are bound to the one or more moiety recognition agent, and amplifying the target first nucleic acid by hybridizing a PCR primer to the PCR primer binding region and extending the primer with a polymerase.

The first nucleic acids and the one or more moiety recognition agents can be localized on a solid substrate (including membranes, beads and other substrates commonly available), or in a gel or other matrix that limits diffusion of the moiety recognition agents or the nucleic acids. The first nucleic acids and the one or more moiety recognition agents can be localized on the solid substrate by a cleavable linker, a chemical linker, a gel, a colloid, a magnetic field, an electrical field, a combination thereof, or the like. In one aspect, the moiety or moiety in contact with the moiety recognition agent can release the nucleic acid, e.g., where the moiety recognition agent cleaves a cleavable linker which attaches the first nucleic acid to a solid substrate.

Typically, the invention can include detecting an activity of the moiety or moiety recognition agent. The one or more first nucleic acid can then be picked with an automated robot, providing for recovery of the nucleic acid and further processing. For example, the one or more first nucleic acid can be picked by placing a capillary on a region comprising the detected activity of the moiety or moiety recognition agent and withdrawing the capillary.

Example: Enrichment Method for In vitro Transcription/Translation Products

Figure 17A:
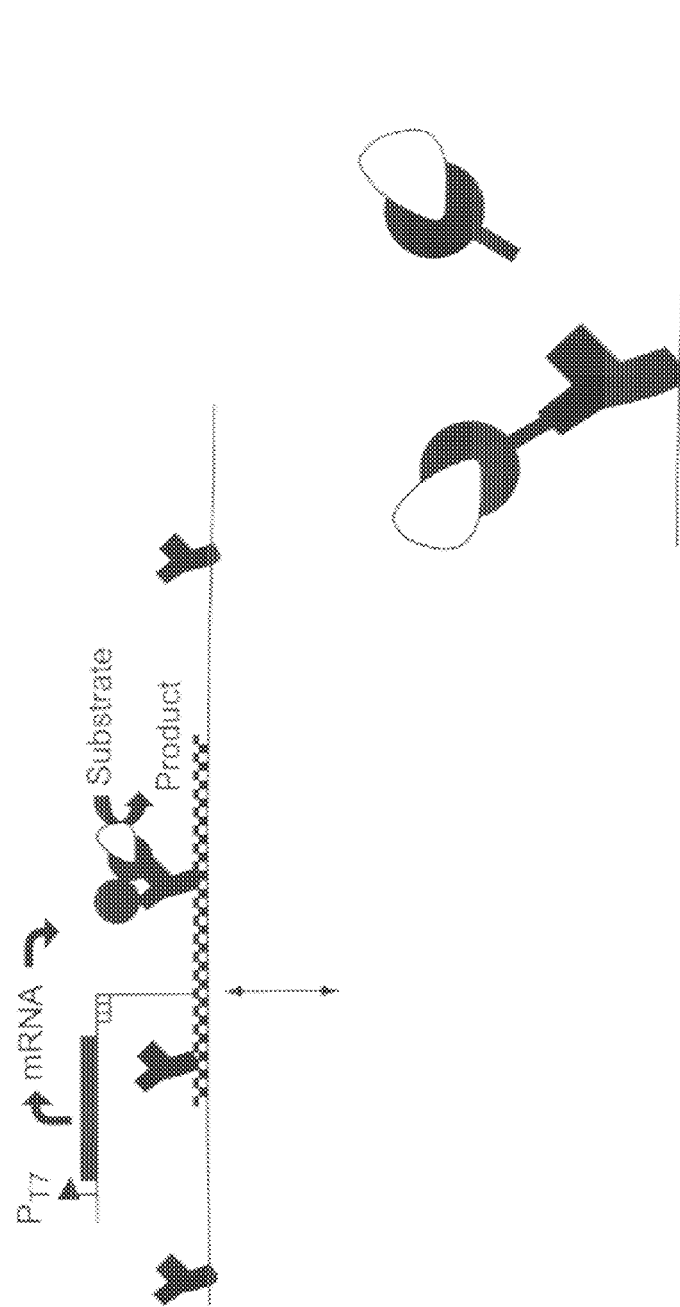
FIG. 17, panels A-E is a schematic of exemplar enrichment methods for in vitro transcription/translation.
Figure 17B:
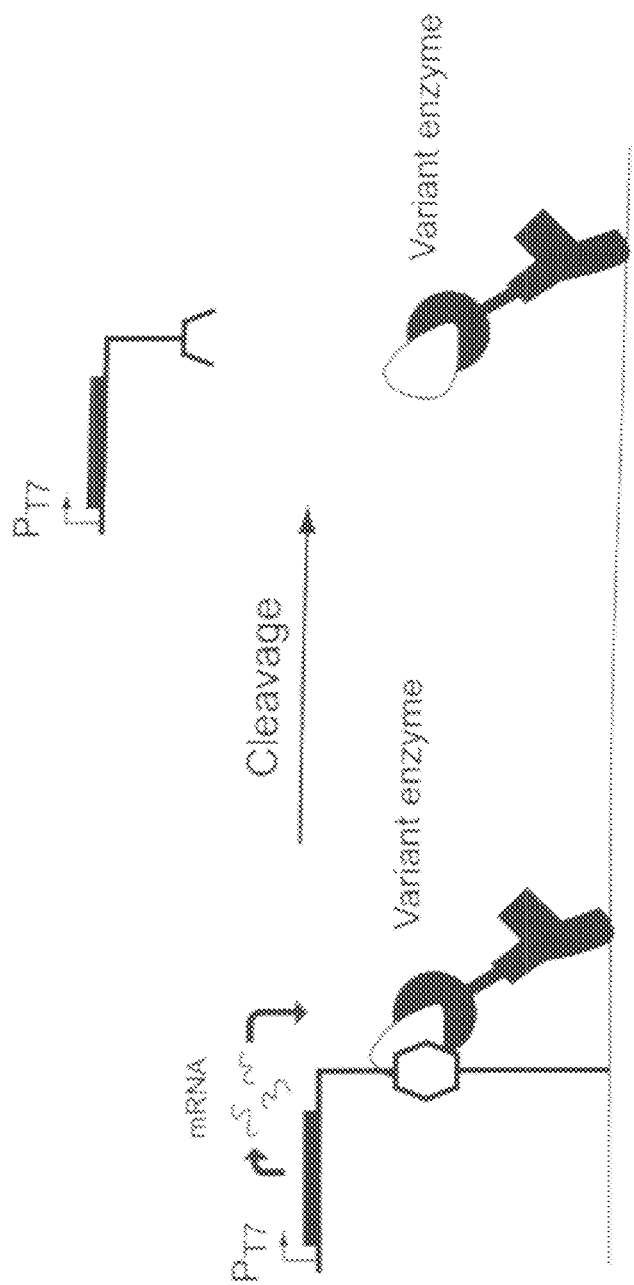
Figure 17C:
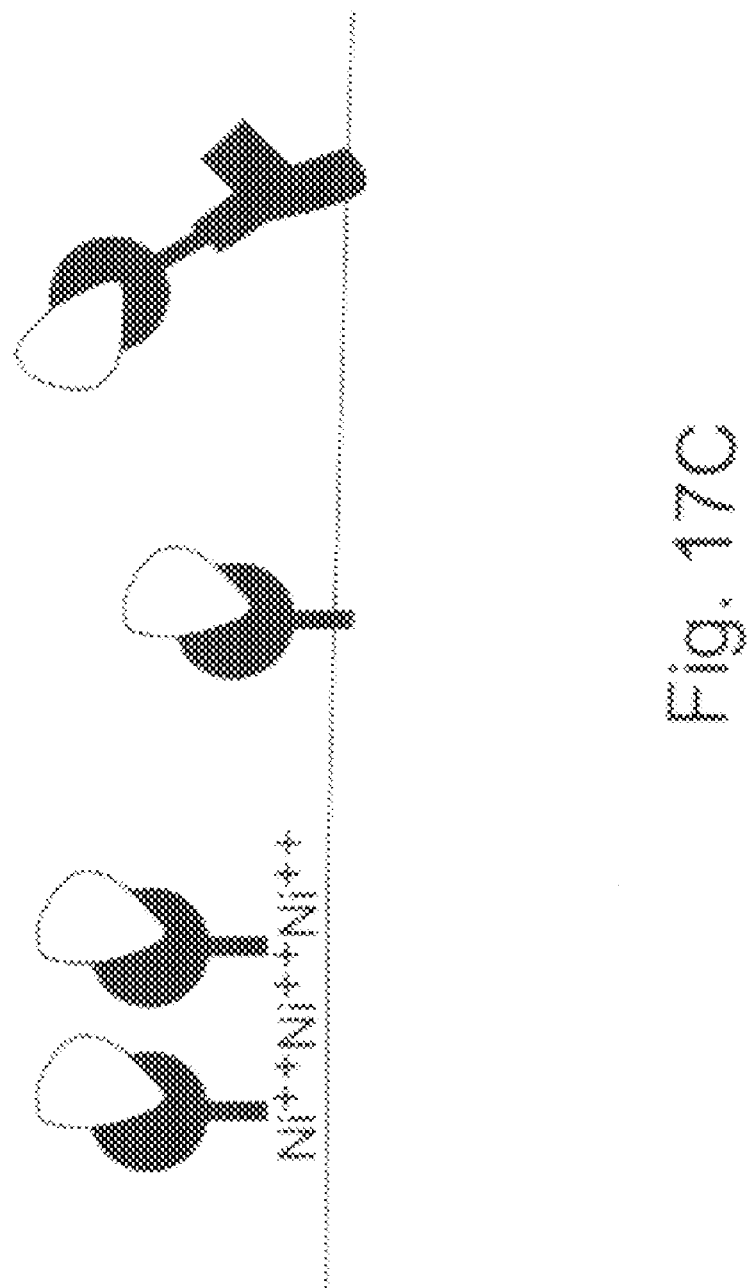

FIG. 17, Panels A-E schematically show an embodiment in which products of in vitro transcription/translation (ivTT) are captured on a solid substrate or in a matrix for further analysis, e.g., via immobilized antibodies or other protein capture mechanisms. As shown, both in vitro transcription and translation products can be captured on a single substrate, providing a mechanism for direct identification and isolation of genes of interest on the substrate.

As shown, an oligonucleotide "hook" is used to capture shuffled or otherwise diversified genes (the hook can hybridize to a region that is held constant in the shuffling or other diversification reaction) to the substrate (which may be any of the substrates herein, including beads, membranes, slides, trays, etc.). Alternately, the oligo can bind a universal epitope on a PCR primer of interest that is incorporated into the gene, e.g., a biotin or other molecule. The gene is in vitro transcribed/translated, with the product being captured by appropriate binding moiety (if the product is a protein, an antibody can be used as the binding moiety; if the product is an RNA, a second capture nucleic acid can be used as the binding moiety). For example, the surface (e.g., plate/bead/well) can be coated with oligos, antibodies, or both. For oligo capture tags, the sequences optionally bind to generic sequence handles. The tags can include a variety of features, including primer sequences for PCR. The oligos can include features for direct capture such as biotin or any other tag that can be linked to the oligo, e.g., through a chemical linkage, which optionally can include a linker region. The oligos can be cleavable (e.g., through incubation with a restriction enzyme). Similarly, cleavage itself can be a marker of activity, e.g., where activity of a restriction enzyme or variant is the molecule to be tested. Similarly, the activity to be tested can be a reporter system that results in cleavage of the capture tag. In the case of antibody tags, the tags can provide for uniform display of active sites and can be used in a project independent fashion, e.g., in any system where the antibody ligand is present.

As shown, the product binds to the binding moiety in proximity to the captured gene. Any activity of the product is then detected. The coding nucleic acid is isolated by its proximity to the detected product, e.g., using a microcapillary or the like. For example, the product can produce a visible signal when active and the system can detect the signal (e.g., by signal region size, signal intensity, etc.) and select the corresponding region for isolation of the coding nucleic acid. In bead-based embodiments, nucleic acids can be selected by FACS or other fluorescence detection methods. The use of the hook to capture DNA offers many control point options, including, e.g., cleavage by a variant.

In one embodiment, which is shown in FIG. 17 B, the product has an activity which results in cleavage of proximal bound coding nucleic acids. However, depending on the nature of the substrate or matrix, any available method can be used for cleavage of the coding nucleic acid, including chemical cleavage, light-directed cleavage, treatment with a restriction enzyme, or the like. The oligonucleotide hook can also include a cleavable linking element, as is common in the art.

As shown, genes are transcribed from a promoter such as a T7 promoter, translated and the activity of the encoded variant enzyme detected. In the format depicted, the variant enzyme includes a capture region that permits immobilization and detection. Free (e.g., soluble) genes transcribed in the same region are isolated. The process is repeated until a desired enrichment is observed. The tether on the gene or the transcribed enzyme or the constant region of the enzyme variant can be cleaved, e.g., specifically. Such specifically cleaved materials can be specifically eluted or otherwise isolated from the system. Examples of such cleavable linkers include a cleavable substrate or substrate analog, e.g., for detection of an activity of the variant protein (e.g., upon binding/cleavage by the protein variant, e.g., where the protein is an enzyme). Similarly, cleavage can be dependent on formation of a desired side product such as peroxide, heat, light, electricity or the like.

It is helpful to limit diffusion in this system, because, as the transcription and/or translation product diffuses away from the tethered coding gene, the association between the tethered gene and the encoded products becomes more difficult to determine. Diffusion can be limited by any available method, including allowing for transcription/translation in a matrix that limits diffusion (e.g., a gel or polymer solution).

FIG. 17, panel C shows details of one embodiment using generic epitope tags. As shown, the tags provide for uniform display of the various active sites of the protein or other bio-molecule of interest. This provides for project independent use of the tags as well as for the use of common reagents. Common tags such as His-tag IMAC can be used, as can any fusion protein comprising a region to be used as tags. The system also provides for common treatment such as free thiol introduction and the like.

As shown in FIG. 17, panel D, a robotic system such as the commercially available Q-bot can be used to pick positive regions of the substrate (e.g., to capture free genes prior to diffusion from a site of interest. Picking can be performed according to any standard hit picking selection criteria, e.g., selection of a particular percentage of variants by the size/intensity produced by a product at a site of activity/expression. Alternately, a bead based protocol can be used in conjunction with FACS if a fluorescent product is formed. In either case, genes which are selected can be used as inputs for subsequent rounds of recombination or mutation (or both) and screening, or can simply be used as product candidates. The products can also be further screened, in pools or as single hits, using any appropriate assay.

As shown in FIG. 17, panel E, DNAs which are recovered are subject to amplification reactions such as PCR or LCR and the amplified products subject to any additional diversity generation, isolation or selection step which is selected by the user or the system. As depicted, recovery in this example is performed via a microcapillary approach (e.g., using the Q-bot) and then subject to RT-PCR to produce products that, again can be used in subsequent recombination/mutation procedures or for any of the other purposes noted herein. It is worth noting that the density of variant genes of interest is inversely proportional to the enrichment of components in the system. Thus, to avoid bystander effects, the density of variant genes should not be too high for accurate selection by whatever selection mechanisms are used (capillary, FACS, etc.).

These methods can also be adapted to in vivo systems by lysing cells and capturing cell components. Systems for cell lysis and capture of nucleic acids such as Xpress-Screen™ from Tropix PE Biosystems (Bedford Mass.) can be adapted for use with this embodiment of the invention.

C. High-Throughput Cloning and Expression

In addition to in vitro transcription/translation, high throughput cloning and expression can be used to generate products to screen for product activity. This approach has the advantage of expressing products in a system that is similar to the eventual intended expression site for many products (e.g., in cells).

Basic cloning methodology is set forth in Sambrook, Ausubel and Berger, supra. In the present high-throughput system, diversified nucleic acids (e.g., a shuffled DNAs) are transformed into cells. The cells are sorted (e.g., by FACS, micro-FACS, visual or fluorescence microscopy) by expression of a marker protein such as GFP, where the marker expression is encoded by a full-length copy of a corresponding nucleic acid, e.g., where the full-length nucleic acid also encodes a full-length product of interest. Cells that have been selected are transferred to a micro-chamber or array where they express the shuffled gene. The micro-chamber or array contains a substrate for the shuffled protein whose optical properties (i.e. absorbance or fluorescence) are changed by catalysis by the enzyme. After a period of time, (e.g., ca. minutes to hours) the array of micro-chambers is "read" with a laser, CCD camera or other high density optical device. Those chambers in which the change in optical properties exceeds some threshold (i.e. a defining activity) are emptied, one into each well of a high density microtitre plate (96, 384, 1500 well etc), and the cells are then grown for the second assay. This provides a high-throughput format as a pre-screen for active clones.

Cells containing shuffled or mutated genes can express a protein or pathway capable of providing a florescent signal directly. In such a case, the cell supplies the translation and, optionally, the transcriptional machinery, and required substrates are loaded by incubating cells in a mixture appropriate for delivering the substrate through the cell wall. Cells expressing either marker or library genes of interest are sorted and arrayed or collected on the basis of the emitted fluorescence signal. Such a signal may also derive from the scattering, or direct emission or absorbance of visible light from the individual cells.

Several alternatives to traditional FACS devices exist and provide particularly unique advantages to the present invention. For example, microfluidic systems (see, e.g.,: Fu A Y, Spence C, Scherer A, Arnold F H and Quake S R., (1999) "A microfabricated fluorescence-activated cell sorter" *Nat. Biotechnol.* 17(11):1109-11) provide an efficient alternative to traditional FACS devices. Such systems are typically microfabricated devices capable of flowing, detecting and sorting cells from a microfluidic stream. Such systems can have several advantages over traditional FACS in that they allow for reversible fluid flow, extraordinarily high sorting accuracy, parallel sorting of multiple samples and the sorting of particles which are below the limit of conventional FACS devices. (e.g. bacteria, phage, phagemids, sub-microparticles, and the like).

In addition, a variety of powerful particle and cell screening methods are available by use of quantitative (e.g. digital) imaging in association with visible or fluorescent microscopy. In such methods, a library of cells producing quantifiable emission(s) are distributed on a surface in such a way as to maintain a reasonably fixed positions. Visualization and quantification of emission of light from each particle or specified sub-area (as in a grid) is conducted by one of a variety of available of microscopic devices operatively linked to and digital imaging camera. Optionally, these components may be linked to a computer or other high-speed computational device equipped with software capable of correcting for lens curvature, unequal background within the field of view, and the like. Such imaging hardware and software can be used to guide (manually or electronically) the selective 'picking' or removal of particles from the surface. Such particles are then processed, characterized and arrayed as described elsewhere within this disclosure. Particularly useful for the selective 'picking' of particles from a surface are micro-manipulation tools such as capillary-actuated or suction-actuated clamping devices, such as find use in ion channel and patch clamp studies, optical and atomic tweezers, micropipets and syringes, and the like.

D. Product Deconvolution

During operation of the device, the array of reaction mixtures produces an array of reaction mixture products (e.g., biologically active nucleic acids or proteins). These biologically active nucleic acids or proteins are screened for at least one property to identify coding nucleic acids of interest. Thus, in one significant aspect, the device or integrated system herein has one or more product identification or purification modules. These product identification/purification modules identify and/or purify one or more members of the array of reaction mixture products.

Common methods of assaying for product activity include any of those available in the art, including enzyme and/or substrate assays, cell-based assays, reporter gene expression, second messenger induction or signaling, etc.

In addition to product identification or purification, product identification or purification modules can also include an instruction set for discriminating between members of the array of reaction products based upon detectable characteristics, such as a physical characteristic of the products, an activity of the products or reactants, and concentrations of the products or reactants. For example "hit picking" software is available which permits the user to select criteria to identify members of an array that display one or more activity which is sufficient to be of interest for further analysis.

The product identification module can include detection and/or selection modules which facilitate detection or selection of array members. Such modules can include, e.g., an array reader which detects one or more member of the array of reaction products. Array readers are commercially available, generally constituting a microscope or CCD and a computer with appropriate software for identifying or recording information. In particular, array readers which are designed to interface with standard microtiter trays and other common array systems are commercially available. In addition to product manufacturer information from many of the various product manufacturers noted herein, detection protocols and systems are well known. For example, basic bioluminescence methods and detection methods which describe e.g., detection methods include LaRossa Ed. (1998) *Bioluminescence Methods and Protocols: Methods in Molecular Biology* Vol. 102, Humana Press, Towata, N.J. Basic Light microscopy methods, including digital image processing is described, e.g., in Shotton (ed) (1993) *Electronic Light Microscopy: Techniques in Modern Biomedical Microscopy* Wiley-Liss, Inc. New York, N.Y. Fluorescence Microscopy methods are described, e.g., in Hergman (1998) *Fluorescence Microscopy* Bios Scientific Publishers, Oxford, England. Specialized imaging instruments and methods for screening large numbers of images have also been described, e.g., "MICROCOLONY IMAGER INSTRUMENT FOR SCREENING CELLS EXPRESSING MUTAGENIZED ENZYMES" U.S. Pat. No. 5,914,245 to Bylina et al.; "ABSORPTION SPECTRA DETERMINATION METHOD FOR HIGH RESOLUTION IMAGING MICROSCOPE . . . " U.S. Pat. No. 5,859, 700 to Yang; "CALIBRATION OF FLUORESCENCE RESONANCE ENERGY IN MICROSCOPY . . . " WO 9855026 (Bylina et al.); "OPTICAL INSTRUMENT HAVING A VARIABLE OPTICAL FILTER" Yang and Youvan U.S. Pat. No. 5,852,498; Youvan (1999) "Imaging Spectroscopy and Solid Phase Screening" *IBC World Congress on Enzyme Technologies*. These systems can be incorporated into the present invention to provide high-throughput screening systems.

Similarly, such modules can include any of: an enzyme which converts one or more member of the array of reaction products into one or more detectable products; a substrate which is converted by the one or more member of the array of reaction products into one or more detectable products; a cell which produces a detectable signal upon incubation with the one or more member of the array of reaction products; a reporter gene which is induced by one or more member of the array of reaction products; a promoter which is induced by one or more member of the array of reaction products, which promoter directs expression of one or more detectable products; an enzyme or receptor cascade which is induced by the one or more member of the array of reaction products or the like.

Further, where a non-standard array format is used, or were non-standard assays are to be detected by the array reader, common detector elements can be used to form an appropriate array reader. For example, common detectors include, e.g., spectrophotometers, fluorescent detectors, microscopes (e.g., for fluorescent microscopy), CCD arrays, scintillation counting devices, pH detectors, calorimetry detectors, photodiodes, cameras, film, and the like, as well as combinations thereof. Examples of suitable detectors are widely available from a variety of commercial sources known to persons of skill.

Signals are preferably monitored by the array reader, e.g., using an optical detection system. For example, fluorescence based signals are typically monitored using, e.g., in laser activated fluorescence detection systems which employ a laser light source at an appropriate wavelength for activating the fluorescent indicator within the system. Fluorescence is then detected using an appropriate detector element, e.g., a photomultiplier tube (PMT), CCD, microscope, or the like. Similarly, for screens employing colorometric signals, spectrophotometric detection systems are employed which detect a light source at the sample and provide a measurement of absorbance or transmissivity of the sample. See also, *The Photonics Design and Applications Handbook*, books 1, 2, 3 and 4, published annually by Laurin Publishing Co., Berkshire Common, P.O. Box 1146, Pittsfield, Mass. for common sources for optical components.

In alternative aspects, the array reader comprises non-optical detectors or sensors for detecting a particular characteristic of the system. Such sensors optionally include temperature sensors (useful, e.g., when a product produces or absorbs heat in a reaction, or when the reaction involves cycles of heat as in PCR or LCR), conductivity, potentiometric (pH, ions), amperometric (for compounds that can be oxidized or reduced, e.g., $O_2$, $H_2O_2$, $I_2$, oxidizable/reducible organic compounds, and the like), mass (mass spectrometry), plasmon resonance (SPR/BIACORE), chromatography detectors (e.g., GC) and the like.

For example, pH indicators which indicate pH effects of receptor-ligand binding can be incorporated into the array reader, where slight pH changes resulting from binding can be detected. See also, Weaver, et al., *Bio/Technology* (1988) 6:1084-1089.

As noted, one conventional system carries light from a specimen field to a CCD camera. A CCD camera includes an array of picture elements (pixels). The light from the specimen is imaged on the CCD. Particular pixels corresponding to regions of the substrate are sampled to obtain light intensity readings for each position. Multiple positions are processed in parallel and the time required for inquiring as to the intensity of light from each position is reduced. Many other suitable detection systems are known to one of skill.

Data obtained (and, optionally, recorded) by the detection device is typically processed, e.g., by digitizing image data and storing and analyzing the image in a computer system. A variety of commercially available peripheral equipment and software is available for digitizing, storing and analyzing a signal or image. A computer is commonly used to transform signals from the detection device into sequence information, reaction rates, or the like. Software for determining reaction rates or monitoring formation of products, are available or can easily be constructed by one of skill using a standard programming language such as Visualbasic, Fortran, Basic, Java, or the like, or can even be programmed into simple end-user applications such as excel or Access. Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive, and other elements. Inputting devices such as a keyboard, mouse or touch screen optionally provide for input from a user.

In addition to array readers, the product deconvolution module can include enzymes which convert one or more member of the array of reaction products into one or more detectable products, or substrates which are converted by the array of reaction products into one or more detectable products, or other features that provide for detection of product activity by direct or indirect detection formats. For example, the module can include cells which produce a detectable signal upon incubation with members of the array of reaction products, and reporter genes which are induced by one or more member of the array of reaction products. Similarly, the module can include promoters which are induced by one or more array member and, e.g., which direct expression of one or more detectable products. Enzyme or receptor cascades can be triggered which are induced by the one or more member of the array of reaction products, with any of the products of the cascade serving as a detectable event.

Any available system for detecting proteins or nucleic acids or other expression products (directly or indirectly) can be incorporated into the module. Common product identification or purification elements include size/charge-based electrophoretic separation units such as gels and capillary-based polymeric solutions, as well as affinity matrices, liposomes, microemulsions, microdroplets, plasmon resonance detectors (e.g., BIACOREs), GC detectors, epifluorescence detectors, fluorescence detectors, fluorescent arrays, CCDs, optical sensors (e.g., an ultraviolet or visible light sensor), FACS detectors, temperature sensors, mass spectrometers, stereo-specific product detectors, coupled $H_2O_2$ detection systems, enzymes, enzyme substrates, Elisa reagents or other antibody-mediated detection components (e.g., an antibody or an antigen), mass spectroscopy, or the like. The particular system to be used depends on the system at issue, the throughput desired and available equipment.

In selected embodiments, the product identification or purification modules include one or more of: a gel, a polymeric solution, a liposome, a microemulsion, a microdroplet, an affinity matrix, a plasmon resonance detector, a BIACORE, a GC detector, an ultraviolet or visible light sensor, an epifluorescence detector, a fluorescence detector, a fluorescent array, a CCD, a digital imager, a scanner, a confocal imaging device, an optical sensor, a FACS detector, a microFACS unit, a temperature sensor, a mass spectrometer, a stereo-specific product detector, an Elisa reagent, an enzyme, an enzyme substrate an antibody, an antigen, mass spectroscopy, a refractive index detector, a polarimeter, a pH detector, a pH-stat device, an ion selective sensor, a calorimeter, a film, a radiation sensor, a Geiger counter, a scintillation counter, a particle counter, or an $H_2O_2$ detection system.

The product detection module can also include a substrate addition module which adds one or more substrate to a plurality of members of the product array or the secondary product array, e.g., where the product has an activity on the substrate. In this embodiment, the device will include a substrate conversion detector which monitors formation of a secondary product produced by contact between the substrate and one or more products. Formation of the product can be monitored directly or indirectly, or formation can be monitored by monitoring the substrate directly or indirectly (e.g., formation of the product can be monitored by monitoring loss of the substrate over time). Primary or secondary product formation can be monitored chemo-, regio- or stereoselectively, or non-selectively.

Formation of the secondary product can be monitored by detecting formation of peroxide, heat, entropy, changes in mass, charge, fluorescence, luminescence, epifluorescence, absorbance or any of the other techniques previously noted in the context of primary product or product activity detection which result from contact between the substrate and the product.

Commonly, the product detector will be a protein detector and the purification module will include protein purification means such as those noted for product purification generally. However, nucleic acids can also be products of the array, and can be similarly detected.

Array members can be moved into proximity to the product identification module, or vice versa. For example, the product identification module can perform an xyz translation of either the identification module or the array (e.g., by conventional robotics as set forth herein), thereby moving the product identification module proximal to the array of reaction products. Similarly, the one or more reaction product array members can be flowed into proximity to the product identification module. In-line or off-line purification systems can purify the one or more reaction product array members from associated materials.

Commonly detected products include one or more polypeptide or polypeptide activity, one or more nucleic acid, one or more catalytic RNA, or one or more biologically active RNA or other nucleic acid (ribozyme, aptamer, anti-sense RNA, etc.).

As noted supra, the present invention provides for array duplication. For example, secondary product arrays can be produced by re-arraying members of the reaction product array at a selected concentration of product members in the secondary product array. The selected concentration can be approximately the same for a plurality of product members in the secondary product array (sometimes all of the array members are plated at the same concentration, but it is also possible to plate members at different concentrations to provide multi-concentration datapoints, e.g., for kinetic analysis). This normalization of concentration simplifies analysis by the product detection module.

Further details on array copy systems, including copying of product arrays are found supra.

In addition to (or in place of) actually re-arraying materials, the detection module (or a separate module) can include an instruction set for determining a correction factor which accounts for variation in product concentration at different positions in the relevant array. For example, where product concentrations are known, a concentration dependent correction can be applied to correct observed activity data.

Example: High Throughput Quantitation Of Ligand Concentrations Using Surface Plasmon Resonance Selective molecular breeding utilizes the ability to measure the biological activities of libraries of shuffled gene products. Quantitative or semi-quantitative high throughput (HTP) screening is used to rank clones with respect to biological activity during each round of shuffling. Automation of this process is useful for decreasing the cost and increasing the speed with which one could do cycles of shuffling and screening.

A common problem with quantitation of libraries of shuffled proteins is that the proteins are expressed at relatively low levels (typically 1 ng to 1 microgram per ml) and in crude mixtures such as bacterial extracts, mammalian transfection supernatants, in vitro translation reactions, etc. The potentially small amounts of the expressed protein relative to the other components in the expression system can make quantitation challenging.

Surface plasmon resonance (SPR) is an established technique for measuring receptor-ligand interaction kinetics. See, e.g., Nieba et al. (1997) "BIACORE analysis of histadine-tagged proteins using a chelating NTA sensor chip" *Anal. Biochem.* 22(2):217-218; Muller et al. (1998) "Tandem Immobilized Metal Ion Affinity Chromatography/Immunoaffinity purification of His-tagged proteins—evaluation of two anti-His-tag monoclonal antibodies" *Anal Biochem.* 259(1): 54-61; Linder et al. (1997) "Specific Detection of His-tagged Proteins with Recombinant anti-His tag scFv-Phosphatase or scFv-phage fusions" *Biotechniques* 22(1):140-149. SPR allows one to measure these kinetics in the presence of complex mixtures such as are present in expression supernatants. If all proteins in a given library are tagged with an "equivalent" epitope tag and if a standard curve is established with an SPR probe, then one can derive the concentration of an unknown tagged protein in a complex supernatant by observing the kinetics of association with an immobilized antibody to the tag.

Surface plasmon resonance (SPR) has been widely exploited to measure the kinetics of a soluble ligand with a cognate receptor immobilized on a surface that is suitable for SPR analysis. This technique is very sensitive (one can easily measure ligands at nanomolar concentrations) and can be performed in the presence of complex mixtures such as are typically present in recombinant protein expression supernatants. The technique measures the kinetics of association and dissociation of the ligand:receptor pair. Given a standard curve, one can use kinetic measurements or equilibrium binding values to estimate absolute concentrations of unknown protein samples which have a constant ligand, such as an epitope tag, that can interact with a receptor immobilized on the sensor.

Preferably, SPR instruments are interfaced with robotic liquid handling apparatus and the detectors are multiplexed so that they can be used in 96-well formats. Although this example focuses on parallel 96-(or other) well SPR formats, a variant approach is to have one (or a few) SPR probe that are sequentially dipped into wells to serially measure protein concentrations in each well. This can be achieved by moving the probe from well to well (with a regeneration step in between) or by moving the plate on a movable stage so that wells are sequentially delivered to the probe.

Figure 18:
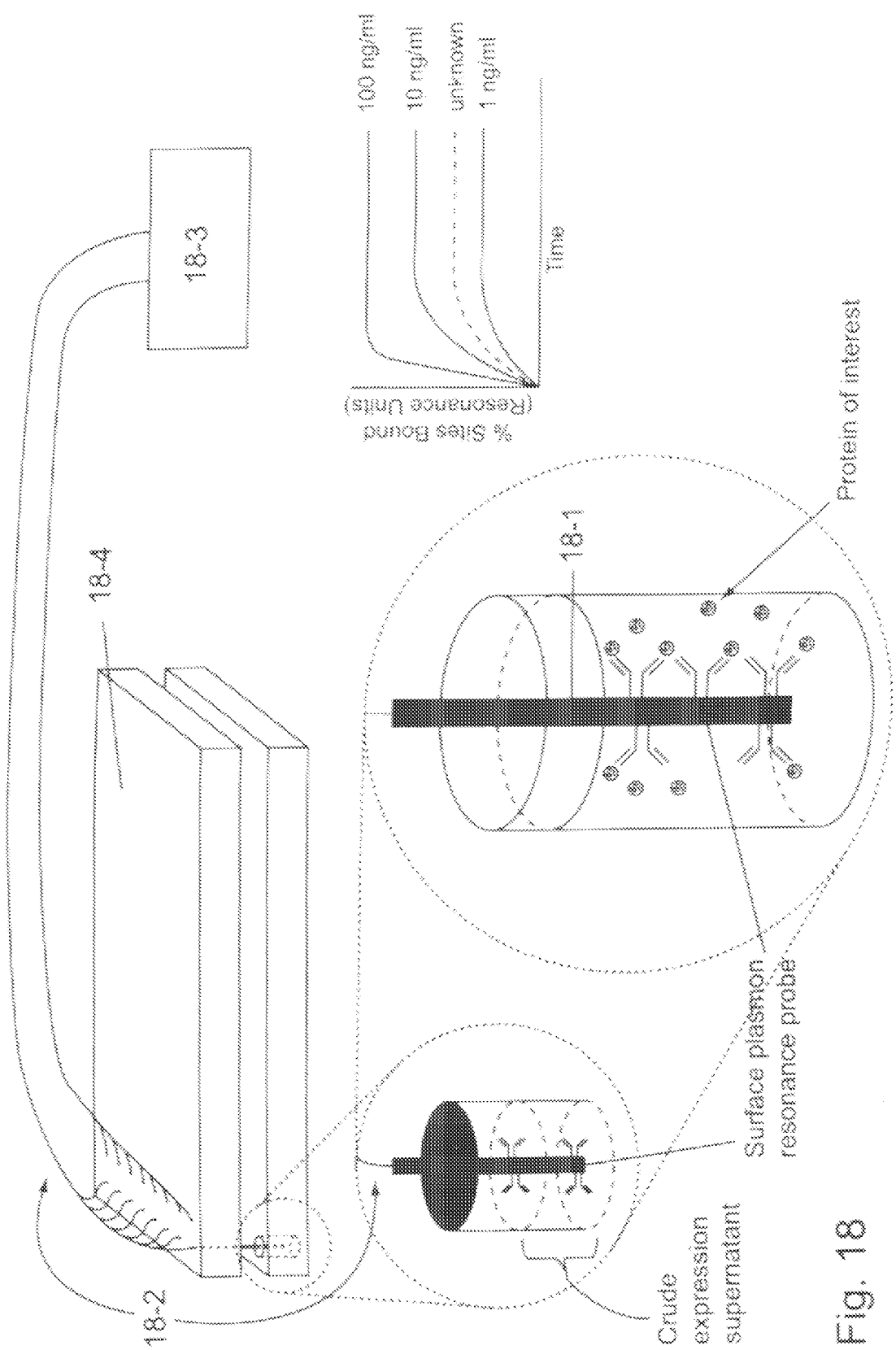
FIG. 18 is a schematic of a high-throughput parallel SPR module.

This example, schematized in FIG. 18, provides for the construction of a microtiter tray compatible SPR device. SPR probe 18-1 is connected by fiber optic cables 18-2 to amplifier/detector 18-3. A 96 (or other)-well array (18-4) of SPR probes is fabricated with an anti-epitope tag (an epitope is attached to proteins in the library) antibody conjugated to the surfaces of each of the SPR probes. The probe array is dipped into a plate containing, e.g., 96 unknown epitope tagged proteins (for a 96 well format) at unknown concentrations. Incident light is beamed from a source, down fiber optic cables to probes. The reflected light is then piped from the probe back to the amplifier where it is quantitated. The fraction of incident light that is reflected is sensitive to the refractive index difference between the probe and the material at the interface between the probe and the unknown solution. Specific binding of protein to the epitope tag increases the local index of refraction and this can be read out as a perturbation in the amount of incident light that is reflected. The probes can be standardized (shown as 1 µg/ml, 10 µg/ml and 100 µg/ml curves) against solutions containing known concentrations of epitope tagged proteins. The standardized probes are then dipped into the microtiter plate of unknown expression system components. The kinetics of association of the expressed proteins with the antibody on the SPR probe are measured and the concentrations of tagged protein in the unknown samples is calculated by comparison with the standard curve.

In addition to SPR, other approaches to protein detection can also be used. For example, the in vitro translated protein of interest can be a fusion protein comprising a fluorescent or luminescent moiety such as a GFP protein. The amount of translated protein is proportional to the level of, e.g., GFP fluorescence and can be read by optical or spectroscopic methods.

Similarly, an epitope tag can be added as an invariant portion of any library (e.g., any shuffled library). A fluorescently labeled antibody to the tag is added to the translation mix and allowed to bind. Either this binding changes fluorescence, e.g., by FRET quenching/dequenching or an on line separation of antibody and protein is achieved by parallel capillary electrophoresis (e.g., in a microfluidic chip format).

In one embodiment, a specific invariant amino acid sequence is added to the library of shuffled proteins that encode an alpha helix which contains 4 Cysteine residues in a tetrahedral array. FlAsH is added to the solution and binds to the epitope with a corresponding increase in fluorescence. There is no fluorescence background and so no separation is required. See also, Tsien et al (1999) "Target Protein Sequences for Binding of Synthetic Biarsenical Molecules" WO 9921013 A1.

E. Array Correspondence/Secondary Diversification Module

The system optionally includes an array correspondence module which identifies, determines or records the location of an identified product in the array of reaction mixture products which is identified by the one or more product identification modules. The array correspondence module can also determine or record the location of at least a first nucleic acid member of an array, or a duplicate thereof, or of an amplified duplicate array, where the member corresponds to the location of one or more member of the array of reaction products. Most commonly, this correspondence module takes the form of a digital system having a query function, and, e.g., a look-up table that records the correspondence information across two or more arrays. For example, the query function can act on a user input to determine correspondence of array members in the look-up table, or the system can be configured automatically to assess correspondence of any array member which meets a selected criteria (e.g., activity determined by the product detection module). Such correspondence modules can easily be programmed using available database or spreadsheet programs such as Microsoft Access™, Microsoft Excel™, Paradox™, Quattro Pro™, or any other available spreadsheet/database program.

This correspondence system can include a one or more secondary selection module which selects at least one array member as a substrate for a further diversification reaction (e.g., by shuffling). The selection is based upon the location of a product identified by the product identification modules and the corresponding location of the corresponding nucleic acid array member identified by the array correspondence member.

In shuffling embodiments, the secondary selection system optionally includes a secondary recombination element which physically contacts members of the starting arrays of nucleic acids, or duplicates or amplicons thereof, to each other or to additional sources of nucleic acids, thereby permitting physical recombination between the first and additional members. In other aspects, all or part of the recombination is performed in silico, and no physical contact is required for recombination (or other diversity generating reactions).

a) Laboratory Information Management System

In general, data tracking can provide maintenance of the associations between array elements and results which correlate to the array elements. For example, sets of results on projects can include association of three relationships:
1. Array member ID—Data Sample ID;
2. Data Sample ID—Data Values;
3. Data Values—Processed Results.

Relationship 1 includes the association of array member names with the identifiers of tested samples (e.g., "Plate 1, well A-4"). Relationship 2 includes the association of device data output with the tested samples. Relationship 3 includes the association of device output values with results.

In order to utilize systems and devices herein, an integrated sample tracking process can be used based on commercially available LIMS (Laboratory Information Management System) products. As each sample goes through many different formats (pooling, deconvolution, dilution, hit picking, assorted assay formats, etc.) it is useful to have a very flexible LIMS to capture that distribution of formats of parental samples and subsequent progeny samples. The generated data for each sample is subsequently integrated with each format and accessible for the user in conjunction with the samples' "pedigree." The data is displayed through any one of many commercially available data analysis software such as SpotFire or ActivityBase to allow monitoring of the process.

For all data-generating devices, the output data can be associated with the sample ID. In other words, each data point can be associated with the well analyzed. This is relatively simple for most systems designed to scan microplates, such as plate readers, but can be more complex for systems where the analytes are sampled from their container, such as in mass spectrometry and HPLC. Where necessary, custom software is used to link data output to sample ID and output the resulting table to the database in a standard format.

HTP screening generates huge amounts of data, which is preferably stored in an organized way. Where the amount of data is too large for easy storage on data servers, a system for data archival and retrieval is also incorporated. The system can include, e.g., a table that tracks datafiles (which can be, e.g., data folders), based on, e.g., name and ID. The table has a column to store both a current location (such as a hard disk), e.g., in URL format, and a location on a backup disk. Backup disks (CD/DVD) themselves have an ID which can be tracked. Archiving can be done automatically, e.g., based on acquisition date or by user triggering. Backed up files are retained on the server and flagged. Once a backup takes place, the user can delete the file from the server.

F. Elements for Arraying and Handling Fluids in the Device

There are a number of common elements to the integrated systems herein which form a "backbone" for the device. For example, the device includes array elements, liquid handling elements, robotics (e.g., for moving microtiter plates) and the like.

(1.) Liquid Handler

The reactant arrays of the invention can be either physical or logical in nature. For the generation of common arrangements involving fluid transfer to or from microtiter plates, a fluid handling station is used. Several "off the shelf" fluid handling stations for performing such transfers are commercially available, including e.g., the Zymate systems from Zymark Corporation (Zymark Center, Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides an interface between standard library formats and chip technologies. Furthermore, the patent and technical literature includes examples of microfluidic systems which can interface directly with microwell plates for fluid handling.

Thus, generally, microfluidic systems are commercially available. In addition, university groups such as Mark Burns' research group at The University of Michigan also describe various microfluidic systems. Accordingly, general fabrication principles and the use of various microfluidic systems is known and can be applied to the integrated systems of the present invention.

(2.) Array Configurations

Any of a variety of array configurations can be used in the systems herein. One common array format for use in the modules herein is a microtiter plate array, in which the array is embodied in the wells of a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use.

In addition to liquid phase arrays, components can be stored in solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by local rehydration (e.g., using a pipette or other fluid handling element) and fluidic transfer, or by scraping the array or cutting out sites of interest on the array.

While arrays are most often thought of as physical elements with a specified spatial-physical relationship, the present invention can also make use of "logical" arrays, which do not have a straightforward spatial organization. For example, a computer system can be used to track the location of one or several components of interest which are located in or on physically disparate components. The computer system creates a logical array by providing a "look-up" table of the physical location of array members. Thus, even components in motion can be part of a logical array, as long as the members of the array can be specified and located.

G. DNA Shuffling on Solid Supports

For clarity, much of the preceding discussion describes the use of liquid phase arrays such as those utilizing microtiter tray formats. However, as noted throughout, solid phase arrays represent an alternative and also preferred format for performing many operations of the systems herein. The following is a description of exemplary solid-phase shuffling formats.

As noted, DNA shuffling is a very powerful technique to generate diverse gene libraries from known gene family members through a combination of recombination, mutagenesis and selection. Current DNA shuffling methods can use primerless PCR assembly, where fragments of genes reassemble based upon the kinetics of oligo re-annealing, which are then extended by DNA polymerase in the presence of dNTPs.

A modification of this DNA shuffling process is performed where oligo annealing and extension by DNA polymerase proceed while the oligonucleotide, or alternatively, the single-stranded template polynucleotide is tethered to a solid support (or substrate). The method below offers advantages to traditional solution based assembly in that assembly occurs sequentially. Therefore, the specific fragments added at each step can be more tightly controlled than solution based assembly. Also, this embodiment optionally combines the assembly and rescue steps, reducing the complexity of the overall shuffling process. This new approach provides novel shuffling methods that utilize technology similar to the combinatorial synthesis of peptides and small molecules.

For example, one may create shuffled libraries by starting assembly using an oligonucleotide(s) that is/are tethered to a solid support. The process typically involves tethering the oligonucleotide(s) to a solid support so that at least about 10-20 nucleotides including the 3' hydroxyl are exposed to solvent. In some embodiments, a synthesizer module is used to synthesize one or more nucleic acid fragment on a solid support. Such fragments are optionally created from one or more parental nucleic acids sequences by a computer operably coupled to the synthesizer module.

In any case, the oligo(s) are then typically annealed to mixtures of single stranded nucleic acid generated, e.g., by the processes discussed herein, for example, partial DNAse digestion of either PCR products of several related genes or genomic or cDNA from homologues of interest. The annealed hybrids are extended, typically with DNA polymerase (for example, with a thermostable DNA polymerase such as Taq DNA polymerase), generating a bound library of extended, solid-support tethered double stranded duplexes. The bound library is denatured to release the second strand. The tethered oligo is reannealed to the released library of DNAse treated fragments and extended. This process is repeated until fragments of desired length are formed. The library of shuffled products is released from the solid support and used as desired, e.g., for in vitro transcription translation or cloning into vectors.

At any of these steps, the solid support allows one to purify the reaction products taking advantage of the properties of the solid support (for example, the solid support can include magnetic beads that can be manipulated by applying a magnetic field.

One feature of this approach is that by using an oligonucleotide of precise length to tether to the support (for example a 38 nt oligo) one has pre-determined the location of the first chimera (in the example, it will begin at nucleotide 39). This is true for the first oligonucleotide. This feature can be useful in keeping parts of the nucleic acid constant, e.g., for cloning purposes or where a feature is not desired to be diversified.

One can use this feature in (at least) two ways. First, if the genes are cloned into a similar vector, the first oligo can anneal to vector sequence (for example immediately adjacent to the gene coding region). In this way, the entirety of new gene combinations are synthesized from DNA fragments with randomly generated ends (e.g., from DNAse treatment), but the vector sequence is kept constant for cloning purposes.

Where one desires to eliminate this feature (where all nucleotides are to be varied for diversity generation purposes), one can tether a mixture of oligonucleotides of varying length to the support (for example, oligos from 35-50 nucleotides give chimeras starting in range of nt36 to nt51), or one can vary the sequences of the tethered oligonucleotides to vary this region, e.g., according to the various in silico and oligonucleotide-mediated methods discussed above.

In typical DNA shuffling, extension of DNAse fragments occurs at any place annealing occurs. In contrast, tethering the oligo to solid supports likely restricts the choice of oligo to those at the ends of the DNA of interest (although one can tether using oligos designed to regions internal to the gene of interest, ultimately the entire DNA of interest is usually, though not always, re-assembled, e.g., to generate a full length, or substantially full length, heterolog).

The addition of DNA fragments to the tethered oligonucleotide is typically sequential. The assembly process can be paused at any step and conditions changed. For example, one can add or subtract gene fragments during the assembly. For example, one can start the assembly with genes 1, 2, and 3, but remove gene 1 after initial round. Similarly, particular blends of genes can be selected at any stage to bias recombination (at any stage) towards one or more parental type. For example, one can change from genes 1-4 to only genes 1 and 4 after 5 extensions; or alter the representation of any gene in the recombination process, e.g., change gene 1, e.g., from 1:4 to 1:2 for the last 3 extensions to bias the recombination, e.g., to achieve selectable gene blending. Alternatively, one can alter PCR conditions for parts of the assembly, e.g., longer extensions at the 3' end. This provides an improved level of control over the progress and outcome of shuffling experiments. For example, one can add DNAse fragments corresponding to the 5' end of genes separately from fragments corresponding to the 3' end.

An additional feature of the invention is that assembly and rescue can occur simultaneously. Also, the sequential nature of the addition of DNA allows for combinatorial DNA shuffling.

DNA shuffling can also be conducted on multiple genes in parallel in a single reaction pot. For example, DNA hybridization is a discrete process; under stringent conditions, oligos from gene A will only recognize DNA from gene A or related sequences, and 'ignore' oligos of non-gene A sequences. Assuming that gene A is unrelated to gene B, one can mix solid supports containing oligos from gene A and gene B, and mix them simultaneously with the DNAse treated fragments. Thus, several genes can be shuffled simultaneously, in the same reaction vessel.

As noted, solid phase shuffling provides several advantages. It is worth noting certain additional advantages. For example, solid phase synthesis of nucleic acids, proteins and other relevant components is straightforward, simplifying automation processes. Similarly, tethering optionally utilizes the attachment of oligos to gene chips, a commercially available technology platform (e.g., from Affymetrix, Santa Clara, Calif.). One may generate gene chips for shuffling or other diversity generation reactions.

Further, since the addition of DNA to the tether (assembly) is stepwise, this step by step process can be controlled (i.e. the reaction can be stopped at any point and conditions changed, such as temperature, salt, extension time, etc).

One can include RNA polymerase promoters on oligos used in the assembly (i.e., an oligo 5' to the coding region), and thereby transcribe RNA in vitro from the solid support linked gene libraries. Since one can transcribe RNA in vitro from these libraries, one can also translate in vitro to directly generate libraries of proteins without cloning. Even if yields of proteins from in vitro translation are low, the translation nonetheless allows very fast screening methods to be employed. Even low levels of expression are sufficient for a variety of methods such as antibody-based screening methods (e.g., ELISA) and enzyme-based detection assays in which signal is amplified in the assay process.

Because tethered DNA is easily purified, libraries can be pre-screened prior to cloning, to select for certain traits, or to select against certain traits (for example hybridization to a gene of interest, or lack of hybridization to the gene of interest), e.g., using appropriate gene chips.

Finally, the technology of using tethered molecules offers advantages in library tracking and cataloging.

Methods to purify only desired shuffled genes can be employed. For example, it is often advantageous to purify only those shuffled genes that are full-length (partial sequences are often less likely to be active). For example, one can synthesize a shuffled library with a tethered oligo that lies 3' to the gene of interest, using an oligo that incorporates a promoter for an RNA polymerase (eg. T7 RNA polymerase) 5' to the coding region in the assembly process. RNA is transcribed using T7 polymerase. The resulting sample is treated with nuclease that destroys single stranded DNA but protects RNA/DNA hybrids (for e.g. S1 or Mung bean nuclease). DNA still linked to the solid support is purified. The sample is heated, or RNAse treated to remove RNA. An oligo that anneals to sequence near the 5' end of the gene (internal to T7 polymerase promoter, but 5' to region of interest) is hybridized. The single stranded DNA product is extended using DNA polymerase to give a double stranded product. The materials is removed from solid support and cloned, or is in vitro transcribed (in place or in another reaction vessel).

Tethering methods include: chemical tethering, biotin-mediated binding, cross-linking to the solid support matrix (e.g., U.V., or florescence activated cross-linking) and the use of 'soluble' matrix, such as PEG, which can be precipitated by ETOH or other solvents to recover bound material (see Wentworth, P., 1999, *TIDTECH* 17:448-452).

(1.) Combinatorial Shuffling Using Solid Supports

By performing diversity generation reactions such as shuffling on solid supports, the variation accumulated in such experiments can be controlled. By using oligos linked to solid supports as outlined above, one can perform sequential additions of DNA by annealing and extension.

In one specific embodiment, this process is performed by: (1) for each family member, PCR amplifying the region of interest, digesting with Dnase, and isolating fragments. (2) Placing Dnased fragments for each gene in a separate 'cup' (i.e., a cup for gene A, a cup for gene B, a cup for gene C, a cup for gene D). Each cup contains DNA fragments representing the whole of each gene, but each gene has its own cup. (3) In the first step, a single stranded oligonucleotide linked to a solid support, (with 10-30 bp of accessible DNA, and an exposed 3' hydroxyl) is divided into several equal fractions (in this example 4 fractions). Each fraction is placed into a separate 'cup' of DNA fragments from either gene A, B, C, or D. The 'cups' are heated to denature any double stranded hybrids present in each cup, then cooled to allow DNA to anneal. During this annealing, fragments homologous to the solid support-linked oligo anneal to this oligo. The annealed products are then extended with DNA polymerase to yield double stranded product, linked to the solid support (in this example, one fourth of the DNA is a 'cup' containing gene A sequence, one fourth in a cup containing gene B sequence, one fourth gene 3, one fourth gene 4; however, an advantage of the system is that any ratios of starting genes may be used, e.g., to bias resulting recombinant nucleic acids towards one parent type). Following the 'extension' reaction, the double stranded DNA fragments are removed by virtue of their solid support linkage (for e.g. magnetic beads), and pooled into one tube (or other container). These hybrids are heated to denature the duplexes, and the unlinked strand washed away.

In a second round, the newly extended single stranded fragments are again randomly divided into pools (in this case 4), and each portion is again placed into one of the available cups (in this case 4 cups, for genes A, B, C, D). The 'cups' are heated to denature any double stranded hybrids present in each cup, then cooled to allow DNA to anneal. During this annealing, fragments homologous to the solid support-linked single stranded polynucleotide anneal. The annealed products are then extended with DNA polymerase to yield double stranded product, linked to the solid support (in this example, one fourth of the DNA was is a 'cup' containing gene A sequence, one fourth in a cup containing gene B sequence, one fourth gene3, one fourth gene 4). Once again the extended products are removed and re-pooled into one container. This container is heated to denature the double stranded duplexes, and the strand unlinked to the support washed away. The support-linked polynucleotide collection is now divided once again, and the process repeated.

After a sufficient number of annealing/extension reactions, the final single stranded DNA products can be converted to double stranded DNA by annealing an oligonucleotide internal to the last oligonucleotide capable of attachment, and extended with DNA polymerase and dNTPs. The double-stranded products are then released from the solid support, and cloned. In order to facilitate cloning, several rounds of PCR amplification may be performed in the tube containing the support linked oligonucleotide, and this may act as a template for PCR while still attached to the solid support. Cloning can also be facilitated by incorporating the recognition sequence for one or several restriction nucleases into the sequence to be incorporated at each end of the assembled gene fragment.

One can design methods to eliminate support-linked oligos that fail to extend in any one step, if this is a source of substantial background.

(2.) Shuffling Using a Tethered Single-Stranded Template

As an alternative to tethering oligonucleotide primers to a solid support, single-stranded template polynucleotides can be immobilized on a solid support as described above (e.g., by: chemical tethering, biotin-mediated binding, cross-linking to the solid support matrix, etc.). In one preferred embodiment, the template polynucleotides are arrayed by depositing a solution containing the template nucleic acids on a glass slide coated with a polycationic polymer such as polylysine or polyarginine (see, e.g., U.S. Pat. Nos. 5,807,522 and 6,110, 426 "METHODS FOR FABRICATING MICROARRAYS OF BIOLOGICAL SAMPLES" to Brown and Shalon. The template polynucleotide can be either DNA or RNA, or a combination of DNA and RNA. A wide variety of suitable templates exist, and can be selected by the practitioner depending on the specific application. For example, desirable template polynucleotides include genomic and/or expressed (e.g., cDNA) sequences including coding, non-coding, anti-sense, naturally occurring, artificial, consensus, synthetic and/or substituted (e.g., dUTP substituted DNA) molecules. In some applications, a population of identical polynucleotides are arrayed on a support. In other applications, templates representing a diverse population of polynucleotides are attached to a support. For example, entire genomes, e.g., bacterial or fungal genomes can be arranged in a physical array on a glass slide or silicon chip. In yet other applications, the expression products of a cell, or a subset thereof are affixed to the support. Such expression products can be RNA or cDNA, and in some cases comprise a library of expression products. The present invention is not limited by the choice of template, or the source of polynucleotide selected. Such routine selections are based on the particular application, and will be readily apparent to one of skill in the art.

Figure 31:
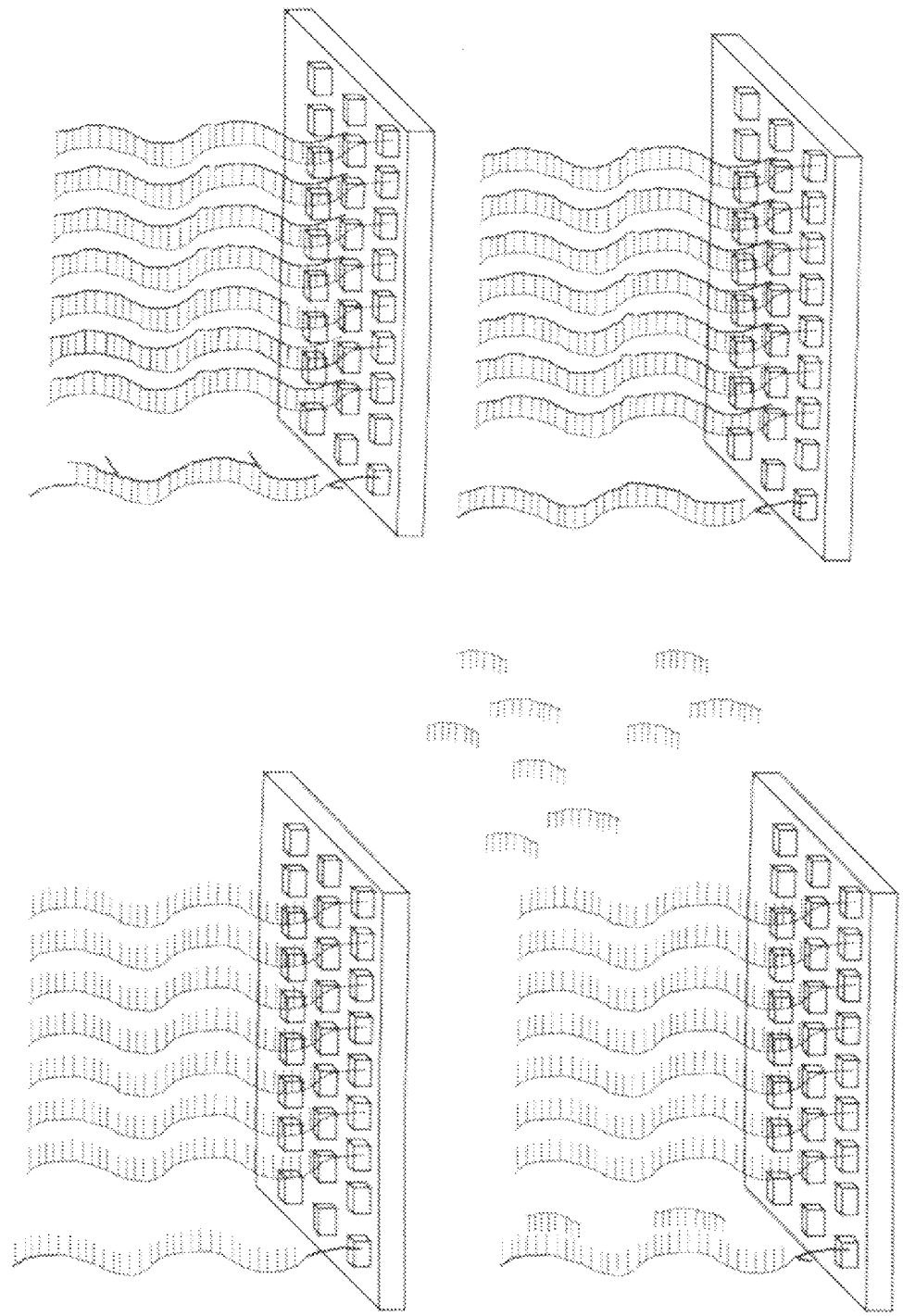
FIG. 31 schematically illustrates recombination of nucleic acids tethered to a solid support.

Diversity is introduced by hybridizing single-stranded nucleic acid fragments to the immobilized template polynucleotide. Typically, the nucleic acid fragments will possess regions of sequence similarity (or identity) as well as regions of dissimilarity. In many cases, annealing of multiple complementary (or partially complementary) fragments results in hybridization of partially overlapping fragments to the immobilized template. A polymerase (e.g., a DNA or RNA polymerase such as a thermostable DNA polymerase) is used to extend the annealed primers generating a heteroduplex made up of the template and a substantially full-length heterolog complementary (i.e., that hybridizes) to the template nucleic acid. Optionally, the unhybridized overhanging regions can be removed, e.g., with a nuclease, prior to or following extension; and/or the gaps between annealed (and extended) fragments joined with a ligase. In some cases, it is desirable to employ a nuclease or ligase with polymerase activity. This process is illustrated in FIG. 31, in which a solid phase-bound template is hybridized to appropriate fragments. As shown, the fragments are extended, if desired, unwanted flaps are digested and breaks in the resulting extended nucleic acids sealed with ligase.

The process can be repeated for multiple cycles by denaturing the heteroduplex and hybridizing the template to a new set (or subset) of nucleic acid fragments. The recombinant heterologs generated in each cycle are optionally recovered between successive cycles of denaturation and reannealing. Most typically, recovery relies on amplification, although other methods such as hybridization and/or cloning are also feasible. Optionally, the recovered heterolog can be used directly in additional diversity generating procedures, as described herein and in the cited references.

Frequently, recovery is facilitated by incorporating a sequence that serves as a primer for the amplification reaction within the template or a fragment nucleic acid sequence. For example, the template can incorporate recognition sequences for "universal" and "reverse" primers at its 5' and 3' ends, respectively. Among the fragments hybridized to the template are included the corresponding universal and reverse primers. Subsequent amplification of recombinant polynucleotides then proceeds according to routine amplification procedures.

Figure 32A:
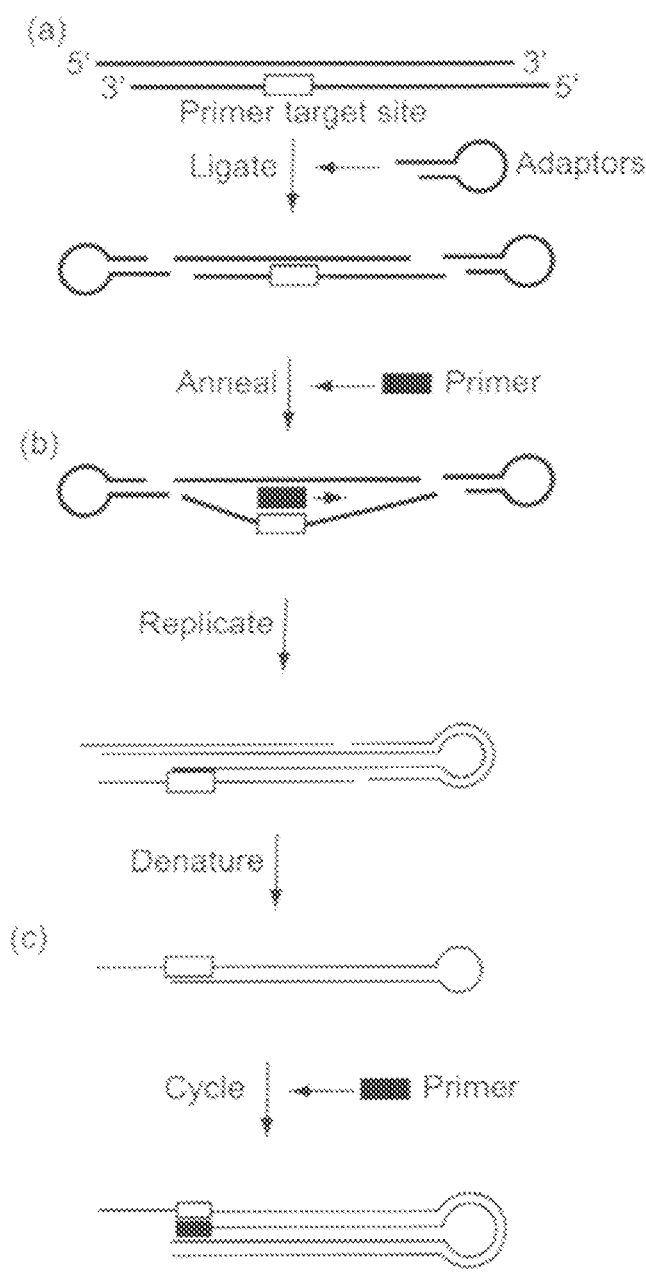
FIGS. 32A and B schematically illustrate recovery procedures using "boomerang" and "vectorette" amplification strategies.

In addition to the commonly used linear sequence primers (such as universal and reverse primers), the present invention makes use of primer sequences with a specialized secondary structure for facilitating recovery of the recombinant heterologs generated by extension of fragments annealed to a specified template. For example, a boomerang DNA amplification reaction is primed by a single primer located internal to recombinant heterolog (for example, a conserved region of the template/fragments can be selected for use as a primer binding site). As illustrated in FIG. 32A, adaptors that assume a hairpin configuration are ligated to the end(s) of the heteroduplex which is optionally released from the solid support. Following denaturation of the heteroduplex, and binding of the internal primer, extension by a DNA polymerase results in extension of a product including sequences identical to the heterolog and the template as an inverted repeat. Typically, a restriction enzyme recognition site is incorporated into the hairpin, permitting separation of the template and heterolog sequences.

Figure 32B:
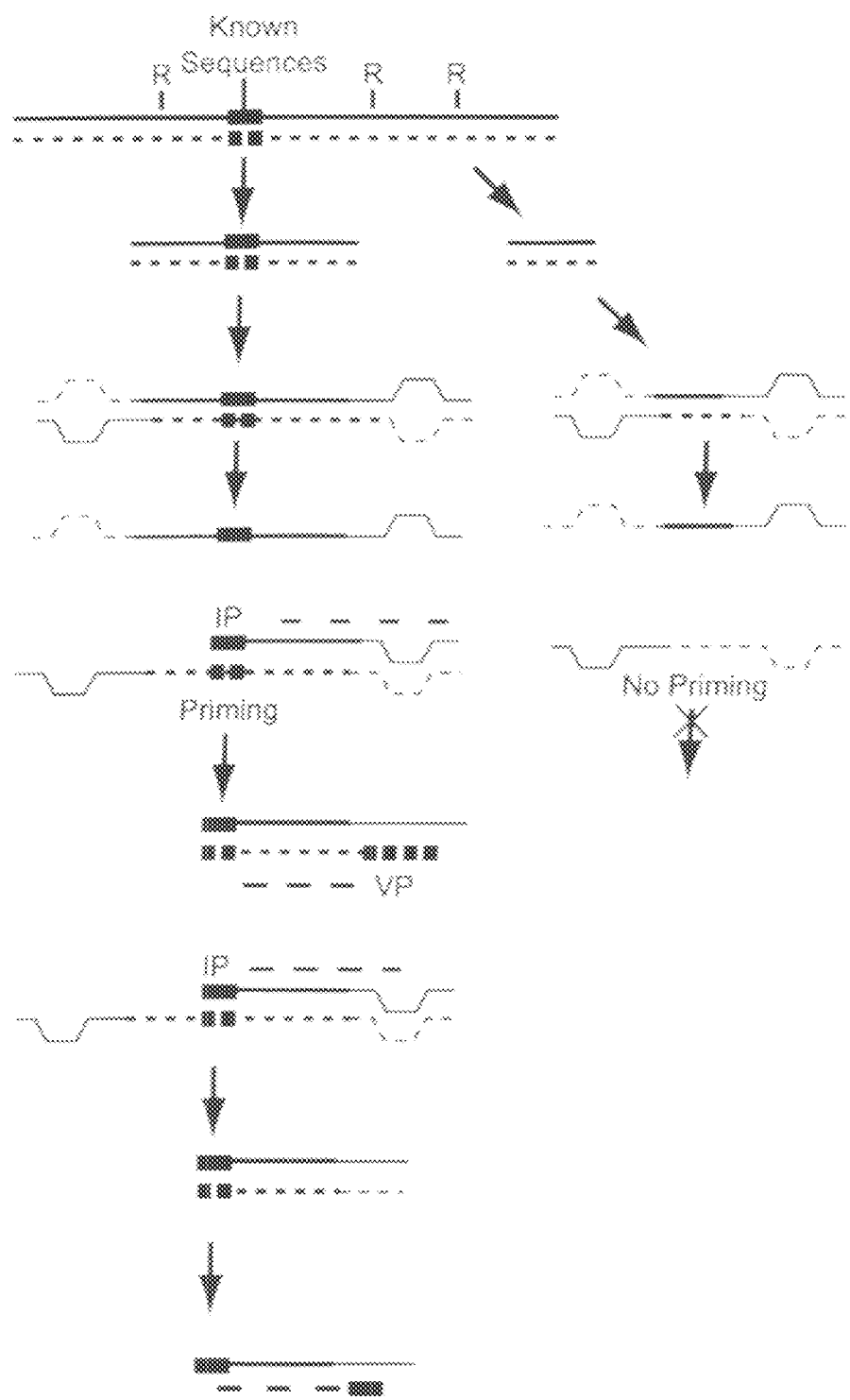

Another alternative is to employ a "vectorette." In this approach, amplification occurs between an internal primer and a primer within the vectorette, a pair of synthetic oligonucleotides having regions of duplexed DNA flanking a central mismatched region that provides a primer binding site, as illustrated in FIG. 32B. If the target nucleic acids are cleaved with a restriction enzyme prior to ligation of the vectorette sequence, only restriction fragments including the internal primer binding site are amplified. A first extension cycle results in a duplex corresponding to the recombinant heterolog which can be simply amplified using the internal and vectorette primers. A variation of this approach is the "splinkerette," in which the vectorette incorporates a looped-back hairpin structure that decreases end-repair priming and reduces non-specific priming. Further details on vectorette use and construction can be found in Arnold et al. (1991) "Vectorette PCR: a novel approach to genomic walking" *PCR methods Appl.* 1:39-42 and Hengen (1995) "Vectorette, splinkerette and boomerang DNA amplification" *Trends Biochem Sci.* 20:372-3.

As previously described, recombinant nucleic acids produced by hybridization and extension of nucleic acids on an array can further be translated to provide reaction products suitable for screening. Alternatively, the recombinant heterologs described above can be transformed and expressed in cells to facilitate screening by structural and/or functional means to identify recombinants with desirable properties. Typically, but not necessarily, the recombinant nucleic acids are introduced into host cells in a vector, such as an expression vector. Vectors and cells incorporating recombinant polynucleotides produced by the above described recombination on a solid phase support are also a feature of the invention.

H. An Example Integrated System for Diversity Generation Via Shuffling

This example "shuffling machine" is an integrated system which converts parent DNA into improved shuffled clones, which are optionally used as parent DNAs for subsequent shuffling. The machine is based upon a set of modules as discussed above that are integrated to improve function and throughput.

The machine performs a number of tasks, using a liquid handling station, a PCR system, a fluorescence/absorbance plate reader, a plate/reservoir storage device and a robotic system for shuttling plates between the modules. This machine performs the entire shuffling process automatically in a microtiter plate format.

Figure 2:
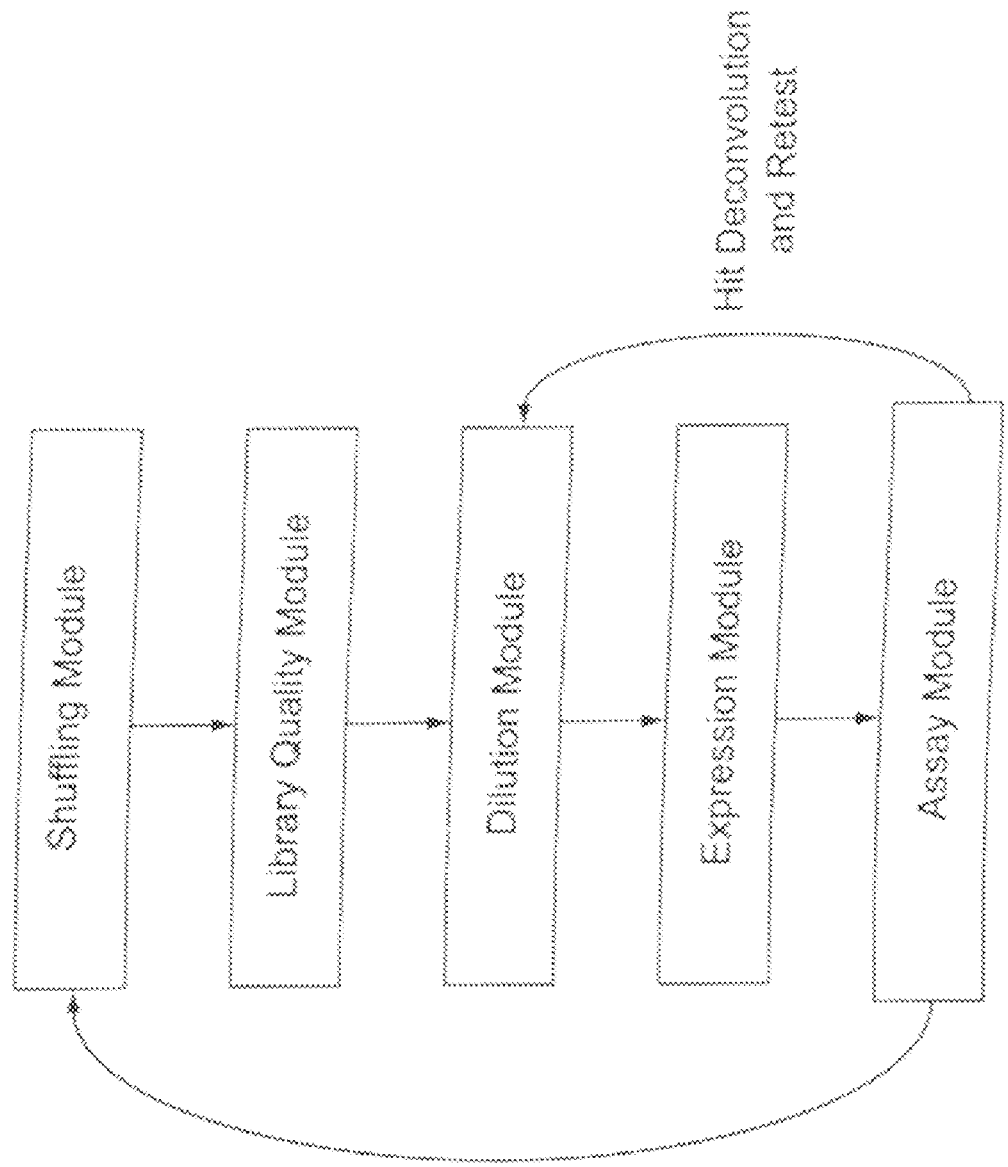
FIG. 2 provides an example schematic of the modules of an integrated shuffling machine.

For clarity of description, the machine is split into a number of modules; however, module functions can be combined in practice to simplify the overall system. An example schematic of the modules of an integrated shuffling machine is provided by FIG. 2. The modules include a shuffling module, a library quality assessment module, a dilution module, a protein expression module, and an assay module. Typical integrated device elements include thermocyclic components, single and multi-well liquid handling, plate readers and plate handlers.

(1.) The Shuffling Module

This example shuffling module uses a liquid handler, a PCR machine, a fluorescent plate reader, and a plate/reservoir handling and storage system to perform an automated shuffling reaction (as noted, shuffling is one preferred diversity generation reaction performed by the methods and systems herein).

Figure 3:
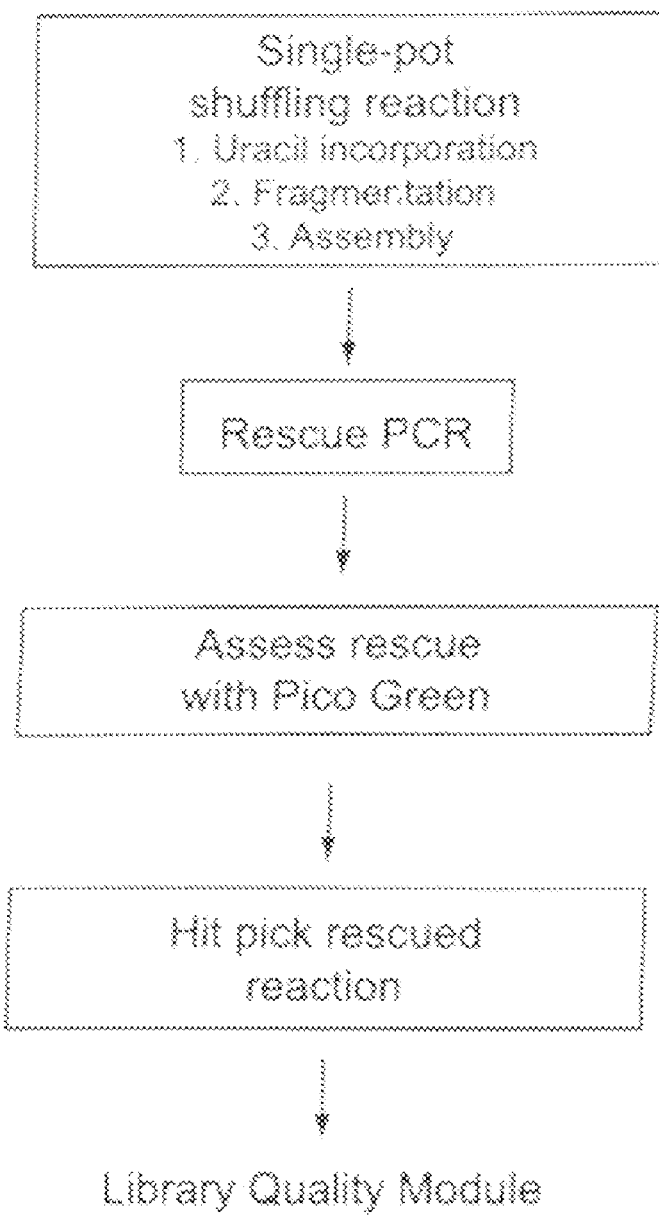
FIG. 3 provides a schematic representation of the steps performed by an exemplar shuffling module. As shown, a single pot reaction is performed, utilizing uracil incorporation, DNA fragmentation and assembly. A rescue PCR is performed, the results assessed with PicoGreen and any wells that test positive for PicoGreen incorporation are rescued and sent to the library quality modules.

FIG. 3 provides a schematic representation of the steps performed by this exemplar shuffling module. In particular, a single pot reaction is performed, utilizing uracil incorporation, DNA fragmentation and assembly. A rescue PCR is performed, the results assessed with PicoGreen and any wells that test positive for PicoGreen incorporation are rescued and sent to the library quality modules.

As noted, DNA fragmentation is achieved using the uracil incorporation strategy noted above. Different wells of a microtiter plate are set up with different reaction conditions, leading to different DNA size fragments and different ratios of parental nucleic acids (the diversity target sequences). The conditions for the uracil fragmentation is defined by the user as are the assembly and rescue protocols.

In other embodiments, the conditions and/or protocols are calculated using a set of computer understandable instructions, e.g., embodied in a computer or web page operably coupled to the shuffling module. Alternatively, the shuffling module is optionally a programmable or programmed module that calculates appropriate conditions, e.g., based on empirical data, theoretical predictions and/or user input.

Once the fragmentation is complete (as selected by the user) the fragmented DNA is transferred to a PCR module for the assembly reaction. An aliquot of the assembled DNA is then transferred to a new PCR plate for a rescue PCR reaction using standard primers.

The success of the shuffling reactions are measured by removing an aliquot from the rescue PCR plate and followed by transfer to a plate containing Pico green dye.

Wells that contain double stranded DNA (i.e., give fluorescence with Pico Green) are collated by the liquid handler, using hit pick software, into plate(s) that contain all the shuffled clones, which are passed on to the library quality module.

The liquid handler then transfers (and, optionally, mixes or otherwise modifies materials) to make up solutions from solvent/reagent reservoirs, setting out an array of reactants. The information as to which solutions are plated in which positions in an array is tracked through subsequent manipulations in all modules, along with the PCR conditions which are used for amplification.

Once the rescue PCR is performed, the success of the recombination is assigned based upon the presence of double stranded DNA as measured by Pico Green fluorescence. Full length ds DNA can also be unambiguously identified and quantified by capillary electrophoresis (e.g., in parallel formats similar to a parallel capillary electrophoresis sequencer such as MEGABASE or by parallel capillary electrophoresis on a chip) with detection by fluorescence. Successful recombination leads to predominantly a single full-length species in the rescue PCR which is proportional to an arbitrary level of fluorescence. As noted above, Pico green is a quantitative measure of the amount of ds DNA present and this information about the DNA concentration in each well is used in the downstream processing modules. The hit picking software takes the positive wells and converts them to new well positions without loss of information. The set of positive wells across all of the plates is referred to as a "collated library."

Another exemplary shuffling module or diversity generation device comprises a programmed thermocycler and fragmentation module operably coupled to the thermocycler. The programmed thermocycler typically comprises a thermocycler operably coupled to a computer comprising one or more instruction set. In other embodiments, the instruction sets are embodied in a web page or in the thermocycler itself, e.g., a Java program. For example, a network card is optionally added to a thermocycler or the internal software of a commercially available thermocycler is altered to provide the instruction sets described below.

The instruction sets typically comprise computer understandable instructions for performing one or more of the following: calculation of an amount of uracil and an amount of thymidine for use in the programmed thermocycler; calculation of one or more crossover region between two or more parental nucleotides; calculation of an annealing temperature; calculation of an extension temperature; and/or selection of one or more parental nucleic acid sequence. These calculations are typically made based on one or more of: user input, empirical data, and theoretical predictions, e.g., of melting temperature. Such melting temperature predictions are well known to those of skill in the art. In addition, predictions are also optionally used to calculate the effect of annealing temperatures on the number of possible crossovers. Typical input data include, but are not limited to, parental nucleic acid sequences, desired fragmentation lengths, crossover lengths, extension temperatures, and annealing temperatures. Empirical data typically comprise comparisons of one or more nucleic acid melting curve or melting temperature.

The computer or programmable thermocycler typically calculates possible crossover regions between parental nucleic acid sequences, depending on the annealing temperature and extension temperatures to be used in the amplification steps. The computer would then set up one or more cycle for the thermocycler. For example, a cycle in the thermocycler typically includes amplification of one or more parental nucleic acid sequence, fragmentation of the one or more parental nucleic acid sequence to produce one or more nucleic acid fragments; reassembly of the one or more nucleic acid fragment to produce one or more shuffled nucleic acid; and, amplification of the one or more shuffled nucleic acid. Various robotics and plate handlers are optionally added to the device as described herein to transfer nucleic acids between the fragmentation module and the thermocycler.

In some embodiments, the thermocycler amplifies the various parental nucleic acids in the presence of uracil and the fragmentation device fragments the parental nucleic acids using various uracil cleaving enzymes. The programmable thermocycler in this embodiment typically directs a pause in the cycle to allow the addition of the enzymes to the reaction mixtures. In addition, the programmed thermocycler is used to calculate the ratio of uracil residues to thymidine residues to produce fragments of a desired mean length or size. For example, a length that leads to an optimized level of diversity in the shuffled nucleic acids is optionally selected. Fragmentation is optionally carried out in the presence of Taq/Pwo and outside primers so that the fragments are used directly in the reassembly/amplification steps of the cycle with appropriately calculated annealing and extension temperatures. Other fragmentation methods optionally used in a fragmentation module of the invention and operably coupled to a programmed thermocycler include, but are not limited to, sonication, DNase II digestion, random primer extension, and the like.

In another embodiment, a diversity generation device comprises a computer, a synthesizer module, e.g., a microarray oligonucleotide synthesizer such as an ink-jet printer head based oligonucleotide synthesizer, and a thermocycler. The computer typically comprises at least a first instruction set for creating one or more nucleic acid fragment sequence from one or more parental nucleic acid sequence. The synthesizer module typically synthesizes the one or more nucleic acid fragment sequence created by the computer; and the thermocycler generates one or more diverse sequence from the one or more nucleic acid fragment sequence, e.g., by performing an assembly/rescue PCR reaction as described above. For example, the synthesizer optionally synthesizes the nucleic acids fragments on a solid support as described above, e.g., using mononucleotide coupling reactions or trinucleotide coupling reactions.

In addition, the computer optionally comprises additional instruction sets, e.g., for determining a set of conditions for the thermocycler, e.g., to perform assembly/rescue PCR reactions.

For example, sequences, e.g., DNA, RNA, or protein sequences, are entered into a computer, e.g., character strings corresponding to the sequences. The computer is then used to generate a number of smaller sequences from which oligonucleotides can be created. These smaller sequences typically encode for some or all of the diversity of the original sequences entered. Typically, the instruction sets, e.g., in a computer, or web page, or both, limit or expand diversity of the one or more nucleic acid fragment sequence, e.g., a parental nucleic acid sequence, by adding or removing one or more amino acid having similar diversity; selecting a frequently used amino acid at one or more specific position; using one or more sequence activity calculation; using a calculated overlap with one or more additional oligonucleotide; based on an amount of degeneracy, or based on a melting temperature. The sequences are then used to drive a synthesizer, e.g., an oligonucleotide synthesizer, to create a physical manifestation of the sequences, e.g., on a support medium or solid support. Once the oligonucleotides are synthesized, the solid support is optionally digested or the oligonucleotides are cleaved from the support, e.g., using the thermocycler. The mix of oligonucleotides is then used in the thermocycler, which creates full length sequences, e.g., shuffled sequences. The computer is also optionally used to determine the best conditions for assembly/rescue reaction and digestion.

The above device allows one to generate synthetic shuffled genes starting with only sequence data in a matter of hours. Combined with a high throughput screening device the genes are all optionally created and screened for desired characteristics in less than a day. Therefore, the devices described above also optionally comprise screening modules, e.g., high-throughput screening modules, for screening the one or more diverse sequence for a desired characteristic. In addition, the computer is optionally used to select the original sequences used to create the fragments for shuffling, as described above.

The above diversity generation devices are typically used to allow rapid shuffling of nucleic acids to create new and diverse nucleic acids, e.g., enzymes. In some embodiments, the devices are incorporated into kits comprising, e.g., the devices, reagents, and appropriate protocols for shuffling. For example, a kit optionally comprises a diversity generation device as described herein, e.g., comprising a pre-programmed PCR machine, and one or more reagent for generating diverse nucleic acids. Reagents include, but are not limited to, E. coli, e.g., a dut-ung strain to make plasmids containing uracil instead of thymidine, PCR reaction mixtures comprising a mixture of uracil and thymidine, one or more uracil cleaving enzyme, a PCR reaction mixture comprising standard dNTPs, polymerases, and the like. Possible uracil cleaving enzymes included in the kit are uracil glycosidase, an endonuclease, such as endonuclease IV, and the like. The uracil/thymidine ratios included with the kit can be optimized to produce fragments of particular size or the protocols and/or diversity generation devices are programmed to calculate the appropriate ratios. Concentrations of dNTPs, Mg and other reagents are also optionally provided in optimized formats. In addition, the number of cycles is also optionally optimized, e.g., by a programmed thermocycler.

Polymerases included with the kits are typically thermostable polymerases, e.g., non-proof reading and proof-reading polymerases. In addition, the kits optionally include artificially evolved enzymes, e.g., artificially evolved polymerases that have a higher fidelity of incorporation for uracil residues, or are more active at 25° C. than those presently available.

The kits and devices above are optionally used to create en entirely automated format for generating diversity, e.g., through shuffling. In addition, they can be combined in a variety of ways with other components described herein, e.g., to create high throughput shuffling and screening capacity.

(2.) Library Quality Module

The library quality module utilizes the liquid handler, the PCR system, the Fluorescence Plate Reader and the Plate/reservoir handling and storage system.

Figure 4:
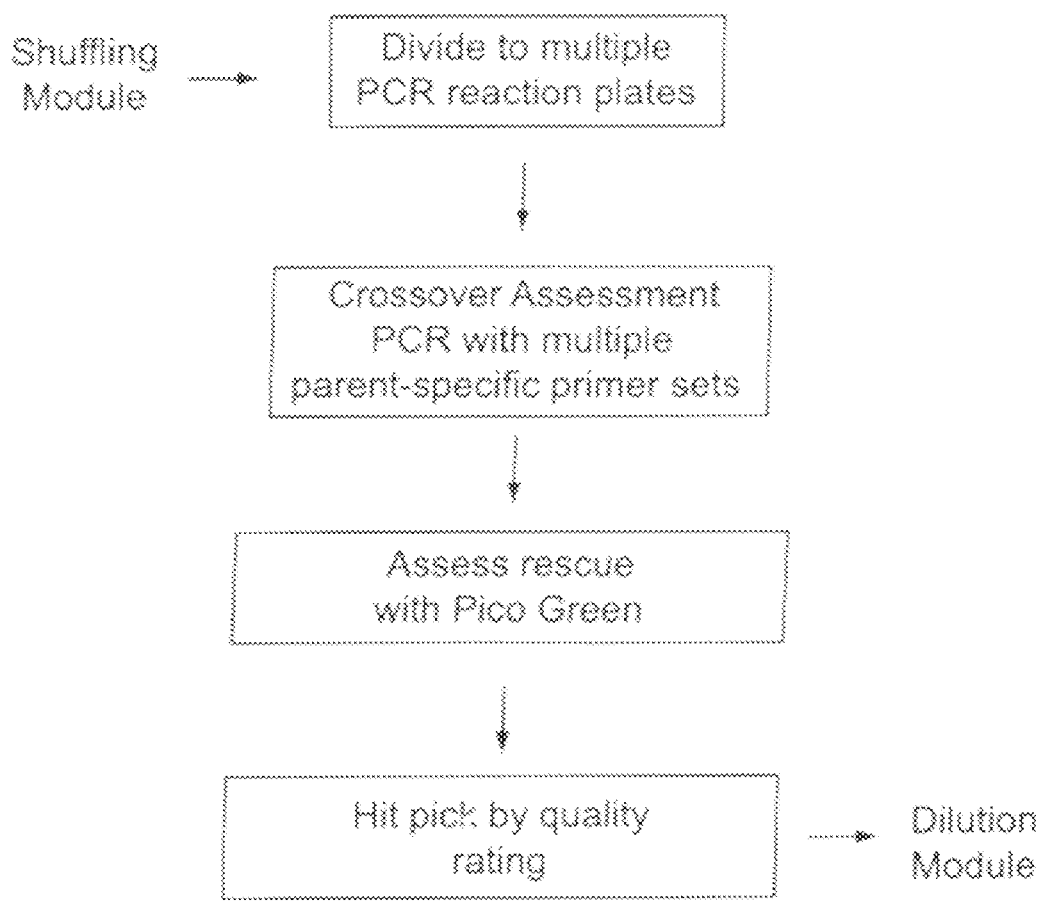
FIG. 4 provides a schematic overview of an exemplar Library Quality Module.

FIG. 4 provides a schematic overview of a Library Quality Module. In particular, the module divides, reactions into multiple plates, performs a crossover assessment, verifies PCR by PicoGreen incorporation and performs a hit pick quality rating.

The collated shuffled library from the shuffling module are diluted into one or more daughter plate to achieve a standard DNA concentration. This daughter plate is used as the source plate for DNA templates in quality assessment PCR reactions. Each parental DNA serves as the template to design forward and reverse PCR primers. These primers are mixed combinatorially such that recombinants can be detected (e.g., by mixing forward primer "A" which uniquely recognizes parent "A" with reverse primer "B" which uniquely recognizes parent "B," etc., covering all possible combinations of primers, or a desired subset thereof). The PCR reactions are transferred to a plate for Pico Green quantitation. The collated libraries are ranked with respect to diversity based on the level of fluorescence in each reaction and the number of PCR reactions that give amplification. The top collated libraries are then (optionally) re-collated to provide diverse collated libraries which are passed onto the in vitro transcription/translation module, or the hits are simply passed onto the in vitro transcription/translation module.

The DNA concentrations determined by the shuffling module is used to normalize template DNA concentrations in this module. The number of different PCR reactions run is determined by the number of starting parental sequences and the amount of information desired (e.g., $2^{no\ of\ parents-1}$ reactions gives good information) to determine the best library. An hypothetical "perfect" library gives the same amplification rate (and hence fluorescence) in each PCR reaction. While this does not give the number of crossover genes per se, it can be used to ensure that the there is a diversity of sequences that have at least one crossover.

(3.) Dilution Module

The dilution module uses the liquid handler, the PCR system, the fluorescence plate reader and the plate reservoir handling/storage system.

Figure 5:
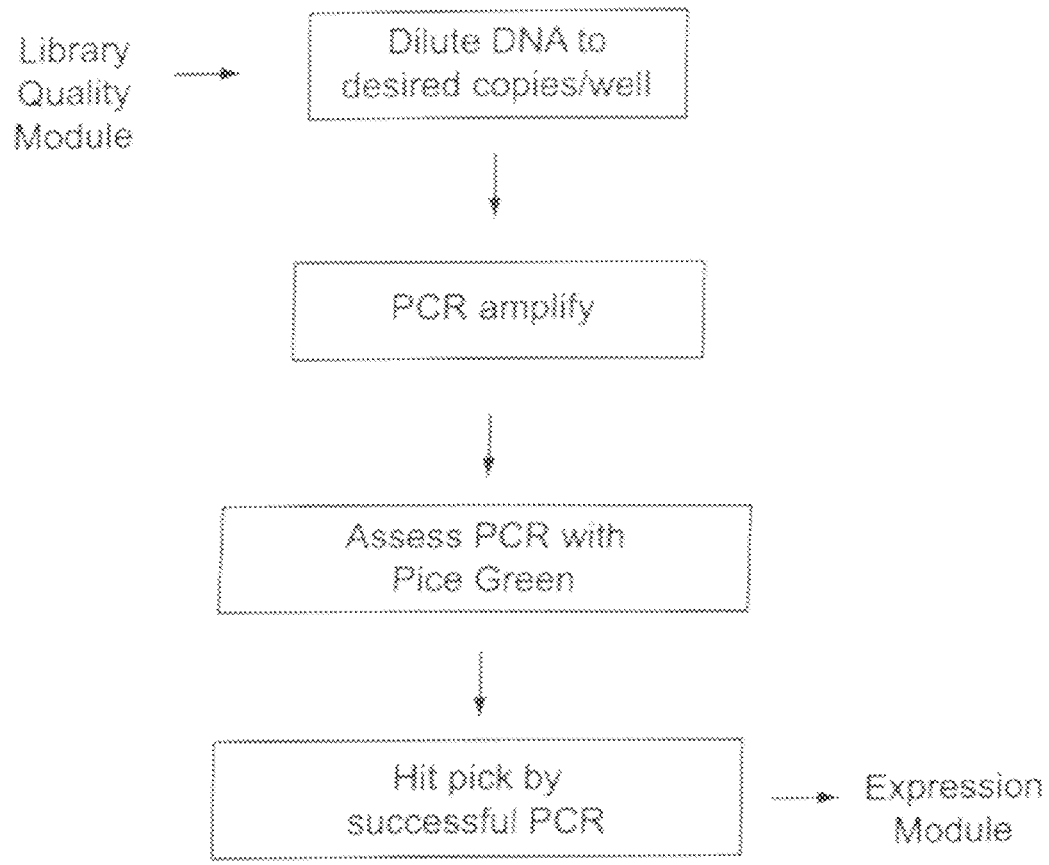
FIG. 5 provides a schematic overview of an exemplar dilution module's activities.

FIG. 5 provides a schematic overview of the dilution module activities. In particular, DNAs are diluted to the desired number of copies per well, PCR amplified, assessed for dsDNA by PicoGreen, and hits are picked.

The top collated libraries are reamplified, incorporating a reporter protein into the library, either as a fusion or as part of a translationally coupled system. An aliquot of this material is removed for quantitation and the library is diluted and dispensed into microtiter wells at an average concentration of about 1-10 DNA molecules/well.

The DNA is amplified by PCR to give enough DNA for efficient in vitro transcription/translation (ivTT) and an aliquot is removed for quantitation with Pico Green. The wells where DNA is amplified are then hit picked into wells ready for transfer to the protein expression module. A number of wells in each plate are filled with standard control constructs (e.g., wild type and a negative control) at the same concentration as the library clone pools.

In general, the dilution which gives a concentration of 1-10 DNA molecules/well is determined from a standard curve. The reporter protein is chosen to give a construct that efficiently undergoes ivTT for a large number of systems. This also standardizes the ivTT procedure for all proteins.

(4.) Protein Expression Module

The Protein expression module uses the liquid handler, the fluorescent plate reader and the plate/reservoir handling and storage system.

Figure 6:
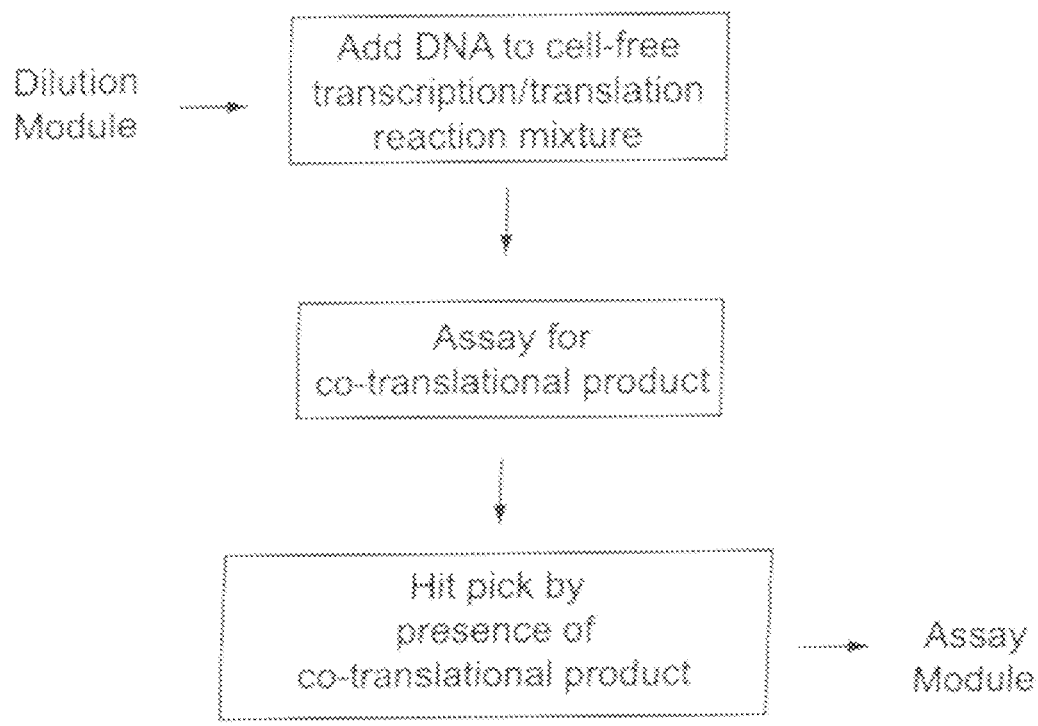
FIG. 6 provides a schematic overview of the activities of an exemplar expression module.

FIG. 6 provides a schematic overview of the activities of the expression module, i.e., the addition of DNA to cell-free ivTT reaction mixtures to form arrays of reaction mixtures, an assay for a co-translational product as a control, and the picking of hits by the presence of the co-translational control product.

The pooled library members are taken from the dilution module and an aliquot is removed in which the DNA concentration is adjusted for optimal ivTT. The rest of the ivTT mix is then added to the wells and protein production is initiated. The efficiency of the ivTT reaction is measured using the activity of the reporter protein. For example, if the reporter is green fluorescence protein (GFP), then efficiency is measured by directly monitoring fluorescence. If the reporter is an enzyme, an aliquot is typically removed for appropriate processing.

The wells which give efficient protein production are then rearrayed into new microtiter plates and passed on to the assay module.

The DNA concentration in each well is determined by the dilution module and therefore the amount of DNA in each well can be normalized to a corrected value for efficient ivTT. The wells which contain the control constructs are tracked so that the activity of the library clones can be compared to the initial wild type.

(5.) Assay Module

The Assay module uses the liquid handler, a fluorescent/colorimetric/luminometer plate reader and the plate/reservoir handling and storage system.

Figure 7:
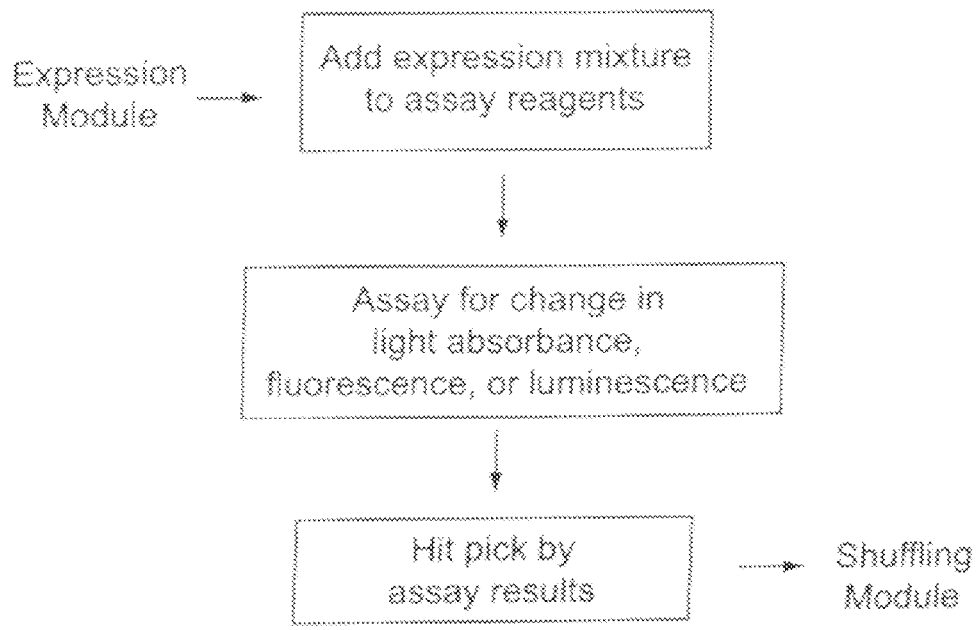
FIG. 7 provides a schematic overview of the activities of an exemplar assay module.

FIG. 7 provides a schematic overview of the exemplar assay module. In particular, expression mixtures are added to assay reagents (or vice versa) and changes in a detectable marker such as absorbance, fluorescence or luminescence are detected and hits picked. Similarly, the assay module can include an autosampler which interfaces with a CE, MS, GE or other system. SPR (surface plasmon Resonance) can also be used to measure protein binding. SPA (Signal Proximity Assay) methods can also be used, e.g., using a luminescence plate reader.

The protein solutions provided by the protein expression module are tested for the properties of interest. The proteins are typically diluted to a standard concentration before the assay, using the level of the reporter protein as a marker.

The protein solutions are aliquoted out and assayed using any format that leads to a spectrophotometric change in the properties of the assay mix. A majority of proteins may be assayed, directly or indirectly, using such formats (e.g., to monitor changes in pH, production of fluorescent product, loss of turbidity on hydrolysis, coupled assays, etc.).

Alternatively, the proteins can be assayed using heat production or oxygen consumption, changes in conductivity (ion production), parallel CE, GC, or the like. These properties of solution are readily quantified, e.g., using microfabricated devices as discussed above.

The proteins that are determined to be better than wild-type according to the criteria of the assay are identified and the position of the clones are determined.

The proteins are normalized to account for expression artifacts in the ivTT reaction. The activity of both the wild type and negative control clones is measured and used as a measure of the range of the assay. The variation in the controls (standard deviation) determines how significant differences are among the hits, as well as providing for statistical comparisons (e.g., standard average deviations as compared to wild type, etc.).

(6.) Deconvolution of Hits and Retesting

The clone pools can be reconfirmed and deconvoluted by submitting them to the dilution module. This separated the pool of about 10 clones into a few hundred wells, with increased stringency (to about 1 molecule/clone per well). The remaining modules then retest each molecule one or more times, verifying the previously identified activity. The assay module can also incorporated a secondary assay to further verify desired activities.

(7.) Second Round Shuffling

The reconfirmed hits are optionally used as substrates in subsequent shuffling reactions, with this process being iteratively (and automatically) repeated by the various modules of the system, until a desired activity level for the target is obtained.

(8.) Example Machine Configuration

Figure 8:
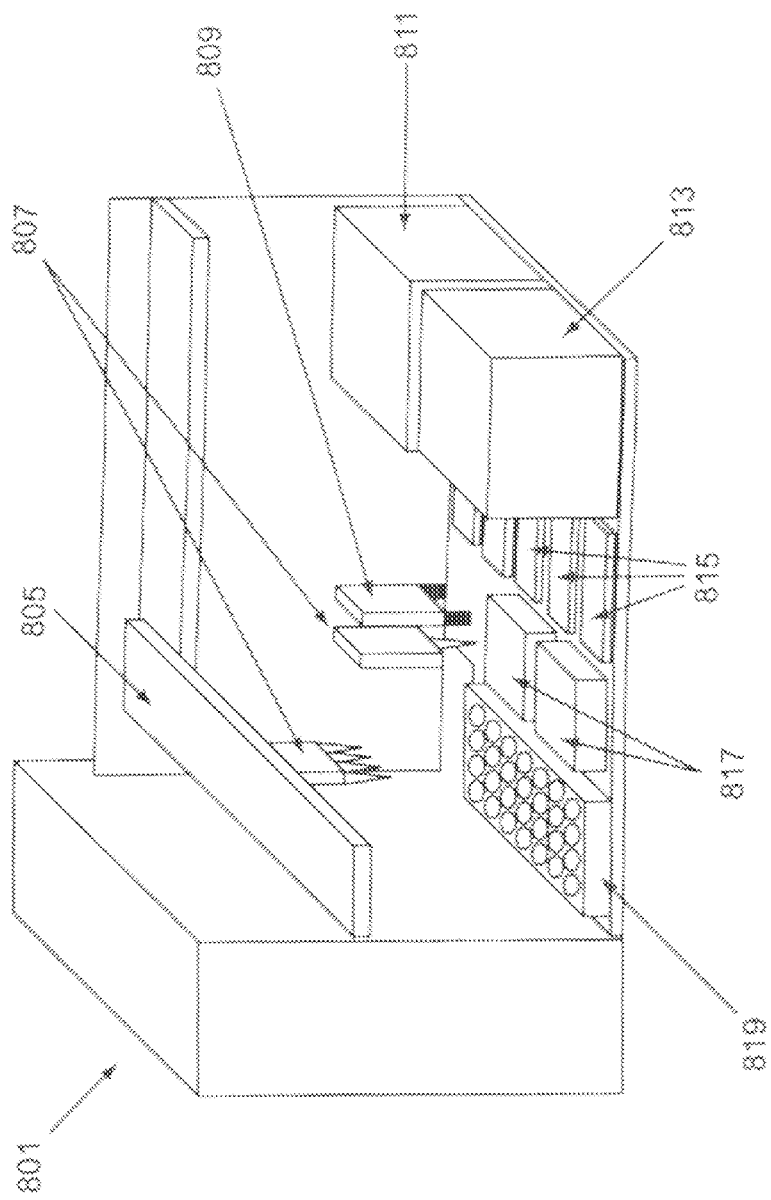
FIG. 8 is a schematic of an example recombination and selection machine.

FIG. 8 provides an exemplar configuration for a recombination and selection machine, showing plate stacker 801, gantry robot 805, pipetting heads 807, plate gripper 809, plate reader 811, thermocycler 813, plate holders 815, solution reservoirs 817 and reagent tubes 819. During operation of the device, plates are transferred from plate stacker 801 by plate gripper 809 to plate holders 815 to the various operation regions such as thermocycler 813 and plate reader 811. Plates are also optionally transferred back to plate stacker 801. Reagents are transferred to and from reagent tubes 819 and solution reservoirs 817 via pipetting heads 807, which also transfer materials between reagent tubes 819, solution reservoirs 817 and any plates used in the system.

(9.) Example Miniature Configuration

Figure 19:
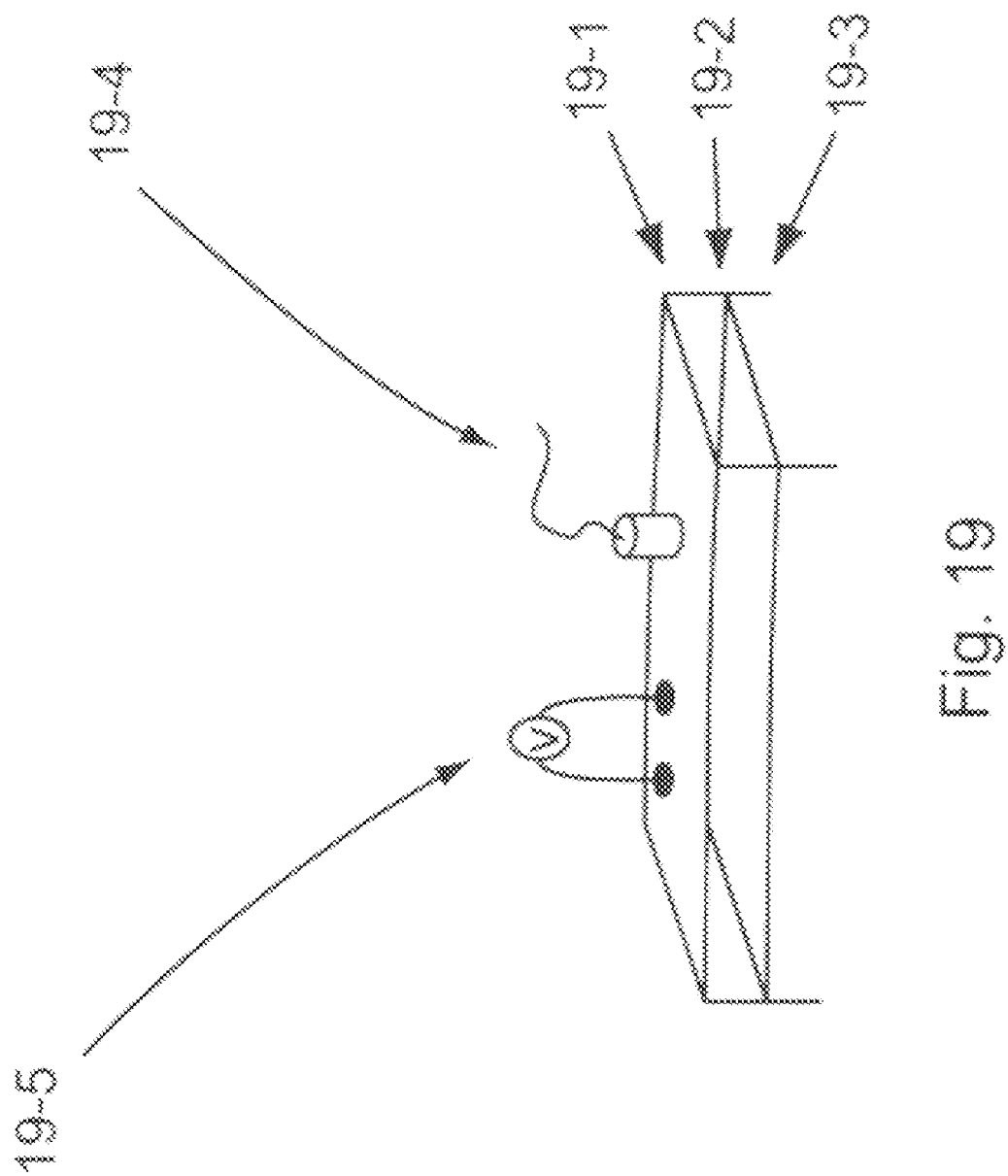
FIG. 19 is a schematic of a shuffling chip.
Figure 20:
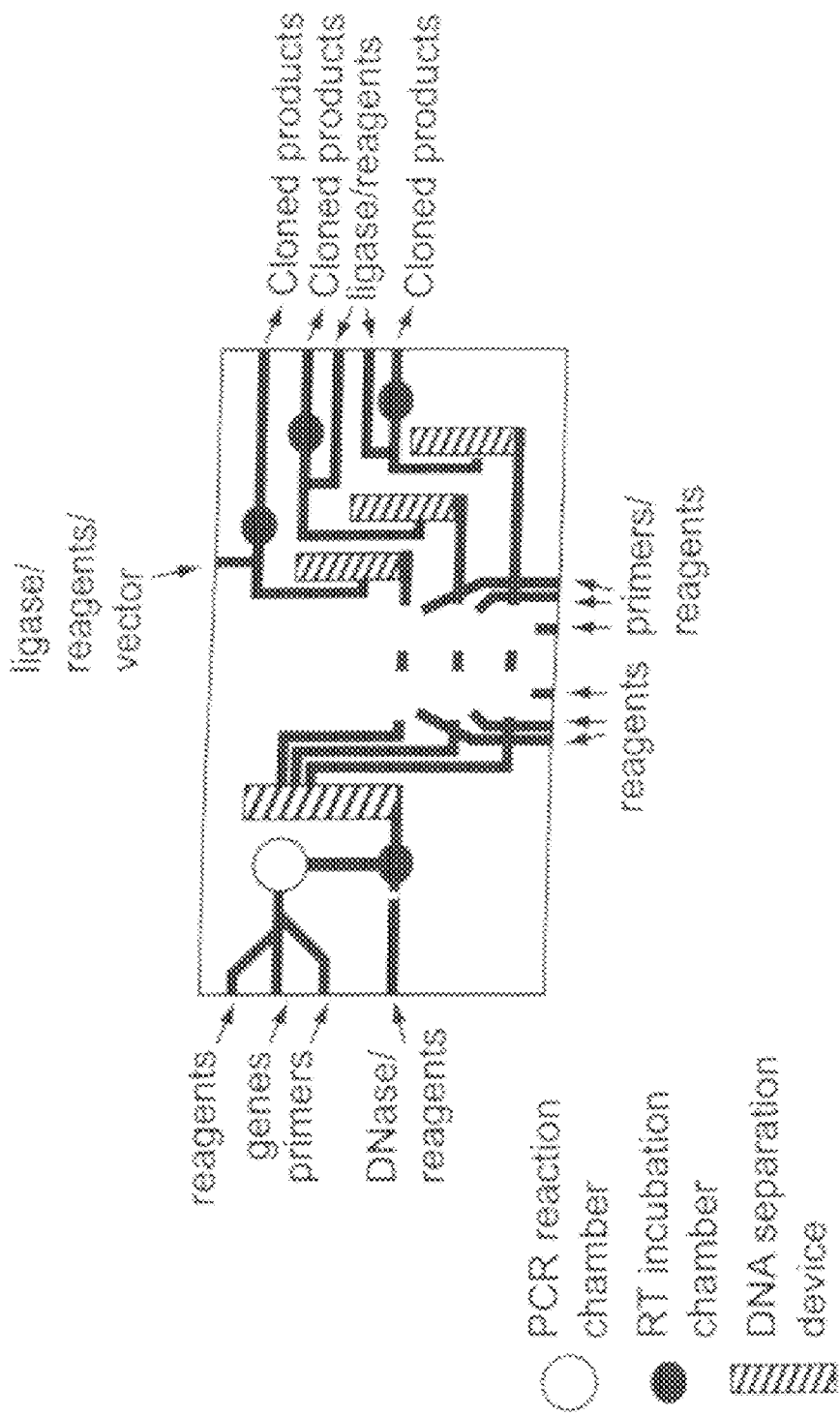
FIG. 20 is a schematic of the fluidics layer of a shuffling system.
Figure 21:
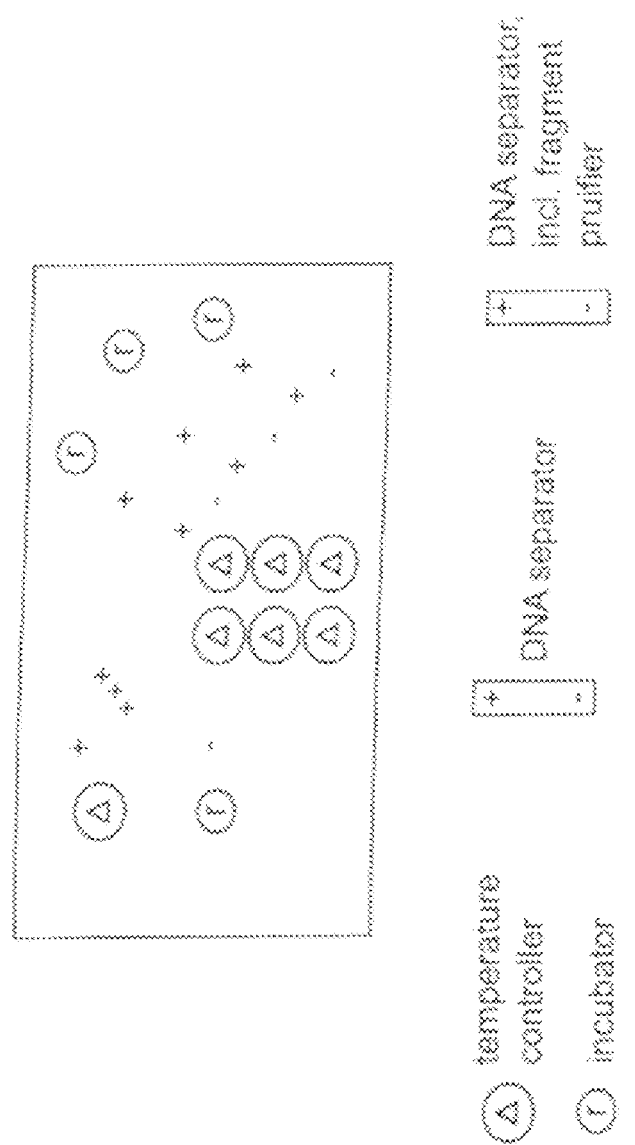
FIG. 21 is a schematic of an environmental control layer.
Figure 22:
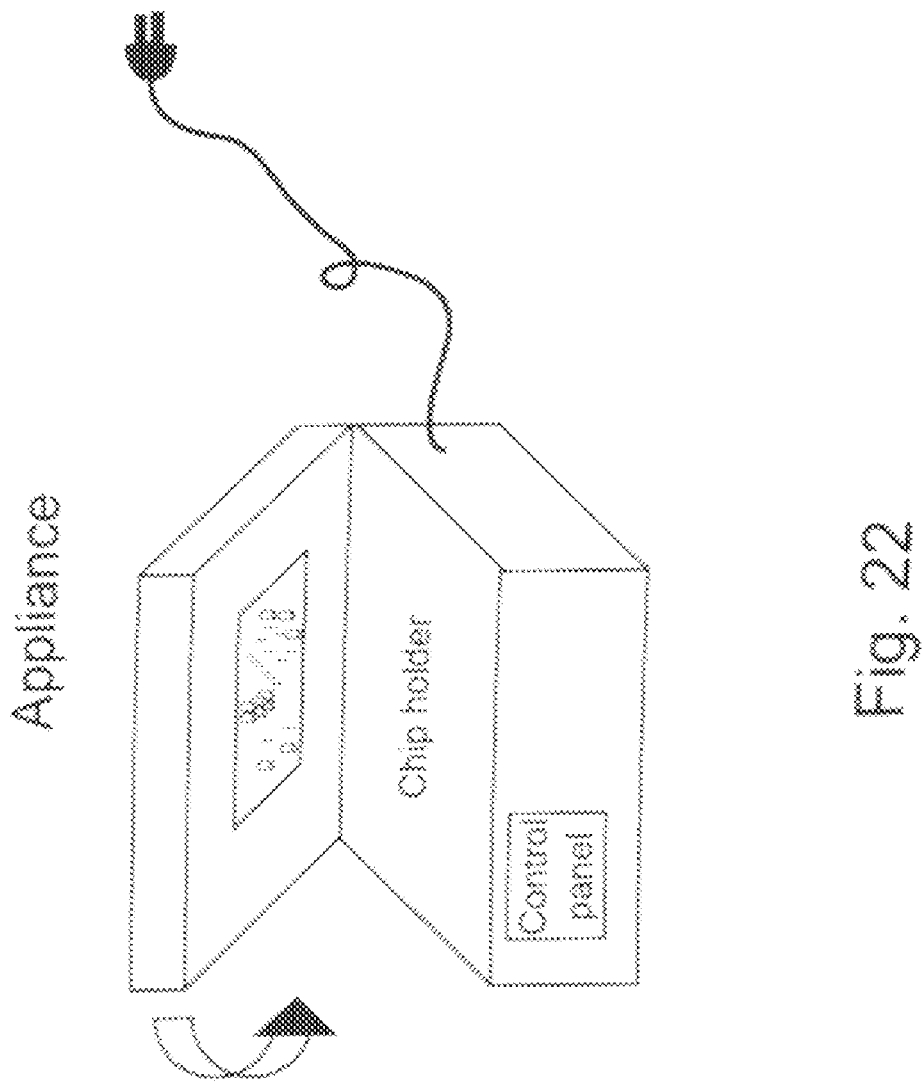
FIG. 22 is a schematic of a microscale appliance.

In this example, a miniature laboratory system is used, e.g., to perform a shuffling reaction. As shown in FIG. 19, the system includes an appliance and a microfluidic chip which has environmental control layer 19-1, microfluidics layer 19-2 and support layer 19-3, as well as optical interface for temperature control 19-4 and power supply 19-5 (see also, FIGS. 20-22). In operation, the miniature laboratory system is used, e.g., in combination with a module that provides reagents and optimal environmental conditions. Starting materials that are provided include DNA (genes/gene fragments, oligonucleotides, etc.), reagents, primers vectors, etc. The product of the system is, e.g., a gene library of diversified genes, operons, etc. Additional steps can be included in the system for additional reactions, if needed. Where purification steps are desired, membrane filters are optionally positioned in the flow lines, e.g., binding reagents or components that are to be removed. The microfluidics system that is used in the miniature laboratory system is used to guide and direct low volume samples containing, e.g., 0.05-100 ng/µl of DNA. Using advanced separation systems and DNA reaction chambers, DNA shuffling can be performed in the miniature laboratory system.

As shown in FIG. 19, in one embodiment, a three-layer chip construction is used to provide the microfluidic portion of the overall system. The bottom layer is for support, the middle layer contains channels that guide DNA and solutions and reagent solutions and the top layer provides contact points for a power supply and a temperature controller (e.g., operating by conductivity or light). Details regarding the top layer are found in FIG. 20. Samples are transported through the system, e.g., by air pulses or other fluid driving means. Details regarding the fluidics layer is set forth in FIG. 21. An appliance (FIG. 22) contains the operation hardware (and optionally software) for the miniature laboratory system, including PCR programs, incubation periods, DNA separation and sample product import/export. The appliance also optionally interfaces with a computer to provide additional control features. The complete system provides means to generate libraries of shuffled genes directly, by supplying starting DNA, reagents, oligonucleotide primers and vectors. The resulting DNA sample is directly introduced into, e.g., a cell of choice by transformation, electroporation, conjugation, particle bombardment, injection, etc.

I. Example DNA Shuffling Machine (Alternate Embodiment)—Comparison Of Alternate Breeding Strategies One way to develop more sophisticated breeding strategies is to empirically compare different breeding strategies. A DNA shuffling machine allows for increased throughput and accuracy in molecular matings.

Standard DNA shuffling is done, e.g., by purifying DNA fragments on gels, assembling fragments in a PCR machine, rescuing fragments in a PCR machine, and then cloning the final rescued product. The essential constraint with this approach is that it requires skilled labor and it is typically costly for a given person to sample a more than a few shuffling variables. However, there are many variables of interest, such as pairwise vs. pooled matings, fragment size, stoichiometry of the parental genes, degree of random mutation vs generating diversity by recombination, etc.

This example provides a solution to this difficulty by automating the shuffling process, providing scalability and other advantages. The example DNA shuffling machine which is the subject of this example is embodied in FIGS. 10 (showing a schematic of the DNA shuffling machine), 11 (showing a schematic of a DNA fragmentation device), 12 (showing a schematic of a DNA fragment analysis and isolation device), 13 (showing a schematic of a DNA fragment preparation device), 14 (showing a schematic of a precision microamplifier), 15 (showing a schematic of a DNA assembly and rescue module), 16 (showing a schematic of a recombination analysis device), and 17 (showing a schematic of a recombination analysis device).

FIG. 10 describes an overall DNA shuffling machine (10-1). This device/system can be built either as an integrated unit, or as a separate module. It can be designed to handle multiple samples in parallel, as each of the modules is scalable. As shown, Input elements including, e.g., plasmids, PCR products, genomic DNAs, primers, etc. are fragmented in DNA fragmentation device or module 10-2. Also included are DNA assembly and rescue device or module 10-3 providing for outputs, e.g., in the form of recombined/shuffled inserts. Finally, recombination and analysis module or device 10-4 provides for recombination analysis on any recombined/shuffled materials (e.g., shuffled insert DNAs).

Figure 11:
FIG. 11 is a schematic of a DNA fragmentation device or module.

FIG. 11 describes a DNA fragmentation device. For the purpose of automation, a reliable, preparation independent method to produce fragments of a desired size is useful. Sonication is a useful method because the fragment length depends on purely physical parameters such as the frequency of sonication and the viscosity of the fluid. However, one issue with this method is the type of ends that are generated, as 3' hydroxyl ends are preferred for subsequent assembly steps to work. The addition of chemical cleaving agents can improve the yield of 3' hydroxyls in the sonication reaction. Enzymatic treatment with a nuclease that is specific for, for example, 3' phosphates, improves the quality of sonicated fragments for DNA shuffling reactions. Other fragmentation methods discussed supra can also be adapted to the present example, such as the use of point-sink shearing methods, synthesis, etc.

Figure 12:
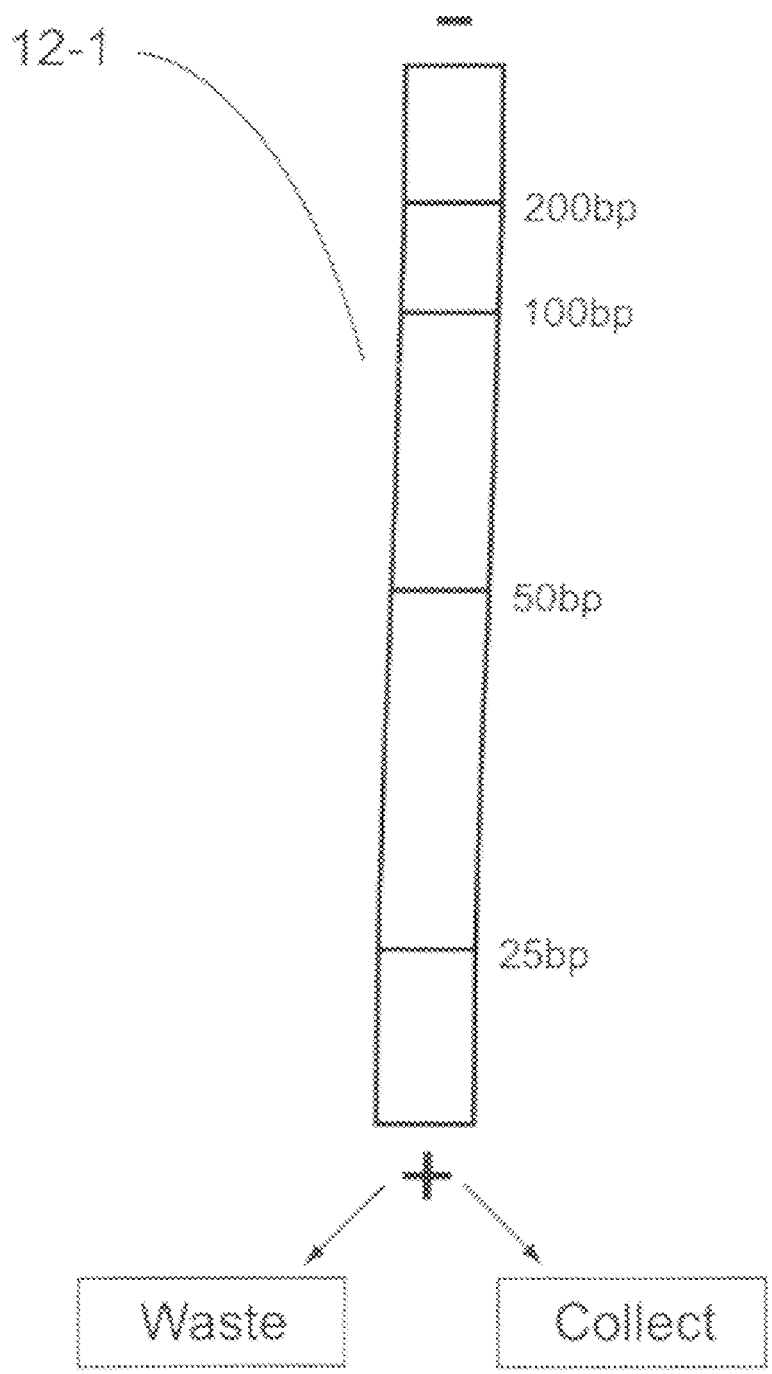
FIG. 12 is a schematic of a DNA fragment analysis and isolation device or module.

FIG. 12 describes a DNA fragment analysis and isolation device. A capillary electrophoresis instrument (e.g., column 12-1) is used to separate the DNA fragments. A detector monitors fluorescently labeled markers on the column to a "waste" or to "collection" reservoir. This allows for automated collection of DNA fragments in the size range that is programmed by the user. An analytical instrument, made of components similar to those used for sequencing gels, can be used for the analytical runs for doing analysis of PCR with recombination oligos or for analysis of raw assemblies to assess the efficiency of assembly. For example, one can collect 25-50 bp fragments.

Figure 13:
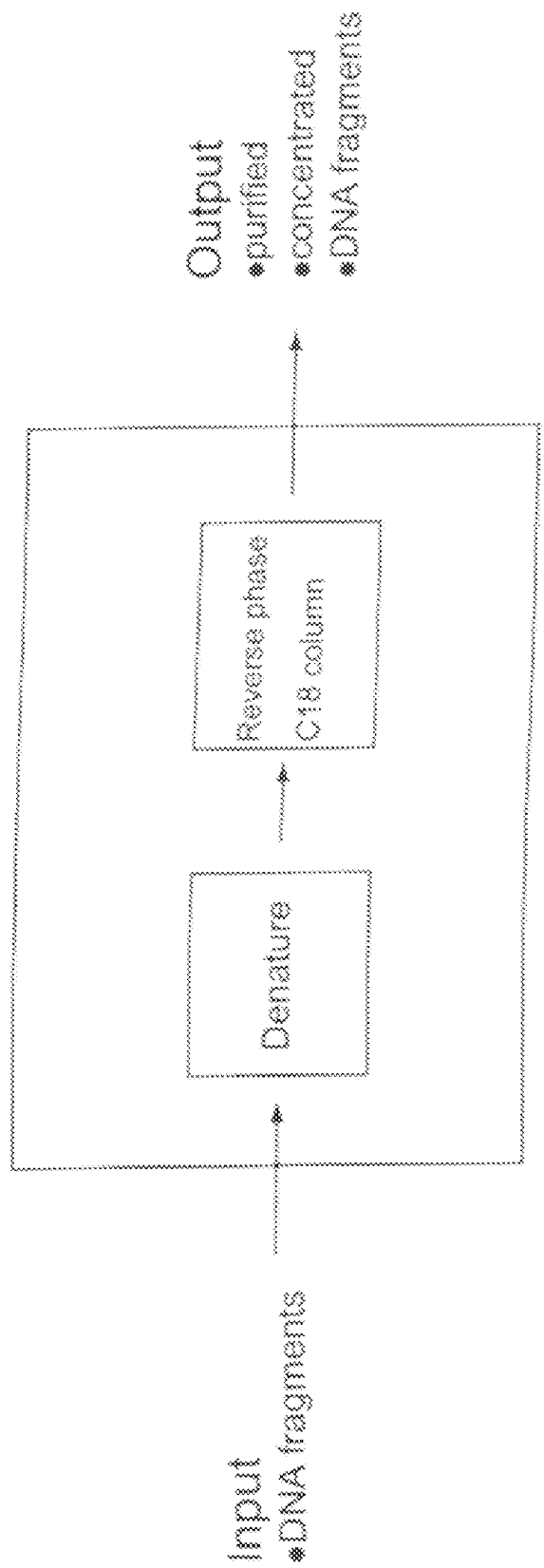
FIG. 13 is a schematic of a DNA fragment prep device.

FIG. 13 describes a DNA fragment prep device. The DNA is denatured to expose or create single stranded DNA that binds efficiently to a C18 hydrophobic column and which can be quantitatively eluted and concentrated. This uses the principle of the SEP-PAK C18 column, but is modified for use in an automated device. Alternatives to this approach include ion exchange chromatography, precipitation, lyophilization, etc.

Figure 14:
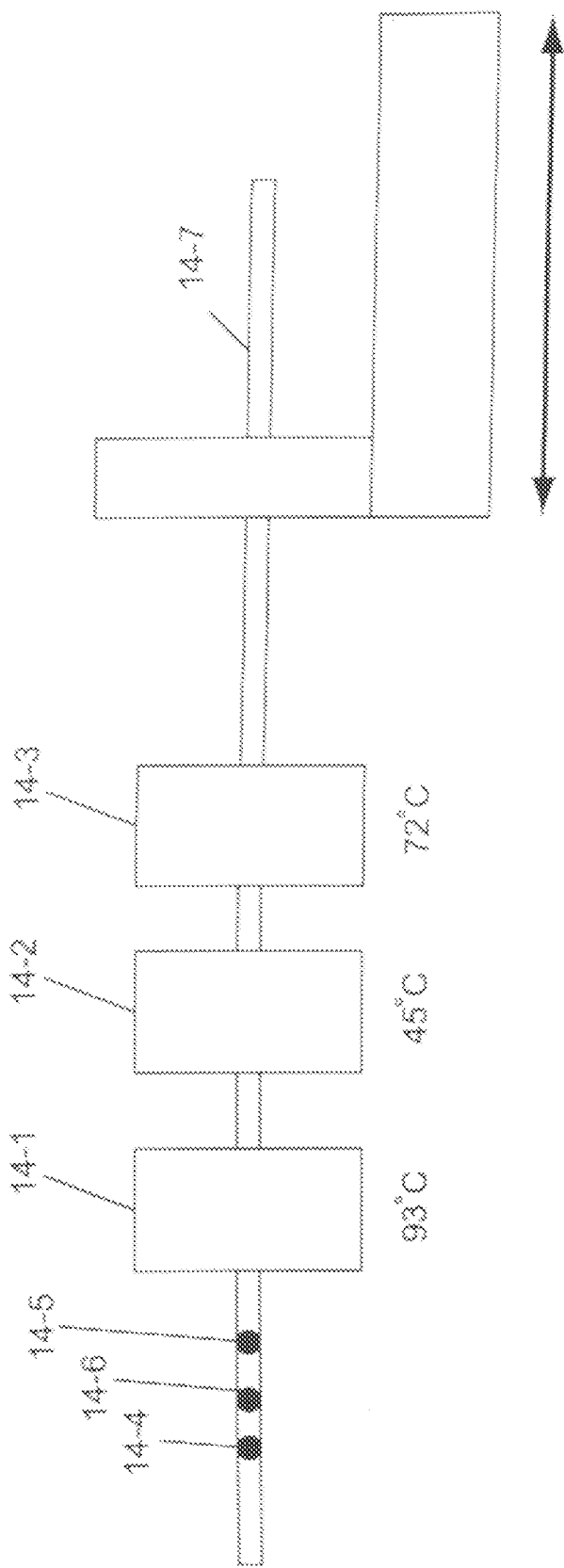
FIG. 14 is a schematic of a precision microamplifier.

FIG. 14 describes a precision microamplifier (PMA). DNA 14-6 is placed in microcapillary 14-7 between two drops of oil (14-4, 14-5) to seal it against evaporation. Typical drop sizes range from 1 nl to 1 μl. The micro-capillary is moved through three resistors (14-1, 14-2, 14-3) whose temperatures are programmed. As depicted, robotic arm 14-8 is used to move the capillary, and thus the DNA droplet, e.g., between resistors 14-1, 14-2, and 14-3. In the simplest case, the resistors are set for, e.g., 93, 45 and 72 degrees centigrade. By moving cyclically through these temperatures, a PCR or assembly reaction can be driven in microdroplet in the microcapillary. A chief advantage of this relative to a standard PCR machine is that the temperature can be controlled more precisely, and, more importantly for DNA shuffling, the volume of the assembly reaction can be driven into the submicroliter range very easily. This allows shuffling using small quantities of fragments, allowing for more molecular "crosses" in the shuffling reactions from a give amount of input DNA.

Figure 15:
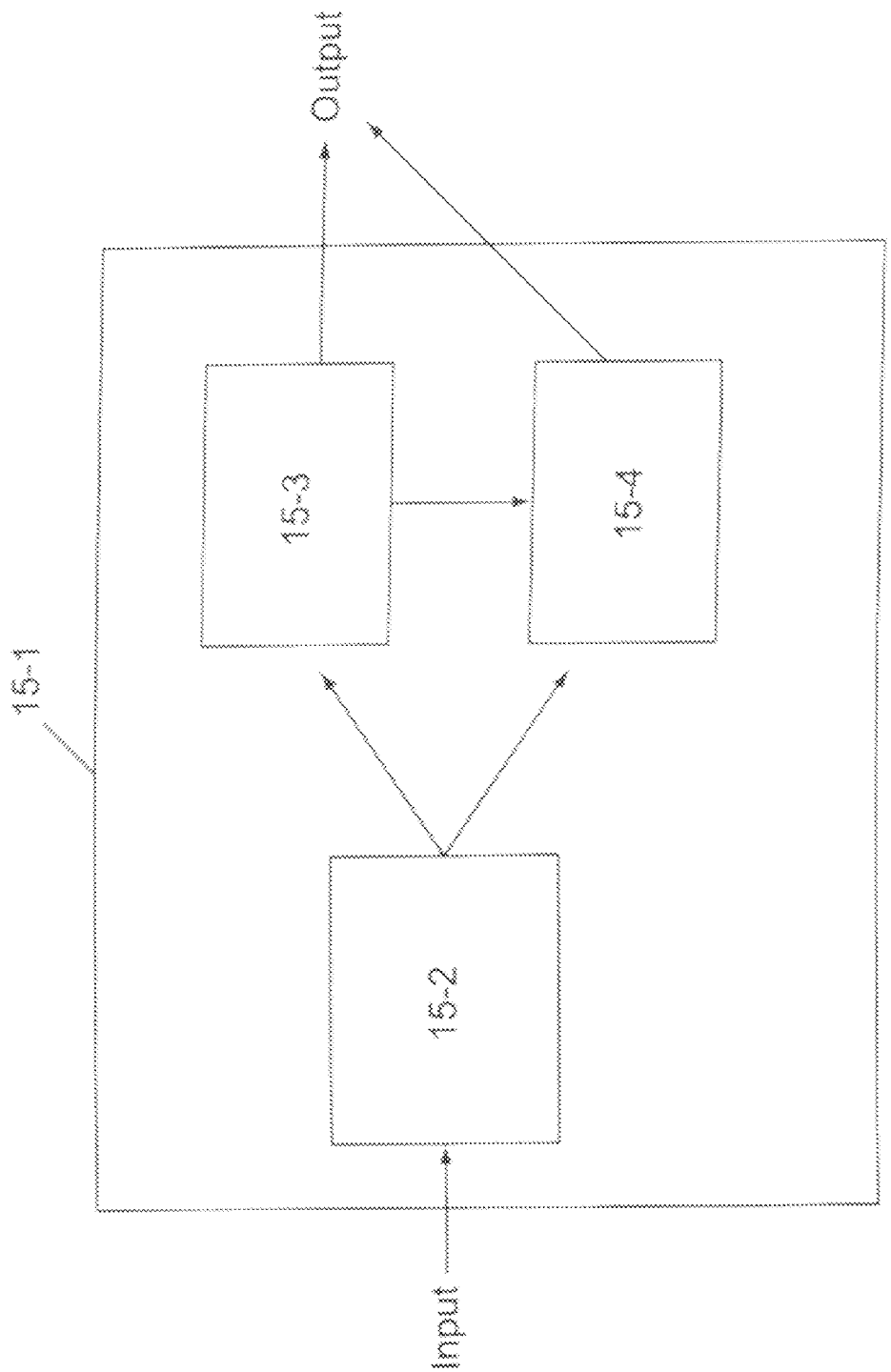
FIG. 15 is a schematic of a DNA assembly and rescue module.

FIG. 15 describes DNA assembly and rescue module 15-1. Assembly is done in a modified PCR machine or in the PMA (depicted as assembler 15-2). The PMA, or similar low-volume/high throughput methods provide one preferred approach, because one can amplify very small volumes which provides for shuffling using a smaller quantity of fragmented DNA. The Analyzer provides a quantitative way to monitor the size and distribution of PCR products and the properties of PCR rescue. A clean and efficient rescue of a unit length of a gene fragment is preferred. The size distribution of assembled product and the properties of the rescue PCR are highly informative for predicting the efficiency of shuffling that has occurred. The analysis can be done by capillary electrophoresis or by mass spec. As depicted, various inputs, including random DNA fragments, overlapping PCR fragments and the like are assembled in assembler 15-2. The assembly and rescue module further includes rescue PCR element 15-3 and analyzer 15-4 (e.g., including a capillary electrophoresis module). Assembly module 15-1 produces outputs including assembled fragments, rescued PCR inserts and the like. Analyzer 15-4 provides profile information including size distribution information.

FIG. 16 describes recombination analysis device/module 16-1. Inputs include raw assembled components and PCR rescued assembled components. Outputs include analysis of the ratio of recombined to parental sequences. In the device, "Crossover oligos" prime one or another parents exclusively, and thus, a 5' oligo from P1 and a 3' oligo from P2 only PCR amplify a recombinant such as F1(B). The analyzer is, for example, a capillary electrophoresis machine that precisely measures the size and intensity of each band. By using multiple fluorophores in the crossover oligos, one can measure, e.g., all four PCR products of the amplification in a single lane, if desired. In the figure, P1=parent #1; P2=parent #2; F1(A) and F1(B) are recombinants with structures with respect to the crossover oligos as shown. The crossover oligos are sets of oligos that exclusively (or at least preferentially) prime the indicated parents. The strategy can be generalized to accommodate multiple pairs of crossover oligos. An advantage of the recombination analysis device is that it allows one to quantitatively monitor the shuffling reaction. For example, if 100-200 base fragments are used in the shuffling, then crossover oligos that are 300 bp apart in the assembled genes are almost fully recombined (recombinants F1(A) and F1(B) bands of only half the intensity of the parental bands.

The DNA fragmentation device and the DNA Fragment Prep Device take the tedium out of preparing gene fragments. They can also increase the yield of fragments of the desired size. The assembly and rescue device allows one to test multiple assembly conditions; e.g., if the precision microamplilier is used for the assembly. The analysis instrument allows one to quantitatively monitor the growth of the shuffled product. This analysis capability is useful for trouble shooting, which ultimately makes the process even more predictably automatable.

The recombination/analysis device allows one to quantitatively measure the frequency of recombination between any known DNA polymorphisms in the parental genes. This analysis is useful in the optimization of shuffling reactions generally. It is similar in effect to measuring recombination frequencies in populations. Importantly, it allows one to make an educated decision as to whether a given shuffling reaction is worth cloning, or in vitro expressing and screening in functional assays, as opposed to doing further work to optimize the shuffling reaction to get a desired spectrum of recombinants. This is of particular value when the number of clones that can be screened is limited or costly.

J. Example: Establishment and Automated Processing of Expression Arrays for Nucleic Acids Derived from a Variety of Sources Identification and characterization of genes from macro- and micro-organisms, enrichment cultures, fermentation broths and uncharacterized environmental isolates, and the like is of commercial value. These genes can be used as substrates in the various diversity generation reactions herein.

Various approaches for using diverse sources of materials in the systems of the present invention are schematically outlined in FIGS. 23-30.

Figure 23:
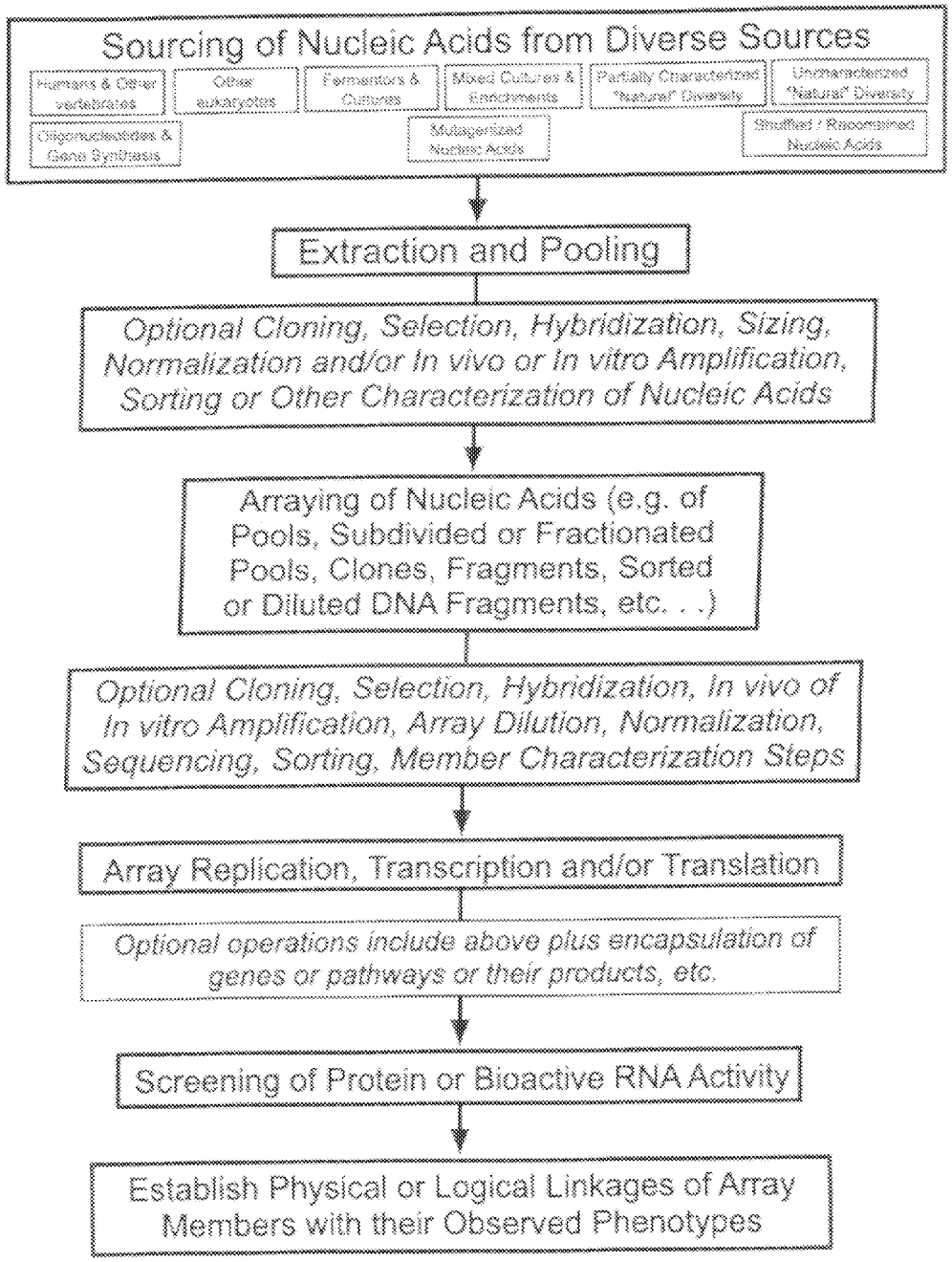
FIG. 23 is a schematic outline of processes for sourcing nucleic acids from diverse sources.

In the process embodiment of FIG. 23, nucleic acids are sourced from any of a variety of diverse sources, including any of those listed in the figure (humans and other vertebrates, other eukaryotes, oligonucleotides and gene synthesis, etc.) The nucleic acids are extracted and/or pooled. Optionally, the pooled nucleic acids are cloned, selected, hybridized, sized, etc. The nucleic acids are then arrayed. The arrayed nucleic acids are then optionally cloned, selected, hybridized, amplified, etc. The arrays are replicated, transcribed and/or translated. The genes can be encapsulated if desired. Proteins or bioactive RNAs are screened for activities of interest. Finally, a physical or logical linkage between the array members and the relevant observed phenotypes is established.

Figure 24:
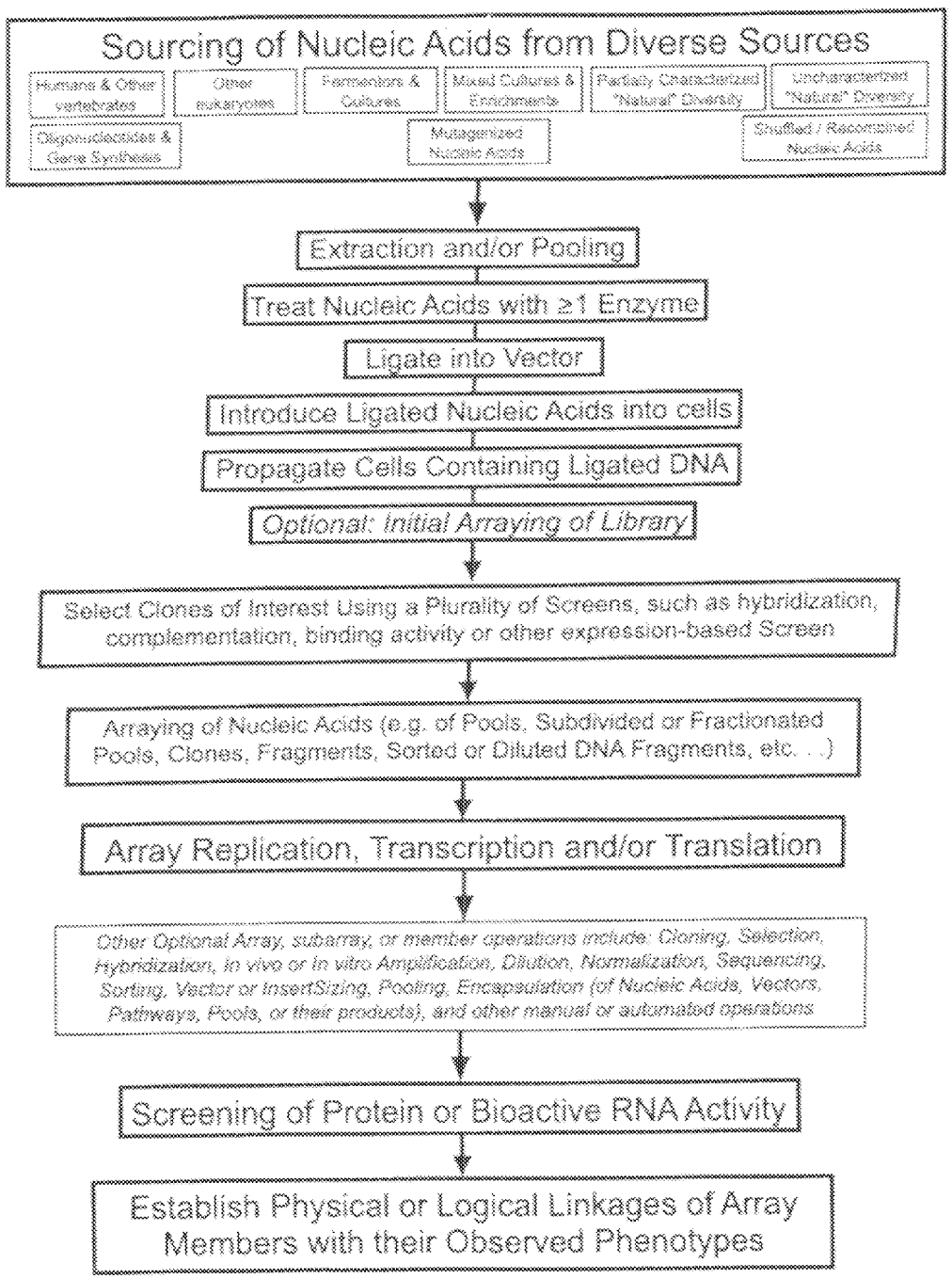
FIG. 24 is an alternative schematic outline of processes for sourcing nucleic acids from diverse sources.

In the process embodiment of FIG. 24, nucleic acids are sourced from any available source, including one or more of those listed in the figure, and extracted/pooled. Nucleic acids are treated with one or more enzyme, ligated into one or more vectors and introduced into cells. Cells are propagated in the cells. Optionally, the cells or expressed nucleic acids can initially be arrayed. Clones of interest are selected using a plurality of screens, such as hybridization, complementation, etc. The selected nucleic acids are arrayed and the arrays replicated. One or more of the replicated arrays is transcribed and/or translated. Optionally, other arrays or array members can be cloned, selected, hybridized, etc. Bioactive RNAs or proteins are selected for one or more activity and, again, a physical or logical linkage between the array members and the relevant observed phenotypes is established.

Figure 25:
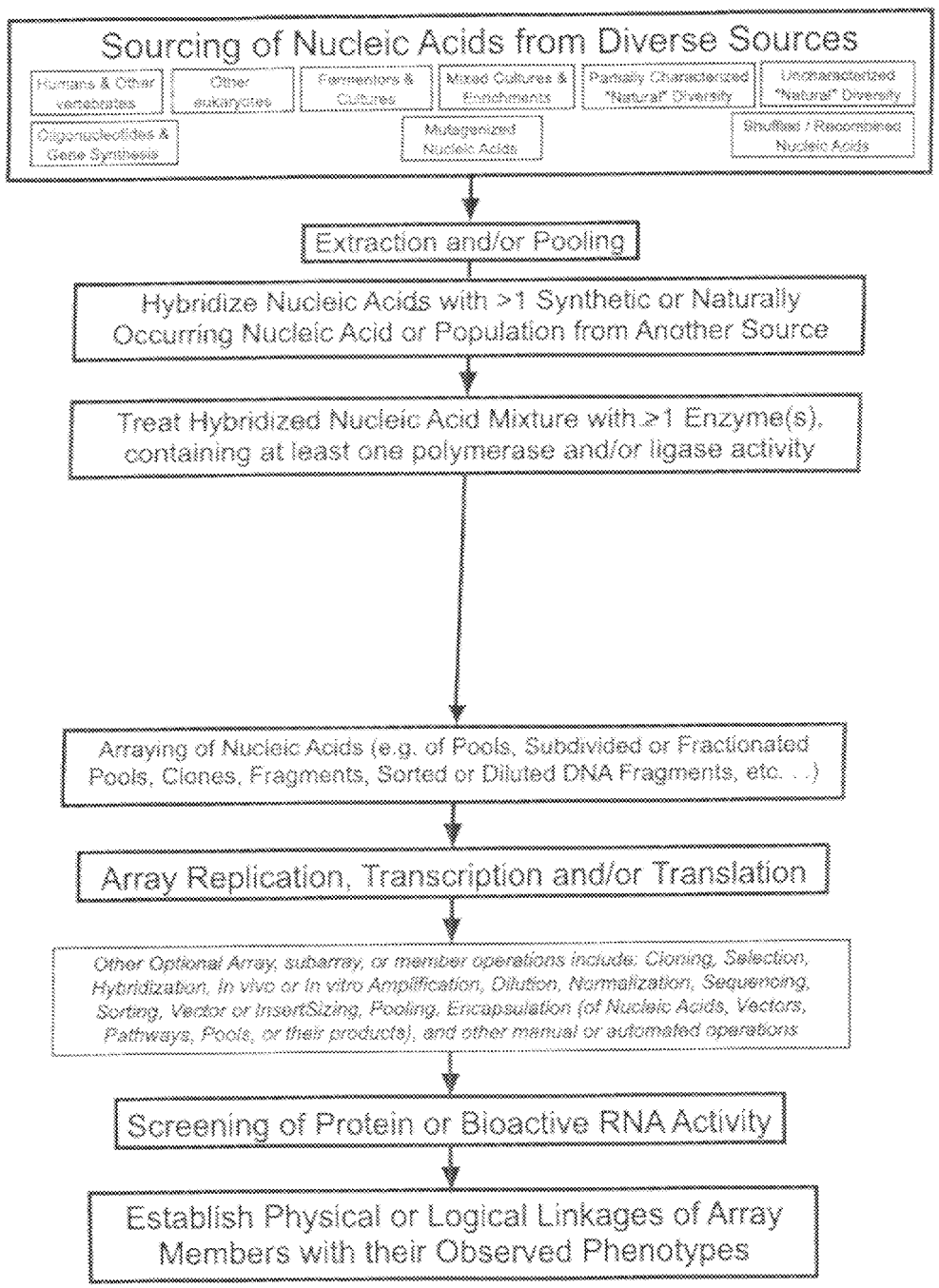
FIG. 25 is an alternative schematic outline of processes for sourcing nucleic acids from diverse sources.

In the process embodiment of FIG. 25, the sourced nucleic acids (again, from any of a variety of diverse sources, including any of those listed in the figure) are extracted and/or pooled, hybridized with at least one synthetic or naturally occurring nucleic acid or population from another source, and treated with at least one enzyme including at least one polymerase or ligase activity. Nucleic acids are arrayed and arrays replicated. Optionally, the arrays or array members include any of a variety of additional operations, including cloning, selection, hybridization, etc. Bioactive RNAs or proteins are selected for one or more activity and, again, a physical or logical linkage between the array members and the relevant observed phenotypes is established.

Figure 26:
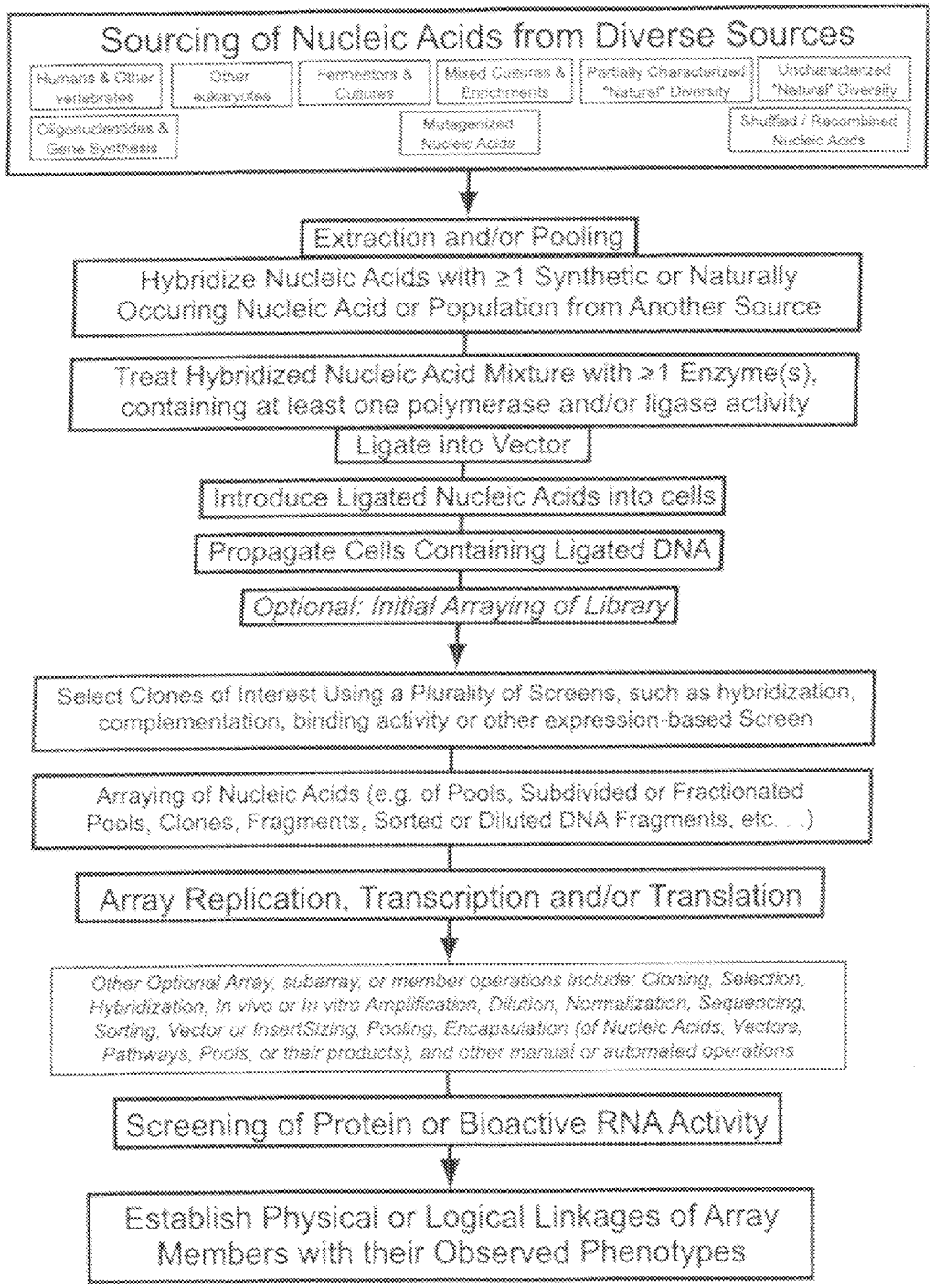
FIG. 26 is an alternative schematic outline of processes for sourcing nucleic acids from diverse sources.

In the process embodiment of FIG. 26, sourced nucleic acids (also from any of a variety of diverse sources, including any of those listed in the figure) are extracted and/or pooled. The resulting nucleic acids are hybridized with at least one synthetic or naturally occurring nucleic acid or population from another source. The resulting hybridization mixture is treated with at least on enzyme containing at least one polymerase and/or ligase activity. The resulting nucleic acids are ligated into a vector, introduced into cells and propagated. Optionally an initial array of the resulting library is performed at this stage of the overall process. Library members (clones) are selected using one or more screens. The selected members are arrayed and the arrays replicated. Bioactive RNAs or proteins are selected for one or more activity and, again, a physical or logical linkage between the array members and the relevant observed phenotypes is established.

Figure 27:
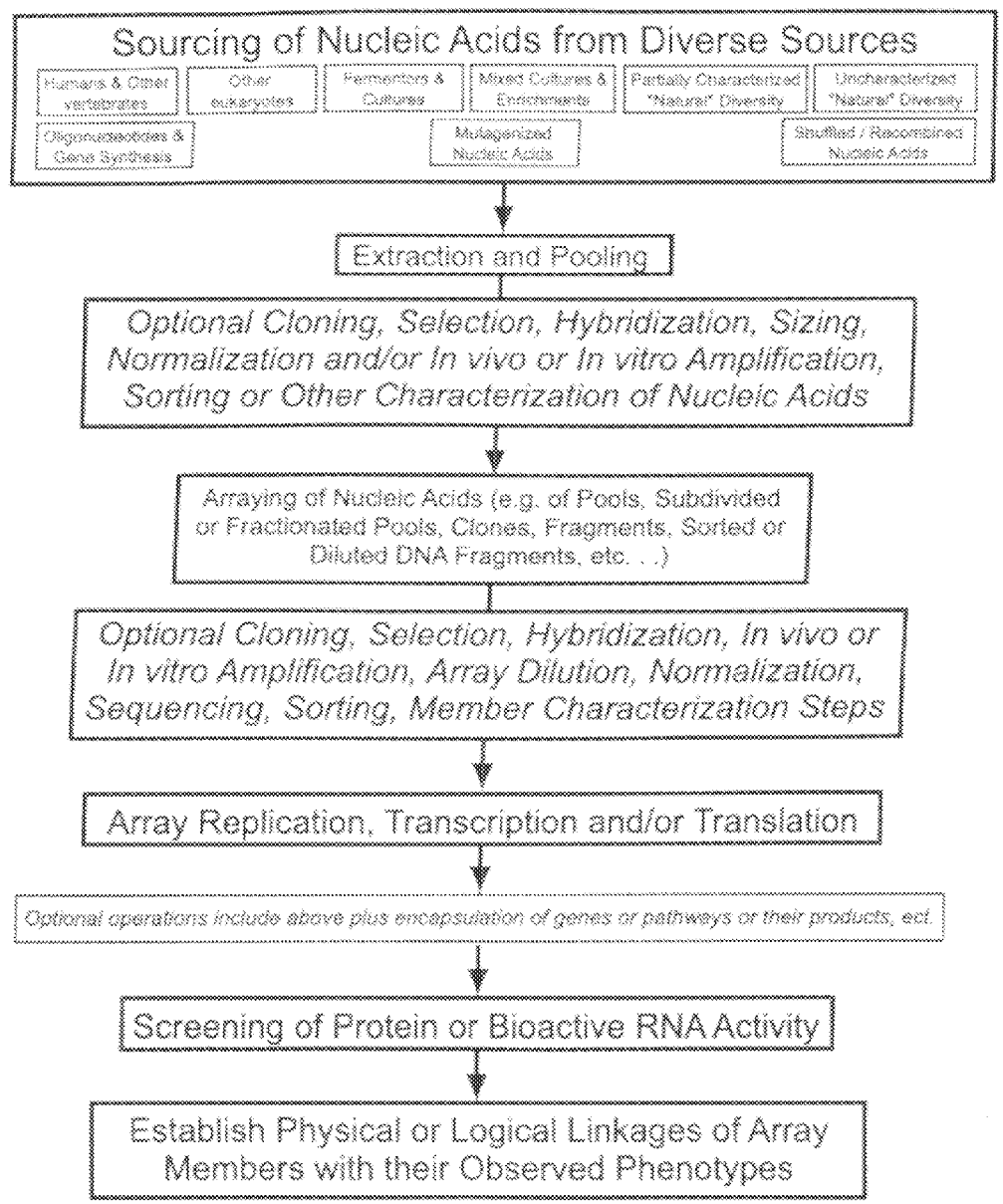
FIG. 27 is an alternative schematic outline of processes for sourcing nucleic acids from diverse sources.

In the process embodiment of FIG. 27, nucleic acids are sourced from any of a variety of diverse sources, including any of those listed in the figure (humans and other vertebrates, other eukaryotes, oligonucleotides and gene synthesis, etc.) The nucleic acids are extracted and/or pooled. Optionally, the pooled nucleic acids are cloned, selected, hybridized, sized, etc. The nucleic acids are then arrayed. The arrayed nucleic acids are then optionally cloned, selected, hybridized, amplified, etc. The arrays are replicated, transcribed and/or translated. The genes can be encapsulated if desired. Proteins or bioactive RNAs are screened for activities of interest. In this embodiment, the properties which are screened include fluorescent or luminescent properties of a particle such as a cell, encapsulated mixture or other matrix, liposome or membrane encapsulated material which incorporates a viral coat protein, or other encapsulated material. The cell or other encapsulated material is used to decide the end locations of such particles on an array comprising at least two designated end locations or chambers. Detection is via FACS, microFACS (with or without a fluorescent signal), fluorescence, visible scanning, transmission or confocal microscopy, digital or high-density signal imaging, thermography, liquid chromatography, combinations thereof, or the like. A physical or logical linkage between the array members and the relevant observed phenotypes is then established.

Figure 28:
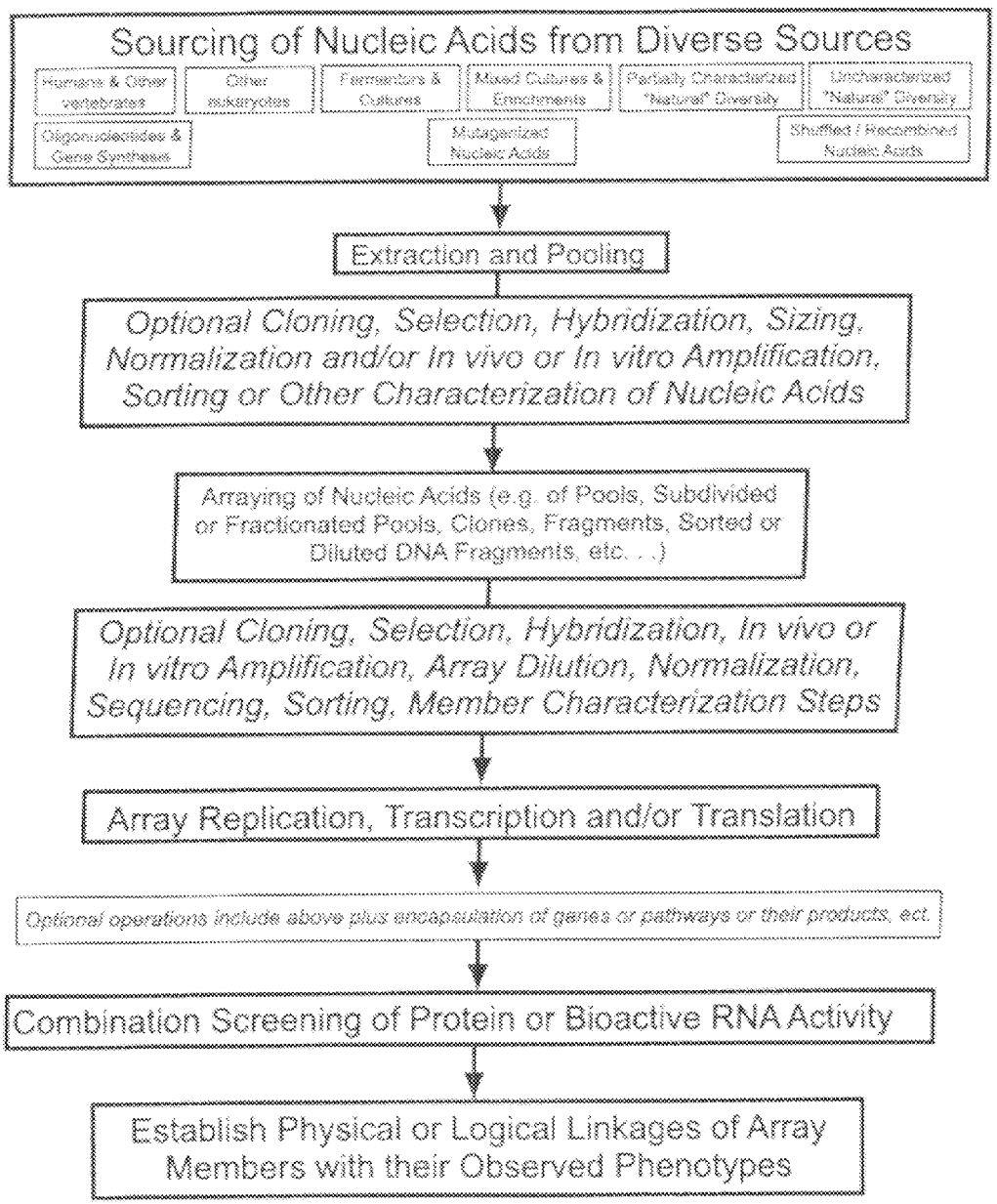
FIG. 28 is an alternative schematic outline of processes for sourcing nucleic acids from diverse sources.

In the process embodiment of FIG. 28, nucleic acids are sourced from any of a variety of diverse sources, including any of those listed in the figure (humans and other vertebrates, other eukaryotes, oligonucleotides and gene synthesis, etc.) The nucleic acids are extracted and/or pooled. Optionally, the pooled nucleic acids are cloned, selected, hybridized, sized, etc. The nucleic acids are then arrayed. The arrayed nucleic acids are then optionally cloned, selected, hybridized, amplified, etc. The arrays are replicated, transcribed and/or translated. The genes can be encapsulated if desired. Proteins or bioactive RNAs are screened for activities of interest. In this embodiment, the screening comprises combination screening of the proteins or bioactive RNAs. Properties which are screened include fluorescent or luminescent properties of a particle such as a cell, encapsulated mixture or other matrix, liposome or membrane encapsulated material which incorporates a viral coat protein, or other encapsulated material. The cell or other encapsulated material is used to decide the end locations of such particles on an array, e.g., comprising at least two designated end locations or chambers. Detection is via FACS, microFACS (with or without a fluorescent signal), fluorescence, visible scanning, transmission or confocal microscopy, digital or high-density signal imaging, thermography, liquid chromatography, combinations thereof, or the like. In addition, the array, e.g., at least one of the end locations, comprises a population of target cells in which a given biological activity is directly assessed, such as cytocidal or antibiotic activities, stimulation or suppression of growth, generation of a detectable signal, or the like. A physical or logical linkage between the array members and the relevant observed phenotypes is then established.

Figure 29:
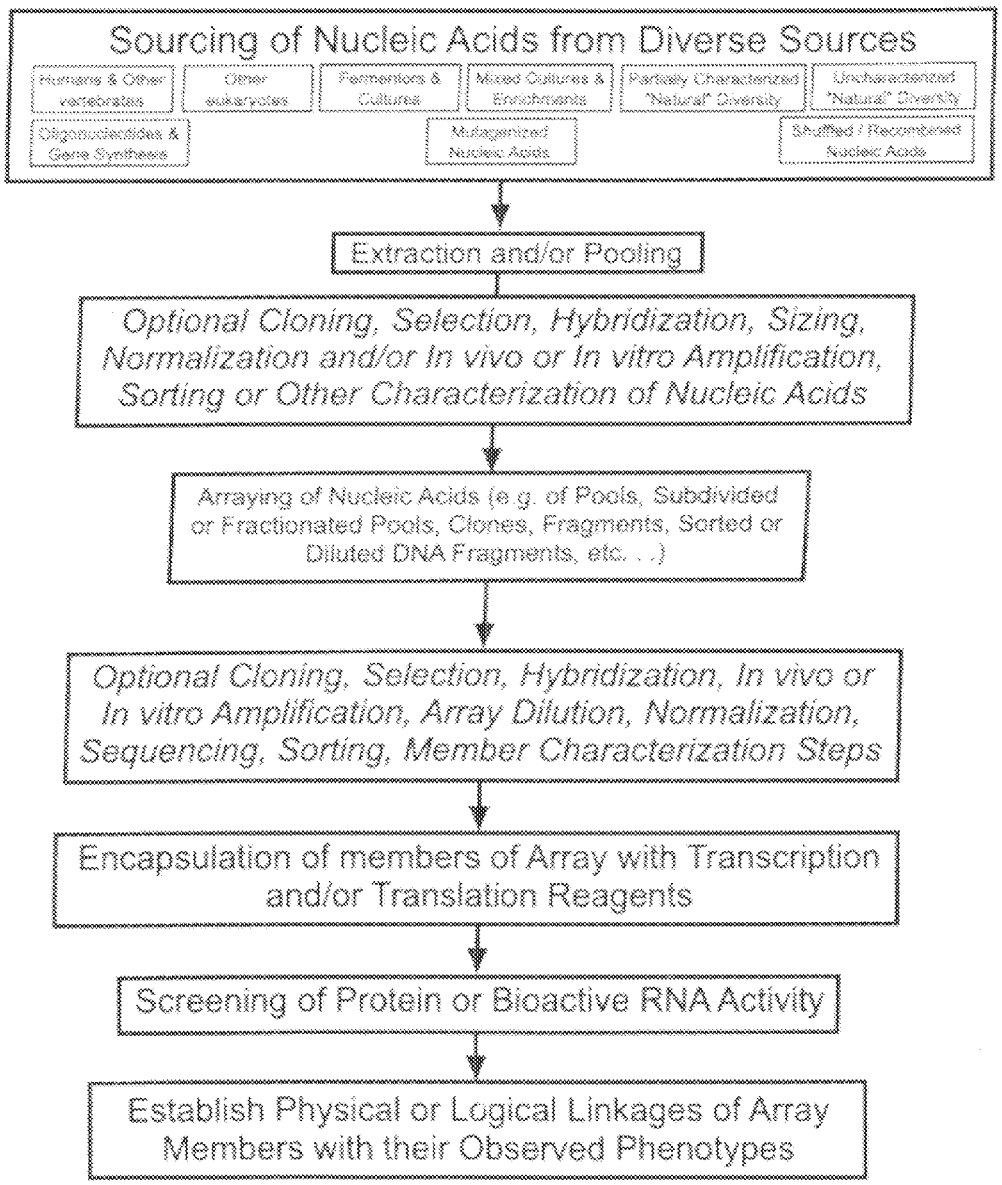
FIG. 29 is an alternative schematic outline of processes for sourcing nucleic acids from diverse sources.

In the process embodiment of FIG. 29, nucleic acids are sourced from any of a variety of diverse sources, including any of those listed in the figure (humans and other vertebrates, other eukaryotes, oligonucleotides and gene synthesis, etc.). The nucleic acids are extracted and/or pooled. Optionally, the pooled nucleic acids are cloned, selected, hybridized, sized, etc. The nucleic acids are then arrayed. The arrayed nucleic acids are then optionally cloned, selected, hybridized, amplified, etc. The arrays are replicated, transcribed and/or translated. The array members are also encapsulated in this embodiment. Proteins or bioactive RNAs are screened for activities of interest. In this embodiment, the properties which are screened can include fluorescent or luminescent properties of a particle, encapsulated mixture, liposome, or mixture encased in a membrane comprising one or more viral coat proteins which are used to decide, e.g., end locations of such particles on an array, e.g., comprising at least two designated end locations or chambers. Such methods include any combination of FACS or microFACS (with of without a fluorescent signal); fluorescent, visible, scanning, transmission and confocal microscopy; digital or high density digital imaging, thermography, liquid chromatography, and the like. A physical or logical linkage between the array members and the relevant observed phenotypes is then established.

Figure 30:
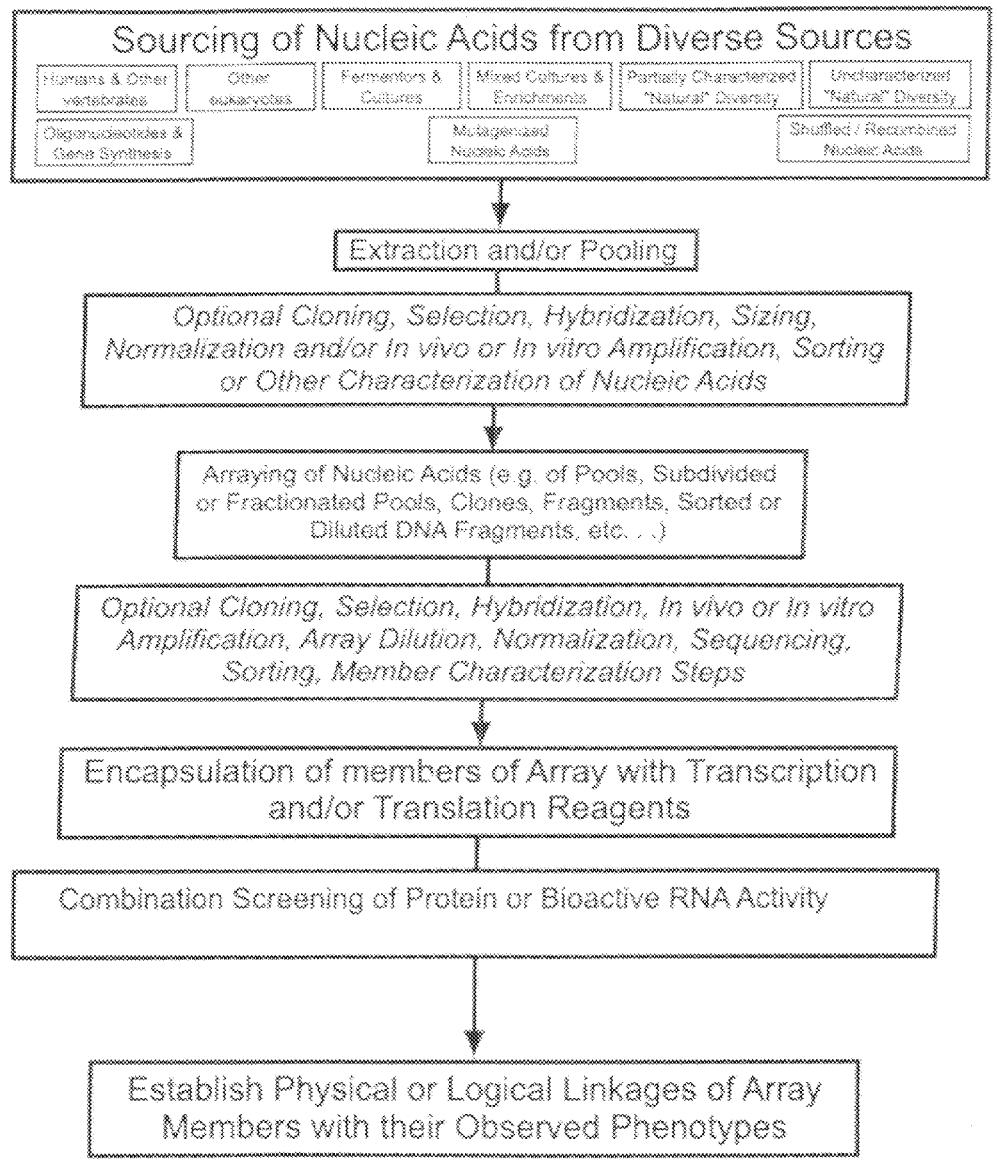
FIG. 30 is an alternative schematic outline of processes for sourcing nucleic acids from diverse sources.

In the process embodiment of FIG. 30, nucleic acids are sourced from any of a variety of diverse sources, including any of those listed in the figure (humans and other vertebrates, other eukaryotes, oligonucleotides and gene synthesis, etc.). The nucleic acids are extracted and/or pooled. Optionally, the pooled nucleic acids are cloned, selected, hybridized, sized, etc. The nucleic acids are then arrayed. The arrayed nucleic acids are then optionally cloned, selected, hybridized, amplified, etc. The arrays are replicated, transcribed and/or translated. The genes can be encapsulated if desired. Proteins or bioactive RNAs are screened for activities of interest. In this embodiment, the screening comprises combination screening of the proteins or bioactive RNAs. Properties which are screened include fluorescent or luminescent properties of a particle such as a cell, encapsulated mixture or other matrix, liposome or membrane encapsulated material which incorporates a viral coat protein, or other encapsulated material. The cell or other encapsulated material is used to decide the end locations of such particles on an array, e.g., comprising at least two designated end locations or chambers. Detection is via FACS, microFACS (with or without a fluorescent signal), fluorescence, visible scanning, transmission or confocal microscopy, digital or high-density signal imaging, thermography, liquid chromatography, combinations thereof, or the like. In addition, the array, e.g., at least one of the end locations, comprises a population of target cells in which a given biological activity is directly assessed, such as cytocidal or antibiotic activities, stimulation or suppression of growth, generation of a detectable signal, or the like. A physical or logical linkage between the array members and the relevant observed phenotypes is then established.

The field of gene isolation is well developed, e.g., in the expression array (e.g., Gene chip™, Affymetrix, Santa Clara, Calif.) and eukaryotic genomics areas, in which, e.g., RNA or genomic DNA is used to detect or sequence novel open reading frames. While tools for sequencing complex genomes of higher organisms has advanced rapidly, less work has been done on sequencing, deconvoluting or otherwise characterizing the genetic properties of microorganisms and microbial systems. Furthermore, while the generation and use of hybridization and sequencing arrays has undergone significant advancement, much of the advances are based on the ability to identify and purify the messenger RNA or intact high MW genomic DNA from higher organisms.

For eukaryotic mRNA, the presence of poly-adenylated tail allows rapid creation and use of convenient EST (expressed sequence tagged) libraries. Since lower organism rarely exhibit such tails, other tools are used for rapid cloning, characterization and analysis.

Recently, methods for extracting nucleic acids at high yield from microbial cultures, broths, pathogen and environmental samples have been described. Where complex, soil-containing or mixed culture systems are targeted for characterization or gene mining, these methods generally use any of a variety of treatments to provide high yield, high purity nucleic acids. For example, a variety of publications and patents describing such methods are listed herein. Examples include Short "PRODUCTION OF ENZYMES HAVING DESIRED ACTIVITIES BY MUTAGENESIS" U.S. Pat. No. 5,939, 250, Thompson, et al. (1998) "METHODS FOR GENERATING AND SCREENING NOVEL METABOLIC PATHWAYS" U.S. Pat. No. 5,824,485 and U.S. Pat. No. 6,783,431; and Carlson, et al. (1999) "METHOD OF RECOVERING A BIOLOGICAL MOLECULE FROM A RECOMBINANT MICROORGANISM" U.S. Pat. Nos. 5,908,765, 5,837,470 and 5,773,221, which allege various methods for creating libraries from, e.g., uncharacterized heterogeneous microbial samples. The present invention provides, e.g., for automation, spatial or logical arrays and associated tools in mediating, improving or replacing these processes.

Often, effective development of a commercially relevant enzyme, protein or biochemical pathway (e.g. for pharmaceutical or industrial applications) involves identifying a plurality of favorable activity parameters be encoded by the candidate gene(s). Having a means of rapidly recruiting and then diversifying a wide variety of starting genes from a wide variety of sources—such as may share a common structural or activity motif—is of importance for rapid gene or pathway development. The present application teaches the application of a family of array operations and automated processing of a wide range of mutagenesis, gene synthesis and recombination and technologies for improving candidate genes.

While preliminary gene recruitment can be done by hybridization or on the basis of logically derived and/or stored hybridization information, hybridization is often not used in confirming the activity or intactness of a given nucleic acid within a physical array. For more refined recruitment or identification of promising candidate genes within an array, it is useful to have at least one other biochemical activity measurement on which to contrast the various members of the storage array. The current invention contemplates and describes a large number of logical and laboratory-based criteria and processes for storing, maintaining and recording that information and its physical of logical linkage with given members of the array. Thus a member of an array is most accurately defined on the basis of its activity in each of the tests performed on it.

A wide variety of phenotypic attributes or combinations of such attributes are useful for identifying genes for suitable for a given application, process, pathway or subsequent evolution toward such applications. In addition to simply creating libraries from diverse samples, expressing such libraries in cells or on phage, and analyzing the results biochemically, the present invention provides, e.g., for automated, integrated or integratable modules for rapidly producing and characterizing expression arrays, e.g., by way of in vitro transcription or translation tools. The present methods also describe the utility and design of automated processes for identifying, cataloging, selecting and subsequently evolving genes from natural or synthetic systems.

One embodiment the present invention describes an automated process for recruiting genes from natural, synthetic or logical sources and storing genetic material suitable for subsequent characterization, mutagenesis, selection and evolution. In another embodiment, it describes the automated devices or modules which carry out such processes.

In addition, the present invention describes a series of general, automatable methods for high-yield extraction of nucleic acids from a wide variety of samples. In these methods, samples containing nucleic acids (e.g., as from diverse or clonal cultured or uncultured cellular populations; tissue sections; sera samples; samples from heterogeneous enrichment cultures, bioreactors or fermentors; samples containing one or more uncharacterized microorganism; environmental isolates; soil, water or microcosm samples) are treated by a method, e.g., comprising the following processes.

First the sample is treated with a plurality of chemical lysing agents (consisting of: chaotropic substance(s), detergent(s), chelator(s), proteinase(s), exo- or endo-glucanase(s), lysozyme(s) and other proteoglycan or cell wall degrading enzymes, etc.) under conditions which allow the lysing agent or agents to come into liquid contact the cell membranes the target cells. The plurality of lysing agents can include a chaotropic agent capable of substantially inactivating a wide variety of nucleases. Similarly, the plurality of lysing agents can include at least one chaotrope and at least one enzyme for lysis. Examples of lysing agents include urea, guanidine and guanidinium, enzymes, etc. Any one or more of these chemical or physical lysing conditions can be used on a given sample, or a sample may be subdivided and subjected to sequential or combinatorial lysis to: a) identify optimal lysing conditions, b) prepare multiple unique extracts from a single sample and/or c) conduct parallel sample preparation, for any purpose.

Second, the samples can be treated with at least one disruptive physical condition(s) or treatment(s) (e.g. freeze-thawing, freeze drying, cold-hot cycling, disruptive (rapid) mixing, sonicating, heating, incubation at pH<5.5 or >8.5, etc.). The at least one disruptive physical condition or treatment can include incubation at a temperature above 37° C. and, e.g. at a temperature of >50° C. The at least one disruptive physical condition or treatment can include at least one freeze-thaw, mixing or sonication step and incubation at a temperature of >50° C. The at least one disruptive physical condition or treatment can include at least one heating or cooling step and at least one step which can cause (such as mixing, vortexing, sonicating or incubating in hypotonic media) physical shearing of cell walls and high molecular weight DNA.

The sample can be subjected to at least one physical-chemical separation step (which may be chosen or achieve similar results such as precipitation, solvent extraction, electrophoretic or chromatographic separation or others) to isolate high purity nucleic acids, e.g., from enriched cultures, natural isolates, cultured cells, tissues or sera. For example at least one alcohol mediated precipitation step or one extraction step can be used. The use of a plurality of physico-chemical separation modes can be used in the extraction process. At least one extraction step and one precipitation or chromatographic step can be used in combination.

In a preferred embodiment, the process described here is conducted under conditions in which a plurality of lysing agents and disruptive physical agents are used on and in which the operation is integrated into an automated device.

The automation of such a method provides a free-standing and uniquely valuable platform from which to conduct high throughput nucleic acid extraction and purification from diverse sample sources. Nucleic acids prepared in such a way can be further characterized or selected, with or without prior cloning, by hybridization-based detection, capture (e.g. 'panning') or direct recombination with other members of the population or exogenous nucleic acids added to the mixture, followed by expression screening.

Expression screening can involve at least one in vitro transcription or translation step. For example, it can involve in vitro transcription preceded by at least one amplification, polymerization or ligation event in which at least one transcriptional regulatory element is operatively linked to the nucleic acids to undergo transcription. In a presently preferred embodiment, the method involves the in vitro translation of library members using transcripts derived from either in vitro, synthetic or cellular sources.

The present invention describes, e.g., the following automated modules for the isolation, detection and evolution of nucleic acids from natural and synthetic isolates: nucleic acid isolation modules, nucleic acid generation modules, nucleic acid sorting or selection modules, dilution modules, array replication modules, expression module, screening modules, etc. Such modules can operate as free-standing devices or as sub-elements of a larger device or other system which links one or more of these modules physically or logically to create, modify, analyze replicate or otherwise manipulate members of interest within the array.

The present invention also provides a logical association for organizing a multiple-phenotype screening array. For example, the present invention provides for detection and screening of genes in a primarily binary process, where individual clones, proteins or enzymes (whether protein or nucleic acid, or both) are identified as either having or not having a specified property or set of properties (resulting in a binary "yes/no" logical operation by the system in evaluating the properties). In addition to strictly binary processes, degrees of activity can also be detected and manipulated by the system.

The invention can also include the organization of multi-phenotype screening in which (one or more) clones in the array are described, organized, screened or otherwise sorted (in physical or computational terms) by their activity fingerprints, such that characterization of the array is open-ended and allows for increasingly diverse layers of characterization to be applied. Such arrays can remain closed-ended with respect to their origin or member nucleic acids. In one embodiment, the array architecture allows for each clone, pool of clones, individual or individual pools of nucleic acids within an array to be described in both (or either) binary and quantitative terms with respect to a given activity or property and provides a means for further isolation, processing or characterization of those members selected on the basis of either Boolean or quantitative queries, or combinations of the two.

While not limited to these, the query-able properties include biological or chemical activities, physical or structural attributes, nucleic acid or amino acid sequences, source, prior processing methods, histories or exposures or physical state within the array. In another embodiment, the present invention provides for the automated or semi-automated amplification, replication and in vitro transcription and/or translation of the physical array to create sub-arrays which can be stored or screened for other properties. In preferred embodiments, the present invention describes a process and a device for isolating nucleic acids from natural or synthetic or computational sources, storing such nucleic acids as logical (or physical) arrays based on a plurality of phenotypes (one of which may be its nucleotide sequence) and the contacting of arrays, with one or more in vitro transcription or translation reagents.

In the present invention, the term 'phenotype' is used to refer to a general or specific set of traits for which a given clone has been screened. The complete complement of phenotypic traits may be derived directly from laboratory data, by logical inference from such data or from stored databases of relevant data (e.g. such as activity, sequence or relational databases). These traits can be directly or indirectly screened, including for stability under natural non-natural physical or chemical conditions, expressibility in a given cell line, strain or in vitro extract, size, solubility, hybridization properties, sequence, associated regulatory elements, catalytic rate, substrate or product selectivity, luminescent, fluorescent, light scattering, x-ray diffracting, sedimentation, binding, calorimetric, refractive or other diverse properties.

The arrays of the invention have value in all areas in which gene products have utility, including pharmaceutical and chemical discovery and manufacturing, agriculture, diagnostics, biofuels, fuel cells and bioelectronics, and many other areas. Such arrays are developed, e.g., from gene libraries extracted from nature or natural sources. They can also be derived computationally or via automated gene or oligonucleotide synthesis. In addition, analogous or derivative arrays may be generated via the application of shuffling or other mutagenesis methods to one or more parental nucleic acids.

While each phenotypic attribute is of value in describing a given member of an array, certain combinations of properties can be particularly useful in characterizing genes for utility in pharmaceutical or chemical manufacturing processes. For example, an array in which at least one physical attribute and at least one selectivity attribute are measured for a plurality of members of that array can be more valuable than one in which only the expression, selectivity or stability attribute has been assessed.

Similarly, an array containing enzymes (or cells expressing such enzymes) which have been quantitatively characterized for their tested for their ability to stereoselectively convert a substrate to a given product under a defined solvent or temperature regime is more informative to the synthetic or process chemist interested in the given conversion than one in which only one of the properties listed has been examined. For synthetic and process chemistry applications physical chemical attributes of interest include many diverse attributes. For example, stability or activity in solvents or mixed water-solvents systems (common solvents would, for example include polar protic and aprotic solvents, nonpolar solvents, alcohols, ethers, esters, alkanes, halogenated solvents, phenols, tetrahydrofuran, benzene and its derivatives, aromatic, fluorinated and perfluorinated solvents, etc. . . . ), stability or activity at elevated or depressed temperatures (e.g. above 50° C. and below 20° C.; e.g., >70° C. or <10° C.), and stability or activity in high or low salt concentrations (e.g. >1 M or <0.050 M sodium, potassium and ammonium containing salts with chloride, bromide, nitrate, nitrite, sulfate, sulfite, carbonate, bicarbonate or amino acid counterions). Similarly, stability or activity at high or low pressure, in oxygen-rich or oxygen deficient environments and/or in the presence of a variety of a one or more agents capable of inactivating proteins by covalent modification (e.g., acylating, alkylating and amide reactive agents), stability of activity in the presence of at least phase transfer or crosslinking agent, or stability or activity within or upon a solid matrix (e.g. by covalent or noncovalent association with a natural or functionalized surface, the surface comprising a hydrophobic or hygroscopic polymer, silica, glass, metal, aluminum, alloy, cellulosic or modified cellulosic, hygroscopic insoluble material a natural biopolymer, a polysaccharide and modified forms of these) can also be of interest.

Selectivity attributes of interest in process and combinatorial chemistry include, but are not limited to, product or substrate chemoselectivity, regioselectivity, stereoselectivity and enantioselectivity; and each of these in combination with a plurality of solvent and physical conditions such as those described above. Thus the present invention describes means of making and using logical and/or physical enzyme arrays in which each member has been characterized on the basis of its activity under at least one nonphysiological physical condition and at least one selectivity attribute. For example, the at least one nonphysiological condition can involve one or more of the following conditions: a nonphysiological thermal, salt, solvent, pressure, or oxygen condition; the presence of active levels of one or more crosslinking agents; or the presence of active levels of one or more potential covalent modifying agents; or immobilization upon on a nonbiological surface.

K. Further Embodiments

In a further aspect, the present invention provides for the use of any apparatus, apparatus component, composition or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent documents (including patent applications) and other references cited in this application are incorporated by reference in their entirety for all purposes to the same extent as if each individual publication, patent, patent document or other reference were individually indicated to be incorporated by reference for all purposes.

What is claimed is:

1. A diversity generation device comprising:
   a fragmentation module configured to fragment parental nucleic acids to produce nucleic acid fragments; and
   a programmed thermocycler operably coupled to the fragmentation module and configured to receive the nucleic acid fragments from the fragmentation module and to reassemble the nucleic acid fragments to produce shuffled nucleic acids,
   wherein the programmed thermocycler comprises a thermocycler operably coupled to a computer,
   wherein the computer comprises one or more instruction sets for:
      calculating one or more crossover regions between two or more parental nucleic acid sequences of the parental nucleic acids;
      using the calculated one or more crossover regions to select the parental nucleic acids for use in the fragmentation module; and
      calculating an amount of uracil and an amount of thymidine based on a desired fragment size.

2. The diversity generation device of claim 1, wherein the one or more instruction sets comprise instructions for receiving user input data and setting up one or more cycles to be performed by the programmed thermocycler.

3. The diversity generation device of claim 2, wherein the input data comprises one or more of the following: one or more parental nucleic acid nucleic acid sequences, a desired crossover frequency, an extension temperature, or an annealing temperature.

4. The diversity generation device of claim 2, wherein the one or more instruction sets further comprise instructions for directing the diversity generation device to perform the one or more cycles comprising:
   selecting the parental nucleic acids;
   amplifying the parental nucleic acids;
   fragmenting the parental nucleic acids to produce the nucleic acid fragments; and
   reassembling the nucleic acid fragments to produce the shuffled nucleic acids, wherein the shuffled nucleic acids are used as the parental nucleic acids in one or more subsequent cycles.

5. The diversity generation device of claim 4, wherein the amplifying operation comprises amplifying the parental nucleic acids in the presence of uracil.

6. The diversity generation device of claim 4, wherein the one or more instruction sets comprise instructions to pause the one or more cycles between the amplifying and fragmenting operations to allow for addition of one or more fragmentation reagents.

7. The diversity generation device of claim 1, wherein the one or more instruction sets comprise instructions for performing one or more calculations based on one or more theoretical predictions of a nucleic acid melting temperature or based on one or more sets of empirical data, the one or more sets of empirical data comprising a comparison of one or more nucleic acid melting temperatures.

8. The diversity generation device of claim 4, wherein the one or more instruction sets comprise instructions to the fragmentation module to fragment the parental nucleic acids to produce the nucleic acid fragments having a desired mean fragment size.

9. The diversity generation device of claim 1, wherein the computer is configured to receive user input data comprising the parental nucleic acids, and wherein the programmed thermocycler comprises software for performing one or more shuffling calculations on the parental nucleic acid sequences, the software embodied on a web page or installed directly on the thermocycler.

10. The diversity generation device of claim 1, wherein the fragmentation module is configured to fragment the parental nucleic acids by sonication, DNase II digestion, random primer extension, or uracil incorporation and is further configured to treat the parental nucleic acids with one or more uracil cleavage enzymes.

11. The diversity generation device of claim 1, wherein the one or more sets of instructions for calculating the one or more crossover regions comprise instructions for identifying sequence windows having a melting temperature greater than a predetermined threshold, the sequence windows are separated by no more than two nucleotides.

12. The diversity generation device of claim 11, wherein the one or more instruction sets further comprise instructions for identifying a shuffleability score and a diversity capture score for the two or more parental nucleic acid sequences based on a number of the identified sequence windows.

13. The diversity generation device of claim 12, wherein the one or more instruction sets further comprise instructions for ranking the two or more parental nucleic acid sequences based on the shuffleability score and the diversity capture score.

14. A diversity generation device comprising:
a fragmentation module configured to fragment parental nucleic acids to produce nucleic acid fragments; and
a programmed thermocycler operably coupled to the fragmentation module and configured to receive the nucleic acid fragments from the fragmentation module and to reassemble the nucleic acid fragments to produce shuffled nucleic acids,
wherein the programmed thermocycler comprises a thermocycler operably coupled to a computer,
wherein the computer comprises one or more instruction sets for:
calculating one or more crossover regions between two or more parental nucleic acid sequences of the parental nucleic acids;
using the calculated one or more crossover regions to select the parental nucleic acids for use in the fragmentation module; and
performing one or more calculations based on one or more theoretical predictions of a nucleic acid melting temperature or based on one or more sets of empirical data, the one or more sets of empirical data comprising a comparison of one or more nucleic acid melting temperatures.

15. A diversity generation device comprising:
a fragmentation module configured to fragment parental nucleic acids to produce nucleic acid fragments; and
a programmed thermocycler operably coupled to the fragmentation module and configured to receive the nucleic acid fragments from the fragmentation module and to reassemble the nucleic acid fragments to produce shuffled nucleic acids,
wherein the programmed thermocycler comprises a thermocycler operably coupled to a computer,
wherein the computer comprises one or more instruction sets for:
calculating one or more crossover regions between two or more parental nucleic acid sequences of the parental nucleic acids;
using the calculated one or more crossover regions to select the parental nucleic acids for use in the fragmentation module; and
calculating the one or more crossover regions comprise instructions for identifying sequence windows having a melting temperature greater than a predetermined threshold, the sequence windows are separated by no more than two nucleotides.

* * * * *